US012123027B2

(12) United States Patent
Hörer et al.

(10) Patent No.: US 12,123,027 B2
(45) Date of Patent: Oct. 22, 2024

(54) LIFE-CYCLE-DEFECTIVE ADENOVIRUS HELPER VIRUSES, THEIR PRODUCTION AND USE FOR PRODUCING rAAV

(71) Applicant: ASCEND GENE AND CELL THERAPIES LTD, Altrincham (GB)

(72) Inventors: Markus Hörer, Gilching (DE); Stefan Kochanek, Blaubeuren (DE); Caroline Hauser, Ehingen (DE); Alexandra Krüger-Haag, Blaustein (DE)

(73) Assignee: Ascend Advanced Therapies Limited, Altrincham (GB)

( * ) Notice: Subject to any disclaimer, the term of this patent is extended or adjusted under 35 U.S.C. 154(b) by 973 days.

(21) Appl. No.: 16/755,283

(22) PCT Filed: Oct. 12, 2018

(86) PCT No.: PCT/EP2018/077945
§ 371 (c)(1),
(2) Date: Apr. 10, 2020

(87) PCT Pub. No.: WO2019/073059
PCT Pub. Date: Apr. 18, 2019

(65) Prior Publication Data
US 2020/0239859 A1 Jul. 30, 2020

(30) Foreign Application Priority Data
Oct. 12, 2017 (DE) ..................... 10 2017 009 489.6

(51) Int. Cl.
*C12N 7/00* (2006.01)
*A61K 35/76* (2015.01)
*C12N 15/86* (2006.01)

(52) U.S. Cl.
CPC ................ *C12N 7/00* (2013.01); *A61K 35/76* (2013.01); *C12N 15/86* (2013.01);
(Continued)

(58) Field of Classification Search
None
See application file for complete search history.

(56) References Cited

FOREIGN PATENT DOCUMENTS

| | | | |
|---|---|---|---|
| WO | WO-9911764 | A2 | 3/1999 |
| WO | WO-9941399 | A1 | 8/1999 |

(Continued)

OTHER PUBLICATIONS

Cepko C L., et al. "Analysis of Ad5 Hexon and 100K is mutants using conformation-specific monoclonal antibodies", Aug. 1, 1983, vol. 129, No. 1 pp. 137-154.

(Continued)

*Primary Examiner* — M Franco G Salvoza
(74) *Attorney, Agent, or Firm* — Klarquist Sparkman, LLP

(57) ABSTRACT

The invention generally concerns the production of defective Adenovirus helper viruses for producing a recombinant adeno-associated virus (rAAV), wherein the Adenovirus helper virus contains at least one mutation selected from (a) an inactivating mutation in the transcription unit coding for the L4-100K protein; (b) an inactivating mutation in the transcription unit coding for the L1-52/55K protein; (c) an inactivating mutation in the transcription unit coding for the preterminal protein (pTP); (d) a mutation in the L4-100K protein in order to render it temperature-sensitive (ts); (e) a mutation in the hexon protein in order to render it temperature-sensitive (ts); and/or (f) a mutation in the L4-00K protein and a mutation in the hexon protein in order to render it temperature-sensitive (ts).

22 Claims, 10 Drawing Sheets

Specification includes a Sequence Listing.

(52) U.S. Cl.
CPC .............. *C12N 2710/10321* (2013.01); *C12N 2710/10322* (2013.01); *C12N 2710/10343* (2013.01); *C12N 2710/10352* (2013.01); *C12N 2750/14122* (2013.01); *C12N 2750/14132* (2013.01); *C12N 2750/14151* (2013.01); *C12N 2750/14152* (2013.01)

(56) References Cited

FOREIGN PATENT DOCUMENTS

| | | | |
|---|---|---|---|
| WO | WO-0012740 | A2 | 3/2000 |
| WO | WO-02098466 | A1 | 12/2002 |
| WO | WO-03092594 | A2 | 11/2003 |

OTHER PUBLICATIONS

Challberg S S., et al. "Deletion mutants of adenovirus 2: Isolation and initial characterization of virus carrying mutations near the right end of the viral genome", Oct. 15, 1981, vol. 114, No. 1, pp. 196-209.

Hodges, B L., et al., "Multiply deleted [E1, polymerase-, and pTP-] adenovirus vector persists despite deletion of the preterminal protein", The Journal of Gene Medicine, vol. 2, No. 4, Jul. 2000, pp. 250-259.

International Search Report and Written Opinion for Corresponding PCT application No. PCT/EP2018/077945 issued Apr. 19, 2019.

Maxwell Ian H., et al., "An adenovirus type 5 mutant with the preterminal rotein gene deleted efficiently provides helper functions for the production of recombinant adeno-associated virus", Journal of Virology, vol. 72, No. 10, Oct. 1998, pp. 8371-8373.

Dolph et al.: Translation by the Adenovirus Tripartite Leader: Elements Which Determine Independence from Cap-Binding Protein Complex. Journal of Virology 64, No. 6 (Jun. 1990): 2669-2677.

Gustin et al.: Encapsidation of Viral DNA Requires the Adenovirus L1 52/55-Kilodalton Protein. Journal of Virology 72, No. 10 (Oct. 1998): 7860-7870.

Hasson et al.: Adenovirus L1 52- and 55-Kilodalton Proteins Are Required for Assembly of Virions. Journal of Virology 63, No. 9 (Sep. 1989): 3612-3621.

Hodges et al., Adenovirus Vectors with the 100K Gene Deleted and Their Potential for Multiple Gene Therapy Applications, J. Virol., 75(13): 5913-5920 (2001).

Kauffman et al.: Characterization of a Temperature-Sensitive, Hexon Transport Mutant of Type 5 Adenovirus. Journal of Virology 19, No. 2 (Aug. 1976): 643-658.

Kruger-Haag, A.: Development of an improved production system for AAV vectors. International Graduate School in Molecular Medicine Ulm, Biannual Report 2016, p. 97.

Oosterom-Dragon et al.: Characterization of two temperature-sensitive mutants of type 5 adenovirus with mutations in the 100,000-dalton protein gene. Journal of Virology 40, No. 2 (Nov. 1981): 491-500.

Perez-Romero et al.: Dependence of the Encapsidation Function of the Adenovirus L1 52/55-Kilodalton Protein on Its Ability to Bind the Packaging Sequence. Journal of Virology 80, No. 4 (Feb. 2006): 1965-1971.

Schaack et al.: Adenovirus Type 5 Precursor Terminal Protein-Expressing 293 and HeLa Cell Lines. Journal of Virology 69, No. 7 (Jul. 1995): 4079-4085.

Schaack et al.: Characterization of a Replication-Incompetent Adenovirus Type 5 Mutant Deleted for the Preterminal Protein Gene. Proceedings of the National Academy of Sciences of the United States of America 93, No. 25 (Dec. 10, 1996): 14686-14691.

Williams et al.: Isolation of Temperature-sensitive Mutants of Adenovirus Type 5. Journal of General Virology 11, No. 2 (1971): 95-101. doi:10.1099/0022-1317-11-2-95.

Wodrich et al.: Switch from Capsid Protein Import to Adenovirus Assembly by Cleavage of Nuclear Transport Signals. The EMBO Journal 22, No. 23 (Dec. 1, 2003): 6245-6255. doi:10.1093/emboj/cdg614.

Fig. 3

(SEQ ID NO: 50)

atggagtcagtcgagaagaaggacagcctaaccgcccctctgagttcgccaccaccgcctccaccgatgccgccaacgc
gcctaccaccttccccgtcgaggcacccccgcttgaggaggaggaagtgattatcgagcaggacccaggttttgtaagcg
aagacgacgaggaccgctcagtaccaacagaggataaaagcaagaccaggacaacgcagaggcaaacgaggaacaagtc
gggcgggggacgaaaggcatggcgactacctagatgtgggagacgacgtgctgttgaagcatctgcagcgccagtgcgc
cattatctgcgacgcgttgcaagagcgcagcgatgtgcccctcgccatagcggatgtcagccttgcctacgaacgccacc
tattctcaccgcgcgtacccccaaacgccaagaaaacggcacatgcgagcccaacccgcgcctcaacttctaccccgta
tttgccgtgccagaggtgcttgccacctatcacatctttttccaaaactgcaagataccccctatcctgccgtgccaaccg
cagccgagcggacaagcagctggccttgcggcagggcgctgtcatacctgatatcgcctcgctcaacgaagtgccaaaaa
tctttgagggtcttggacgcgacgagaagcgcgcggcaaacgctctgcaacaggaaaacagcgaaaatgaaagtcactct
ggagtgttggtggaactcgagggtgacaacgcgcgcctagccgtactaaaacgcagcaTCGAGGTCACCCACTTTGCCTA
CCCGGCACTTAACCTACCCCCCAAGGTCTTGCCTACCACTCTGACATAATGGAAGACGTGAGCGGTGACGGTCTACTGga
gtgtcactgtcgctgcaacctatgcacccccgcaccgctccctggtttgcaattcgcagctgcttaacgaaagtcaaatta
tcggtacctttgagctgcagggtccctcgcctgacgaaaagtccgcggctccggggttgaaactcactccggggctgtgg
acgtcggcttaccttcgcaaatttgtacctgaggactaccacgcccacgagattaggttctacgaagaccaatcccgccc
gccaaatgcggagcttaccgcctgcgtcattacccagggccacattcttggccaattgcaagccatcaacaaagcccgcc
aagagtttctgctacgaaagggacgggggtttacttggacccccagtccggcgaggagctcaacccaatcccccgccg
ccgcagccctatcagcagcagccgcgggcccttgcttcccaggatggcacccaaaaagaagctgcagctgccgccgccac
ccacggacgaggaggaatactgggacagtcaggcagaggaggtttggacgaggaggaggaggacatgatggaagactgg
gagagcctagacgaggaagcttccgaggtcgaagaggtgtcagacgaaacaccgtcaccctcggtcgcattcccctcgcc
ggcgcccccagaaatcggcaaccggttccagcatggctacaacctccgctcctcaggcgccgccggcactgcccgttcgcc
gacccaaccgtag (SEQ ID NO: 51)

CAGCTGGGGCCGGACCTGGGCTGGCGGTGGCACCCGCGCGCGCTGGCAACgtcggcggcgtggaggaatatgacgaggac gatgagtacgagccagaggacggcgagtactaa

Fig. 11A

SEQ ID NO: 52 ctaaaagcggtgacgcgggcgagcccccggaggtagggggggctccggacccgccgggagaggggcaggggcacgtcgg
cgccgcgcgcgggcaggagctggtgctgcgcgcgtaggttgctggcgaacgcgacgacgcggcggttgatctcctgaatc
tggcgcctctgcgtgaagacgacgggcccggtgagcttgagcctgaaagagagttcgacagaatcaatttcggtgtcgtt
gacggcggcctggcgcaaaatctcctgcacgtctcctgagttgtcttgataggcgatctcggccatgaactgctcgatct
cttcctcctggagatctccgcgtccggctcgctccacggtggcggcgaggtcgttggaaatgcgggccatgagctgcgag
aaggcgttgaggcctccctcgttccagacgcggctgtagaccacgccccccttcggcatcgcgggcgcgcatgaccacctg
cgcgagattgagctccacgtgccgggcgaagacggcgtagtttcgcaggcgctgaaagaggtagttgagggtggtggcgg
tgtgttctgccacgaagaagtacataacccagcgtcgcaacgtggattcgttgatatcccccaaggcctcaaggcgctcc
atggcctcgtagaagtccacggcgaagttgaaaaactgggagttgcgcgccgacacggttaactcctcctccagaagacg
gatgagctcggcgacagtgtcgcgcacctcgcgctcaaaggctacaggggcctcttcttcttcttcaatctcctcttcca
taagggcctccccttcttcttcttctggcggcggtgggggaggggggacacggcggcgacgacggcgcaccgggaggcgg
tcgacaaagcgctcgatcatctccccgcggcgacggcgcatggtctcggtgacggcgcggccgttctcgcgggggcgcag
ttggaagacgccgcccgtcatgtcccggttatgggttggcgggggctgccatgcggcagggatacggcgctaacgatgc
atctcaacaattgttgtgtaggtactccgccgccgagggacctgagcgagtccgcatcgaccggatcggaaaacctctcg
agaaaggcgtctaaccagtcacagtcgcaaggtaggctgagcaccgtggcgggcggcagcgggcggcggtcggggttgtt
tctggcggaggtgctgctgatgatgtaattaaagtaggcggtcttgagacggcggatggtcgacagaagcaCCATGTCCT
TGGGTCCGGCCTGCTGAATGCGCAGGCGGTCGGCCATGCCCCTAGACCGTGCAAAAGGAGAGCCTGTAAGCGGGCACTCT
TCCGTGGTCTGgtggataaattcgcaagggtatcatggcggacgaccggggttcgagccccgtatccggccgtccgccgt
gatccatgcggttaccgcccgcgtgtcgaacccaggtgtgcgacgtcagacaacgggggagtgctccttttggcttcctt
ccaggcgcggcggctgctgcgctagcttttttggccactggccgcgcgcagcgtaagcggttaggctggaaagcgaaagc
attaagtggctcgctccctgtagccggagggttattttccaagggttgagtcgcgggacccccggttcgagtctcggacc
ggccggactgcggcgaacgggggtttgcctccccgtcatgcaagaccccgcttgcaaattcctccggaaacagggacgag
cccctttttttgcttttcccagatgcatccggtgctgcggcagatgcgcccccctcctcagcagcggcaagagcaagagca
gcggcagacatgcagggcaccctcccctcctcctaccgcgtcaggaggggcgacatccgcggttgacgcggcagcagatg
gtgattacgaacccccgcggcgccgggcccggcactacctggacttggaggagggcgagggcctggcgcggctaggagcg
ccctctcctgagcggtacccaaggtgcagctgaagcgtgatacgcgtgaggcgtacgtgccgcggcagaacctgtttcg
cgaccgcgagggagaggagcccgaggagatgcgggatcgaaagttccacgcagggcgcgagctgcggcatggcctgaatc
gcgagcggttgctgcgcgaggaggactttgagcccgacgcgcgaaccgggattagtcccgtggcgggccgcgacctggt
aaccgcatacgagcagacggtgaaccaggagattaactttcaagcgcgcgcacaaaagctttaacaaccacgtgcgtac
gcttgtggcgcgcgaggaggtggctataggactgatgcatctgtgggactttgtaagcgcgctggagcaaaacccaaata
gcaagccgctcatggcgcagctgttccttatagtgcagcacagcagggacaacgaggcattcagggatgcgctgctaaac
atagtagagcccgagggccgctggctgctcgatttgataaacatcctgcagagcatagtggtgcaggagcgcagcttgag
cctggctgacaaggtggccgccatcaactattccatgcttagcctgggcaagtttttacgcccgcaagatataccataccc
cttacgttcccatagacaaggaggtaaagatcgaggggttctacatgcgcatggcgctgaaggtgcttaccttgagcgac
gacctgggcgtttatcgcaacgagcgcatccacaaggccgtgagcgtgagccggcggcgcgagctcagcgaccgcgagct
gatgcacagcctgcaaagggccctggctggcacgggcagcggcgatagagaggccgagtcctactttgacgcgggcgctg

Fig. 11B acctgcgctgggccccaagccgacgcgccctggaggcagctggggccggacctgggctggcggtggcaccgcgcgcgct
ggcaacgtcggcggcgtggaggaatatgacgaggacgatgagtacgagccagaggacggcgagtactaagcgggtgatgtt
tctgatcagatgatgcaagacgcaacggacccggcggtgcggggcggcgctgcagagccagccgtccggccttaactccac
ggacgactggcgccaggtcatggaccgcatcatgtcgctgactgcgcgcaatcctgacgcgttccggcagcagccgcagg
ccaaccggctctccgcaattctggaagcggtggtcccggcgcgcgcaaaccccacgcacgagaaggtgctggcgatcgta
aacgcgctggccgaaaacagggccatccggcccgacgaggccggcctggtctacgacgcgctgcttcagcgcgtggctcg
ttacaacagcggcaacgtgcagaccaacctggaccggctggtgggggatgtgcgcgaggccgtggcgcagcgtgagcgcg
cgcagcagcagggcaacctgggctccatggttgcactaaacgccttcctgagtacacagcccgccaacgtgccgcgggga
caggaggactacaccaactttgtgagcgcactgcggctaatggtgactgagacaccgcaaagtgaggtgtaccagtctgg
gccagactattttttccagaccagtagacaaggcctgcagaccgtaaacctgagccaggctttcaaaaacttgcaggggc
tgtggggggtgcgggctcccacaggcgaccgcgcgaccgtgtctagcttgctgacgcccaactcgcgcctgttgctgctg
ctaatagcgcccttcaggacagtggcagcgtgtcccgggacacatacctaggtcacttgctgacactgtaccgcgaggc
cataggtcaggcgcatgtggacgagcatactttccaggagattacaagtgtcagccgcgcgctggggcaggaggacacgg
gcagcctggaggcaaccctaaactacctgctgaccaaccggcggcagaagatcccctcgttgcacagtttaaacagcgag
gaggagcgcattttgcgctacgtgcagcagagcgtgagccttaacctgatgcgcgacggggtaacgcccagcgtggcgct
ggacatgaccgcgcgcaacatggaaccgggcatgtatgcctcaaaccggccgtttatcaaccgcctaatggactacttgc
atcgcgcggccgccgtgaaccccgagtatttcaccaatgccatcttgaacccgcactggctaccgccccctggtttctac
accgggggattcgaggtgcccgagggtaacgatggattcctctgggacgacatagacgacagcgtgttttccccgcaacc
gcagaccctgctagagttgcaacagcgcgagcaggcagaggcggcgctgcgaaaggaaagcttccgcaggccaagcagct
tgtccgatctaggcgctgcggccccgcggtcagatgctagtagcccatttccaagcttgatagggtctcttaccagcact
cgcaccacccgcccgcgcctgctgggcgaggaggagtacctaaacaactcgctgctgcagccgcagcgcgaaaaaaacct
gcctccggcatttcccaacaacgggatagagagcctagtggacaagatgagtagatggaagacgtacgcgcaggagcaca
gggacgtgccaggcccgcgcccgcccacccgtcgtcaaaggcacgaccgtcagcggggtctggtgtgggaggacgatgac
tcggcagacgacagcagcgtcctggatttgggagggagtggcaacccgtttgcgcaccttcgcccaggctggggagaat
gttttaaaaaaaaaaaagcatgatgcaaaataaaaaactcaccaaggccat

SEQUENCE LISTING

<160> NUMBER OF SEQ ID NOS: 49

<210> SEQ ID NO 1
<211> LENGTH: 1613
<212> TYPE: DNA
<213> ORGANISM: Artificial sequence
<220> FEATURE:
<223> OTHER INFORMATION: Nucleic acid encoding the L4-100K mutant

<400> SEQUENCE: 1
atggagtcag tcgagaagaa ggacagccta accgccccct ctgagttcgc caccaccgcc 60
tccaccgatg ccgccaacgc gcctaccacc ttccccgtcg aggcaccccc gcttgaggag 120
gaggaagtga ttatcgagca ggacccaggt tttgtaagcg aagacgacga ggaccgctca 180
gtaccaacag aggataaaaa gcaagaccag gacaacgcag aggcaaacga ggaacaagtc 240
gggcgggggg acgaaaggca tggcgactac ctagatgtgg gagacgacgt gctgttgaag 300
catctgcagc gccagtgcgc cattatctgc gacgcgttgc aagagcgcag cgatgtgccc 360
ctcgccatag cggatgtcag ccttgcctac gaacgccacc tattctcacc gcgcgtaccc 420
cccaaacgcc aagaaaacgg cacatgcgag cccaacccgc gcctcaactt ctaccccgta 480
tttgccgtgc cagaggtgct tgccacctat cacatctttt tccaaaactg caagataccc 540
ctatcctgcc gtgccaaccg cagccgagcg gacaagcagc tggccttgcg gcagggcgct 600
gtcatacctg atatcgcctc gctcaacgaa gtgccaaaaa tctttgaggg tcttggacgc 660
gacgagaagc gcgcggcaaa cgctctgcaa caggaaaaca gcgaaaatga aagtcactct 720
ggagtgttgg tggaactcga gggtgacaac gcgcgcctag ccgtactaaa acgcagcatc 780
gaggtcaccc actttgccta cccggcactt aacctacccc ccaaggtctt gcctaccact 840
ctgacataat ggaagacgtg agcggtgacg gtctactgga gtgtcactgt cgctgcaacc 900
tatgcacccc gcaccgctcc ctggtttgca attcgcagct gcttaacgaa agtcaaatta 960
tcggtacctt tgagctgcag ggtccctcgc ctgacgaaaa gtccgcggct ccggggttga 1020
aactcactcc ggggctgtgg acgtcggctt accttcgcaa atttgtacct gaggactacc 1080
acgcccacga gattaggttc tacgaagacc aatcccgccc gccaaatgcg gagcttaccg 1140
cctgcgtcat tacccagggc cacattcttg gccaattgca agccatcaac aaagcccgcc 1200
aagagtttct gctacgaaag ggacgggggg tttacttgga cccccagtcc ggcgaggagc 1260
tcaacccaat ccccccgccg ccgcagccct atcagcagca gccgcgggcc cttgcttccc 1320
aggatggcac ccaaaaagaa gctgcagctg ccgccgccac ccacggacga ggaggaatac 1380
tgggacagtc aggcagagga ggttttggac gaggaggagg aggacatgat ggaagactgg 1440
gagagcctag acgaggaagc ttccgaggtc gaagaggtgt cagacgaaac accgtcaccc 1500
tcggtcgcat tcccctcgcc ggcgccccag aaatcggcaa ccggttccag catggctaca 1560
acctccgctc ctcaggcgcc gccggcactg cccgttcgcc gacccaaccg tag 1613

<210> SEQ ID NO 2
<211> LENGTH: 113
<212> TYPE: DNA

<213> ORGANISM: Artificial sequence
<220> FEATURE:
<223> OTHER INFORMATION: Nucleic acid encoding the L1-52/55K mutant

<400> SEQUENCE: 2

```
cagctggggc cggacctggg ctggcggtgg cacccgcgcg cgctggcaac gtcggcggcg     60

tggaggaata tgacgaggac gatgagtacg agccagagga cggcgagtac taa           113
```

<210> SEQ ID NO 3
<211> LENGTH: 4851
<212> TYPE: DNA
<213> ORGANISM: Artificial sequence
<220> FEATURE:
<223> OTHER INFORMATION: Nucleic acid encoding the pTP mutant

<400> SEQUENCE: 3

```
ctaaaagcgg tgacgcgggc gagcccccgg aggtaggggg ggctccggac ccgccgggag     60

agggggcagg ggcacgtcgg cgccgcgcgc gggcaggagc tggtgctgcg cgcgtaggtt    120

gctggcgaac gcgacgacgc ggcggttgat ctcctgaatc tggcgcctct gcgtgaagac    180

gacgggcccg gtgagcttga gcctgaaaga gagttcgaca gaatcaattt cggtgtcgtt    240

gacggcggcc tggcgcaaaa tctcctgcac gtctcctgag ttgtcttgat aggcgatctc    300

ggccatgaac tgctcgatct cttcctcctg gagatctccg cgtccggctc gctccacggt    360

ggcggcgagg tcgttggaaa tgcgggccat gagctgcgag aaggcgttga ggcctccctc    420

gttccagacg cggctgtaga ccacgccccc ttcggcatcg cgggcgcgca tgaccacctg    480

cgcgagattg agctccacgt gccgggcgaa gacggcgtag tttcgcaggc gctgaaagag    540

gtagttgagg gtggtggcgg tgtgttctgc cacgaagaag tacataaccc agcgtcgcaa    600

cgtggattcg ttgatatccc ccaaggcctc aaggcgctcc atggcctcgt agaagtccac    660

ggcgaagttg aaaaactggg agttgcgcgc cgacacggtt aactcctcct ccagaagacg    720

gatgagctcg gcgacagtgt cgcgcacctc gcgctcaaag gctacagggg cctcttcttc    780

ttcttcaatc tcctcttcca taagggcctc cccttcttct tcttctggcg gcggtggggg    840

agggggggaca cggcggcgac gacggcgcac cgggaggcgg tcgacaaagc gctcgatcat    900

ctccccgcgg cgacggcgca tggtctcggt gacggcgcgg ccgttctcgc gggggcgcag    960

ttggaagacg ccgcccgtca tgtcccggtt atgggttggc ggggggctgc catgcggcag   1020

ggatacggcg ctaacgatgc atctcaacaa ttgttgtgta ggtactccgc cgccgaggga   1080

cctgagcgag tccgcatcga ccggatcgga aaacctctcg agaaaggcgt ctaaccagtc   1140

acagtcgcaa ggtaggctga gcaccgtggc gggcggcagc gggcggcggt cggggttgtt   1200

tctggcggag gtgctgctga tgatgtaatt aaagtaggcg gtcttgagac ggcggatggt   1260

cgacagaagc accatgtcct tgggtccggc ctgctgaatg cgcaggcggt cggccatgcc   1320

cctagaccgt gcaaaaggag agcctgtaag cgggcactct tccgtggtct ggtggataaa   1380

ttcgcaaggg tatcatggcg gacgaccggg gttcgagccc cgtatccggc cgtccgccgt   1440

gatccatgcg gttaccgccc gcgtgtcgaa cccaggtgtg cgacgtcaga caacggggga   1500

gtgctccttt tggcttcctt ccaggcgcgg cggctgctgc gctagctttt ttggccactg   1560

gccgcgcgca gcgtaagcgg ttaggctgga aagcgaaagc attaagtggc tcgctccctg   1620

tagccggagg gttattttcc aagggttgag tcgcgggacc cccggttcga gtctcggacc   1680

ggccggactg cggcgaacgg gggtttgcct ccccgtcatg caagaccccg cttgcaaatt   1740

cctccggaaa cagggacgag ccccttttt gcttttccca gatgcatccg gtgctgcggc   1800
```

-continued

```
agatgcgccc ccctcctcag cagcggcaag agcaagagca gcggcagaca tgcagggcac   1860
cctcccctcc tcctaccgcg tcaggagggg cgacatccgc ggttgacgcg gcagcagatg   1920
gtgattacga acccccgcgg cgccgggccc ggcactacct ggacttggag gagggcgagg   1980
gcctggcgcg gctaggagcg ccctctcctg agcggtaccc aagggtgcag ctgaagcgtg   2040
atacgcgtga ggcgtacgtg ccgcggcaga acctgtttcg cgaccgcgag ggagaggagc   2100
ccgaggagat gcgggatcga aagttccacg cagggcgcga gctgcggcat ggcctgaatc   2160
gcgagcggtt gctgcgcgag gaggactttg agcccgacgc gcgaaccggg attagtcccc   2220
gtggcggccg ccgacctggt aaccgcatac gagcagacgg tgaaccagga gattaacttt   2280
caagcgcgcg cacaaaaagc tttaacaacc acgtgcgtac gcttgtggcg cgcgaggagg   2340
tggctatagg actgatgcat ctgtgggact ttgtaagcgc gctggagcaa aacccaaata   2400
gcaagccgct catggcgcag ctgttcctta tagtgcagca cagcagggac aacgaggcat   2460
tcagggatgc gctgctaaac atagtagagc ccgagggccg ctggctgctc gatttgataa   2520
acatcctgca gagcatagtg gtgcaggagc gcagcttgag cctggctgac aaggtggccg   2580
ccatcaacta ttccatgctt agcctgggca agttttacgc ccgcaagata taccataccc   2640
cttacgttcc catagacaag gaggtaaaga tcgaggggtt ctacatgcgc atggcgctga   2700
aggtgcttac cttgagcgac gacctgggcg tttatcgcaa cgagcgcatc cacaaggccg   2760
tgagcgtgag ccggcggcgc gagctcagcg accgcgagct gatgcacagc ctgcaaaggg   2820
ccctggctgg cacgggcagc ggcgatagag aggccgagtc ctactttgac gcgggcgctg   2880
acctgcgctg ggccccaagc cgacgcgccc tggaggcagc tggggccgga cctgggctgg   2940
cggtggcacc cgcgcgcgct ggcaacgtcg gcggcgtgga ggaatatgac gaggacgatg   3000
agtacgagcc agaggacggc gagtactaag cggtgatgtt tctgatcaga tgatgcaaga   3060
cgcaacggac ccggcggtgc gggcggcgct gcagagccag ccgtccggcc ttaactccac   3120
ggacgactgg cgccaggtca tggaccgcat catgtcgctg actgcgcgca atcctgacgc   3180
gttccggcag cagccgcagg ccaaccggct ctccgcaatt ctggaagcgg tggtcccggc   3240
gcgcgcaaac cccacgcacg agaaggtgct ggcgatcgta aacgcgctgg ccgaaaacag   3300
ggccatccgg cccgacgagg ccggcctggt ctacgacgcg ctgcttcagc gcgtggctcg   3360
ttacaacagc ggcaacgtgc agaccaacct ggaccggctg gtgggggatg tgcgcgaggc   3420
cgtggcgcag cgtgagcgcg cgcagcagca gggcaacctg ggctccatgg ttgcactaaa   3480
cgccttcctg agtacacagc ccgccaacgt gccgcgggga caggaggact acaccaactt   3540
tgtgagcgca ctgcggctaa tggtgactga gacaccgcaa agtgaggtgt accagtctgg   3600
gccagactat tttttccaga ccagtagaca aggcctgcag accgtaaacc tgagccaggc   3660
tttcaaaaac ttgcaggggc tgtggggggt gcgggctccc acaggcgacc gcgcgaccgt   3720
gtctagcttg ctgacgccca actcgcgcct gttgctgctg ctaatagcgc ccttcacgga   3780
cagtggcagc gtgtcccggg acacatacct aggtcacttg ctgacactgt accgcgaggc   3840
cataggtcag gcgcatgtgg acgagcatac tttccaggag attacaagtg tcagccgcgc   3900
gctggggcag gaggacacgg gcagcctgga ggcaacccta aactacctgc tgaccaaccg   3960
gcggcagaag atcccctcgt tgcacagttt aaacagcgag gaggagcgca ttttgcgcta   4020
cgtgcagcag agcgtgagcc ttaacctgat gcgcgacggg gtaacgccca gcgtggcgct   4080
ggacatgacc gcgcgcaaca tggaaccggg catgtatgcc tcaaaccggc cgtttatcaa   4140
```

-continued

```
ccgcctaatg gactacttgc atcgcgcggc cgccgtgaac cccgagtatt tcaccaatgc   4200
catcttgaac ccgcactggc taccgccccc tggtttctac accgggggat tcgaggtgcc   4260
cgagggtaac gatggattcc tctgggacga catagacgac agcgtgtttt ccccgcaacc   4320
gcagaccctg ctagagttgc aacagcgcga gcaggcagag gcggcgctgc gaaaggaaag   4380
cttccgcagg ccaagcagct tgtccgatct aggcgctgcg gccccgcggt cagatgctag   4440
tagcccattt ccaagcttga tagggtctct taccagcact cgcaccaccc gcccgcgcct   4500
gctgggcgag gaggagtacc taaacaactc gctgctgcag ccgcagcgcg aaaaaaacct   4560
gcctccggca tttcccaaca acgggataga gagcctagtg gacaagatga gtagatggaa   4620
gacgtacgcg caggagcaca gggacgtgcc aggcccgcgc ccgcccaccc gtcgtcaaag   4680
gcacgaccgt cagcggggtc tggtgtggga ggacgatgac tcggcagacg acagcagcgt   4740
cctggatttg ggagggagtg gcaacccgtt tgcgcacctt cgccccaggc tggggagaat   4800
gttttaaaaa aaaaaaagca tgatgcaaaa taaaaaactc accaaggcca t            4851
```

<210> SEQ ID NO 4
<211> LENGTH: 42148
<212> TYPE: DNA
<213> ORGANISM: Artificial sequence
<220> FEATURE:
<223> OTHER INFORMATION: Sequence pBEL066 Ad5 wt (42148 bp)

<400> SEQUENCE: 4

```
attattatag tcagctgacg tgtagtgtat ttatacccgg tgagttcctc aagaggccac     60
tcttgagtgc cagcgagtag agttttctcc tccgagccgc tccgacaccg ggactgaaaa    120
tgagacatat tatctgccac ggaggtgtta ttaccgaaga aatggccgcc agtcttttgg    180
accagctgat cgaagaggta ctggctgata atcttccacc tcctagccat tttgaaccac    240
ctacccttca cgaactgtat gatttagacg tgacggcccc cgaagatccc aacgaggagg    300
cggtttcgca gatttttccc gactctgtaa tgttggcggt gcaggaaggg attgacttac    360
tcacttttcc gccggcgccc ggttctccgg agccgcctca cctttcccgg cagcccgagc    420
agccggagca gagagccttg ggtccggttt ctatgccaaa ccttgtaccg gaggtgatcg    480
atcttacctg ccacgaggct ggctttccac ccagtgacga cgaggatgaa gagggtgagg    540
agtttgtgtt agattatgtg gagcaccccg ggcacggttg caggtcttgt cattatcacc    600
ggaggaatac gggggaccca gatattatgt gttcgctttg ctatatgagg acctgtggca    660
tgtttgtcta cagtaagtga aaattatggg cagtgggtga tagagtggtg ggtttggtgt    720
ggtaattttt tttttaattt ttacagtttt gtggtttaaa gaattttgta ttgtgatttt    780
tttaaaaggt cctgtgtctg aacctgagcc tgagcccgag ccagaaccgg agcctgcaag    840
acctacccgc cgtcctaaaa tggcgcctgc tatcctgaga cgcccgacat cacctgtgtc    900
tagagaatgc aatagtagta cggatagctg tgactccggt ccttctaaca cacctcctga    960
gatacacccg gtggtcccgc tgtgccccat taaaccagtt gccgtgagag ttggtgggcg   1020
tcgccaggct gtggaatgta tcgaggactt gcttaacgag cctgggcaac ctttggactt   1080
gagctgtaaa cgccccaggc cataaggtgt aaacctgtga ttgcgtgtgt ggttaacgcc   1140
tttgtttgct gaatgagttg atgtaagttt aataaagggt gagataatgt ttaacttgca   1200
tggcgtgtta aatggggcgg ggcttaaagg gtatataatg cgccgtgggc taatcttggt   1260
tacatctgac ctcatggagg cttgggagtg tttggaagat ttttctgctg tgcgtaactt   1320
gctggaacag agctctaaca gtacctcttg gttttggagg tttctgtggg gctcatccca   1380
```

-continued

```
ggcaaagtta gtctgcagaa ttaaggagga ttacaagtgg gaatttgaag agcttttgaa   1440
atcctgtggt gagctgtttg attctttgaa tctgggtcac caggcgcttt tccaagagaa   1500
ggtcatcaag actttggatt tttccacacc ggggcgcgct gcggctgctg ttgctttttt   1560
gagttttata aaggataaat ggagcgaaga aacccatctg agcggggggt acctgctgga   1620
ttttctggcc atgcatctgt ggagagcggt tgtgagacac aagaatcgcc tgctactgtt   1680
gtcttccgtc cgcccggcga taataccgac ggaggagcag cagcagcagc aggaggaagc   1740
caggcggcgg cggcaggagc agagcccatg gaacccgaga gccggcctgg accctcggga   1800
atgaatgttg tacaggtggc tgaactgtat ccagaactga gacgcatttt gacaattaca   1860
gaggatgggc aggggctaaa gggggtaaag agggagcggg gggcttgtga ggctacagag   1920
gaggctagga atctagcttt tagcttaatg accagacacc gtcctgagtg tattactttt   1980
caacagatca aggataattg cgctaatgag cttgatctgc tggcgcagaa gtattccata   2040
gagcagctga ccacttactg gctgcagcca ggggatgatt ttgaggaggc tattagggta   2100
tatgcaaagg tggcacttag gccagattgc aagtacaaga tcagcaaact tgtaaatatc   2160
aggaattgtt gctacatttc tgggaacggg gccgaggtgg agatagatac ggaggatagg   2220
gtggccttta gatgtagcat gataaatatg tggccggggg tgcttggcat ggacggggtg   2280
gttattatga atgtaaggtt tactggcccc aattttagcg gtacggtttt cctggccaat   2340
accaacctta tcctacacgg tgtaagcttc tatgggttta acaatacctg tgtggaagcc   2400
tggaccgatg taagggttcg ggctgtgcc ttttactgct gctggaaggg ggtggtgtgt   2460
cgccccaaaa gcagggcttc aattaagaaa tgcctctttg aaaggtgtac cttgggtatc   2520
ctgtctgagg gtaactccag ggtgcgccac aatgtggcct ccgactgtgg ttgcttcatg   2580
ctagtgaaaa gcgtggctgt gattaagcat aacatggtat gtggcaactg cgaggacagg   2640
gcctctcaga tgctgacctg ctcggacggc aactgtcacc tgctgaagac cattcacgta   2700
gccagccact ctcgcaaggc ctggccagtg tttgagcata acatactgac ccgctgttcc   2760
ttgcatttgg gtaacaggag gggggtgttc ctaccttacc aatgcaattt gagtcacact   2820
aagatattgc ttgagcccga gagcatgtcc aaggtgaacc tgaacggggt gtttgacatg   2880
accatgaaga tctggaaggt gctgaggtac gatgagaccc gcaccaggtg cagaccctgc   2940
gagtgtggcg gtaaacatat taggaaccag cctgtgatgc tggatgtgac cgaggagctg   3000
aggcccgatc acttggtgct ggcctgcacc cgcgctgagt ttggctctag cgatgaagat   3060
acagattgag gtactgaaat gtgtgggcgt ggcttaaggg tgggaaagaa tatataaggt   3120
gggggtctta tgtagttttg tatctgtttt gcagcagccg ccgccgccat gagcaccaac   3180
tcgtttgatg gaagcattgt gagctcatat ttgacaacgc gcatgccccc atgggccggg   3240
gtgcgtcaga atgtgatggg ctccagcatt gatggtcgcc ccgtcctgcc cgcaaactct   3300
actaccttga cctacgagac cgtgtctgga acgccgttgg agactgcagc ctccgccgcc   3360
gcttcagccg ctgcagccac cgcccgcggg attgtgactg actttgcttt cctgagcccg   3420
cttgcaagca gtgcagcttc ccgttcatcc gcccgcgatg acaagttgac ggctcttttg   3480
gcacaattgg attctttgac ccgggaactt aatgtcgttt ctcagcagct gttggatctg   3540
cgccagcagg tttctgccct gaaggcttcc tcccctccca atgcggttta aaacataaat   3600
aaaaaaccag actctgtttg gatttggatc aagcaagtgt cttgctgtct ttatttaggg   3660
gttttgcgcg cgcggtaggc ccgggaccag cggtctcggt cgttgagggt cctgtgtatt   3720
```

-continued

```
ttttccagga cgtggtaaag gtgactctgg atgttcagat acatgggcat aagcccgtct   3780
ctggggtgga ggtagcacca ctgcagagct tcatgctgcg gggtggtgtt gtagatgatc   3840
cagtcgtagc aggagcgctg ggcgtggtgc ctaaaaatgt ctttcagtag caagctgatt   3900
gccaggggca ggcccttggt gtaagtgttt acaaagcggt taagctggga tgggtgcata   3960
cgtggggata tgagatgcat cttggactgt atttttaggt tggctatgtt cccagccata   4020
tccctccggg gattcatgtt gtgcagaacc accagcacag tgtatccggt gcacttggga   4080
aatttgtcat gtagcttaga aggaaatgcg tggaagaact tggagacgcc cttgtgacct   4140
ccaagatttt ccatgcattc gtccataatg atggcaatgg gcccacgggc ggcggcctgg   4200
gcgaagatat ttctgggatc actaacgtca tagttgtgtt ccaggatgag atcgtcatag   4260
gccattttta caaagcgcgg gcggagggtg ccagactgcg gtataatggt tccatccggc   4320
ccaggggcgt agttaccctc acagatttgc atttcccacg ctttgagttc agatgggggg   4380
atcatgtcta cctgcggggc gatgaagaaa acggtttccg ggtaggggga gatcagctgg   4440
gaagaaagca ggttcctgag cagctgcgac ttaccgcagc cggtgggccc gtaaatcaca   4500
cctattaccg ggtgcaactg gtagttaaga gagctgcagc tgccgtcatc cctgagcagg   4560
ggggccactt cgttaagcat gtccctgact cgcatgtttt ccctgaccaa atccgccaga   4620
aggcgctcgc cgcccagcga tagcagttct tgcaaggaag caaagttttt caacggtttg   4680
agaccgtccg ccgtaggcat gcttttgagc gtttgaccaa gcagttccag gcggtcccac   4740
agctcggtca cctgctctac ggcatctcga tccagcatat ctcctcgttt cgcgggttgg   4800
ggcggctttc gctgtacggc agtagtcggt gctcgtccag acgggccagg gtcatgtctt   4860
tccacgggcg cagggtcctc gtcagcgtag tctgggtcac ggtgaagggg tgcgctccgg   4920
gctgcgcgct ggccagggtg cgcttgaggc tggtcctgct ggtgctgaag cgctgccggt   4980
cttcgccctg cgcgtcggcc aggtagcatt tgaccatggt gtcatagtcc agcccctccg   5040
cggcgtggcc cttggcgcgc agcttgccct tggaggaggc gccgcacgag gggcagtgca   5100
gacttttgag ggcgtagagc ttgggcgcga gaaataccga ttccggggag taggcatccg   5160
cgccgcaggc cccgcagacg gtctcgcatt ccacgagcca ggtgagctct ggccgttcgg   5220
ggtcaaaaac caggtttccc ccatgctttt tgatgcgttt cttacctctg gtttccatga   5280
gccggtgtcc acgctcggtg acgaaaaggc tgtccgtgtc cccgtataca gacttgagag   5340
gcctgtcctc gagcggtgtt ccgcggtcct cctcgtatag aaactcggac cactctgaga   5400
caaaggctcg cgtccaggcc agcacgaagg aggctaagtg ggaggggtag cggtcgttgt   5460
ccactagggg gtccactcgc tccagggtgt gaagacacat gtcgccctct tcggcatcaa   5520
ggaaggtgat tggtttgtag gtgtaggcca cgtgaccggg tgttcctgaa ggggggctat   5580
aaaagggggt gggggcgcgt tcgtcctcac tctcttccgc atcgctgtct gcgagggcca   5640
gctgttgggg tgagtactcc ctctgaaaag cgggcatgac ttctgcgcta agattgtcag   5700
tttccaaaaa cgaggaggat ttgatattca cctggcccgc ggtgatgcct ttgagggtgg   5760
ccgcatccat ctggtcagaa aagacaatct ttttgttgtc aagcttggtg gcaaacgacc   5820
cgtagagggc gttggacagc aacttggcga tggagcgcag ggtttggttt ttgtcgcgat   5880
cggcgcgctc cttggccgcg atgtttagct gcacgtattc gcgcgcaacg caccgccatt   5940
cgggaaagac ggtggtgcgc tcgtcgggca ccaggtgcac gcgccaaccg cggttgtgca   6000
gggtgacaag gtcaacgctg gtggctacct ctccgcgtag gcgctcgttg gtccagcaga   6060
ggcggccgcc cttgcgcgag cagaatggcg gtagggggtc tagctgcgtc tcgtccgggg   6120
```

-continued

```
ggtctgcgtc cacggtaaag accccgggca gcaggcgcgc gtcgaagtag tctatcttgc   6180
atccttgcaa gtctagcgcc tgctgccatg cgcgggcggc aagcgcgcgc tcgtatgggt   6240
tgagtggggg accccatggc atggggtggg tgagcgcgga ggcgtacatg ccgcaaatgt   6300
cgtaaacgta gaggggctct ctgagtattc caagatatgt agggtagcat cttccaccgc   6360
ggatgctggc gcgcacgtaa tcgtatagtt cgtgcgaggg agcgaggagg tcgggaccga   6420
ggttgctacg ggcgggctgc tctgctcgga agactatctg cctgaagatg gcatgtgagt   6480
tggatgatat ggttggacgc tggaagacgt tgaagctggc gtctgtgaga cctaccgcgt   6540
cacgcacgaa ggaggcgtag gagtcgcgca gcttgttgac cagctcggcg gtgacctgca   6600
cgtctagggc gcagtagtcc agggtttcct tgatgatgtc atacttatcc tgtccctttt   6660
ttttccacag ctcgcggttg aggacaaact cttcgcggtc tttccagtac tcttggatcg   6720
gaaacccgtc ggcctccgaa cggtaagagc ctagcatgta gaactggttg acggcctggt   6780
aggcgcagca tccctttttct acgggtagcg cgtatgcctg cgcggccttc cggagcgagg   6840
tgtgggtgag cgcaaaggtg tccctgacca tgactttgag gtactggtat ttgaagtcag   6900
tgtcgtcgca tccgccctgc tcccagagca aaaagtccgt gcgctttttg gaacgcggat   6960
ttggcagggc gaaggtgaca tcgttgaaga gtatctttcc cgcgcgaggc ataaagttgc   7020
gtgtgatgcg gaagggtccc ggcacctcgg aacggttgtt aattacctgg gcggcgagca   7080
cgatctcgtc aaagccgttg atgttgtggc ccacaatgta aagttccaag aagcgcggga   7140
tgcccttgat ggaaggcaat tttttaagtt cctcgtaggt gagctcttca ggggagctga   7200
gcccgtgctc tgaaagggcc cagtctgcaa gatgagggtt ggaagcgacg aatgagctcc   7260
acaggtcacg ggccattagc atttgcaggt ggtcgcgaaa ggtcctaaac tggcgaccta   7320
tggccatttt ttctggggtg atgcagtaga aggtaagcgg gtcttgttcc cagcggtccc   7380
atccaaggtt cgcggctagg tctcgcgcgg cagtcactag aggctcatct ccgccgaact   7440
tcatgaccag catgaagggc acgagctgct tcccaaaggc ccccatccaa gtataggtct   7500
ctacatcgta ggtgacaaag agacgctcgg tgcgaggatg cgagccgatc gggaagaact   7560
ggatctcccg ccaccaattg gaggagtggc tattgatgtg gtgaaagtag aagtccctgc   7620
gacgggccga acactcgtgc tggcttttgt aaaaacgtgc gcagtactgg cagcggtgca   7680
cgggctgtac atcctgcacg aggttgacct gacgaccgcg cacaaggaag cagagtggga   7740
atttgagccc ctcgcctggc gggtttggct ggtggtcttc tacttcggct gcttgtcctt   7800
gaccgtctgg ctgctcgagg ggagttacgg tggatcggac caccacgccg cgcgagccca   7860
aagtccagat gtccgcgcgc ggcggtcgga gcttgatgac aacatcgcgc agatgggagc   7920
tgtccatggt ctggagctcc cgcggcgtca ggtcaggcgg gagctcctgc aggtttacct   7980
cgcatagacg ggtcagggcg cgggctagat ccaggtgata cctaatttcc aggggctggt   8040
tggtggcggc gtcgatggct tgcaagaggc cgcatccccg cggcgcgact acggtaccgc   8100
gcggcgggcg gtgggccgcg ggggtgtcct tggatgatgc atctaaaagc ggtgacgcgg   8160
gcgagccccc ggaggtaggg ggggctccgg acccgccggg agagggggca ggggcacgtc   8220
ggcgccgcgc gcgggcagga gctggtgctg cgcgcgtagg ttgctggcga acgcgacgac   8280
gcggcggttg atctcctgaa tctggcgcct ctgcgtgaag acgacgggcc cggtgagctt   8340
gagcctgaaa gagagttcga cagaatcaat ttcggtgtcg ttgacggcgg cctggcgcaa   8400
aatctcctgc acgtctcctg agttgtcttg ataggcgatc tcggccatga actgctcgat   8460
```

-continued

```
ctcttcctcc tggagatctc cgcgtccggc tcgctccacg gtggcggcga ggtcgttgga   8520
aatgcgggcc atgagctgcg agaaggcgtt gaggcctccc tcgttccaga cgcggctgta   8580
gaccacgccc ccttcggcat cgcgggcgcg catgaccacc tgcgcgagat tgagctccac   8640
gtgccgggcg aagacggcgt agtttcgcag gcgctgaaag aggtagttga gggtggtggc   8700
ggtgtgttct gccacgaaga agtacataac ccagcgtcgc aacgtggatt cgttgatatc   8760
ccccaaggcc tcaaggcgct ccatggcctc gtagaagtcc acggcgaagt tgaaaaactg   8820
ggagttgcgc gccgacacgg ttaactcctc ctccagaaga cggatgagct cggcgacagt   8880
gtcgcgcacc tcgcgctcaa aggctacagg ggcctcttct tcttcttcaa tctcctcttc   8940
cataagggcc tccccttctt cttcttctgg cggcggtggg ggaggggggga cacggcggcg   9000
acgacggcgc accgggaggc ggtcgacaaa gcgctcgatc atctccccgc ggcgacggcg   9060
catggtctcg gtgacggcgc ggccgttctc gcgggggcgc agttggaaga cgccgcccgt   9120
catgtcccgg ttatgggttg gcgggggggct gccatgcggc agggatacgg cgctaacgat   9180
gcatctcaac aattgttgtg taggtactcc gccgccgagg gacctgagcg agtccgcatc   9240
gaccggatcg gaaaacctct cgagaaaggc gtctaaccag tcacagtcgc aaggtaggct   9300
gagcaccgtg gcgggcggca gcgggcggcg gtcggggttg tttctggcgg aggtgctgct   9360
gatgatgtaa ttaaagtagg cggtcttgag acggcggatg gtcgacagaa gcaccatgtc   9420
cttgggtccg gcctgctgaa tgcgcaggcg gtcggccatg ccccaggctt cgttttgaca   9480
tcggcgcagg tctttgtagt agtcttgcat gagcctttct accggcactt cttcttctcc   9540
ttcctcttgt cctgcatctc ttgcatctat cgctgcggcg gcggcggagt ttggccgtag   9600
gtggcgccct cttcctccca tgcgtgtgac cccgaagccc ctcatcggct gaagcagggc   9660
taggtcggcg acaacgcgct cggctaatat ggcctgctgc acctgcgtga gggtagactg   9720
gaagtcatcc atgtccacaa agcggtggta tgcgcccgtg ttgatggtgt aagtgcagtt   9780
ggccataacg gaccagttaa cggtctggtg acccggctgc gagagctcgg tgtacctgag   9840
acgcgagtaa gccctcgagt caaatacgta gtcgttgcaa gtccgcacca ggtactggta   9900
tcccaccaaa aagtgcggcg gcggctggcg gtagaggggc cagcgtaggg tggccggggc   9960
tccgggggcg agatcttcca acataaggcg atgatatccg tagatgtacc tggacatcca  10020
ggtgatgccg gcggcggtgg tggaggcgcg cggaaagtcg cggacgcggt tccagatgtt  10080
gcgcagcggc aaaaagtgct ccatggtcgg gacgctctgg ccggtcaggc gcgcgcaatc  10140
gttgacgctc tagaccgtgc aaaaggagag cctgtaagcg ggcactcttc cgtggtctgg  10200
tggataaatt cgcaagggta tcatggcgga cgaccggggt tcgagccccg tatccggccg  10260
tccgccgtga tccatgcggt taccgcccgc gtgtcgaacc caggtgtgcg acgtcagaca  10320
acgggggagt gctccttttg gcttccttcc aggcgcggcg gctgctgcgc tagctttttt  10380
ggccactggc cgcgcgcagc gtaagcggtt aggctggaaa gcgaaagcat taagtggctc  10440
gctccctgta gccggagggt tattttccaa gggttgagtc gcgggacccc cggttcgagt  10500
ctcggaccgg ccggactgcg gcgaacgggg gtttgcctcc ccgtcatgca agaccccgct  10560
tgcaaattcc tccggaaaca gggacgagcc cctttttgc ttttcccaga tgcatccggt  10620
gctgcggcag atgcgccccc ctcctcagca gcggcaagag caagagcagc ggcagacatg  10680
cagggcaccc tcccctcctc ctaccgcgtc aggaggggcg acatccgcgg ttgacgcggc  10740
agcagatggt gattacgaac cccgcggcg ccgggcccgg cactacctgg acttggagga  10800
gggcgagggc ctggcgcggc taggagcgcc ctctcctgag cggtacccaa gggtgcagct  10860
```

-continued gaagcgtgat acgcgtgagg cgtacgtgcc gcggcagaac ctgtttcgcg accgcgaggg 10920
agaggagccc gaggagatgc gggatcgaaa gttccacgca gggcgcgagc tgcggcatgg 10980
cctgaatcgc gagcggttgc tgcgcgagga ggactttgag cccgacgcgc gaaccgggat 11040
tagtccccgt ggcggccgcc gacctggtaa ccgcatacga gcagacggtg aaccaggaga 11100
ttaactttca agcgcgcgca caaaaagctt taacaaccac gtgcgtacgc ttgtggcgcg 11160
cgaggaggtg gctataggac tgatgcatct gtgggacttt gtaagcgcgc tggagcaaaa 11220
cccaaatagc aagccgctca tggcgcagct gttccttata gtgcagcaca gcagggacaa 11280
cgaggcattc agggatgcgc tgctaaacat agtagagccc gagggccgct ggctgctcga 11340
tttgataaac atcctgcaga gcatagtggt gcaggagcgc agcttgagcc tggctgacaa 11400
ggtggccgcc atcaactatt ccatgcttag cctgggcaag ttttacgccc gcaagatata 11460
ccatacccct tacgttccca tagacaagga ggtaaagatc gaggggttct acatgcgcat 11520
ggcgctgaag gtgcttacct tgagcgacga cctgggcgtt tatcgcaacg agcgcatcca 11580
caaggccgtg agcgtgagcc ggcggcgcga gctcagcgac cgcgagctga tgcacagcct 11640
gcaaagggcc ctggctggca cgggcagcgg cgatagagag gccgagtcct actttgacgc 11700
gggcgctgac ctgcgctggg ccccaagccg acgcgccctg gaggcagctg gggccggacc 11760
tgggctggcg gtggcacccg cgcgcgctgg caacgtcggc ggcgtggagg aatatgacga 11820
ggacgatgag tacgagccag aggacggcga gtactaagcg gtgatgtttc tgatcagatg 11880
atgcaagacg caacggaccc ggcggtgcgg gcggcgctgc agagccagcc gtccggcctt 11940
aactccacgg acgactggcg ccaggtcatg gaccgcatca tgtcgctgac tgcgcgcaat 12000
cctgacgcgt tccggcagca gccgcaggcc aaccggctct ccgcaattct ggaagcggtg 12060
gtcccggcgc gcgcaaaccc cacgcacgag aaggtgctgg cgatcgtaaa cgcgctggcc 12120
gaaaacaggg ccatccggcc cgacgaggcc ggcctggtct acgacgcgct gcttcagcgc 12180
gtggctcgtt acaacagcgg caacgtgcag accaacctgg accggctggt gggggatgtg 12240
cgcgaggccg tggcgcagcg tgagcgcgcg cagcagcagg gcaacctggg ctccatggtt 12300
gcactaaacg ccttcctgag tacacagccc gccaacgtgc cgcggggaca ggaggactac 12360
accaactttg tgagcgcact gcggctaatg gtgactgaga caccgcaaag tgaggtgtac 12420
cagtctgggc cagactattt tttccagacc agtagacaag gcctgcagac cgtaaacctg 12480
agccaggctt tcaaaaactt gcaggggctg tggggggtgc gggctcccac aggcgaccgc 12540
gcgaccgtgt ctagcttgct gacgcccaac tcgcgcctgt tgctgctgct aatagcgccc 12600
ttcacggaca gtggcagcgt gtcccgggac acatacctag gtcacttgct gacactgtac 12660
cgcgaggcca taggtcaggc gcatgtggac gagcatactt tccaggagat tacaagtgtc 12720
agccgcgcgc tggggcagga ggacacgggc agcctggagg caaccctaaa ctacctgctg 12780
accaaccggc ggcagaagat cccctcgttg cacagtttaa acagcgagga ggagcgcatt 12840
ttgcgctacg tgcagcagag cgtgagcctt aacctgatgc gcgacggggt aacgcccagc 12900
gtggcgctgg acatgaccgc gcgcaacatg gaaccgggca tgtatgcctc aaaccggccg 12960
tttatcaacc gcctaatgga ctacttgcat cgcgcggccg ccgtgaaccc cgagtatttc 13020
accaatgcca tcttgaaccc gcactggcta ccgccccctg gtttctacac cgggggattc 13080
gaggtgcccg agggtaacga tggattcctc tgggacgaca tagacgacag cgtgttttcc 13140
ccgcaaccgc agaccctgct agagttgcaa cagcgcgagc aggcagaggc ggcgctgcga 13200

-continued

```
aaggaaagct tccgcaggcc aagcagcttg tccgatctag gcgctgcggc cccgcggtca  13260
gatgctagta gcccatttcc aagcttgata gggtctctta ccagcactcg caccacccgc  13320
ccgcgcctgc tgggcgagga ggagtaccta aacaactcgc tgctgcagcc gcagcgcgaa  13380
aaaaacctgc ctccggcatt tcccaacaac gggatagaga gcctagtgga caagatgagt  13440
agatggaaga cgtacgcgca ggagcacagg gacgtgccag gcccgcgccc gcccacccgt  13500
cgtcaaaggc acgaccgtca gcggggtctg gtgtgggagg acgatgactc ggcagacgac  13560
agcagcgtcc tggatttggg agggagtggc aacccgtttg cgcaccttcg ccccaggctg  13620
gggagaatgt tttaaaaaaa aaaaagcatg atgcaaaata aaaaactcac caaggccatg  13680
gcaccgagcg ttggttttct tgtattcccc ttagtatgcg gcgcgcggcg atgtatgagg  13740
aaggtcctcc tccctcctac gagagtgtgg tgagcgcggc gccagtggcg gcggcgctgg  13800
gttctccctt cgatgctccc ctggacccgc cgtttgtgcc tccgcggtac ctgcggccta  13860
ccggggggag aaacagcatc cgttactctg agttggcacc cctattcgac accacccgtg  13920
tgtacctggt ggacaacaag tcaacggatg tggcatccct gaactaccag aacgaccaca  13980
gcaactttct gaccacggtc attcaaaaca atgactacag cccgggggag gcaagcacac  14040
agaccatcaa tcttgacgac cggtcgcact ggggcggcga cctgaaaacc atcctgcata  14100
ccaacatgcc aaatgtgaac gagttcatgt ttaccaataa gtttaaggcg cgggtgatgg  14160
tgtcgcgctt gcctactaag gacaatcagg tggagctgaa atacgagtgg gtggagttca  14220
cgctgcccga gggcaactac tccgagacca tgaccataga ccttatgaac aacgcgatcg  14280
tggagcacta cttgaaagtg ggcagacaga acggggttct ggaaagcgac atcggggtaa  14340
agtttgacac ccgcaacttc agactggggt ttgaccccgt cactggtctt gtcatgcctg  14400
gggtatatac aaacgaagcc ttccatccag acatcatttt gctgccagga tgcggggtgg  14460
acttcaccca cagccgcctg agcaacttgt tgggcatccg caagcggcaa cccttccagg  14520
agggctttag gatcacctac gatgatctgg agggtggtaa cattcccgca ctgttggatg  14580
tggacgccta ccaggcgagc ttgaaagatg acaccgaaca gggcgggggt ggcgcaggcg  14640
gcagcaacag cagtggcagc ggcgcggaag agaactccaa cgcggcagcc gcggcaatgc  14700
agccggtgga ggacatgaac gatcatgcca ttcgcggcga cacctttgcc acacgggctg  14760
aggagaagcg cgctgaggcc gaagcagcgg ccgaagctgc cgccccccgct gcgcaacccg  14820
aggtcgagaa gcctcagaag aaaccggtga tcaaacccct gacagaggac agcaagaaac  14880
gcagttacaa cctaataagc aatgacagca ccttcaccca gtaccgcagc tggtaccttg  14940
catacaacta cggcgaccct cagaccggaa tccgctcatg gaccctgctt tgcactcctg  15000
acgtaacctg cggctcggag caggtctact ggtcgttgcc agacatgatg caagaccccg  15060
tgaccttccg ctccacgcgc cagatcagca actttccggt ggtgggcgcc gagctgttgc  15120
ccgtgcactc caagagcttc tacaacgacc aggccgtcta ctcccaactc atccgccagt  15180
ttacctctct gacccacgtg ttcaatcgct ttcccgagaa ccagattttg gcgcgcccgc  15240
cagcccccac catcaccacc gtcagtgaaa acgttcctgc tctcacagat cacgggacgc  15300
taccgctgcg caacagcatc ggaggagtcc agcgagtgac cattactgac gccagacgcc  15360
gcacctgccc ctacgtttac aaggccctgg gcatagtctc gccgcgcgtc ctatcgagcc  15420
gcactttttg agcaagcatg tccatcctta tatcgcccag caataacaca ggctggggcc  15480
tgcgcttccc aagcaagatg tttggcgggg ccaagaagcg ctccgaccaa cacccagtgc  15540
gcgtgcgcgg gcactaccgc gcgccctggg gcgcgcacaa acgcggccgc actgggcgca  15600
```

-continued ccaccgtcga tgacgccatc gacgcggtgg tggaggaggc gcgcaactac acgcccacgc 15660
cgccaccagt gtccacagtg gacgcggcca ttcagaccgt ggtgcgcgga gcccggcgct 15720
atgctaaaat gaagagacgg cggaggcgcg tagcacgtcg ccaccgccgc cgacccggca 15780
ctgccgccca acgcgcggcg gcggccctgc ttaaccgcgc acgtcgcacc ggccgacggg 15840
cggccatgcg ggccgctcga aggctggccg cgggtattgt cactgtgccc cccaggtcca 15900
ggcgacgagc ggccgccgca gcagccgcgg ccattagtgc tatgactcag ggtcgcaggg 15960
gcaacgtgta ttgggtgcgc gactcggtta gcggcctgcg cgtgcccgtg cgcacccgcc 16020
ccccgcgcaa ctagattgca agaaaaaact acttagactc gtactgttgt atgtatccag 16080
cggcggcggc gcgcaacgaa gctatgtcca agcgcaaaat caaagaagag atgctccagg 16140
tcatcgcgcc ggagatctat ggcccccga agaaggaaga gcaggattac aagccccgaa 16200
agctaaagcg ggtcaaaaag aaaaagaaag atgatgatga tgaacttgac gacgaggtgg 16260
aactgctgca cgctaccgcg cccaggcgac gggtacagtg gaaaggtcga cgcgtaaaac 16320
gtgttttgcg acccggcacc accgtagtct ttacgcccgg tgagcgctcc acccgcacct 16380
acaagcgcgt gtatgatgag gtgtacggcg acgaggacct gcttgagcag gccaacgagc 16440
gcctcgggga gtttgcctac ggaaagcggc ataaggacat gctggcgttg ccgctggacg 16500
agggcaaccc aacacctagc ctaaagcccg taacactgca gcaggtgctg cccgcgcttg 16560
caccgtccga agaaaagcgc ggcctaaagc gcgagtctgg tgacttggca cccaccgtgc 16620
agctgatggt acccaagcgc cagcgactgg aagatgtctt ggaaaaaatg accgtggaac 16680
ctgggctgga gcccgaggtc cgcgtgcggc caatcaagca ggtggcgccg ggactgggcg 16740
tgcagaccgt ggacgttcag atacccacta ccagtagcac cagtattgcc accgccacag 16800
agggcatgga gacacaaacg tccccggttg cctcagcggt ggcggatgcc gcggtgcagg 16860
cggtcgctgc ggccgcgtcc aagacctcta cggaggtgca aacggacccg tggatgtttc 16920
gcgtttcagc cccccggcgc ccgcgcggtt cgaggaagta cggcgccgcc agcgcgctac 16980
tgcccgaata tgccctacat ccttccattg cgcctacccc cggctatcgt ggctacacct 17040
accgccccag aagacgagca actacccgac gccgaaccac cactggaacc cgccgccgcc 17100
gtcgccgtcg ccagcccgtg ctggccccga tttccgtgcg cagggtggct cgcgaaggag 17160
gcaggaccct ggtgctgcca acagcgcgct accaccccag catcgtttaa aagccggtct 17220
ttgtggttct tgcagatatg gccctcacct gccgcctccg tttcccggtg ccgggattcc 17280
gaggaagaat gcaccgtagg aggggcatgg ccggccacgg cctgacgggc ggcatgcgtc 17340
gtgcgcacca ccggcggcgg cgcgcgtcgc accgtcgcat gcgcggcggt atcctgcccc 17400
tccttattcc actgatcgcc gcggcgattg gcgccgtgcc cggaattgca tccgtggcct 17460
tgcaggcgca gagacactga ttaaaaacaa gttgcatgtg gaaaaatcaa aataaaaagt 17520
ctggactctc acgctcgctt ggtcctgtaa ctattttgta gaatggaaga catcaacttt 17580
gcgtctctgg ccccgcgaca cggctcgcgc ccgttcatgg gaaactggca agatatcggc 17640
accagcaata tgagcggtgg cgccttcagc tggggctcgc tgtggagcgg cattaaaaat 17700
ttcggttcca ccgttaagaa ctatggcagc aaggcctgga acagcagcac aggccagatg 17760
ctgagggata agttgaaaga gcaaaatttc caacaaaagg tggtagatgg cctggcctct 17820
ggcattagcg gggtggtgga cctggccaac caggcagtgc aaaataagat taacagtaag 17880
cttgatcccc gccctcccgt agaggagcct ccaccggccg tggagacagt gtctccagag 17940

-continued

```
gggcgtggcg aaaagcgtcc gcgccccgac agggaagaaa ctctggtgac gcaaatagac  18000
gagcctccct cgtacgagga ggcactaaag caaggcctgc ccaccacccg tcccatcgcg  18060
cccatggcta ccggagtgct gggccagcac acacccgtaa cgctggacct gcctcccccc  18120
gccgacaccc agcagaaacc tgtgctgcca ggcccgaccg ccgttgttgt aacccgtcct  18180
agccgcgcgt ccctgcgccg cgccgccagc ggtccgcgat cgttgcggcc cgtagccagt  18240
ggcaactggc aaagcacact gaacagcatc gtgggtctgg gggtgcaatc cctgaagcgc  18300
cgacgatgct tctgaatagc taacgtgtcg tatgtgtgtc atgtatgcgt ccatgtcgcc  18360
gccagaggag ctgctgagcc gccgcgcgcc cgctttccaa gatggctacc ccttcgatga  18420
tgccgcagtg gtcttacatg cacatctcgg gccaggacgc ctcggagtac ctgagccccg  18480
ggctggtgca gtttgcccgc gccaccgaga cgtacttcag cctgaataac aagtttagaa  18540
accccacggt ggcgcctacg cacgacgtga ccacagaccg gtcccagcgt ttgacgctgc  18600
ggttcatccc tgtggaccgt gaggatactg cgtactcgta caaggcgcgg ttcaccctag  18660
ctgtgggtga taaccgtgtg ctggacatgg cttccacgta ctttgacatc cgcggcgtgc  18720
tggacagggg ccctactttt aagccctact ctggcactgc ctacaacgcc ctggctccca  18780
agggtgcccc aaatccttgc gaatgggatg aagctgctac tgctcttgaa ataaacctag  18840
aagaagagga cgatgacaac gaagacgaag tagacgagca agctgagcag caaaaaactc  18900
acgtatttgg gcaggcgcct tattctggta taaatattac aaaggagggt attcaaatag  18960
gtgtcgaagg tcaaacacct aaatatgccg ataaaacatt tcaacctgaa cctcaaatag  19020
gagaatctca gtggtacgaa actgaaatta atcatgcagc tgggagagtc cttaaaaaga  19080
ctaccccaat gaaaccatgt tacggttcat atgcaaaacc cacaaatgaa aatggagggc  19140
aaggcattct tgtaaagcaa caaaatggaa agctagaaag tcaagtggaa atgcaatttt  19200
tctcaactac tgaggcgacc gcaggcaatg gtgataactt gactcctaaa gtggtattgt  19260
acagtgaaga tgtagatata gaaaccccag acactcatat ttcttacatg cccactatta  19320
aggaaggtaa ctcacgagaa ctaatgggcc aacaatctat gcccaacagg cctaattaca  19380
ttgcttttag ggacaatttt attggtctaa tgtattacaa cagcacgggt aatatgggtg  19440
ttctggcggg ccaagcatcg cagttgaatg ctgttgtaga tttgcaagac agaaacacag  19500
agctttcata ccagcttttg cttgattcca ttggtgatag aaccaggtac ttttctatgt  19560
ggaatcaggc tgttgacagc tatgatccag atgttagaat tattgaaaat catggaactg  19620
aagatgaact tccaaattac tgctttccac tgggaggtgt gattaataca gagactctta  19680
ccaaggtaaa acctaaaaca ggtcaggaaa atggatggga aaaagatgct acagaatttt  19740
cagataaaaa tgaaataaga gttggaaata attttgccat ggaaatcaat ctaaatgcca  19800
acctgtggag aaatttcctg tactccaaca tagcgctgta tttgcccgac aagctaaagt  19860
acagtccttc caacgtaaaa atttctgata acccaaacac ctacgactac atgaacaagc  19920
gagtggtggc tcccgggtta gtggactgct acattaacct tggagcacgc tggtcccttg  19980
actatatgga caacgtcaac ccatttaacc accaccgcaa tgctggcctg cgctaccgct  20040
caatgttgct gggcaatggt cgctatgtgc ccttccacat ccaggtgcct cagaagttct  20100
ttgccattaa aaacctcctt ctcctgccgg gctcatacac ctacgagtgg aacttcagga  20160
aggatgttaa catggttctg cagagctccc taggaaatga cctaagggtt gacggagcca  20220
gcattaagtt tgatagcatt tgcctttacg ccaccttctt ccccatggcc cacaacaccg  20280
cctccacgct tgaggccatg cttagaaacg acaccaacga ccagtccttt aacgactatc  20340
```

tctccgccgc caacatgctc taccctatac ccgccaacgc taccaacgtg cccatatcca 20400
tcccctcccg caactgggcg gctttccgcg gctgggcctt cacgcgcctt aagactaagg 20460
aaaccccatc actgggctcg ggctacgacc cttattacac ctactctggc tctataccct 20520
acctagatgg aacctttttac ctcaaccaca cctttaagaa ggtggccatt acctttgact 20580
cttctgtcag ctggcctggc aatgaccgcc tgcttacccc caacgagttt gaaattaagc 20640
gctcagttga cggggagggt tacaacgttg cccagtgtaa catgaccaaa gactggttcc 20700
tggtacaaat gctagctaac tacaacattg gctaccaggg cttctatatc ccagagagct 20760
acaaggaccg catgtactcc ttctttagaa acttccagcc catgagccgt caggtggtgg 20820
atgatactaa atacaaggac taccaacagg tgggcatcct acaccaacac aacaactctg 20880
gatttgttgg ctaccttgcc cccaccatgc gcgaaggaca ggcctaccct gctaacttcc 20940
cctatccgct tataggcaag accgcagttg acagcattac ccagaaaaag tttctttgcg 21000
atcgcaccct ttggcgcatc ccattctcca gtaactttat gtccatgggc gcactcacag 21060
acctgggcca aaaccttctc tacgccaact ccgcccacgc gctagacatg acttttgagg 21120
tggatcccat ggacgagccc acccttcttt atgttttgtt tgaagtcttt gacgtggtcc 21180
gtgtgcaccg gccgcaccgc ggcgtcatcg aaaccgtgta cctgcgcacg cccttctcgg 21240
ccggcaacgc cacaacataa agaagcaagc aacatcaaca acagctgccg ccatgggctc 21300
cagtgagcag gaactgaaag ccattgtcaa agatcttggt tgtgggccat attttttggg 21360
cacctatgac aagcgctttc caggctttgt ttctccacac aagctcgcct gcgccatagt 21420
caatacggcc ggtcgcgaga ctgggggcgt acactggatg gcctttgcct ggaacccgca 21480
ctcaaaaaca tgctacctct ttgagccctt tggcttttct gaccagcgac tcaagcaggt 21540
ttaccagttt gagtacgagt cactcctgcg ccgtagcgcc attgcttctt cccccgaccg 21600
ctgtataacg ctggaaaagt ccacccaaag cgtacagggg cccaactcgg ccgcctgtgg 21660
actattctgc tgcatgtttc tccacgcctt tgccaactgg ccccaaactc ccatggatca 21720
caaccccacc atgaacctta ttaccggggt acccaactcc atgctcaaca gtccccaggt 21780
acagcccacc ctgcgtcgca accaggaaca gctctacagc ttcctggagc gccactcgcc 21840
ctacttccgc agccacagtg cgcagattag gagcgccact tctttttgtc acttgaaaaa 21900
catgtaaaaa taatgtacta gagacacttt caataaaggc aaatgctttt atttgtacac 21960
tctcgggtga ttatttaccc ccacccttgc cgtctgcgcc gtttaaaaat caaaggggtt 22020
ctgccgcgca tcgctatgcg ccactggcag ggacacgttg cgatactggt gtttagtgct 22080
ccacttaaac tcaggcacaa ccatccgcgg cagctcggtg aagttttcac tccacaggct 22140
gcgcaccatc accaacgcgt ttagcaggtc gggcgccgat atcttgaagt cgcagttggg 22200
gcctccgccc tgcgcgcgcg agttgcgata cacagggttg cagcactgga acactatcag 22260
cgccgggtgg tgcacgctgg ccagcacgct cttgtcggag atcagatccg cgtccaggtc 22320
ctccgcgttg ctcagggcga acggagtcaa ctttggtagc tgccttccca aaaagggcgc 22380
gtgcccaggc tttgagttgc actcgcaccg tagtggcatc aaaaggtgac cgtgcccggt 22440
ctgggcgtta ggatacagcg cctgcataaa agccttgatc tgcttaaaag ccacctgagc 22500
ctttgcgcct tcagagaaga acatgccgca agacttgccg gaaaactgat tggccggaca 22560
ggccgcgtcg tgcacgcagc accttgcgtc ggtgttggag atctgcacca catttcggcc 22620
ccaccggttc ttcacgatct tggccttgct agactgctcc ttcagcgcgc gctgcccgtt 22680

-continued

```
ttcgctcgtc acatccattt caatcacgtg ctccttattt atcataatgc ttccgtgtag  22740
acacttaagc tcgccttcga tctcagcgca gcggtgcagc cacaacgcgc agcccgtggg  22800
ctcgtgatgc ttgtaggtca cctctgcaaa cgactgcagg tacgcctgca ggaatcgccc  22860
catcatcgtc acaaaggtct tgttgctggt gaaggtcagc tgcaacccgc ggtgctcctc  22920
gttcagccag gtcttgcata cggccgccag agcttccact tggtcaggca gtagtttgaa  22980
gttcgccttt agatcgttat ccacgtggta cttgtccatc agcgcgcgcg cagcctccat  23040
gcccttctcc cacgcagaca cgatcggcac actcagcggg ttcatcaccg taatttcact  23100
ttccgcttcg ctgggctctt cctcttcctc ttgcgtccgc ataccacgcg ccactgggtc  23160
gtcttcattc agccgccgca ctgtgcgctt acctcctttg ccatgcttga ttagcaccgg  23220
tgggttgctg aaacccacca tttgtagcgc cacatcttct ctttcttcct cgctgtccac  23280
gattacctct ggtgatggcg ggcgctcggg cttgggagaa gggcgcttct ttttcttctt  23340
gggcgcaatg gccaaatccg ccgccgaggt cgatggccgc gggctgggtg tgcgcggcac  23400
cagcgcgtct tgtgatgagt cttcctcgtc ctcggactcg atacgccgcc tcatccgctt  23460
ttttgggggc gcccggggag gcggcggcga cggggacggg gacgacacgt cctccatggt  23520
tgggggacgt cgcgccgcac cgcgtccgcg ctcgggggtg gtttcgcgct gctcctcttc  23580
ccgactggcc atttccttct cctataggca gaaaaagatc atggagtcag tcgagaagaa  23640
ggacagccta accgcccccct ctgagttcgc caccaccgcc tccaccgatg ccgccaacgc  23700
gcctaccacc ttccccgtcg aggcaccccc gcttgaggag gaggaagtga ttatcgagca  23760
ggacccaggt tttgtaagcg aagacgacga ggaccgctca gtaccaacag aggataaaaa  23820
gcaagaccag gacaacgcag aggcaaacga ggaacaagtc gggcgggggg acgaaaggca  23880
tggcgactac ctagatgtgg gagacgacgt gctgttgaag catctgcagc gccagtgcgc  23940
cattatctgc gacgcgttgc aagagcgcag cgatgtgccc ctcgccatag cggatgtcag  24000
ccttgcctac gaacgccacc tattctcacc gcgcgtaccc cccaaacgcc aagaaaacgg  24060
cacatgcgag cccaacccgc gcctcaactt ctaccccgta tttgccgtgc cagaggtgct  24120
tgccacctat cacatctttt tccaaaactg caagataccc ctatcctgcc gtgccaaccg  24180
cagccgagcg gacaagcagc tggccttgcg gcagggcgct gtcatacctg atatcgcctc  24240
gctcaacgaa gtgccaaaaa tctttgaggg tcttggacgc gacgagaagc gcgcggcaaa  24300
cgctctgcaa caggaaaaca gcgaaaatga aagtcactct ggagtgttgg tggaactcga  24360
gggtgacaac gcgcgcctag ccgtactaaa acgcagcatc gaggtcaccc actttgccta  24420
cccggcactt aacctacccc ccaaggtcat gagcacagtc atgagtgagc tgatcgtgcg  24480
ccgtgcgcag cccctggaga gggatgcaaa tttgcaagaa caaacagagg agggcctacc  24540
cgcagttggc gacgagcagc tagcgcgctg gcttcaaacg cgcgagcctg ccgacttgga  24600
ggagcgacgc aaactaatga tggccgcagt gctcgttacc gtggagcttg agtgcatgca  24660
gcggttcttt gctgacccgg agatgcagcg caagctagag gaaacattgc actacacctt  24720
tcgacagggc tacgtacgcc aggcctgcaa gatctccaac gtggagctct gcaacctggt  24780
ctcctacctt ggaattttgc acgaaaaccg ccttgggcaa aacgtgcttc attccacgct  24840
caagggcgag gcgcgccgcg actacgtccg cgactgcgtt tacttatttc tatgctacac  24900
ctggcagacg gccatgggcg tttggcagca gtgcttggag gagtgcaacc tcaaggagct  24960
gcagaaactg ctaaagcaaa acttgaagga cctatggacg gccttcaacg agcgctccgt  25020
ggccgcgcac ctggcggaca tcattttccc cgaacgcctg cttaaaaccc tgcaacaggg  25080
```

```
tctgccagac ttcaccagtc aaagcatgtt gcagaacttt aggaacttta tcctagagcg  25140
ctcaggaatc ttgcccgcca cctgctgtgc acttcctagc gactttgtgc ccattaagta  25200
ccgcgaatgc cctccgccgc tttggggcca ctgctacctt ctgcagctag ccaactacct  25260
tgcctaccac tctgacataa tggaagacgt gagcggtgac ggtctactgg agtgtcactg  25320
tcgctgcaac ctatgcaccc cgcaccgctc cctggtttgc aattcgcagc tgcttaacga  25380
aagtcaaatt atcggtacct ttgagctgca gggtccctcg cctgacgaaa agtccgcggc  25440
tccggggttg aaactcactc cggggctgtg gacgtcggct taccttcgca aatttgtacc  25500
tgaggactac cacgcccacg agattaggtt ctacgaagac caatcccgcc cgccaaatgc  25560
ggagcttacc gcctgcgtca ttacccaggg ccacattctt ggccaattgc aagccatcaa  25620
caaagcccgc caagagtttc tgctacgaaa gggacggggg gtttacttgg acccccagtc  25680
cggcgaggag ctcaacccaa tcccccgcc gccgcagccc tatcagcagc agccgcgggc  25740
ccttgcttcc caggatggca cccaaaaaga agctgcagct gccgccgcca cccacggacg  25800
aggaggaata ctgggacagt caggcagagg aggttttgga cgaggaggag gaggacatga  25860
tggaagactg ggagagccta gacgaggaag cttccgaggt cgaagaggtg tcagacgaaa  25920
caccgtcacc ctcggtcgca ttcccctcgc cggcgcccca gaaatcggca accggttcca  25980
gcatggctac aacctccgct cctcaggcgc cgccggcact gcccgttcgc cgacccaacc  26040
gtagatggga caccactgga accagggccg gtaagtccaa gcagccgccg ccgttagccc  26100
aagagcaaca acagcgccaa ggctaccgct catggcgcgg gcacaagaac gccatagttg  26160
cttgcttgca agactgtggg ggcaacatct ccttcgcccg ccgctttctt ctctaccatc  26220
acggcgtggc cttcccccgt aacatcctgc attactaccg tcatctctac agcccatact  26280
gcaccggcgg cagcggcagc ggcagcaaca gcagcggcca cacagaagca aaggcgaccg  26340
gatagcaaga ctctgacaaa gcccaagaaa tccacagcgg cggcagcagc aggaggagga  26400
gcgctgcgtc tggcgcccaa cgaacccgta tcgacccgcg agcttagaaa caggattttt  26460
cccactctgt atgctatatt tcaacagagc aggggccaag aacaagagct gaaaataaaa  26520
aacaggtctc tgcgatccct cacccgcagc tgcctgtatc acaaaagcga agatcagctt  26580
cggcgcacgc tggaagacgc ggaggctctc ttcagtaaat actgcgcgct gactcttaag  26640
gactagtttc gcgccctttc tcaaatttaa gcgcgaaaac tacgtcatct ccagcggcca  26700
cacccggcgc cagcacctgt cgtcagcgcc attatgagca aggaaattcc cacgccctac  26760
atgtggagtt accagccaca aatgggactt gcggctggag ctgcccaaga ctactcaacc  26820
cgaataaact acatgagcgc gggaccccac atgatatccc gggtcaacgg aatccgcgcc  26880
caccgaaacc gaattctctt ggaacaggcg gctattacca ccacacctcg taataacctt  26940
aatccccgta gttggcccgc tgccctggtg taccaggaaa gtcccgctcc caccactgtg  27000
gtacttccca gagacgccca ggccgaagtt cagatgacta actcaggggc gcagcttgcg  27060
ggcggctttc gtcacagggt gcggtcgccc gggcagggta taactcacct gacaatcaga  27120
gggcgaggta ttcagctcaa cgacgagtcg gtgagctcct cgcttggtct ccgtccggac  27180
gggacatttc agatcggcgg cgccggccgt ccttcattca cgcctcgtca ggcaatccta  27240
actctgcaga cctcgtcctc tgagccgcgc tctggaggca ttggaactct gcaatttatt  27300
gaggagtttg tgccatcggt ctactttaac cccttctcgg gacctcccgg ccactatccg  27360
gatcaattta ttcctaactt tgacgcggta aaggactcgg cggacggcta cgactgaatg  27420
```

-continued

```
ttaagtggag aggcagagca actgcgcctg aaacacctgg tccactgtcg ccgccacaag  27480
tgctttgccc gcgactccgg tgagttttgc tactttgaat tgcccgagga tcatatcgag  27540
ggcccggcgc acggcgtccg gcttaccgcc cagggagagc ttgcccgtag cctgattcgg  27600
gagtttaccc agcgccccct gctagttgag cgggacaggg gaccctgtgt tctcactgtg  27660
atttgcaact gtcctaacct tggattacat caagatcttt gttgccatct ctgtgctgag  27720
tataataaat acagaaatta aaatatactg gggctcctat cgccatcctg taaacgccac  27780
cgtcttcacc cgcccaagca aaccaaggcg aaccttacct ggtactttta acatctctcc  27840
ctctgtgatt tacaacagtt tcaacccaga cggagtgagt ctacgagaga acctctccga  27900
gctcagctac tccatcagaa aaaacaccac cctccttacc tgccgggaac gtacgagtgc  27960
gtcaccggcc gctgcaccac acctaccgcc tgaccgtaaa ccagactttt tccggacaga  28020
cctcaataac tctgtttacc agaacaggag gtgagcttag aaaacccctta gggtattagg  28080
ccaaaggcgc agctactgtg gggtttatga acaattcaag caactctacg ggctattcta  28140
attcaggttt ctctagaatc ggggttgggg ttattctctg tcttgtgatt ctctttattc  28200
ttatactaac gcttctctgc ctaaggctcg ccgcctgctg tgtgcacatt tgcatttatt  28260
gtcagctttt taaacgctgg ggtcgccacc caagatgatt aggtacataa tcctaggttt  28320
actcaccctt gcgtcagccc acggtaccac ccaaaaggtg gattttaagg agccagcctg  28380
taatgttaca ttcgcagctg aagctaatga gtgcaccact cttataaaat gcaccacaga  28440
acatgaaaag ctgcttattc gccacaaaaa caaaattggc aagtatgctg tttatgctat  28500
ttggcagcca ggtgacacta cagagtataa tgttacagtt ttccagggta aaagtcataa  28560
aacttttatg tatacttttc cattttatga aatgtgcgac attaccatgt acatgagcaa  28620
acagtataag ttgtggcccc cacaaaattg tgtggaaaac actggcactt tctgctgcac  28680
tgctatgcta attacagtgc tcgctttggt ctgtacccta ctctatatta aatacaaaag  28740
cagacgcagc tttattgagg aaaagaaaat gccttaattt actaagttac aaagctaatg  28800
tcaccactaa ctgctttact cgctgcttgc aaaacaaatt caaaaagtta gcattataat  28860
tagaatagga tttaaacccc ccggtcattt cctgctcaat accattcccc tgaacaattg  28920
actctatgtg ggatatgctc cagcgctaca accttgaagt caggcttcct ggatgtcagc  28980
atctgacttt ggccagcacc tgtcccgcgg atttgttcca gtccaactac agcgacccac  29040
cctaacagag atgaccaaca caaccaacgc ggccgccgct accggactta catctaccac  29100
aaatacaccc caagtttctg cctttgtcaa taactgggat aacttgggca tgtggtggtt  29160
ctccatagcg cttatgtttg tatgccttat tattatgtgg ctcatctgct gcctaaagcg  29220
caaacgcgcc cgaccaccca tctatagtcc catcattgtg ctacacccaa acaatgatgg  29280
aatccataga ttggacggac tgaaacacat gttcttttct cttacagtat gattaaatga  29340
gacatgattc ctcgagtttt tatattactg acccttgttg cgcttttttg tgcgtgctcc  29400
acattggctg cggtttctca catcgaagta gactgcattc cagccttcac agtctatttg  29460
ctttacggat ttgtcaccct cacgctcatc tgcagcctca tcactgtggt catcgccttt  29520
atccagtgca ttgactgggt ctgtgtgcgc tttgcatatc tcagacacca tccccagtac  29580
agggacagga ctatagctga gcttcttaga attctttaat tatgaaattt actgtgactt  29640
ttctgctgat tatttgcacc ctatctgcgt tttgttcccc gacctccaag cctcaaagac  29700
atatatcatg cagattcact cgtatatgga atattccaag ttgctacaat gaaaaaagcg  29760
atctttccga agcctggtta tatgcaatca tctctgttat ggtgttctgc agtaccatct  29820
```

```
tagccctagc tatatatccc taccttgaca ttggctggaa acgaatagat gccatgaacc  29880
acccaacttt ccccgcgccc gctatgcttc cactgcaaca agttgttgcc ggcggctttg  29940
tcccagccaa tcagcctcgc cccacttctc ccaccccac tgaaatcagc tactttaatc  30000
taacaggagg agatgactga caccctagat ctagaaatgg acggaattat tacagagcag  30060
cgcctgctag aaagacgcag ggcagcggcc gagcaacagc gcatgaatca agagctccaa  30120
gacatggtta acttgcacca gtgcaaaagg ggtatctttt gtctggtaaa gcaggccaaa  30180
gtcacctacg acagtaatac caccggacac cgccttagct acaagttgcc aaccaagcgt  30240
cagaaattgg tggtcatggt gggagaaaag cccattacca taactcagca ctcggtagaa  30300
accgaaggct gcattcactc accttgtcaa ggacctgagg atctctgcac ccttattaag  30360
accctgtgcg gtctcaaaga tcttattccc tttaactaat aaaaaaaaat aataaagcat  30420
cacttactta aaatcagtta gcaaatttct gtccagttta ttcagcagca cctccttgcc  30480
ctcctcccag ctctggtatt gcagcttcct cctggctgca aactttctcc acaatctaaa  30540
tggaatgtca gtttcctcct gttcctgtcc atccgcaccc actatcttca tgttgttgca  30600
gatgaagcgc gcaagaccgt ctgaagatac cttcaacccc gtgtatccat atgacacgga  30660
aaccggtcct ccaactgtgc cttttcttac tcctcccttt gtatccccca atgggtttca  30720
agagagtccc cctggggtac tctctttgcg cctatccgaa cctctagtta cctccaatgg  30780
catgcttgcg ctcaaaatgg gcaacggcct ctctctggac gaggccggca accttacctc  30840
ccaaaatgta accactgtga gcccacctct caaaaaaacc aagtcaaaca taaacctgga  30900
aatatctgca cccctcacag ttacctcaga agccctaact gtggctgccg ccgcacctct  30960
aatggtcgcg ggcaacacac tcaccatgca atcacaggcc ccgctaaccg tgcacgactc  31020
caaacttagc attgccaccc aaggacccct cacagtgtca gaaggaaagc tagccctgca  31080
aacatcaggc cccctcacca ccaccgatag cagtaccctt actatcactg cctcaccccc  31140
tctaactact gccactggta gcttgggcat tgacttgaaa gagcccattt atacacaaaa  31200
tggaaaacta ggactaaagt acggggctcc tttgcatgta acagacgacc taaacacttt  31260
gaccgtagca actggtccag gtgtgactat taataatact tccttgcaaa ctaaagttac  31320
tggagccttg ggttttgatt cacaaggcaa tatgcaactt aatgtagcag gaggactaag  31380
gattgattct caaaacagac gccttatact tgatgttagt tatccgtttg atgctcaaaa  31440
ccaactaaat ctaagactag gacagggccc tctttttata aactcagccc acaacttgga  31500
tattaactac aacaaaggcc tttacttgtt tacagcttca aacaattcca aaaagcttga  31560
ggttaaccta agcactgcca aggggttgat gtttgacgct acagccatag ccattaatgc  31620
aggagatggg cttgaatttg gttcacctaa tgcaccaaac acaaatcccc tcaaaacaaa  31680
aattggccat ggcctagaat ttgattcaaa caaggctatg gttcctaaac taggaactgg  31740
ccttagtttt gacagcacag gtgccattac agtaggaaac aaaaataatg ataagctaac  31800
tttgtggacc acaccagctc catctcctaa ctgtagacta aatgcagaga aagatgctaa  31860
actcactttg gtcttaacaa aatgtggcag tcaaatactt gctacagttt cagttttggc  31920
tgttaaaggc agtttggctc caatatctgg aacagttcaa agtgctcatc ttattataag  31980
atttgacgaa aatggagtgc tactaaacaa ttccttcctg gacccagaat attggaactt  32040
tagaaatgga gatcttactg aaggcacagc ctatacaaac gctgttggat ttatgcctaa  32100
cctatcagct tatccaaaat ctcacggtaa aactgccaaa agtaacattg tcagtcaagt  32160
```

-continued

```
ttacttaaac ggagacaaaa ctaaacctgt aacactaacc attacactaa acggtacaca  32220
ggaaacagga gacacaactc caagtgcata ctctatgtca ttttcatggg actggtctgg  32280
ccacaactac attaatgaaa tatttgccac atcctcttac actttttcat acattgccca  32340
agaataaaga atcgtttgtg ttatgtttca acgtgtttat ttttcaattg cagaaaattt  32400
caagtcattt ttcattcagt agtatagccc caccaccaca tagcttatac agatcaccgt  32460
accttaatca aactcacaga accctagtat tcaacctgcc acctccctcc caacacacag  32520
agtacacagt cctttctccc cggctggcct taaaaagcat catatcatgg gtaacagaca  32580
tattcttagg tgttatattc cacacggttt cctgtcgagc caaacgctca tcagtgatat  32640
taataaactc cccgggcagc tcacttaagt tcatgtcgct gtccagctgc tgagccacag  32700
gctgctgtcc aacttgcggt tgcttaacgg gcggcgaagg agaagtccac gcctacatgg  32760
gggtagagtc ataatcgtgc atcaggatag ggcggtggtg ctgcagcagc gcgcgaataa  32820
actgctgccg ccgccgctcc gtcctgcagg aatacaacat ggcagtggtc tcctcagcga  32880
tgattcgcac cgcccgcagc ataaggcgcc ttgtcctccg ggcacagcag cgcaccctga  32940
tctcacttaa atcagcacag taactgcagc acagcaccac aatattgttc aaaatcccac  33000
agtgcaaggc gctgtatcca aagctcatgg cggggaccac agaacccacg tggccatcat  33060
accacaagcg caggtagatt aagtggcgac ccctcataaa cacgctggac ataaacatta  33120
cctcttttgg catgttgtaa ttcaccacct cccggtacca tataaacctc tgattaaaca  33180
tggcgccatc caccaccatc ctaaaccagc tggccaaaac ctgcccgccg gctatacact  33240
gcagggaacc gggactggaa caatgacagt ggagagccca ggactcgtaa ccatggatca  33300
tcatgctcgt catgatatca atgttggcac aacacaggca cacgtgcata cacttcctca  33360
ggattacaag ctcctcccgc gttagaacca tatcccaggg aacaacccat tcctgaatca  33420
gcgtaaatcc cacactgcag ggaagacctc gcacgtaact cacgttgtgc attgtcaaag  33480
tgttacattc gggcagcagc ggatgatcct ccagtatggt agcgcgggtt tctgtctcaa  33540
aaggaggtag acgatcccta ctgtacggag tgcgccgaga caaccgagat cgtgttggtc  33600
gtagtgtcat gccaaatgga acgccggacg tagtcatatt tcctgaagca aaaccaggtg  33660
cgggcgtgac aaacagatct gcgtctccgg tctcgccgct tagatcgctc tgtgtagtag  33720
ttgtagtata tccactctct caaagcatcc aggcgccccc tggcttcggg ttctatgtaa  33780
actccttcat gcgccgctgc cctgataaca tccaccaccg cagaataagc cacacccagc  33840
caacctacac attcgttctg cgagtcacac acgggaggag cgggaagagc tggaagaacc  33900
atgttttttt ttttattcca aaagattatc caaaacctca aaatgaagat ctattaagtg  33960
aacgcgctcc cctccggtgg cgtggtcaaa ctctacagcc aaagaacaga taatggcatt  34020
tgtaagatgt tgcacaatgg cttccaaaag gcaaacggcc ctcacgtcca agtggacgta  34080
aaggctaaac ccttcagggt gaatctcctc tataaacatt ccagcacctt caaccatgcc  34140
caaataattc tcatctcgcc accttctcaa tatatctcta agcaaatccc gaatattaag  34200
tccggccatt gtaaaaatct gctccagagc gccctccacc ttcagcctca agcagcgaat  34260
catgattgca aaaattcagg ttcctcacag acctgtataa gattcaaaag cggaacatta  34320
acaaaaatac cgcgatcccg taggtccctt cgcagggcca gctgaacata atcgtgcagg  34380
tctgcacgga ccagcgcggc cacttccccg ccaggaacct tgacaaaaga acccacactg  34440
attatgacac gcatactcgg agctatgcta accagcgtag ccccgatgta agctttgttg  34500
catgggcggc gatataaaat gcaaggtgct gctcaaaaaa tcaggcaaag cctcgcgcaa  34560
```

-continued

```
aaaagaaagc acatcgtagt catgctcatg cagataaagg caggtaagct ccggaaccac  34620
cacagaaaaa gacaccattt ttctctcaaa catgtctgcg ggtttctgca taaacacaaa  34680
ataaaataac aaaaaaacat ttaaacatta gaagcctgtc ttacaacagg aaaaacaacc  34740
cttataagca taagacggac tacggccatg ccggcgtgac cgtaaaaaaa ctggtcaccg  34800
tgattaaaaa gcaccaccga cagctcctcg gtcatgtccg gagtcataat gtaagactcg  34860
gtaaacacat caggttgatt catcggtcag tgctaaaaag cgaccgaaat agcccggggg  34920
aatacatacc cgcaggcgta gagacaacat tacagccccc ataggaggta taacaaaatt  34980
aataggagag aaaaacacat aaacacctga aaaaccctcc tgcctaggca aaatagcacc  35040
ctcccgctcc agaacaacat acagcgcttc acagcggcag cctaacagtc agccttacca  35100
gtaaaaaaga aaacctatta aaaaaacacc actcgacacg gcaccagctc aatcagtcac  35160
agtgtaaaaa agggccaagt gcagagcgag tatatatagg actaaaaaat gacgtaacgg  35220
ttaaagtcca caaaaaaacac ccagaaaacc gcacgcgaac ctacgcccag aaacgaaagc  35280
caaaaaaccc acaacttcct caaatcgtca cttccgtttt cccacgttac gtaacttccc  35340
attttaagaa aactacaatt cccaacacat acaagttact ccgccctaaa acctacgtca  35400
cccgccccgt tcccacgccc cgcgccacgt cacaaactcc accccctcat tatcatattg  35460
gcttcaatcc aaaataaggt atattattga tgatgattta aatgccgcag tactgttgta  35520
attcattaag cattctgccg acatggaagc catcacaaac ggcatgatga acctgaatcg  35580
ccagcggcat cagcaccttg tcgccttgcg tataatattt gcccatggtg aaaacggggg  35640
cgaagaagtt gtccatattg gccacgttta aatcaaaact ggtgaaactc acccagggat  35700
tggctgagac gaaaaacata ttctcaataa accctttagg gaaataggcc aggttttcac  35760
cgtaacacgc cacatcttgc gaatatatgt gtagaaactg ccggaaatcg tcgtggtatt  35820
cactccagag cgatgaaaac gtttcagttt gctcatggaa aacggtgtaa caagggtgaa  35880
cactatccca tatcaccagc tcaccgtctt tcattgccat acggaattcc ggatgagcat  35940
tcatcaggcg ggcaagaatg tgaataaagg ccggataaaa cttgtgctta tttttcttta  36000
cggtctttaa aaaggccgta atatccagct gaacggtctg gttataggta cattgagcaa  36060
ctgactgaaa tgcctcaaaa tgttctttac gatgccattg ggatatatca acggtggtat  36120
atccagtgat ttttttctcc attttagctt ccttagctcc tgaaaatctc gataactcaa  36180
aaaatacgcc cggtagtgat cttatttcat tatggtgaaa gttggaacct cttacgtgcc  36240
gatcaacgtc tcattttcgc caaaagttgg cccagggctt cccggtatca acagggacac  36300
caggatttat ttattctgcg aagtgatctt ccgtcacagg tatttattcg cgataagctc  36360
atggagcggc gtaaccgtcg cacaggaagg acagagaaag cgcggatctg ggaagtgacg  36420
gacagaacgg tcaggacctg gattggggag gcggttgccg ccgctgctgc tgacggtgtg  36480
acgttctctg ttccggtcac accacatacg ttccgccatt cctatgcgat gcacatgctg  36540
tatgccggta taccgctgaa agttctgcaa agcctgatgg gacataagtc catcagttca  36600
acggaagtct acacgaaggt ttttgcgctg gatgtggctg cccggcaccg ggtgcagttt  36660
gcgatgccgg agtctgatgc ggttgcgatg ctgaaacaat tatcctgaga ataaatgcct  36720
tggcctttat atggaaatgt ggaactgagt ggatatgctg tttttgtctg ttaaacagag  36780
aagctggctg ttatccactg agaagcgaac gaaacagtcg ggaaaatctc ccattatcgt  36840
agagatccgc attattaatc tcaggagcct gtgtagcgtt tataggaagt agtgttctgt  36900
```

-continued

```
catgatgcct gcaagcggta acgaaaacga tttgaatatg ccttcaggaa caatagaaat  36960
cttcgtgcgg tgttacgttg aagtggagcg gattatgtca gcaatggaca gaacaaccta  37020
atgaacacag aaccatgatg tggtctgtcc ttttacagcc agtagtgctc gccgcagtcg  37080
agcgacaggg cgaagccctc gagtgagcga ggaagcacca gggaacagca cttatatatt  37140
ctgcttacac acgatgcctg aaaaaacttc ccttggggtt atccacttat ccacggggat  37200
atttttataa ttattttttt tatagttttt agatcttctt ttttagagcg ccttgtaggc  37260
ctttatccat gctggttcta gagaaggtgt tgtgacaaat tgccctttca gtgtgacaaa  37320
tcaccctcaa atgacagtcc tgtctgtgac aaattgccct taaccctgtg acaaattgcc  37380
ctcagaagaa gctgtttttt cacaaagtta tccctgctta ttgactcttt tttatttagt  37440
gtgacaatct aaaaacttgt cacacttcac atggatctgt catggcggaa acagcggtta  37500
tcaatcacaa gaaacgtaaa aatagcccgc gaatcgtcca gtcaaacgac ctcactgagg  37560
cggcatatag tctctcccgg gatcaaaaac gtatgctgta tctgttcgtt gaccagatca  37620
gaaaatctga tggcacccta caggaacatg acggtatctg cgagatccat gttgctaaat  37680
atgctgaaat attcggattg acctctgcgg aagccagtaa ggatatacgg caggcattga  37740
agagtttcgc ggggaaggaa gtggtttttt atcgccctga agaggatgcc ggcgatgaaa  37800
aaggctatga atcttttcct tggtttatca aacgtgcgca cagtccatcc agagggcttt  37860
acagtgtaca tatcaaccca tatctcattc ccttctttat cgggttacag aaccggttta  37920
cgcagtttcg gcttagtgaa acaaaagaaa tcaccaatcc gtatgccatg cgtttatacg  37980
aatccctgtg tcagtatcgt aagccggatg gctcaggcat cgtctctctg aaaatcgact  38040
ggatcataga gcgttaccag ctgcctcaaa gttaccagcg tatgcctgac ttccgccgcc  38100
gcttcctgca ggtctgtgtt aatgagatca acagcagaac tccaatgcgc ctctcataca  38160
ttgagaaaaa gaaaggccgc cagacgactc atatcgtatt ttccttccgc gatatcactt  38220
ccatgacgac aggatagtct gagggttatc tgtcacagat ttgagggtgg ttcgtcacat  38280
ttgttctgac ctactgaggg taatttgtca cagttttgct gtttccttca gcctgcatgg  38340
attttctcat actttttgaa ctgtaatttt taaggaagcc aaatttgagg gcagtttgtc  38400
acagttgatt tccttctctt tcccttcgtc atgtgacctg atatcggggg ttagttcgtc  38460
atcattgatg agggttgatt atcacagttt attactctga attggctatc cgcgtgtgta  38520
cctctacctg gagtttttcc cacggtggat atttcttctt gcgctgagcg taagagctat  38580
ctgacagaac agttcttctt tgcttcctcg ccagttcgct cgctatgctc ggttacacgg  38640
ctgcggcgag cgctagtgat aataagtgac tgaggtatgt gctcttctta tctccttttg  38700
tagtgttgct cttattttaa acaactttgc ggtttttttga tgactttgcg attttgttgt  38760
tgctttgcag taaattgcaa gatttaataa aaaaacgcaa agcaatgatt aaaggatgtt  38820
cagaatgaaa ctcatggaaa cacttaacca gtgcataaac gctggtcatg aaatgacgaa  38880
ggctatcgcc attgcacagt ttaatgatga cagcccggaa gcgaggaaaa taacccggcg  38940
ctggagaata ggtgaagcag cggatttagt tggggtttct tctcaggcta tcagagatgc  39000
cgagaaagca gggcgactac cgcacccgga tatggaaatt cgaggacggg ttgagcaacg  39060
tgttggttat acaattgaac aaattaatca tatgcgtgat gtgtttggta cgcgattgcg  39120
acgtgctgaa gacgtatttc caccggtgat cggggttgct gcccataaag gtggcgttta  39180
caaaacctca gtttctgttc atcttgctca ggatctggct ctgaaggggc tacgtgtttt  39240
gctcgtggaa ggtaacgacc cccagggaac agcctcaatg tatcacggat gggtaccaga  39300
```

-continued

```
tcttcatatt catgcagaag acactctcct gcctttctat cttggggaaa aggacgatgt  39360
cacttatgca ataaagccca cttgctggcc ggggcttgac attattcctt cctgtctggc  39420
tctgcaccgt attgaaactg agttaatggg caaatttgat gaaggtaaac tgcccaccga  39480
tccacacctg atgctccgac tggccattga aactgttgct catgactatg atgtcatagt  39540
tattgacagc gcgcctaacc tgggtatcgg cacgattaat gtcgtatgtg ctgctgatgt  39600
gctgattgtt cccacgcctg ctgagttgtt tgactacacc tccgcactgc agtttttcga  39660
tatgcttcgt gatctgctca agaacgttga tcttaaaggg ttcgagcctg atgtacgtat  39720
tttgcttacc aaatacagca atagtaatgg ctctcagtcc ccgtggatgg aggagcaaat  39780
tcgggatgcc tggggaagca tggttctaaa aaatgttgta cgtgaaacgg atgaagttgg  39840
taaaggtcag atccggatga gaactgtttt tgaacaggcc attgatcaac gctcttcaac  39900
tggtgcctgg agaaatgctc tttctatttg ggaacctgtc tgcaatgaaa ttttcgatcg  39960
tctgattaaa ccacgctggg agattagata atgaagcgtg cgcctgttat tccaaaacat  40020
acgctcaata ctcaaccggt tgaagatact tcgttatcga caccagctgc cccgatggtg  40080
gattcgttaa ttgcgcgcgt aggagtaatg gctcgcggta atgccattac tttgcctgta  40140
tgtggtcggg atgtgaagtt tactcttgaa gtgctccggg gtgatagtgt tgagaagacc  40200
tctcgggtat ggtcaggtaa tgaacgtgac caggagctgc ttactgagga cgcactggat  40260
gatctcatcc cttcttttct actgactggt caacagacac cggcgttcgg tcgaagagta  40320
tctggtgtca tagaaattgc cgatgggagt cgccgtcgta aagctgctgc acttaccgaa  40380
agtgattatc gtgttctggt tggcgagctg gatgatgagc agatggctgc attatccaga  40440
ttgggtaacg attatcgccc aacaagtgct tatgaacgtg gtcagcgtta tgcaagccga  40500
ttgcagaatg aatttgctgg aaatatttct gcgctggctg atgcggaaaa tatttcacgt  40560
aagattatta cccgctgtat caacaccgcc aaattgccta aatcagttgt tgctcttttt  40620
tctcaccccg gtgaactatc tgcccggtca ggtgatgcac ttcaaaaagc ctttacagat  40680
aaagaggaat tacttaagca gcaggcatct aaccttcatg agcagaaaaa agctggggtg  40740
atatttgaag ctgaagaagt tatcactctt ttaacttctg tgcttaaaac gtcatctgca  40800
tcaagaacta gtttaagctc acgacatcag tttgctcctg gagcgacagt attgtataag  40860
ggcgataaaa tggtgcttaa cctggacagg tctcgtgttc caactgagtg tatagagaaa  40920
attgaggcca ttcttaagga acttgaaaag ccagcaccct gatgcgacca cgttttagtc  40980
tacgtttatc tgtctttact taatgtcctt tgttacaggc cagaaagcat aactggcctg  41040
aatattctct ctgggcccac tgttccactt gtatcgtcgg tctgataatc agactgggac  41100
cacggtccca ctcgtatcgt cggtctgatt attagtctgg gaccacggtc ccactcgtat  41160
cgtcggtctg attattagtc tgggaccacg gtcccactcg tatcgtcggt ctgataatca  41220
gactgggacc acggtcccac tcgtatcgtc ggtctgatta ttagtctggg accatggtcc  41280
cactcgtatc gtcggtctga ttattagtct gggaccacgg tcccactcgt atcgtcggtc  41340
tgattattag tctggaacca cggtcccact cgtatcgtcg gtctgattat tagtctggga  41400
ccacggtccc actcgtatcg tcggtctgat tattagtctg ggaccacgat cccactcgtg  41460
ttgtcggtct gattatcggt ctgggaccac ggtcccactt gtattgtcga tcagactatc  41520
agcgtgagac tacgattcca tcaatgcctg tcaagggcaa gtattgacat gtcgtcgtaa  41580
cctgtagaac ggagtaacct cggtgtgcgg ttgtatgcct gctgtggatt gctgctgtgt  41640
```

-continued

```
cctgcttatc cacaacattt tgcgcacggt tatgtggaca aaatacctgt taccatttcc  41700
atttaaatca tcatcaataa tataccttat tttggattga agccaatatg ataatgaggg  41760
ggtggagttt gtgacgtggc gcggggcgtg ggaacggggc gggtgacgta gtagtgtggc  41820
ggaagtgtga tgttgcaagt gtggcggaac acatgtaagc gacggatgtg gcaaaagtga  41880
cgtttttggt gtgcgccggt gtacacagga agtgacaatt ttcgcgcggt tttaggcgga  41940
tgttgtagta aatttgggcg taaccgagta agatttggcc attttcgcgg gaaaactgaa  42000
taagaggaag tgaaatctga ataattttgt gttactcata gcgcgtaata tttgtctagg  42060
gccgcgggga ctttgaccgt ttacgtggag actcgcccag gtgtttttct caggtgtttt  42120
ccgcgttccg ggtcaaagtt ggcgtttt                                    42148
```

<210> SEQ ID NO 5
<211> LENGTH: 35789
<212> TYPE: DNA
<213> ORGANISM: Artificial sequence
<220> FEATURE:
<223> OTHER INFORMATION: Sequence pGS66 (35789 bp)

<400> SEQUENCE: 5

```
ttcgaaattt aaatcatcat caataatata ccttattttg gattgaagcc aatatgataa     60
tgagggggtg gagtttgtga cgtggcgcgg ggcgtgggaa cggggcgggt gacgtagtag    120
tgtggcggaa gtgtgatgtt gcaagtgtgg cggaacacat gtaagcgacg gatgtggcaa    180
aagtgacgtt tttggtgtgc gccggtgtac acaggaagtg acaattttcg cgcggtttta    240
ggcggatgtt gtagtaaatt tgggcgtaac cgagtaagat ttggccattt tcgcgggaaa    300
actgaataag aggaagtgaa atctgaataa ttttgtgtta ctcatagcgc gtaatatttg    360
tctagggccg cggggacttt gaccgtttac gtggagactc gcccaggtgt ttttctcagg    420
tgttttccgc gttccgggtc aaagttggcg ttttgatggc gtcccttaat taaggatcca    480
gatctgtggg cgtggcttaa gggtgggaaa gaatatataa ggtgggggtc ttatgtagtt    540
ttgtatctgt tttgcagcag ccgccgccgc catgagcacc aactcgtttg atggaagcat    600
tgtgagctca tatttgacaa cgcgcatgcc cccatgggcc ggggtgcgtc agaatgtgat    660
gggctccagc attgatggtc gccccgtcct gcccgcaaac tctactacct tgacctacga    720
gaccgtgtct ggaacgccgt tggagactgc agcctccgcc gccgcttcag ccgctgcagc    780
caccgcccgc gggattgtga ctgactttgc tttcctgagc ccgcttgcaa gcagtgcagc    840
ttcccgttca tccgcccgcg atgacaagtt gacggctctt ttggcacaat tggattcttt    900
gacccgggaa cttaatgtcg tttctcagca gctgttggat ctgcgccagc aggtttctgc    960
cctgaaggct tcctcccctc ccaatgcggt ttaaaacata aataaaaaac cagactctgt   1020
ttggatttgg atcaagcaag tgtcttgctg tctttattta ggggttttgc gcgcgcggta   1080
ggcccgggac cagcggtctc ggtcgttgag ggtcctgtgt atttttttcca ggacgtggta   1140
aaggtgactc tggatgttca gatacatggg cataagcccg tctctggggt ggaggtagca   1200
ccactgcaga gcttcatgct gcggggtggt gttgtagatg atccagtcgt agcaggagcg   1260
ctgggcgtgg tgcctaaaaa tgtctttcag tagcaagctg attgccaggg gcaggccctt   1320
ggtgtaagtg tttacaaagc ggttaagctg ggatgggtgc atacgtgggg atatgagatg   1380
catcttggac tgtattttta ggttggctat gttcccagcc atatccctcc ggggattcat   1440
gttgtgcaga accaccagca cagtgtatcc ggtgcacttg ggaaatttgt catgtagctt   1500
agaaggaaat gcgtggaaga acttggagac gcccttgtga cctccaagat tttccatgca   1560
```

-continued

```
ttcgtccata atgatggcaa tgggcccacg ggcggcggcc tgggcgaaga tatttctggg   1620
atcactaacg tcatagttgt gttccaggat gagatcgtca taggccattt ttacaaagcg   1680
cgggcggagg gtgccagact gcggtataat ggttccatcc ggcccagggg cgtagttacc   1740
ctcacagatt tgcatttccc acgctttgag ttcagatggg gggatcatgt ctacctgcgg   1800
ggcgatgaag aaaacggttt ccggggtagg ggagatcagc tgggaagaaa gcaggttcct   1860
gagcagctgc gacttaccgc agccggtggg cccgtaaatc acacctatta ccgggtgcaa   1920
ctggtagtta agagagctgc agctgccgtc atccctgagc aggggggcca cttcgttaag   1980
catgtccctg actcgcatgt tttccctgac caaatccgcc agaaggcgct cgccgcccag   2040
cgatagcagt tcttgcaagg aagcaaagtt tttcaacggt ttgagaccgt ccgccgtagg   2100
catgcttttg agcgtttgac caagcagttc caggcggtcc cacagctcgg tcacctgctc   2160
tacggcatct cgatccagca tatctcctcg tttcgcgggt tggggcggct ttcgctgtac   2220
ggcagtagtc ggtgctcgtc cagacgggcc agggtcatgt ctttccacgg gcgcagggtc   2280
ctcgtcagcg tagtctgggt cacggtgaag ggtgcgctc cgggctgcgc gctggccagg   2340
gtgcgcttga ggctggtcct gctggtgctg aagcgctgcc ggtcttcgcc ctgcgcgtcg   2400
gccaggtagc atttgaccat ggtgtcatag tccagcccct ccgcggcgtg gcccttggcg   2460
cgcagcttgc ccttggagga ggcgccgcac gaggggcagt gcagactttt gagggcgtag   2520
agcttgggcg cgagaaatac cgattccggg gagtaggcat ccgcgccgca ggccccgcag   2580
acggtctcgc attccacgag ccaggtgagc tctggccgtt cggggtcaaa aaccaggttt   2640
cccccatgct ttttgatgcg tttcttacct ctggtttcca tgagccggtg tccacgctcg   2700
gtgacgaaaa ggctgtccgt gtccccgtat acagacttga gaggcctgtc ctcgagcggt   2760
gttccgcggt cctcctcgta tagaaactcg gaccactctg agacaaaggc tcgcgtccag   2820
gccagcacga aggaggctaa gtgggagggg tagcggtcgt tgtccactag ggggtccact   2880
cgctccaggg tgtgaagaca catgtcgccc tcttcggcat caaggaaggt gattggtttg   2940
taggtgtagg ccacgtgacc gggtgttcct gaaggggggc tataaaaggg ggtgggggcg   3000
cgttcgtcct cactctcttc cgcatcgctg tctgcgaggg ccagctgttg gggtgagtac   3060
tccctctgaa aagcgggcat gacttctgcg ctaagattgt cagtttccaa aaacgaggag   3120
gatttgatat tcacctggcc cgcggtgatg cctttgaggg tggccgcatc catctggtca   3180
gaaaagacaa tctttttgtt gtcaagcttg gtggcaaacg acccgtagag ggcgttggac   3240
agcaacttgg cgatggagcg cagggtttgg tttttgtcgc gatcggcgcg ctccttggcc   3300
gcgatgttta gctgcacgta ttcgcgcgca acgcaccgcc attcgggaaa gacggtggtg   3360
cgctcgtcgg gcaccaggtg cacgcgccaa ccgcggttgt gcagggtgac aaggtcaacg   3420
ctggtggcta cctctccgcg taggcgctcg ttggtccagc agaggcggcc gcccttgcgc   3480
gagcagaatg gcggtagggg gtctagctgc gtctcgtccg gggggtctgc gtccacggta   3540
aagaccccgg gcagcaggcg cgcgtcgaag tagtctatct tgcatccttg caagtctagc   3600
gcctgctgcc atgcgcgggc ggcaagcgcg cgctcgtatg ggttgagtgg gggaccccat   3660
ggcatggggt gggtgagcgc ggaggcgtac atgccgcaaa tgtcgtaaac gtagaggggc   3720
tctctgagta ttccaagata tgtagggtag catcttccac cgcggatgct ggcgcgcacg   3780
taatcgtata gttcgtgcga gggagcgagg aggtcgggac cgaggttgct acgggcgggc   3840
tgctctgctc ggaagactat ctgcctgaag atggcatgtg agttggatga tatggttgga   3900
```

```
cgctggaaga cgttgaagct ggcgtctgtg agacctaccg cgtcacgcac gaaggaggcg   3960
taggagtcgc gcagcttgtt gaccagctcg gcggtgacct gcacgtctag ggcgcagtag   4020
tccagggttt ccttgatgat gtcatactta tcctgtccct tttttttcca cagctcgcgg   4080
ttgaggacaa actcttcgcg gtctttccag tactcttgga tcggaaaccc gtcggcctcc   4140
gaacggtaag agcctagcat gtagaactgg ttgacggcct ggtaggcgca gcatcccttt   4200
tctacgggta gcgcgtatgc ctgcgcggcc ttccggagcg aggtgtgggt gagcgcaaag   4260
gtgtccctga ccatgacttt gaggtactgg tatttgaagt cagtgtcgtc gcatccgccc   4320
tgctcccaga gcaaaaagtc cgtgcgcttt ttggaacgcg gatttggcag ggcgaaggtg   4380
acatcgttga agagtatctt tcccgcgcga ggcataaagt tgcgtgtgat gcggaagggt   4440
cccggcacct cggaacggtt gttaattacc tgggcggcga gcacgatctc gtcaaagccg   4500
ttgatgttgt ggcccacaat gtaaagttcc aagaagcgcg ggatgccctt gatggaaggc   4560
aattttttaa gttcctcgta ggtgagctct tcaggggagc tgagcccgtg ctctgaaagg   4620
gcccagtctg caagatgagg gttggaagcg acgaatgagc tccacaggtc acgggccatt   4680
agcatttgca ggtggtcgcg aaaggtccta aactggcgac ctatggccat tttttctggg   4740
gtgatgcagt agaaggtaag cgggtcttgt tcccagcggt cccatccaag gttcgcggct   4800
aggtctcgcg cggcagtcac tagaggctca tctccgccga acttcatgac cagcatgaag   4860
ggcacgagct gcttcccaaa ggcccccatc caagtatagg tctctacatc gtaggtgaca   4920
aagagacgct cggtgcgagg atgcgagccg atcgggaaga actggatctc ccgccaccaa   4980
ttggaggagt ggctattgat gtggtgaaag tagaagtccc tgcgacgggc cgaacactcg   5040
tgctggcttt tgtaaaaacg tgcgcagtac tggcagcggt gcacgggctg tacatcctgc   5100
acgaggttga cctgacgacc gcgcacaagg aagcagagtg ggaatttgag cccctcgcct   5160
ggcgggtttg gctggtggtc ttctacttcg gctgcttgtc cttgaccgtc tggctgctcg   5220
aggggagtta cggtggatcg gaccaccacg ccgcgcgagc ccaaagtcca gatgtccgcg   5280
cgcggcggtc ggagcttgat gacaacatcg cgcagatggg agctgtccat ggtctggagc   5340
tcccgcggcg tcaggtcagg cgggagctcc tgcaggttta cctcgcatag acgggtcagg   5400
gcgcgggcta gatccaggtg atacctaatt tccaggggct ggttggtggc ggcgtcgatg   5460
gcttgcaaga ggccgcatcc ccgcggcgcg actacggtac cgcgcggcgg gcggtgggcc   5520
gcgggggtgt ccttggatga tgcatctaaa agcggtgacg cgggcgagcc cccggaggta   5580
gggggggctc cggacccgcc gggagagggg gcaggggcac gtcggcgccg cgcgcgggca   5640
ggagctggtg ctgcgcgcgt aggttgctgg cgaacgcgac gacgcggcgg ttgatctcct   5700
gaatctggcg cctctgcgtg aagacgacgg gcccggtgag cttgagcctg aaagagagtt   5760
cgacagaatc aatttcggtg tcgttgacgg cggcctggcg caaaatctcc tgcacgtctc   5820
ctgagttgtc ttgataggcg atctcggcca tgaactgctc gatctcttcc tcctggagat   5880
ctccgcgtcc ggctcgctcc acggtggcgg cgaggtcgtt ggaaatgcgg gccatgagct   5940
gcgagaaggc gttgaggcct ccctcgttcc agacgcggct gtagaccacg ccccccttcgg  6000
catcgcgggc gcgcatgacc acctgcgcga gattgagctc cacgtgccgg gcgaagacgg   6060
cgtagtttcg caggcgctga aagaggtagt tgagggtggt ggcggtgtgt tctgccacga   6120
agaagtacat aacccagcgt cgcaacgtgg attcgttgat atcccccaag gcctcaaggc   6180
gctccatggc ctcgtagaag tccacggcga agttgaaaaa ctgggagttg cgcgccgaca   6240
cggttaactc ctcctccaga agacggatga gctcggcgac agtgtcgcgc acctcgcgct   6300
```

```
caaaggctac aggggcctct tcttcttctt caatctcctc ttccataagg gcctcccctt   6360
cttcttcttc tggcggcggt gggggagggg ggacacggcg gcgacgacgg cgcaccggga   6420
ggcggtcgac aaagcgctcg atcatctccc cgcggcgacg gcgcatggtc tcggtgacgg   6480
cgcggccgtt ctcgcggggg cgcagttgga agacgccgcc cgtcatgtcc cggttatggg   6540
ttggcggggg gctgccatgc ggcagggata cggcgctaac gatgcatctc aacaattgtt   6600
gtgtaggtac tccgccgccg agggacctga gcgagtccgc atcgaccgga tcggaaaacc   6660
tctcgagaaa ggcgtctaac cagtcacagt cgcaaggtag gctgagcacc gtggcgggcg   6720
gcagcgggcg gcggtcgggg ttgtttctgg cggaggtgct gctgatgatg taattaaagt   6780
aggcggtctt gagacggcgg atggtcgaca gaagcaccat gtccttgggt ccggcctgct   6840
gaatgcgcag gcggtcggcc atgccccagg cttcgttttg acatcggcgc aggtctttgt   6900
agtagtcttg catgagcctt tctaccggca cttcttcttc tccttcctct tgtcctgcat   6960
ctcttgcatc tatcgctgcg gcggcggcgg agtttggccg taggtggcgc cctcttcctc   7020
ccatgcgtgt gaccccgaag cccctcatcg gctgaagcag ggctaggtcg gcgacaacgc   7080
gctcggctaa tatggcctgc tgcacctgcg tgagggtaga ctggaagtca tccatgtcca   7140
caaagcggtg gtatgcgccc gtgttgatgg tgtaagtgca gttggccata acggaccagt   7200
taacggtctg gtgacccggc tgcgagagct cggtgtacct gagacgcgag taagccctcg   7260
agtcaaatac gtagtcgttg caagtccgca ccaggtactg gtatcccacc aaaaagtgcg   7320
gcggcggctg gcggtagagg ggccagcgta gggtggccgg ggctccgggg gcgagatctt   7380
ccaacataag gcgatgatat ccgtagatgt acctggacat ccaggtgatg ccggcggcgg   7440
tggtggaggc gcgcggaaag tcgcggacgc ggttccagat gttgcgcagc ggcaaaaagt   7500
gctccatggt cgggacgctc tggccggtca ggcgcgcgca atcgttgacg ctctagaccg   7560
tgcaaaagga gagcctgtaa gcgggcactc ttccgtggtc tggtggataa attcgcaagg   7620
gtatcatggc ggacgaccgg ggttcgagcc ccgtatccgg ccgtccgccg tgatccatgc   7680
ggttaccgcc cgcgtgtcga acccaggtgt gcgacgtcag acaacggggg agtgctcctt   7740
ttggcttcct tccaggcgcg gcggctgctg cgctagcttt tttggccact ggccgcgcgc   7800
agcgtaagcg gttaggctgg aaagcgaaag cattaagtgg ctcgctccct gtagccggag   7860
ggttattttc caagggttga gtcgcgggac ccccggttcg agtctcggac cggccggact   7920
gcggcgaacg gggtttgcc tccccgtcat gcaagacccc gcttgcaaat tcctccggaa   7980
acagggacga gcccctttt tgcttttccc agatgcatcc ggtgctgcgg cagatgcgcc   8040
cccctcctca gcagcggcaa gagcaagagc agcggcagac atgcagggca ccctcccctc   8100
ctcctaccgc gtcaggaggg gcgacatccg cggttgacgc ggcagcagat ggtgattacg   8160
aacccccgcg gcgccgggcc cggcactacc tggacttgga ggagggcgag ggcctggcgc   8220
ggctaggagc gccctctcct gagcggcacc caagggtgca gctgaagcgt gatacgcgtg   8280
aggcgtacgt gccgcggcag aacctgtttc gcgaccgcga gggagaggag cccgaggaga   8340
tgcgggatcg aaagttccac gcagggcgcg agctgcggca tggcctgaat cgcgagcggt   8400
tgctgcgcga ggaggacttt gagcccgacg cgcgaaccgg gattagtccc gcgcgcgcac   8460
acgtggcggc cgccgacctg gtaaccgcat acgagcagac ggtgaaccag gagattaact   8520
ttcaaaaaag ctttaacaac cacgtgcgta cgcttgtggc gcgcgaggag gtggctatag   8580
gactgatgca tctgtgggac tttgtaagcg cgctggagca aaacccaaat agcaagccgc   8640
```

-continued

```
tcatggcgca gctgttcctt atagtgcagc acagcaggga caacgaggca ttcagggatg   8700
cgctgctaaa catagtagag cccgagggcc gctggctgct cgatttgata aacatcctgc   8760
agagcatagt ggtgcaggag cgcagcttga gcctggctga caaggtggcc gccatcaact   8820
attccatgct tagcctgggc aagttttacg cccgcaagat ataccatacc ccttacgttc   8880
ccatagacaa ggaggtaaag atcgaggggt tctacatgcg catggcgctg aaggtgctta   8940
ccttgagcga cgacctgggc gtttatcgca acgagcgcat ccacaaggcc gtgagcgtga   9000
gccggcggcg cgagctcagc gaccgcgagc tgatgcacag cctgcaaagg gccctggctg   9060
gcacgggcag cggcgataga gaggccgagt cctactttga cgcgggcgct gacctgcgct   9120
gggccccaag ccgacgcgcc ctggaggcag ctggggccgg acctgggctg gcggtggcac   9180
ccgcgcgcgc tggcaacgtc ggcggcgtgg aggaatatga cgaggacgat gagtacgagc   9240
cagaggacgg cgagtactaa gcggtgatgt ttctgatcag atgatgcaag acgcaacgga   9300
cccggcggtg cgggcggcgc tgcagagcca gccgtccggc cttaactcca cggacgactg   9360
gcgccaggtc atggaccgca tcatgtcgct gactgcgcgc aatcctgacg cgttccggca   9420
gcagccgcag gccaaccggc tctccgcaat tctggaagcg gtggtcccgg cgcgcgcaaa   9480
ccccacgcac gagaaggtgc tggcgatcgt aaacgcgctg gccgaaaaca gggccatccg   9540
gcccgacgag gccggcctgg tctacgacgc gctgcttcag cgcgtggctc gttacaacag   9600
cggcaacgtg cagaccaacc tggaccggct ggtgggggat gtgcgcgagg ccgtggcgca   9660
gcgtgagcgc gcgcagcagc agggcaacct gggctccatg gttgcactaa acgccttcct   9720
gagtacacag cccgccaacg tgccgcgggg acaggaggac tacaccaact ttgtgagcgc   9780
actgcggcta atggtgactg agacaccgca aagtgaggtg taccagtctg ggccagacta   9840
tttttttccag accagtagac aaggcctgca gaccgtaaac ctgagccagg ctttcaaaaa   9900
cttgcagggg ctgtgggggg tgcgggctcc cacaggcgac cgcgcgaccg tgtctagctt   9960
gctgacgccc aactcgcgcc tgttgctgct gctaatagcg cccttcacgg acagtggcag  10020
cgtgtcccgg gacacatacc taggtcactt gctgacactg taccgcgagg ccataggtca  10080
ggcgcatgtg gacgagcata ctttccagga gattacaagt gtcagccgcg cgctggggca  10140
ggaggacacg ggcagcctgg aggcaaccct aaactacctg ctgaccaacc ggcggcagaa  10200
gatcccctcg ttgcacagtt taaacagcga ggaggagcgc attttgcgct acgtgcagca  10260
gagcgtgagc cttaacctga tgcgcgacgg ggtaacgccc agcgtggcgc tggacatgac  10320
cgcgcgcaac atggaaccgg gcatgtatgc ctcaaaccgg ccgtttatca accgcctaat  10380
ggactacttg catcgcgcgg ccgccgtgaa ccccgagtat ttcaccaatg ccatcttgaa  10440
cccgcactgg ctaccgcccc ctggtttcta caccggggga ttcgaggtgc ccgagggtaa  10500
cgatggattc ctctgggacg acatagacga cagcgtgttt tccccgcaac cgcagaccct  10560
gctagagttg caacagcgcg agcaggcaga ggcggcgctg cgaaaggaaa gcttccgcag  10620
gccaagcagc ttgtccgatc taggcgctgc ggccccgcgg tcagatgcta gtagcccatt  10680
tccaagcttg atagggtctc ttaccagcac tcgcaccacc cgcccgcgcc tgctgggcga  10740
ggaggagtac ctaaacaact cgctgctgca gccgcagcgc gaaaaaaacc tgcctccggc  10800
atttcccaac aacgggatag agagcctagt ggacaagatg agtagatgga agacgtacgc  10860
gcaggagcac agggacgtgc caggcccgcg cccgcccacc cgtcgtcaaa ggcacgaccg  10920
tcagcggggt ctggtgtggg aggacgatga ctcggcagac gacagcagcg tcctggattt  10980
gggagggagt ggcaacccgt ttgcgcacct tcgccccagg ctggggagaa tgttttaaaa  11040
```

-continued

```
aaaaaaaagc atgatgcaaa ataaaaaact caccaaggcc atggcaccga gcgttggttt  11100
tcttgtattc cccttagtat gcggcgcgcg gcgatgtatg aggaaggtcc tcctccctcc  11160
tacgagagtg tggtgagcgc ggcgccagtg gcggcggcgc tgggttctcc cttcgatgct  11220
cccctggacc cgccgtttgt gcctccgcgg tacctgcggc ctaccggggg gagaaacagc  11280
atccgttact ctgagttggc acccctattc gacaccaccc gtgtgtacct ggtggacaac  11340
aagtcaacgg atgtggcatc cctgaactac cagaacgacc acagcaactt tctgaccacg  11400
gtcattcaaa acaatgacta cagcccgggg gaggcaagca cacagaccat caatcttgac  11460
gaccggtcgc actggggcgg cgacctgaaa accatcctgc ataccaacat gccaaatgtg  11520
aacgagttca tgtttaccaa taagtttaag gcgcgggtga tggtgtcgcg cttgcctact  11580
aaggacaatc aggtggagct gaaatacgag tgggtggagt tcacgctgcc cgagggcaac  11640
tactccgaga ccatgaccat agaccttatg aacaacgcga tcgtggagca ctacttgaaa  11700
gtgggcagac agaacggggt tctggaaagc gacatcgggg taaagtttga cacccgcaac  11760
ttcagactgg ggtttgaccc cgtcactggt cttgtcatgc ctggggtata tacaaacgaa  11820
gccttccatc cagacatcat tttgctgcca ggatgcgggg tggacttcac ccacagccgc  11880
ctgagcaact tgttgggcat ccgcaagcgg caacccttcc aggagggctt taggatcacc  11940
tacgatgatc tggagggtgg taacattccc gcactgttgg atgtggacgc ctaccaggcg  12000
agcttgaaag atgacaccga acagggcggg ggtggcgcag gcggcagcaa cagcagtggc  12060
agcggcgcgg aagagaactc caacgcggca gccgcggcaa tgcagccggt ggaggacatg  12120
aacgatcatg ccattcgcgg cgacaccttt gccacacggg ctgaggagaa gcgcgctgag  12180
gccgaagcag cggccgaagc tgccgccccc gctgcgcaac ccgaggtcga gaagcctcag  12240
aagaaaccgg tgatcaaacc cctgacagag gacagcaaga aacgcagtta caacctaata  12300
agcaatgaca gcaccttcac ccagtaccgc agctggtacc ttgcatacaa ctacggcgac  12360
cctcagaccg gaatccgctc atggaccctg ctttgcactc ctgacgtaac ctgcggctcg  12420
gagcaggtct actggtcgtt gccagacatg atgcaagacc ccgtgacctt ccgctccacg  12480
cgccagatca gcaactttcc ggtggtgggc gccgagctgt tgcccgtgca ctccaagagc  12540
ttctacaacg accaggccgt ctactcccaa ctcatccgcc agtttacctc tctgacccac  12600
gtgttcaatc gctttcccga gaaccagatt ttggcgcgcc cgccagcccc caccatcacc  12660
accgtcagtg aaaacgttcc tgctctcaca gatcacggga cgctaccgct gcgcaacagc  12720
atcggaggag tccagcgagt gaccattact gacgccagac gccgcacctg cccctacgtt  12780
tacaaggccc tgggcatagt ctcgccgcgc gtcctatcga gccgcacttt ttgagcaagc  12840
atgtccatcc ttatatcgcc cagcaataac acaggctggg gcctgcgctt cccaagcaag  12900
atgtttggcg gggccaagaa gcgctccgac caacacccag tgcgcgtgcg cgggcactac  12960
cgcgcgccct ggggcgcgca caaacgcggc cgcactgggc gcaccaccgt cgatgacgcc  13020
atcgacgcgg tggtggagga ggcgcgcaac tacacgccca cgccgccacc agtgtccaca  13080
gtggacgcgg ccattcagac cgtggtgcgc ggagcccggc gctatgctaa aatgaagaga  13140
cggcggaggc gcgtagcacg tcgccaccgc cgccgacccg gcactgccgc ccaacgcgcg  13200
gcggcggccc tgcttaaccg cgcacgtcgc accggccgac gggcggccat gcgggccgct  13260
cgaaggctgg ccgcgggtat tgtcactgtg ccccccaggt ccaggcgacg agcggccgcc  13320
gcagcagccg cggccattag tgctatgact cagggtcgca ggggcaacgt gtattgggtg  13380
```

-continued

```
cgcgactcgg ttagcggcct gcgcgtgccc gtgcgcaccc gccccccgcg caactagatt  13440
gcaagaaaaa actacttaga ctcgtactgt tgtatgtatc cagcggcggc ggcgcgcaac  13500
gaagctatgt ccaagcgcaa aatcaaagaa gagatgctcc aggtcatcgc gccggagatc  13560
tatggccccc cgaagaagga agagcaggat tacaagcccc gaaagctaaa gcgggtcaaa  13620
aagaaaaaga aagatgatga tgatgaactt gacgacgagg tggaactgct gcacgctacc  13680
gcgcccaggc gacgggtaca gtggaaaggt cgacgcgtaa aacgtgtttt gcgacccggc  13740
accaccgtag tctttacgcc cggtgagcgc tccacccgca cctacaagcg cgtgtatgat  13800
gaggtgtacg gcgacgagga cctgcttgag caggccaacg agcgcctcgg ggagtttgcc  13860
tacggaaagc ggcataagga catgctggcg ttgccgctgg acgagggcaa cccaacacct  13920
agcctaaagc ccgtaacact gcagcaggtg ctgcccgcgc ttgcaccgtc cgaagaaaag  13980
cgcggcctaa agcgcgagtc tggtgacttg gcacccaccg tgcagctgat ggtacccaag  14040
cgccagcgac tggaagatgt cttggaaaaa atgaccgtgg aacctgggct ggagcccgag  14100
gtccgcgtgc ggccaatcaa gcaggtggcg ccgggactgg gcgtgcagac cgtggacgtt  14160
cagataccca ctaccagtag caccagtatt gccaccgcca cagagggcat ggagacacaa  14220
acgtccccgg ttgcctcagc ggtggcggat gccgcggtgc aggcggtcgc tgcggccgcg  14280
tccaagacct ctacggaggt gcaaacggac ccgtggatgt ttcgcgtttc agcccccccgg  14340
cgcccgcgcg gttcgaggaa gtacggcgcc gccagcgcgc tactgcccga atatgcccta  14400
catccttcca ttgcgcctac ccccggctat cgtggctaca cctaccgccc cagaagacga  14460
gcaactaccc gacgccgaac caccactgga acccgccgcc gccgtcgccg tcgccagccc  14520
gtgctggccc cgatttccgt gcgcagggtg gctcgcgaag gaggcaggac cctggtgctg  14580
ccaacagcgc gctaccaccc cagcatcgtt taaaagccgg tctttgtggt tcttgcagat  14640
atggccctca cctgccgcct ccgtttcccg gtgccgggat tccgaggaag aatgcaccgt  14700
aggaggggca tggccggcca cggcctgacg ggcggcatgc gtcgtgcgca ccaccggcgg  14760
cggcgcgcgt cgcaccgtcg catgcgcggc ggtatcctgc ccctccttat tccactgatc  14820
gccgcggcga ttggcgccgt gcccggaatt gcatccgtgg ccttgcaggc gcagagacac  14880
tgattaaaaa caagttgcat gtggaaaaat caaaataaaa agtctggact ctcacgctcg  14940
cttggtcctg taactatttt gtagaatgga agacatcaac tttgcgtctc tggccccgcg  15000
acacggctcg cgcccgttca tgggaaactg gcaagatatc ggcaccagca atatgagcgg  15060
tggcgccttc agctggggct cgctgtggag cggcattaaa aatttcggtt ccaccgttaa  15120
gaactatggc agcaaggcct ggaacagcag cacaggccag atgctgaggg ataagttgaa  15180
agagcaaaat ttccaacaaa aggtggtaga tggcctggcc tctggcatta gcggggtggt  15240
ggacctggcc aaccaggcag tgcaaaataa gattaacagt aagcttgatc cccgccctcc  15300
cgtagaggag cctccaccgg ccgtggagac agtgtctcca gaggggcgtg gcgaaaagcg  15360
tccgcgcccc gacagggaag aaactctggt gacgcaaata gacgagcctc cctcgtacga  15420
ggaggcacta aagcaaggcc tgcccaccac ccgtcccatc gcgcccatgg ctaccggagt  15480
gctgggccag cacacacccg taacgctgga cctgcctccc cccgccgaca cccagcagaa  15540
acctgtgctg ccaggcccga ccgccgttgt tgtaacccgt cctagccgcg cgtccctgcg  15600
ccgcgccgcc agcggtccgc gatcgttgcg gcccgtagcc agtggcaact ggcaaagcac  15660
actgaacagc atcgtgggtc tgggggtgca atccctgaag cgccgacgat gcttctgaat  15720
agctaacgtg tcgtatgtgt gtcatgtatg cgtccatgtc gccgccagag gagctgctga  15780
```

gccgccgcgc gcccgctttc caagatggct acccccttcga tgatgccgca gtggtcttac 15840
atgcacatct cgggccagga cgcctcggag tacctgagcc ccgggctggt gcagtttgcc 15900
cgcgccaccg agacgtactt cagcctgaat aacaagttta gaaaccccac ggtggcgcct 15960
acgcacgacg tgaccacaga ccggtcccag cgtttgacgc tgcggttcat ccctgtggac 16020
cgtgaggata ctgcgtactc gtacaaggcg cggttcaccc tagctgtggg tgataaccgt 16080
gtgctggaca tggcttccac gtactttgac atccgcggcg tgctggacag gggccctact 16140
tttaagccct actctggcac tgcctacaac gccctggctc ccaagggtgc cccaaatcct 16200
tgcgaatggg atgaagctgc tactgctctt gaaataaacc tagaagaaga ggacgatgac 16260
aacgaagacg aagtagacga gcaagctgag cagcaaaaaa ctcacgtatt tgggcaggcg 16320
ccttattctg gtataaatat tacaaaggag ggtattcaaa taggtgtcga aggtcaaaca 16380
cctaaatatg ccgataaaac atttcaacct gaacctcaaa taggagaatc tcagtggtac 16440
gaaactgaaa ttaatcatgc agctgggaga gtccttaaaa agactacccc aatgaaacca 16500
tgttacggtt catatgcaaa acccacaaat gaaaatggag ggcaaggcat tcttgtaaag 16560
caacaaaatg gaaagctaga aagtcaagtg gaaatgcaat tttctcaac tactgaggca 16620 gccgcaggca atggtgataa cttgactcct aaagtggtat tgtacagtga agatgtagat 16680
atagaaaccc cagacactca tatttcttac atgcccacta ttaaggaagg taactcacga 16740
gaactaatgg gccaacaatc tatgcccaac aggcctaatt acattgcttt tagggacaat 16800
tttattggtc taatgtatta caacagcacg ggtaatatgg gtgttctggc gggccaagca 16860
tcgcagttga atgctgttgt agatttgcaa gacagaaaca cagagctttc ataccagctt 16920
ttgcttgatt ccattggtga tagaaccagg tacttttcta tgtggaatca ggctgttgac 16980
agctatgatc cagatgttag aattattgaa aatcatggaa ctgaagatga acttccaaat 17040
tactgctttc cactgggagg tgtgattaat acagagactc ttaccaaggt aaaacctaaa 17100
acaggtcagg aaaatggatg ggaaaaagat gctacagaat tttcagataa aaatgaaata 17160
agagttggaa ataattttgc catggaaatc aatctaaatg ccaacctgtg gagaaatttc 17220
ctgtactcca acatagcgct gtatttgccc gacaagctaa agtacagtcc ttccaacgta 17280
aaaatttctg ataacccaaa cacctacgac tacatgaaca agcgagtggt ggctcccggg 17340
ttagtggact gctacattaa ccttggagca cgctggtccc ttgactatat ggacaacgtc 17400
aacccattta accaccaccg caatgctggc ctgcgctacc gctcaatgtt gctgggcaat 17460
ggtcgctatg tgcccttcca catccaggtg cctcagaagt tctttgccat taaaaacctc 17520
cttctcctgc cgggctcata cacctacgag tggaacttca ggaaggatgt taacatggtt 17580
ctgcagagct ccctaggaaa tgacctaagg gttgacggag ccagcattaa gtttgatagc 17640
atttgccttt acgccacctt cttccccatg gcccacaaca ccgcctccac gcttgaggcc 17700
atgcttagaa acgacaccaa cgaccagtcc tttaacgact atctctccgc cgccaacatg 17760
ctctacccta tacccgccaa cgctaccaac gtgcccatat ccatcccctc ccgcaactgg 17820
gcggctttcc gcggctgggc cttcacgcgc cttaagacta aggaaacccc atcactgggc 17880
tcgggctacg acccttatta cacctactct ggctctatac cctacctaga tggaaccttt 17940
tacctcaacc acacctttaa gaaggtggcc attacctttg actcttctgt cagctggcct 18000
ggcaatgacc gcctgcttac ccccaacgag tttgaaatta agcgctcagt tgacggggag 18060
ggttacaacg ttgcccagtg taacatgacc aaagactggt tcctggtaca aatgctagct 18120

-continued

```
aactacaaca ttggctacca gggcttctat atcccagaga gctacaagga ccgcatgtac  18180
tccttcttta gaaacttcca gcccatgagc cgtcaggtgg tggatgatac taaatacaag  18240
gactaccaac aggtgggcat cctacaccaa cacaacaact ctggatttgt tggctacctt  18300
gcccccacca tgcgcgaagg acaggcctac cctgctaact tcccctatcc gcttataggc  18360
aagaccgcag ttgacagcat tacccagaaa aagtttcttt gcgatcgcac cctttggcgc  18420
atcccattct ccagtaactt tatgtccatg ggcgcactca cagacctggg ccaaaacctt  18480
ctctacgcca actccgccca cgcgctagac atgacttttg aggtggatcc catggacgag  18540
cccacccttc tttatgtttt gtttgaagtc tttgacgtgg tccgtgtgca ccggccgcac  18600
cgcggcgtca tcgaaaccgt gtacctgcgc acgcccttct cggccggcaa cgccacaaca  18660
taaagaagca agcaacatca acaacagctg ccgccatggg ctccagtgag caggaactga  18720
aagccattgt caaagatctt ggttgtgggc catatttttt gggcacctat gacaagcgct  18780
ttccaggctt tgtttctcca cacaagctcg cctgcgccat agtcaatacg gccggtcgcg  18840
agactggggg cgtacactgg atggcctttg cctggaaccc gcactcaaaa acatgctacc  18900
tctttgagcc ctttggcttt tctgaccagc gactcaagca ggtttaccag tttgagtacg  18960
agtcactcct gcgccgtagc gccattgctt cttcccccga ccgctgtata acgctggaaa  19020
agtccaccca aagcgtacag gggcccaact cggccgcctg tggactattc tgctgcatgt  19080
ttctccacgc ctttgccaac tggccccaaa ctcccatgga tcacaacccc accatgaacc  19140
ttattaccgg ggtacccaac tccatgctca acagtcccca ggtacagccc accctgcgtc  19200
gcaaccagga acagctctac agcttcctgg agcgccactc gccctacttc cgcagccaca  19260
gtgcgcagat taggagcgcc acttcttttt gtcacttgaa aaacatgtaa aaataatgta  19320
ctagagacac tttcaataaa ggcaaatgct tttatttgta cactctcggg tgattattta  19380
cccccaccct tgccgtctgc gccgtttaaa aatcaaaggg gttctgccgc gcatcgctat  19440
gcgccactgg cagggacacg ttgcgatact ggtgtttagt gctccactta aactcaggca  19500
caaccatccg cggcagctcg gtgaagtttt cactccacag gctgcgcacc atcaccaacg  19560
cgtttagcag gtcgggcgcc gatatcttga agtcgcagtt ggggcctccg ccctgcgcgc  19620
gcgagttgcg atacacaggg ttgcagcact ggaacactat cagcgccggg tggtgcacgc  19680
tggccagcac gctcttgtcg gagatcagat ccgcgtccag gtcctccgcg ttgctcaggg  19740
cgaacggagt caactttggt agctgccttc ccaaaaaggg cgcgtgccca ggctttgagt  19800
tgcactcgca ccgtagtggc atcaaaaggt gaccgtgccc ggtctgggcg ttaggataca  19860
gcgcctgcat aaaagccttg atctgcttaa aagccacctg agcctttgcg ccttcagaga  19920
agaacatgcc gcaagacttg ccggaaaact gattggccgg acaggccgcg tcgtgcacgc  19980
agcaccttgc gtcggtgttg gagatctgca ccacatttcg gccccaccgg ttcttcacga  20040
tcttggcctt gctagactgc tccttcagcg cgcgctgccc gttttcgctc gtcacatcca  20100
tttcaatcac gtgctcctta tttatcataa tgcttccgtg tagacactta agctcgcctt  20160
cgatctcagc gcagcggtgc agccacaacg cgcagcccgt gggctcgtga tgcttgtagg  20220
tcacctctgc aaacgactgc aggtacgcct gcaggaatcg ccccatcatc gtcacaaagg  20280
tcttgttgct ggtgaaggtc agctgcaacc cgcggtgctc ctcgttcagc caggtcttgc  20340
atacggccgc cagagcttcc acttggtcag gcagtagttt gaagttcgcc tttagatcgt  20400
tatccacgtg gtacttgtcc atcagcgcgc gcgcagcctc catgcccttc tcccacgcag  20460
acacgatcgg cacactcagc gggttcatca ccgtaatttc actttccgct tcgctgggct  20520
```

-continued

```
cttcctcttc ctcttgcgtc cgcataccac gcgccactgg gtcgtcttca ttcagccgcc  20580
gcactgtgcg cttacctcct ttgccatgct tgattagcac cggtgggttg ctgaaaccca  20640
ccatttgtag cgccacatct tctctttctt cctcgctgtc cacgattacc tctggtgatg  20700
gcgggcgctc gggcttggga gaagggcgct tctttttctt cttgggcgca atggccaaat  20760
ccgccgccga ggtcgatggc cgcgggctgg gtgtgcgcgg caccagcgcg tcttgtgatg  20820
agtcttcctc gtcctcggac tcgatacgcc gcctcatccg ctttttgggg ggcgcccggg  20880
gaggcggcgg cgacggggac ggggacgaca cgtcctccat ggttgggggga cgtcgcgccg  20940
caccgcgtcc gcgctcgggg gtggtttcgc gctgctcctc ttcccgactg gccatttcct  21000
tctcctatag gcagaaaaag atcatggagt cagtcgagaa gaaggacagc ctaaccgccc  21060
cctctgagtt cgccaccacc gcctccaccg atgccgccaa cgcgcctacc accttccccg  21120
tcgaggcacc cccgcttgag gaggaggaag tgattatcga gcaggaccca ggttttgtaa  21180
gcgaagacga cgaggaccgc tcagtaccaa cagaggataa aaagcaagac caggacaacg  21240
cagaggcaaa cgaggaacaa gtcgggcggg gggacgaaag gcatggcgac tacctagatg  21300
tgggagacga cgtgctgttg aagcatctgc agcgccagtg cgccattatc tgcgacgcgt  21360
tgcaagagcg cagcgatgtg cccctcgcca tagcggatgt cagccttgcc tacgaacgcc  21420
acctattctc accgcgcgta ccccccaaac gccaagaaaa cggcacatgc gagcccaacc  21480
cgcgcctcaa cttctacccc gtatttgccg tgccagaggt gcttgccacc tatcacatct  21540
tttccaaaa ctgcaagata cccctatcct gccgtgccaa ccgcagccga gcggacaagc  21600
agctggcctt gcggcagggc gctgtcatac ctgatatcgc ctcgctcaac gaagtgccaa  21660
aaatctttga gggtcttgga cgcgacgaga agcgcgcggc aaacgctctg caacaggaaa  21720
acagcgaaaa tgaaagtcac tctggagtgt tggtggaact cgagggtgac aacgcgcgcc  21780
tagccgtact aaaacgcagc atcgaggtca cccactttgc ctacccggca cttaacctac  21840
cccccaaggt catgagcaca gtcatgagtg agctgatcgt gcgccgtgcg cagcccctgg  21900
agagggatgc aaatttgcaa gaacaaacag aggagggcct acccgcagtt ggcgacgagc  21960
agctagcgcg ctggcttcaa acgcgcgagc ctgccgactt ggaggagcga cgcaaactaa  22020
tgatggccgc agtgctcgtt accgtggagc ttgagtgcat gcagcggttc tttgctgacc  22080
cggagatgca gcgcaagcta gaggaaacat tgcactacac ctttcgacag ggctacgtac  22140
gccaggcctg caagatctcc aacgtggagc tctgcaacct ggtctcctac cttggaattt  22200
tgcacgaaaa ccgccttggg caaaacgtgc ttcattccac gctcaagggc gaggcgcgcc  22260
gcgactacgt ccgcgactgc gtttacttat ttctatgcta cacctggcag acggccatgg  22320
gcgtttggca gcagtgcttg gaggagtgca acctcaagga gctgcagaaa ctgctaaagc  22380
aaaacttgaa ggacctatgg acggccttca acgagcgctc cgtggccgcg cacctggcgg  22440
acatcatttt ccccgaacgc ctgcttaaaa ccctgcaaca gggtctgcca gacttcacca  22500
gtcaaagcat gttgcagaac tttaggaact ttatcctaga gcgctcagga atcttgcccg  22560
ccacctgctg tgcacttcct agcgactttg tgcccattaa gtaccgcgaa tgccctccgc  22620
cgctttgggg ccactgctac cttctgcagc tagccaacta ccttgcctac cactctgaca  22680
taatggaaga cgtgagcggt gacggtctac tggagtgtca ctgtcgctgc aacctatgca  22740
ccccgcaccg ctccctggtt tgcaattcgc agctgcttaa cgaaagtcaa attatcggta  22800
cctttgagct gcagggtccc tcgcctgacg aaaagtccgc ggctccgggg ttgaaactca  22860
```

-continued

```
ctccggggct gtggacgtcg gcttaccttc gcaaatttgt acctgaggac taccacgccc  22920
acgagattag gttctacgaa gaccaatccc gcccgccaaa tgcggagctt accgcctgcg  22980
tcattaccca gggccacatt cttggccaat tgcaagccat caacaaagcc cgccaagagt  23040
ttctgctacg aaagggacgg ggggtttact tggaccccca gtccggcgag gagctcaacc  23100
caatcccccc gccgccgcag ccctatcagc agcagccgcg ggcccttgct tcccaggatg  23160
gcacccaaaa agaagctgca gctgccgccg ccacccacgg acgaggagga atactgggac  23220
agtcaggcag aggaggtttt ggacgaggag gaggaggaca tgatggaaga ctgggagagc  23280
ctagacgagg aagcttccga ggtcgaagag gtgtcagacg aaacaccgtc accctcggtc  23340
gcattcccct cgccggcgcc ccagaaatcg gcaaccggtt ccagcatggc tacaacctcc  23400
gctcctcagg cgccgccggc actgcccgtt cgccgaccca accgtagatg ggacaccact  23460
ggaaccaggg ccggtaagtc caagcagccg ccgccgttag cccaagagca acaacagcgc  23520
caaggctacc gctcatggcg cgggcacaag aacgccatag ttgcttgctt gcaagactgt  23580
gggggcaaca tctccttcgc ccgccgcttt cttctctacc atcacggcgt ggccttcccc  23640
cgtaacatcc tgcattacta ccgtcatctc tacagcccat actgcaccgg cggcagcggc  23700
agcggcagca acagcagcgg ccacacagaa gcaaaggcga ccggatagca agactctgac  23760
aaagcccaag aaatccacag cggcggcagc agcaggagga ggagcgctgc gtctggcgcc  23820
caacgaaccc gtatcgaccc gcgagcttag aaacaggatt tttcccactc tgtatgctat  23880
atttcaacag agcaggggcc aagaacaaga gctgaaaata aaaaacaggt ctctgcgatc  23940
cctcacccgc agctgcctgt atcacaaaag cgaagatcag cttcggcgca cgctggaaga  24000
cgcggaggct ctcttcagta aatactgcgc gctgactctt aaggactagt ttcgcgccct  24060
ttctcaaatt taagcgcgaa aactacgtca tctccagcgg ccacacccgg cgccagcacc  24120
tgtcgtcagc gccattatga gcaaggaaat tcccacgccc tacatgtgga gttaccagcc  24180
acaaatggga cttgcggctg gagctgccca agactactca acccgaataa actacatgag  24240
cgcgggaccc cacatgatat cccgggtcaa cggaatccgc gcccaccgaa accgaattct  24300
cttggaacag gcggctatta ccaccacacc tcgtaataac cttaatcccc gtagttggcc  24360
cgctgccctg gtgtaccagg aaagtcccgc tcccaccact gtggtacttc ccagagacgc  24420
ccaggccgaa gttcagatga ctaactcagg ggcgcagctt gcgggcggct ttcgtcacag  24480
ggtgcggtcg cccgggcagg gtataactca cctgacaatc agagggcgag gtattcagct  24540
caacgacgag tcggtgagct cctcgcttgg tctccgtccg gacgggacat ttcagatcgg  24600
cggcgccggc cgtccttcat tcacgcctcg tcaggcaatc ctaactctgc agacctcgtc  24660
ctctgagccg cgctctggag gcattggaac tctgcaattt attgaggagt ttgtgccatc  24720
ggtctacttt aacccccttct cgggacctcc cggccactat ccggatcaat ttattcctaa  24780
ctttgacgcg gtaaaggact cggcggacgg ctacgactga atgttaagtg gagaggcaga  24840
gcaactgcgc ctgaaacacc tggtccactg tcgccgccac aagtgctttg cccgcgactc  24900
cggtgagttt tgctactttg aattgcccga ggatcatatc gagggcccgg cgcacggcgt  24960
ccggcttacc gcccagggag agcttgcccg tagcctgatt cgggagttta cccagcgccc  25020
cctgctagtt gagcgggaca ggggaccctg tgttctcact gtgatttgca actgtcctaa  25080
ccttggatta catcaagatc tttgttgcca tctctgtgct gagtataata aatacagaaa  25140
ttaaaatata ctggggctcc tatcgccatc ctgtaaacgc caccgtcttc acccgcccaa  25200
gcaaaccaag gcgaacctta cctggtactt ttaacatctc tccctctgtg atttacaaca  25260
```

-continued gtttcaaccc agacggagtg agtctacgag agaacctctc cgagctcagc tactccatca 25320
gaaaaaacac caccctcctt acctgccggg aacgtacgag tgcgtcaccg gccgctgcac 25380
cacacctacc gcctgaccgt aaaccagact ttttccggac agacctcaat aactctgttt 25440
accagaacag gaggtgagct tagaaaaccc ttagggtatt aggccaaagg cgcagctact 25500
gtggggttta tgaacaattc aagcaactct acgggctatt ctaattcagg tttctctaga 25560
atcggggttg gggttattct ctgtcttgtg attctcttta ttcttatact aacgcttctc 25620
tgcctaaggc tcgccgcctg ctgtgtgcac atttgcattt attgtcagct ttttaaacgc 25680
tggggtcgcc acccaagatg attaggtaca taatcctagg tttactcacc cttgcgtcag 25740
cccacggtac cacccaaaag gtggatttta aggagccagc ctgtaatgtt acattcgcag 25800
ctgaagctaa tgagtgcacc actcttataa aatgcaccac agaacatgaa aagctgctta 25860
ttcgccacaa aaacaaaatt ggcaagtatg ctgtttatgc tatttggcag ccaggtgaca 25920
ctacagagta taatgttaca gttttccagg gtaaaagtca taaaactttt atgtatactt 25980
ttccatttta tgaaatgtgc gacattacca tgtacatgag caaacagtat aagttgtggc 26040
ccccacaaaa ttgtgtggaa aacactggca ctttctgctg cactgctatg ctaattacag 26100
tgctcgcttt ggtctgtacc ctactctata ttaaatacaa aagcagacgc agctttattg 26160
aggaaaagaa aatgccttaa tttactaagt tacaaagcta atgtcaccac taactgcttt 26220
actcgctgct tgcaaaacaa attcaaaaag ttagcattat aattagaata ggatttaaac 26280
cccccggtca tttcctgctc aataccattc ccctgaacaa ttgactctat gtgggatatg 26340
ctccagcgct acaaccttga agtcaggctt cctggatgtc agcatctgac tttggccagc 26400
acctgtcccg cggatttgtt ccagtccaac tacagcgacc caccctaaca gagatgacca 26460
acacaaccaa cgcggccgcc gctaccggac ttacatctac cacaaataca ccccaagttt 26520
ctgcctttgt caataactgg gataacttgg gcatgtggtg gttctccata gcgcttatgt 26580
ttgtatgcct tattattatg tggctcatct gctgcctaaa gcgcaaacgc gcccgaccac 26640
ccatctatag tcccatcatt gtgctacacc caaacaatga tggaatccat agattggacg 26700
gactgaaaca catgttcttt tctcttacag tatgattaaa tgagacatga ttcctcgagt 26760
ttttatatta ctgacccttg ttgcgctttt ttgtgcgtgc tccacattgg ctgcggtttc 26820
tcacatcgaa gtagactgca ttccagcctt cacagtctat ttgctttacg gatttgtcac 26880
cctcacgctc atctgcagcc tcatcactgt ggtcatcgcc tttatccagt gcattgactg 26940
ggtctgtgtg cgctttgcat atctcagaca ccatccccag tacagggaca ggactatagc 27000
tgagcttctt agaattcttt aattatgaaa tttactgtga cttttctgct gattatttgc 27060
accctatctg cgtttgttc cccgacctcc aagcctcaaa gacatatatc atgcagattc 27120
actcgtatat ggaatattcc aagttgctac aatgaaaaaa gcgatctttc cgaagcctgg 27180
ttatatgcaa tcatctctgt tatggtgttc tgcagtacca tcttagccct agctatatat 27240
ccctaccttg acattggctg gaaacgaata gatgccatga accacccaac tttccccgcg 27300
cccgctatgc ttccactgca acaagttgtt gccggcggct ttgtcccagc caatcagcct 27360
cgccccactt ctcccacccc cactgaaatc agctacttta atctaacagg aggagatgac 27420
tgacacccta gatctagaaa tggacggaat tattacagag cagcgcctgc tagaaagacg 27480
cagggcagcg gccgagcaac agcgcatgaa tcaagagctc caagacatgg ttaacttgca 27540
ccagtgcaaa aggggtatct tttgtctggt aaagcaggcc aaagtcacct acgacagtaa 27600

-continued

```
taccaccgga caccgcctta gctacaagtt gccaaccaag cgtcagaaat tggtggtcat  27660
ggtgggagaa aagcccatta ccataactca gcactcggta gaaaccgaag gctgcattca  27720
ctcaccttgt caaggacctg aggatctctg caccccttatt aagaccctgt gcggtctcaa  27780
agatcttatt ccctttaact aataaaaaaa aataataaag catcacttac ttaaaatcag  27840
ttagcaaatt tctgtccagt ttattcagca gcacctcctt gccctcctcc cagctctggt  27900
attgcagctt cctcctggct gcaaactttc tccacaatct aaatggaatg tcagtttcct  27960
cctgttcctg tccatccgca cccactatct tcatgttgtt gcagatgaag cgcgcaagac  28020
cgtctgaaga taccttcaac cccgtgtatc catatgacac ggaaaccggt cctccaactg  28080
tgccttttct tactcctccc tttgtatccc ccaatgggtt tcaagagagt ccccctgggg  28140
tactctcttt gcgcctatcc gaacctctag ttacctccaa tggcatgctt gcgctcaaaa  28200
tgggcaacgg cctctctctg gacgaggccg gcaaccttac ctcccaaaat gtaaccactg  28260
tgagcccacc tctcaaaaaa accaagtcaa acataaacct ggaaatatct gcacccctca  28320
cagttacctc agaagcccta actgtggctg ccgccgcacc tctaatggtc gcgggcaaca  28380
cactcaccat gcaatcacag gccccgctaa ccgtgcacga ctccaaactt agcattgcca  28440
cccaaggacc cctcacagtg tcagaaggaa agctagccct gcaaacatca ggcccccctca  28500
ccaccaccga tagcagtacc cttactatca ctgcctcacc ccctctaact actgccactg  28560
gtagcttggg cattgacttg aaagagccca tttatacaca aaatggaaaa ctaggactaa  28620
agtacggggc tcctttgcat gtaacagacg acctaaacac tttgaccgta gcaactggtc  28680
caggtgtgac tattaataat acttccttgc aaactaaagt tactggagcc ttgggttttg  28740
attcacaagg caatatgcaa cttaatgtag caggaggact aaggattgat tctcaaaaca  28800
gacgccttat acttgatgtt agttatccgt ttgatgctca aaaccaacta aatctaagac  28860
taggacaggg ccctcttttt ataaactcag cccacaactt ggatattaac tacaacaaag  28920
gcctttactt gtttacagct tcaaacaatt ccaaaaagct tgaggttaac ctaagcactg  28980
ccaaggggtt gatgtttgac gctacagcca tagccattaa tgcaggagat gggcttgaat  29040
ttggttcacc taatgcacca aacacaaatc ccctcaaaac aaaaattggc catggcctag  29100
aatttgattc aaacaaggct atggttccta aactaggaac tggccttagt tttgacagca  29160
caggtgccat tacagtagga aacaaaaata atgataagct aactttgtgg accacaccag  29220
ctccatctcc taactgtaga ctaaatgcag agaaagatgc taaactcact ttggtcttaa  29280
caaaatgtgg cagtcaaata cttgctacag tttcagtttt ggctgttaaa ggcagtttgg  29340
ctccaatatc tggaacagtt caaagtgctc atcttattat aagatttgac gaaaatggag  29400
tgctactaaa caattccttc ctggacccag aatattggaa ctttagaaat ggagatctta  29460
ctgaaggcac agcctataca aacgctgttg gatttatgcc taacctatca gcttatccaa  29520
aatctcacgg taaaactgcc aaaagtaaca ttgtcagtca agtttactta aacggagaca  29580
aaactaaacc tgtaacacta accattacac taaacggtac acaggaaaca ggagacacaa  29640
ctccaagtgc atactctatg tcattttcat gggactggtc tggccacaac tacattaatg  29700
aaatatttgc cacatcctct tacacttttt catacattgc ccaagaataa agaatcgttt  29760
gtgttatgtt tcaacgtgtt tatttttcaa ttgcagaaaa tttcaagtca tttttcattc  29820
agtagtatag ccccaccacc acatagctta tacagatcac cgtaccttaa tcaaactcac  29880
agaaccctag tattcaacct gccacctccc tcccaacaca cagagtacac agtcctttct  29940
ccccggctgg ccttaaaaag catcatatca tgggtaacag acatattctt aggtgttata  30000
```

-continued ttccacacgg tttcctgtcg agccaaacgc tcatcagtga tattaataaa ctccccgggc 30060
agctcactta agttcatgtc gctgtccagc tgctgagcca caggctgctg tccaacttgc 30120
ggttgcttaa cgggcggcga aggagaagtc cacgcctaca tgggggtaga gtcataatcg 30180
tgcatcagga tagggcggtg gtgctgcagc agcgcgcgaa taaactgctg ccgccgccgc 30240
tccgtcctgc aggaatacaa catggcagtg gtctcctcag cgatgattcg caccgcccgc 30300
agcataaggc gccttgtcct ccgggcacag cagcgcaccc tgatctcact taaatcagca 30360
cagtaactgc agcacagcac cacaatattg ttcaaaatcc cacagtgcaa ggcgctgtat 30420
ccaaagctca tggcggggac cacagaaccc acgtggccat cataccacaa gcgcaggtag 30480
attaagtggc gacccctcat aaacacgctg gacataaaca ttacctcttt tggcatgttg 30540
taattcacca cctcccggta ccatataaac ctctgattaa acatggcgcc atccaccacc 30600
atcctaaacc agctggccaa aacctgcccg ccggctatac actgcaggga accgggactg 30660
gaacaatgac agtggagagc ccaggactcg taaccatgga tcatcatgct cgtcatgata 30720
tcaatgttgg cacaacacag gcacacgtgc atacacttcc tcaggattac aagctcctcc 30780
cgcgttagaa ccatatccca gggaacaacc cattcctgaa tcagcgtaaa tcccacactg 30840
cagggaagac ctcgcacgta actcacgttg tgcattgtca aagtgttaca ttcgggcagc 30900
agcggatgat cctccagtat ggtagcgcgg gtttctgtct caaaaggagg tagacgatcc 30960
ctactgtacg gagtgcgccg agacaaccga gatcgtgttg gtcgtagtgt catgccaaat 31020
ggaacgccgg acgtagtcat atttcctgaa gcaaaaccag gtgcgggcgt gacaaacaga 31080
tctgcgtctc cggtctcgcc gcttagatcg ctctgtgtag tagttgtagt atatccactc 31140
tctcaaagca tccaggcgcc ccctggcttc gggttctatg taaactcctt catgcgccgc 31200
tgccctgata acatccacca ccgcagaata agccacaccc agccaaccta cacattcgtt 31260
ctgcgagtca cacacgggag gagcgggaag agctggaaga accatgtttt tttttttatt 31320
ccaaaagatt atccaaaacc tcaaaatgaa gatctattaa gtgaacgcgc tcccctccgg 31380
tggcgtggtc aaactctaca gccaaagaac agataatggc atttgtaaga tgttgcacaa 31440
tggcttccaa aaggcaaacg gccctcacgt ccaagtggac gtaaaggcta aacccttcag 31500
ggtgaatctc ctctataaac attccagcac cttcaaccat gcccaaataa ttctcatctc 31560
gccaccttct caatatatct ctaagcaaat cccgaatatt aagtccggcc attgtaaaaa 31620
tctgctccag agcgccctcc accttcagcc tcaagcagcg aatcatgatt gcaaaaattc 31680
aggttcctca cagacctgta taagattcaa aagcggaaca ttaacaaaaa taccgcgatc 31740
ccgtaggtcc cttcgcaggg ccagctgaac ataatcgtgc aggtctgcac ggaccagcgc 31800
ggccacttcc ccgccaggaa ccttgacaaa agaacccaca ctgattatga cacgcatact 31860
cggagctatg ctaaccagcg tagccccgat gtaagctttg ttgcatgggc ggcgatataa 31920
aatgcaaggt gctgctcaaa aaatcaggca aagcctcgcg caaaaaagaa agcacatcgt 31980
agtcatgctc atgcagataa aggcaggtaa gctccggaac caccacagaa aaagacacca 32040
tttttctctc aaacatgtct gcgggtttct gcataaacac aaaataaaat aacaaaaaaa 32100
catttaaaca ttagaagcct gtcttacaac aggaaaaaca acccttataa gcataagacg 32160
gactacggcc atgccggcgt gaccgtaaaa aaactggtca ccgtgattaa aaagcaccac 32220
cgacagctcc tcggtcatgt ccggagtcat aatgtaagac tcggtaaaca catcaggttg 32280
attcatcggt cagtgctaaa aagcgaccga aatagcccgg gggaatacat acccgcaggc 32340

-continued

```
gtagagacaa cattacagcc cccataggag gtataacaaa attaatagga gagaaaaaca  32400
cataaacacc tgaaaaaccc tcctgcctag gcaaaatagc accctcccgc tccagaacaa  32460
catacagcgc ttcacagcgg cagcctaaca gtcagcctta ccagtaaaaa agaaaaccta  32520
ttaaaaaaac accactcgac acggcaccag ctcaatcagt cacagtgtaa aaaagggcca  32580
agtgcagagc gagtatatat aggactaaaa aatgacgtaa cggttaaagt ccacaaaaaa  32640
cacccagaaa accgcacgcg aacctacgcc cagaaacgaa agccaaaaaa cccacaactt  32700
cctcaaatcg tcacttccgt tttcccacgt tacgtaactt cccattttaa gaaaactaca  32760
attcccaaca catacaagtt actccgccct aaaacctacg tcacccgccc cgttcccacg  32820
ccccgcgcca cgtcacaaac tccacccccct cattatcata ttggcttcaa tccaaaataa  32880
ggtatattat tgatgatgat ttaaatggat ccatttaaat cggtacccag cttttgttcc  32940
ctttagtgag ggttaattgc gcgcttggcg taatcatggt catagctgtt tcctgtgtga  33000
aattgttatc cgctcacaat tccacacaac atacgagccg gaagcataaa gtgtaaagcc  33060
tggggtgcct aatgagtgag ctaactcaca ttaattgcgt tgcgctcact gcccgctttc  33120
cagtcgggaa acctgtcgtg ccagctgcat taatgaatcg gccaacgcgc ggggagaggc  33180
ggtttgcgta ttgggcgctc ttccgcttcc tcgctcactg actcgctgcg ctcggtcgtt  33240
cggctgcggc gagcggtatc agctcactca aaggcggtaa tacggttatc cacagaatca  33300
ggggataacg caggaaagaa catgtgagca aaaggccagc aaaaggccag gaaccgtaaa  33360
aaggccgcgt tgctggcgtt tttccatagg ctccgccccc ctgacgagca tcacaaaaat  33420
cgacgctcaa gtcagaggtg gcgaaacccg acaggactat aaagatacca ggcgtttccc  33480
cctggaagct ccctcgtgcg ctctcctgtt ccgaccctgc cgcttaccgg atacctgtcc  33540
gcctttctcc cttcgggaag cgtggcgctt tctcatagct cacgctgtag gtatctcagt  33600
tcggtgtagg tcgttcgctc caagctgggc tgtgtgcacg aaccccccgt tcagcccgac  33660
cgctgcgcct tatccggtaa ctatcgtctt gagtccaacc cggtaagaca cgacttatcg  33720
ccactggcag cagccactgg taacaggatt agcagagcga ggtatgtagg cggtgctaca  33780
gagttcttga agtggtggcc taactacggc tacactagaa ggacagtatt tggtatctgc  33840
gctctgctga agccagttac cttcggaaaa agagttggta gctcttgatc cggcaaacaa  33900
accaccgctg gtagcggtgg tttttttgtt tgcaagcagc agattacgcg cagaaaaaaa  33960
ggatctcaag aagatccttt gatcttttct acggggtctg acgctcagtg gaacgaaaac  34020
tcacgttaag ggattttggt catgagatta tcaaaaagga tcttcaccta gatcctttta  34080
aattaaaaat gaagttttaa atcaatctaa agtatatatg agtaaacttg gtctgacagt  34140
taccaatgct taatcagtga ggcacctatc tcagcgatct gtctatttcg ttcatccata  34200
gttgcctgac tccccgtcgt gtagataact acgatacggg agggcttacc atctggcccc  34260
agtgctgcaa tgataccgcg agacccacgc tcaccggctc cagatttatc agcaataaac  34320
cagccagccg gaagggccga gcgcagaagt ggtcctgcaa ctttatccgc ctccatccag  34380
tctattaatt gttgccggga agctagagta agtagttcgc cagttaatag tttgcgcaac  34440
gttgttgcca ttgctacagg catcgtggtg tcacgctcgt cgtttggtat ggcttcattc  34500
agctccggtt cccaacgatc aaggcgagtt acatgatccc ccatgttgtg caaaaaagcg  34560
gttagctcct tcggtcctcc gatcgttgtc agaagtaagt tggccgcagt gttatcactc  34620
atggttatgg cagcactgca taattctctt actgtcatgc catccgtaag atgcttttct  34680
gtgactggtg agtactcaac caagtcattc tgagaatagt gtatgcggcg accgagttgc  34740
```

-continued

```
tcttgcccgg cgtcaatacg ggataatacc gcgccacata gcagaacttt aaaagtgctc  34800
atcattggaa aacgttcttc ggggcgaaaa ctctcaagga tcttaccgct gttgagatcc  34860
agttcgatgt aacccactcg tgcacccaac tgatcttcag catcttttac tttcaccagc  34920
gtttctgggt gagcaaaaac aggaaggcaa aatgccgcaa aaaagggaat aagggcgaca  34980
cggaaatgtt gaatactcat actcttcctt tttcaatatt attgaagcat ttatcagggt  35040
tattgtctca tgagcggata catatttgaa tgtatttaga aaaataaaca aataggggtt  35100
ccgcgcacat ttccccgaaa agtgccacct aaattgtaag cgttaatatt ttgttaaaat  35160
tcgcgttaaa tttttgttaa atcagctcat tttttaacca ataggccgaa atcggcaaaa  35220
tcccttataa atcaaaagaa tagaccgaga tagggttgag tgttgttcca gtttggaaca  35280
agagtccact attaaagaac gtggactcca acgtcaaagg gcgaaaaacc gtctatcagg  35340
gcgatggccc actacgtgaa ccatcaccct aatcaagttt tttggggtcg aggtgccgta  35400
aagcactaaa tcggaaccct aaagggagcc cccgatttag agcttgacgg ggaaagccgg  35460
cgaacgtggc gagaaaggaa gggaagaaag cgaaaggagc gggcgctagg gcgctggcaa  35520
gtgtagcggt cacgctgcgc gtaaccacca cacccgccgc gcttaatgcg ccgctacagg  35580
gcgcgtccca ttcgccattc aggctgcgca actgttggga agggcgatcg gtgcgggcct  35640
cttcgctatt acgccagctg gcgaaagggg gatgtgctgc aaggcgatta agttgggtaa  35700
cgccagggtt ttcccagtca cgacgttgta aaacgacggc cagtgagcgc gcgtaatacg  35760
actcactata gggcgaattg gagctccac                                   35789
```

<210> SEQ ID NO 6
<211> LENGTH: 6690
<212> TYPE: DNA
<213> ORGANISM: Artificial sequence
<220> FEATURE:
<223> OTHER INFORMATION: Sequence pBSK-CMV-TPLIn-100K (6690 bp)

<400> SEQUENCE: 6

```
cacctaaatt gtaagcgtta atattttgtt aaaattcgcg ttaaattttt gttaaatcag     60
ctcatttttt aaccaatagg ccgaaatcgg caaaatccct tataaatcaa aagaatagac    120
cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
accctaatca agttttttgg ggtcgaggtg ccgtaaagca ctaaatcgga accctaaagg    300
gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tgggtaccat    660
ttaaatacgc gtagatcttc aatattggcc attagccata ttattcattg gttatatagc    720
ataaatcaat attggctatt ggccattgca tacgttgtat ctatatcata atatgtacat    780
ttatattggc tcatgtccaa tatgaccgcc atgttggcat tgattattga ctagttatta    840
atagtaatca attacggggt cattagttca tagcccatat atggagttcc gcgttacata    900
acttacggta aatggcccgc ctggctgacc gcccaacgac ccccgcccat tgacgtcaat    960
```

-continued

```
aatgacgtat gttcccatag taacgccaat agggactttc cattgacgtc aatgggtgga   1020
gtatttacgg taaactgccc acttggcagt acatcaagtg tatcatatgc caagtccgcc   1080
ccctattgac gtcaatgacg gtaaatggcc cgcctggcat tatgcccagt acatgacctt   1140
acgggacttt cctacttggc agtacatcta cgtattagtc atcgctatta ccatggtgat   1200
gcggttttgg cagtacacca atgggcgtgg atagcggttt gactcacggg gatttccaag   1260
tctccacccc attgacgtca atgggagttt gttttggcac caaaatcaac gggactttcc   1320
aaaatgtcgt aataaccccg ccccgttgac gcaaatgggc ggtaggcgtg tacggtggga   1380
ggtctatata agcagagctc gtttagtgaa ccgtcagatc actagaagct tactctcttc   1440
cgcatcgctg tctgcgaggg ccagctgttg ggctcgcggt tgaggacaaa ctcttcgcgg   1500
tctttccagt actcttggat cggaaacccg tcggcctccg aacggtactc cgccgccgag   1560
ggacctgagc gagtccgcat cgaccggatc ggaaaacctc tcgagaaagg cgtctaacca   1620
gtcacagtcg caaggtaagt atcaaggtta caagacaggt ttaaggagac caatagaaac   1680
tgggcttgtc gagacagaga agactcttgc gtttctgata ggcacctatt ggtcttactg   1740
acatccactt tgcctttctc tccacaggtg cggccgcgac catggagtca gtcgagaaga   1800
aggacagcct aaccgccccc tctgagttcg ccaccaccgc ctccaccgat gccgccaacg   1860
cgcctaccac cttccccgtc gaggcacccc cgcttgagga ggaggaagtg attatcgagc   1920
aggacccagg ttttgtaagc gaagacgacg aggaccgctc agtaccaaca gaggataaaa   1980
agcaagacca ggacaacgca gaggcaaacg aggaacaagt cgggcggggg gacgaaaggc   2040
atggcgacta cctagatgtg ggagacgacg tgctgttgaa gcatctgcag cgccagtgcg   2100
ccattatctg cgacgcgttg caagagcgca gcgatgtgcc cctcgccata gcggatgtca   2160
gccttgccta cgaacgccac ctattctcac cgcgcgtacc ccccaaacgc caagaaaacg   2220
gcacatgcga gcccaacccg cgcctcaact tctaccccgt atttgccgtg ccagaggtgc   2280
ttgccaccta tcacatcttt ttccaaaact gcaagatacc cctatcctgc cgtgccaacc   2340
gcagccgagc ggacaagcag ctggccttgc ggcagggcgc tgtcatacct gatatcgcct   2400
cgctcaacga agtgccaaaa atctttgagg gtcttggacg cgacgagaag cgcgcggcaa   2460
acgctctgca acaggaaaac agcgaaaatg aaagtcactc tggagtgttg gtggaactcg   2520
agggtgacaa cgcgcgccta gccgtactaa aacgcagcat cgaggtcacc cactttgcct   2580
acccggcact taacctaccc cccaaggtca tgagcacagt catgagtgag ctgatcgtgc   2640
gccgtgcgca gcccctggag agggatgcaa atttgcaaga acaaacagag gagggcctac   2700
ccgcagttgg cgacgagcag ctagcgcgct ggcttcaaac gcgcgagcct gccgacttgg   2760
aggagcgacg caaactaatg atggccgcag tgctcgttac cgtggagctt gagtgcatgc   2820
agcggttctt tgctgacccg gagatgcagc gcaagctaga ggaaacattg cactacacct   2880
ttcgacaggg ctacgtacgc caggcctgca agatctccaa cgtggagctc tgcaacctgg   2940
tctcctacct tggaattttg cacgaaaacc gccttgggca aaacgtgctt cattccacgc   3000
tcaagggcga ggcgcgccgc gactacgtcc gcgactgcgt ttacttattt ctatgctaca   3060
cctggcagac ggccatgggc gtttggcagc agtgcttgga ggagtgcaac ctcaaggagc   3120
tgcagaaact gctaaagcaa aacttgaagg acctatggac ggccttcaac gagcgctccg   3180
tggccgcgca cctggcggac atcattttcc ccgaacgcct gcttaaaacc ctgcaacagg   3240
gtctgccaga cttcaccagt caaagcatgt tgcagaactt taggaacttt atcctagagc   3300
gctcaggaat cttgcccgcc acctgctgtg cacttcctag cgactttgtg cccattaagt   3360
```

accgcgaatg ccctccgccg ctttggggcc actgctacct tctgcagcta gccaactacc 3420
ttgcctacca ctctgacata atggaagacg tgagcggtga cggtctactg gagtgtcact 3480
gtcgctgcaa cctatgcacc ccgcaccgct ccctggtttg caattcgcag ctgcttaacg 3540
aaagtcaaat tatcggtacc tttgagctgc agggtccctc gcctgacgaa aagtccgcgg 3600
ctccggggtt gaaactcact ccggggctgt ggacgtcggc ttaccttcgc aaatttgtac 3660
ctgaggacta ccacgcccac gagattaggt tctacgaaga ccaatcccgc ccgccaaatg 3720
cggagcttac cgcctgcgtc attacccagg gccacattct tggccaattg caagccatca 3780
acaaagcccg ccaagagttt ctgctacgaa agggacgggg ggtttacttg gacccccagt 3840
ccggcgagga gctcaaccca atcccccgc cgccgcagcc ctatcagcag cagccgcggg 3900
cccttgcttc ccaggatggc acccaaaaag aagctgcagc tgccgccgcc acccacggac 3960
gaggaggaat actgggacag tcaggcagag gaggttttgg acgaggagga ggaggacatg 4020
atggaagact gggagagcct agacgaggaa gcttccgagg tcgaagaggt gtcagacgaa 4080
acaccgtcac cctcggtcgc attcccctcg ccggcgcccc agaaatcggc aaccggttcc 4140
agcatggcta caacctccgc tcctcaggcg ccgccggcac tgcccgttcg ccgacccaac 4200
cgtagcccgg gaatatcggc cgcttcgagc agacatgata agatacattg atgagtttgg 4260
acaaaccaca actagaatgc agtgaaaaaa atgctttatt tgtgaaattt gtgatgctat 4320
tgctttattt gtaaccatta taagctgcaa taaacaagtt aacaacaaca attgcattca 4380
ttttatgttt caggttcagg gggagatgtg ggaggttttt taaagcaagt aaaacctcta 4440
caaatgtggt aaaatcgata aggatctgcg gccggccgca tttaaatagc tccagctttt 4500
gttcccttta gtgagggtta atttcgagct tggcgtaatc atggtcatag ctgtttcctg 4560
tgtgaaattg ttatccgctc acaattccac acaacatacg agccggaagc ataaagtgta 4620
aagcctgggg tgcctaatga gtgagctaac tcacattaat tgcgttgcgc tcactgcccg 4680
ctttccagtc gggaaacctg tcgtgccagc tgcattaatg aatcggccaa cgcgcgggga 4740
gaggcggttt gcgtattggg cgctcttccg cttcctcgct cactgactcg ctgcgctcgg 4800
tcgttcggct gcggcgagcg gtatcagctc actcaaaggc ggtaatacgg ttatccacag 4860
aatcagggga taacgcagga aagaacatgt gagcaaaagg ccagcaaaag gccaggaacc 4920
gtaaaaaggc cgcgttgctg gcgtttttcc ataggctccg cccccctgac gagcatcaca 4980
aaaatcgacg ctcaagtcag aggtggcgaa acccgacagg actataaaga taccaggcgt 5040
ttccccctgg aagctccctc gtgcgctctc ctgttccgac cctgccgctt accggatacc 5100
tgtccgcctt tctcccttcg ggaagcgtgg cgctttctca tagctcacgc tgtaggtatc 5160
tcagttcggt gtaggtcgtt cgctccaagc tgggctgtgt gcacgaaccc cccgttcagc 5220
ccgaccgctg cgccttatcc ggtaactatc gtcttgagtc caacccggta agacacgact 5280
tatcgccact ggcagcagcc actggtaaca ggattagcag agcgaggtat gtaggcggtg 5340
ctacagagtt cttgaagtgg tggcctaact acggctacac tagaaggaca gtatttggta 5400
tctgcgctct gctgaagcca gttaccttcg gaaaaagagt tggtagctct tgatccggca 5460
aacaaaccac cgctggtagc ggtggttttt ttgtttgcaa gcagcagatt acgcgcagaa 5520
aaaaaggatc tcaagaagat cctttgatct tttctacggg gtctgacgct cagtggaacg 5580
aaaactcacg ttaagggatt ttggtcatga gattatcaaa aaggatcttc acctagatcc 5640
ttttaaatta aaaatgaagt tttaaatcaa tctaaagtat atatgagtaa acttggtctg 5700

-continued

```
acagttacca atgcttaatc agtgaggcac ctatctcagc gatctgtcta tttcgttcat   5760
ccatagttgc ctgactcccc gtcgtgtaga taactacgat acgggagggc ttaccatctg   5820
gccccagtgc tgcaatgata ccgcgagacc cacgctcacc ggctccagat ttatcagcaa   5880
taaaccagcc agccggaagg gccgagcgca gaagtggtcc tgcaacttta tccgcctcca   5940
tccagtctat taattgttgc cgggaagcta gagtaagtag ttcgccagtt aatagtttgc   6000
gcaacgttgt tgccattgct acaggcatcg tggtgtcacg ctcgtcgttt ggtatggctt   6060
cattcagctc cggttcccaa cgatcaaggc gagttacatg atcccccatg ttgtgcaaaa   6120
aagcggttag ctccttcggt cctccgatcg ttgtcagaag taagttggcc gcagtgttat   6180
cactcatggt tatggcagca ctgcataatt ctcttactgt catgccatcc gtaagatgct   6240
tttctgtgac tggtgagtac tcaaccaagt cattctgaga atagtgtatg cggcgaccga   6300
gttgctcttg cccggcgtca atacgggata ataccgcgcc acatagcaga actttaaaag   6360
tgctcatcat tggaaaacgt tcttcggggc gaaaactctc aaggatctta ccgctgttga   6420
gatccagttc gatgtaaccc actcgtgcac ccaactgatc ttcagcatct tttactttca   6480
ccagcgtttc tgggtgagca aaaacaggaa ggcaaaatgc cgcaaaaaag ggaataaggg   6540
cgacacggaa atgttgaata ctcatactct tcctttttca atattattga agcatttatc   6600
agggttattg tctcatgagc ggatacatat ttgaatgtat ttagaaaaat aaacaaatag   6660
gggttccgcg cacatttccc cgaaaagtgc                                    6690
```

<210> SEQ ID NO 7
<211> LENGTH: 41337
<212> TYPE: DNA
<213> ORGANISM: Artificial sequence
<220> FEATURE:
<223> OTHER INFORMATION: Bacmid sequence Ad5delta100K (41337 bp)

<400> SEQUENCE: 7

```
attattatag tcagctgacg tgtagtgtat ttatacccgg tgagttcctc aagaggccac     60
tcttgagtgc cagcgagtag agttttctcc tccgagccgc tccgacaccg ggactgaaaa    120
tgagacatat tatctgccac ggaggtgtta ttaccgaaga aatggccgcc agtcttttgg    180
accagctgat cgaagaggta ctggctgata atcttccacc tcctagccat tttgaaccac    240
ctacccttca cgaactgtat gatttagacg tgacggcccc cgaagatccc aacgaggagg    300
cggtttcgca gatttttccc gactctgtaa tgttggcggt gcaggaaggg attgacttac    360
tcacttttcc gccggcgccc ggttctccgg agccgcctca cctttcccgg cagcccgagc    420
agccggagca gagagccttg ggtccggttt ctatgccaaa ccttgtaccg gaggtgatcg    480
atcttacctg ccacgaggct ggctttccac ccagtgacga cgaggatgaa gagggtgagg    540
agtttgtgtt agattatgtg gagcaccccg ggcacggttg caggtcttgt cattatcacc    600
ggaggaatac gggggaccca gatattatgt gttcgctttg ctatatgagg acctgtggca    660
tgtttgtcta cagtaagtga aaattatggg cagtgggtga tagagtggtg ggtttggtgt    720
ggtaattttt tttttaattt ttacagtttt gtggtttaaa gaattttgta ttgtgatttt    780
tttaaaaggt cctgtgtctg aacctgagcc tgagcccgag ccagaaccgg agcctgcaag    840
acctacccgc cgtcctaaaa tggcgcctgc tatcctgaga cgcccgacat cacctgtgtc    900
tagagaatgc aatagtagta cggatagctg tgactccggt ccttctaaca cacctcctga    960
gatacacccg gtggtcccgc tgtgccccat taaaccagtt gccgtgagag ttggtgggcg   1020
tcgccaggct gtggaatgta tcgaggactt gcttaacgag cctgggcaac ctttggactt   1080
```

-continued gagctgtaaa cgccccaggc cataaggtgt aaacctgtga ttgcgtgtgt ggttaacgcc 1140
tttgtttgct gaatgagttg atgtaagttt aataaagggt gagataatgt ttaacttgca 1200
tggcgtgtta aatggggcgg ggcttaaagg gtatataatg cgccgtgggc taatcttggt 1260
tacatctgac ctcatggagg cttgggagtg tttggaagat ttttctgctg tgcgtaactt 1320
gctggaacag agctctaaca gtacctcttg gttttggagg tttctgtggg gctcatccca 1380
ggcaaagtta gtctgcagaa ttaaggagga ttacaagtgg gaatttgaag agcttttgaa 1440
atcctgtggt gagctgtttg attctttgaa tctgggtcac caggcgcttt tccaagagaa 1500
ggtcatcaag actttggatt tttccacacc ggggcgcgct gcggctgctg ttgctttttt 1560
gagttttata aaggataaat ggagcgaaga aacccatctg agcggggggt acctgctgga 1620
ttttctggcc atgcatctgt ggagagcggt tgtgagacac aagaatcgcc tgctactgtt 1680
gtcttccgtc cgcccggcga taataccgac ggaggagcag cagcagcagc aggaggaagc 1740
caggcggcgg cggcaggagc agagcccatg gaacccgaga gccggcctgg accctcggga 1800
atgaatgttg tacaggtggc tgaactgtat ccagaactga gacgcatttt gacaattaca 1860
gaggatgggc aggggctaaa gggggtaaag agggagcggg gggcttgtga ggctacagag 1920
gaggctagga atctagcttt tagcttaatg accagacacc gtcctgagtg tattactttt 1980
caacagatca aggataattg cgctaatgag cttgatctgc tggcgcagaa gtattccata 2040
gagcagctga ccacttactg gctgcagcca ggggatgatt ttgaggaggc tattagggta 2100
tatgcaaagg tggcacttag gccagattgc aagtacaaga tcagcaaact tgtaaatatc 2160
aggaattgtt gctacatttc tgggaacggg gccgaggtgg agatagatac ggaggatagg 2220
gtggccttta gatgtagcat gataaatatg tggccggggg tgcttggcat ggacggggtg 2280
gttattatga atgtaaggtt tactggcccc aattttagcg gtacggtttt cctggccaat 2340
accaacctta tcctacacgg tgtaagcttc tatgggttta acaatacctg tgtggaagcc 2400
tggaccgatg taagggttcg gggctgtgcc ttttactgct gctggaaggg ggtggtgtgt 2460
cgccccaaaa gcagggcttc aattaagaaa tgcctctttg aaaggtgtac cttgggtatc 2520
ctgtctgagg gtaactccag ggtgcgccac aatgtggcct ccgactgtgg ttgcttcatg 2580
ctagtgaaaa gcgtggctgt gattaagcat aacatggtat gtggcaactg cgaggacagg 2640
gcctctcaga tgctgacctg ctcggacggc aactgtcacc tgctgaagac cattcacgta 2700
gccagccact ctcgcaaggc ctggccagtg tttgagcata acatactgac ccgctgttcc 2760
ttgcatttgg gtaacaggag gggggtgttc ctaccttacc aatgcaattt gagtcacact 2820
aagatattgc ttgagcccga gagcatgtcc aaggtgaacc tgaacggggt gtttgacatg 2880
accatgaaga tctggaaggt gctgaggtac gatgagaccc gcaccaggtg cagaccctgc 2940
gagtgtggcg gtaaacatat taggaaccag cctgtgatgc tggatgtgac cgaggagctg 3000
aggcccgatc acttggtgct ggcctgcacc cgcgctgagt ttggctctag cgatgaagat 3060
acagattgag gtactgaaat gtgtgggcgt ggcttaaggg tgggaaagaa tatataaggt 3120
gggggtctta tgtagttttg tatctgtttt gcagcagccg ccgccgccat gagcaccaac 3180
tcgtttgatg gaagcattgt gagctcatat ttgacaacgc gcatgccccc atgggccggg 3240
gtgcgtcaga atgtgatggg ctccagcatt gatggtcgcc ccgtcctgcc cgcaaactct 3300
actaccttga cctacgagac cgtgtctgga acgccgttgg agactgcagc ctccgccgcc 3360
gcttcagccg ctgcagccac cgcccgcggg attgtgactg actttgcttt cctgagcccg 3420

-continued

```
cttgcaagca gtgcagcttc ccgttcatcc gcccgcgatg acaagttgac ggctcttttg   3480
gcacaattgg attctttgac ccgggaactt aatgtcgttt ctcagcagct gttggatctg   3540
cgccagcagg tttctgccct gaaggcttcc tcccctccca atgcggttta aaacataaat   3600
aaaaaaccag actctgtttg gatttggatc aagcaagtgt cttgctgtct ttatttaggg   3660
gttttgcgcg cgcggtaggc ccgggaccag cggtctcggt cgttgagggt cctgtgtatt   3720
ttttccagga cgtggtaaag gtgactctgg atgttcagat acatgggcat aagcccgtct   3780
ctggggtgga ggtagcacca ctgcagagct tcatgctgcg gggtggtgtt gtagatgatc   3840
cagtcgtagc aggagcgctg ggcgtggtgc ctaaaaatgt ctttcagtag caagctgatt   3900
gccaggggca ggcccttggt gtaagtgttt acaaagcggt taagctggga tgggtgcata   3960
cgtggggata tgagatgcat cttggactgt atttttaggt tggctatgtt cccagccata   4020
tccctccggg gattcatgtt gtgcagaacc accagcacag tgtatccggt gcacttggga   4080
aatttgtcat gtagcttaga aggaaatgcg tggaagaact tggagacgcc cttgtgacct   4140
ccaagatttt ccatgcattc gtccataatg atggcaatgg gcccacgggc ggcggcctgg   4200
gcgaagatat ttctgggatc actaacgtca tagttgtgtt ccaggatgag atcgtcatag   4260
gccattttta caaagcgcgg gcggagggtg ccagactgcg gtataatggt tccatccggc   4320
ccaggggcgt agttaccctc acagatttgc atttcccacg ctttgagttc agatgggggg   4380
atcatgtcta cctgcggggc gatgaagaaa acggtttccg ggtaggggga gatcagctgg   4440
gaagaaagca ggttcctgag cagctgcgac ttaccgcagc cggtgggccc gtaaatcaca   4500
cctattaccg ggtgcaactg gtagttaaga gagctgcagc tgccgtcatc cctgagcagg   4560
ggggccactt cgttaagcat gtccctgact cgcatgtttt ccctgaccaa atccgccaga   4620
aggcgctcgc cgcccagcga tagcagttct tgcaaggaag caaagttttt caacggtttg   4680
agaccgtccg ccgtaggcat gcttttgagc gtttgaccaa gcagttccag gcggtcccac   4740
agctcggtca cctgctctac ggcatctcga tccagcatat ctcctcgttt cgcgggttgg   4800
ggcggctttc gctgtacggc agtagtcggt gctcgtccag acgggccagg gtcatgtctt   4860
tccacgggcg cagggtcctc gtcagcgtag tctgggtcac ggtgaagggg tgcgctccgg   4920
gctgcgcgct ggccagggtg cgcttgaggc tggtcctgct ggtgctgaag cgctgccggt   4980
cttcgccctg cgcgtcggcc aggtagcatt tgaccatggt gtcatagtcc agcccctccg   5040
cggcgtggcc cttggcgcgc agcttgccct tggaggaggc gccgcacgag gggcagtgca   5100
gacttttgag ggcgtagagc ttgggcgcga gaaataccga ttccggggag taggcatccg   5160
cgccgcaggc cccgcagacg gtctcgcatt ccacgagcca ggtgagctct ggccgttcgg   5220
ggtcaaaaac caggtttccc ccatgctttt tgatgcgttt cttacctctg gtttccatga   5280
gccggtgtcc acgctcggtg acgaaaaggc tgtccgtgtc cccgtataca gacttgagag   5340
gcctgtcctc gagcggtgtt ccgcggtcct cctcgtatag aaactcggac cactctgaga   5400
caaaggctcg cgtccaggcc agcacgaagg aggctaagtg ggaggggtag cggtcgttgt   5460
ccactagggg gtccactcgc tccagggtgt gaagacacat gtcgccctct tcggcatcaa   5520
ggaaggtgat tggtttgtag gtgtaggcca cgtgaccggg tgttcctgaa ggggggctat   5580
aaaagggggt gggggcgcgt tcgtcctcac tctcttccgc atcgctgtct gcgagggcca   5640
gctgttgggg tgagtactcc ctctgaaaag cgggcatgac ttctgcgcta agattgtcag   5700
tttccaaaaa cgaggaggat ttgatattca cctggcccgc ggtgatgcct ttgagggtgg   5760
ccgcatccat ctggtcagaa aagacaatct tttgttgtc aagcttggtg gcaaacgacc   5820
```

```
cgtagagggc gttggacagc aacttggcga tggagcgcag ggtttggttt ttgtcgcgat   5880
cggcgcgctc cttggccgcg atgtttagct gcacgtattc gcgcgcaacg caccgccatt   5940
cgggaaagac ggtggtgcgc tcgtcgggca ccaggtgcac gcgccaaccg cggttgtgca   6000
gggtgacaag gtcaacgctg gtggctacct ctccgcgtag gcgctcgttg gtccagcaga   6060
ggcggccgcc cttgcgcgag cagaatggcg gtagggggtc tagctgcgtc tcgtccgggg   6120
ggtctgcgtc cacggtaaag accccgggca gcaggcgcgc gtcgaagtag tctatcttgc   6180
atccttgcaa gtctagcgcc tgctgccatg cgcgggcggc aagcgcgcgc tcgtatgggt   6240
tgagtggggg accccatggc atggggtggg tgagcgcgga ggcgtacatg ccgcaaatgt   6300
cgtaaacgta gaggggctct ctgagtattc caagatatgt agggtagcat cttccaccgc   6360
ggatgctggc gcgcacgtaa tcgtatagtt cgtgcgaggg agcgaggagg tcgggaccga   6420
ggttgctacg ggcgggctgc tctgctcgga agactatctg cctgaagatg gcatgtgagt   6480
tggatgatat ggttggacgc tggaagacgt tgaagctggc gtctgtgaga cctaccgcgt   6540
cacgcacgaa ggaggcgtag gagtcgcgca gcttgttgac cagctcggcg gtgacctgca   6600
cgtctagggc gcagtagtcc agggtttcct tgatgatgtc atacttatcc tgtccctttt   6660
ttttccacag ctcgcggttg aggacaaact cttcgcggtc tttccagtac tcttggatcg   6720
gaaacccgtc ggcctccgaa cggtaagagc ctagcatgta gaactggttg acggcctggt   6780
aggcgcagca tccctttttct acgggtagcg cgtatgcctg cgcggccttc cggagcgagg   6840
tgtgggtgag cgcaaaggtg tccctgacca tgactttgag gtactggtat ttgaagtcag   6900
tgtcgtcgca tccgccctgc tcccagagca aaaagtccgt gcgctttttg gaacgcggat   6960
ttggcagggc gaaggtgaca tcgttgaaga gtatctttcc cgcgcgaggc ataaagttgc   7020
gtgtgatgcg gaagggtccc ggcacctcgg aacggttgtt aattacctgg gcggcgagca   7080
cgatctcgtc aaagccgttg atgttgtggc ccacaatgta aagttccaag aagcgcggga   7140
tgcccttgat ggaaggcaat tttttaagtt cctcgtaggt gagctcttca ggggagctga   7200
gcccgtgctc tgaaagggcc cagtctgcaa gatgagggtt ggaagcgacg aatgagctcc   7260
acaggtcacg ggccattagc atttgcaggt ggtcgcgaaa ggtcctaaac tggcgaccta   7320
tggccatttt ttctggggtg atgcagtaga aggtaagcgg gtcttgttcc cagcggtccc   7380
atccaaggtt cgcggctagg tctcgcgcgg cagtcactag aggctcatct ccgccgaact   7440
tcatgaccag catgaagggc acgagctgct tcccaaaggc ccccatccaa gtataggtct   7500
ctacatcgta ggtgacaaag agacgctcgg tgcgaggatg cgagccgatc gggaagaact   7560
ggatctcccg ccaccaattg gaggagtggc tattgatgtg gtgaaagtag aagtccctgc   7620
gacgggccga acactcgtgc tggcttttgt aaaaacgtgc gcagtactgg cagcggtgca   7680
cgggctgtac atcctgcacg aggttgacct gacgaccgcg cacaaggaag cagagtggga   7740
atttgagccc ctcgcctggc gggtttggct ggtggtcttc tacttcggct gcttgtcctt   7800
gaccgtctgg ctgctcgagg ggagttacgg tggatcggac caccacgccg cgcgagccca   7860
aagtccagat gtccgcgcgc ggcggtcgga gcttgatgac aacatcgcgc agatgggagc   7920
tgtccatggt ctggagctcc cgcggcgtca ggtcaggcgg gagctcctgc aggtttacct   7980
cgcatagacg ggtcagggcg cgggctagat ccaggtgata cctaatttcc aggggctggt   8040
tggtggcggc gtcgatggct tgcaagaggc cgcatccccg cggcgcgact acggtaccgc   8100
gcggcgggcg gtgggccgcg ggggtgtcct tggatgatgc atctaaaagc ggtgacgcgg   8160
```

-continued gcgagccccc ggaggtaggg ggggctccgg acccgccggg agaggggca ggggcacgtc 8220 ggcgccgcgc gcgggcagga gctggtgctg cgcgcgtagg ttgctggcga acgcgacgac 8280
gcggcggttg atctcctgaa tctggcgcct ctgcgtgaag acgacgggcc cggtgagctt 8340
gagcctgaaa gagagttcga cagaatcaat ttcggtgtcg ttgacggcgg cctggcgcaa 8400
aatctcctgc acgtctcctg agttgtcttg ataggcgatc tcggccatga actgctcgat 8460
ctcttcctcc tggagatctc cgcgtccggc tcgctccacg gtggcggcga ggtcgttgga 8520
aatgcgggcc atgagctgcg agaaggcgtt gaggcctccc tcgttccaga cgcggctgta 8580
gaccacgccc ccttcggcat cgcgggcgcg catgaccacc tgcgcgagat tgagctccac 8640
gtgccgggcg aagacggcgt agtttcgcag gcgctgaaag aggtagttga gggtggtggc 8700
ggtgtgttct gccacgaaga agtacataac ccagcgtcgc aacgtggatt cgttgatatc 8760
ccccaaggcc tcaaggcgct ccatggcctc gtagaagtcc acggcgaagt tgaaaaactg 8820
ggagttgcgc gccgacacgg ttaactcctc ctccagaaga cggatgagct cggcgacagt 8880
gtcgcgcacc tcgcgctcaa aggctacagg ggcctcttct tcttcttcaa tctcctcttc 8940
cataagggcc tccccttctt cttcttctgg cggcggtggg ggagggggga cacggcggcg 9000
acgacggcgc accgggaggc ggtcgacaaa gcgctcgatc atctccccgc ggcgacggcg 9060
catggtctcg gtgacggcgc ggccgttctc gcgggggcgc agttggaaga cgccgcccgt 9120
catgtcccgg ttatgggttg gcgggggct gccatgcggc agggatacgg cgctaacgat 9180
gcatctcaac aattgttgtg taggtactcc gccgccgagg gacctgagcg agtccgcatc 9240
gaccggatcg gaaaacctct cgagaaaggc gtctaaccag tcacagtcgc aaggtaggct 9300
gagcaccgtg gcgggcggca gcgggcggcg gtcggggttg tttctggcgg aggtgctgct 9360
gatgatgtaa ttaaagtagg cggtcttgag acggcggatg gtcgacagaa gcaccatgtc 9420
cttgggtccg gcctgctgaa tgcgcaggcg gtcggccatg ccccaggctt cgttttgaca 9480
tcggcgcagg tctttgtagt agtcttgcat gagcctttct accggcactt cttcttctcc 9540
ttcctcttgt cctgcatctc ttgcatctat cgctgcggcg gcggcggagt ttggccgtag 9600
gtggcgccct cttcctccca tgcgtgtgac cccgaagccc ctcatcggct gaagcagggc 9660
taggtcggcg acaacgcgct cggctaatat ggcctgctgc acctgcgtga gggtagactg 9720
gaagtcatcc atgtccacaa agcggtggta tgcgcccgtg ttgatggtgt aagtgcagtt 9780
ggccataacg gaccagttaa cggtctggtg acccggctgc gagagctcgg tgtacctgag 9840
acgcgagtaa gccctcgagt caaatacgta gtcgttgcaa gtccgcacca ggtactggta 9900
tcccaccaaa aagtgcggcg gcggctggcg gtagaggggc cagcgtaggg tggccggggc 9960
tccgggggcg agatcttcca acataaggcg atgatatccg tagatgtacc tggacatcca 10020
ggtgatgccg gcggcggtgg tggaggcgcg cggaaagtcg cggacgcggt tccagatgtt 10080
gcgcagcggc aaaaagtgct ccatggtcgg gacgctctgg ccggtcaggc gcgcgcaatc 10140
gttgacgctc tagaccgtgc aaaaggagag cctgtaagcg ggcactcttc cgtggtctgg 10200
tggataaatt cgcaagggta tcatggcgga cgaccggggt tcgagccccg tatccggccg 10260
tccgccgtga tccatgcggt taccgcccgc gtgtcgaacc caggtgtgcg acgtcagaca 10320
acgggggagt gctccttttg gcttccttcc aggcgcggcg gctgctgcgc tagcttttt 10380 ggccactggc cgcgcgcagc gtaagcggtt aggctggaaa gcgaaagcat taagtggctc 10440
gctccctgta gccggagggt tattttccaa gggttgagtc gcgggacccc cggttcgagt 10500
ctcggaccgg ccggactgcg gcgaacgggg gtttgcctcc ccgtcatgca agaccccgct 10560
tgcaaattcc tccggaaaca gggacgagcc cctttttttgc ttttcccaga tgcatccggt 10620
gctgcggcag atgcgccccc ctcctcagca gcggcaagag caagagcagc ggcagacatg 10680
cagggcaccc tcccctcctc ctaccgcgtc aggaggggcg acatccgcgg ttgacgcggc 10740
agcagatggt gattacgaac cccgcggcg ccgggcccgg cactacctgg acttggagga 10800
gggcgagggc ctggcgcggc taggagcgcc ctctcctgag cggtacccaa gggtgcagct 10860
gaagcgtgat acgcgtgagg cgtacgtgcc gcggcagaac ctgtttcgcg accgcgaggg 10920
agaggagccc gaggagatgc gggatcgaaa gttccacgca gggcgcgagc tgcggcatgg 10980
cctgaatcgc gagcggttgc tgcgcgagga ggactttgag cccgacgcgc gaaccgggat 11040
tagtccccgt ggcggccgcc gacctggtaa ccgcatacga gcagacggtg aaccaggaga 11100
ttaactttca agcgcgcgca caaaaagctt taacaaccac gtgcgtacgc ttgtggcgcg 11160
cgaggaggtg gctataggac tgatgcatct gtgggacttt gtaagcgcgc tggagcaaaa 11220
cccaaatagc aagccgctca tggcgcagct gttccttata gtgcagcaca gcagggacaa 11280
cgaggcattc agggatgcgc tgctaaacat agtagagccc gagggccgct ggctgctcga 11340
tttgataaac atcctgcaga gcatagtggt gcaggagcgc agcttgagcc tggctgacaa 11400
ggtggccgcc atcaactatt ccatgcttag cctgggcaag ttttacgccc gcaagatata 11460
ccatacccct tacgttccca tagacaagga ggtaaagatc gaggggttct acatgcgcat 11520
ggcgctgaag gtgcttacct tgagcgacga cctgggcgtt tatcgcaacg agcgcatcca 11580
caaggccgtg agcgtgagcc ggcggcgcga gctcagcgac cgcgagctga tgcacagcct 11640
gcaaagggcc ctggctggca cgggcagcgg cgatagagag gccgagtcct actttgacgc 11700
gggcgctgac ctgcgctggg ccccaagccg acgcgccctg gaggcagctg ggccggacc 11760 tgggctggcg gtggcacccg cgcgcgctgg caacgtcggc ggcgtggagg aatatgacga 11820
ggacgatgag tacgagccag aggacggcga gtactaagcg gtgatgtttc tgatcagatg 11880
atgcaagacg caacggaccc ggcggtgcgg gcggcgctgc agagccagcc gtccggcctt 11940
aactccacgg acgactggcg ccaggtcatg gaccgcatca tgtcgctgac tgcgcgcaat 12000
cctgacgcgt tccggcagca gccgcaggcc aaccggctct ccgcaattct ggaagcggtg 12060
gtcccggcgc gcgcaaaccc cacgcacgag aaggtgctgg cgatcgtaaa cgcgctggcc 12120
gaaaacaggg ccatccggcc cgacgaggcc ggcctggtct acgacgcgct gcttcagcgc 12180
gtggctcgtt acaacagcgg caacgtgcag accaacctgg accggctggt gggggatgtg 12240
cgcgaggccg tggcgcagcg tgagcgcgcg cagcagcagg gcaacctggg ctccatggtt 12300
gcactaaacg ccttcctgag tacacagccc gccaacgtgc cgcggggaca ggaggactac 12360
accaactttg tgagcgcact gcggctaatg gtgactgaga caccgcaaag tgaggtgtac 12420
cagtctgggc cagactattt tttccagacc agtagacaag gcctgcagac cgtaaacctg 12480
agccaggctt tcaaaaactt gcaggggctg tgggggggtgc gggctcccac aggcgaccgc 12540
gcgaccgtgt ctagcttgct gacgcccaac tcgcgcctgt tgctgctgct aatagcgccc 12600
ttcacggaca gtggcagcgt gtcccgggac acatacctag gtcacttgct gacactgtac 12660
cgcgaggcca taggtcaggc gcatgtggac gagcatactt tccaggagat tacaagtgtc 12720
agccgcgcgc tggggcagga ggacacgggc agcctggagg caaccctaaa ctacctgctg 12780
accaaccggc ggcagaagat cccctcgttg cacagtttaa acagcgagga ggagcgcatt 12840
ttgcgctacg tgcagcagag cgtgagcctt aacctgatgc gcgacggggt aacgcccagc 12900

-continued

```
gtggcgctgg acatgaccgc gcgcaacatg gaaccgggca tgtatgcctc aaaccggccg  12960
tttatcaacc gcctaatgga ctacttgcat cgcgcggccg ccgtgaaccc cgagtatttc  13020
accaatgcca tcttgaaccc gcactggcta ccgccccctg gtttctacac cgggggattc  13080
gaggtgcccg agggtaacga tggattcctc tgggacgaca tagacgacag cgtgttttcc  13140
ccgcaaccgc agaccctgct agagttgcaa cagcgcgagc aggcagaggc ggcgctgcga  13200
aaggaaagct tccgcaggcc aagcagcttg tccgatctag gcgctgcggc cccgcggtca  13260
gatgctagta gcccatttcc aagcttgata gggtctctta ccagcactcg caccacccgc  13320
ccgcgcctgc tgggcgagga ggagtaccta aacaactcgc tgctgcagcc gcagcgcgaa  13380
aaaaacctgc ctccggcatt tcccaacaac gggatagaga gcctagtgga caagatgagt  13440
agatggaaga cgtacgcgca ggagcacagg gacgtgccag gcccgcgccc gcccacccgt  13500
cgtcaaaggc acgaccgtca gcggggtctg gtgtgggagg acgatgactc ggcagacgac  13560
agcagcgtcc tggatttggg agggagtggc aacccgtttg cgcaccttcg ccccaggctg  13620
gggagaatgt tttaaaaaaa aaaaagcatg atgcaaaata aaaaactcac caaggccatg  13680
gcaccgagcg ttggttttct tgtattcccc ttagtatgcg gcgcgcggcg atgtatgagg  13740
aaggtcctcc tccctcctac gagagtgtgg tgagcgcggc gccagtggcg gcggcgctgg  13800
gttctccctt cgatgctccc ctggacccgc cgtttgtgcc tccgcggtac ctgcggccta  13860
ccggggggag aaacagcatc cgttactctg agttggcacc cctattcgac accacccgtg  13920
tgtacctggt ggacaacaag tcaacggatg tggcatccct gaactaccag aacgaccaca  13980
gcaactttct gaccacggtc attcaaaaca atgactacag cccgggggag gcaagcacac  14040
agaccatcaa tcttgacgac cggtcgcact ggggcggcga cctgaaaacc atcctgcata  14100
ccaacatgcc aaatgtgaac gagttcatgt ttaccaataa gtttaaggcg cgggtgatgg  14160
tgtcgcgctt gcctactaag gacaatcagg tggagctgaa atacgagtgg gtggagttca  14220
cgctgcccga gggcaactac tccgagacca tgaccataga ccttatgaac aacgcgatcg  14280
tggagcacta cttgaaagtg ggcagacaga acggggttct ggaaagcgac atcggggtaa  14340
agtttgacac ccgcaacttc agactggggt ttgaccccgt cactggtctt gtcatgcctg  14400
gggtatatac aaacgaagcc ttccatccag acatcatttt gctgccagga tgcggggtgg  14460
acttcaccca cagccgcctg agcaacttgt tgggcatccg caagcggcaa cccttccagg  14520
agggctttag gatcacctac gatgatctgg agggtggtaa cattcccgca ctgttggatg  14580
tggacgccta ccaggcgagc ttgaaagatg acaccgaaca gggcgggggt ggcgcaggcg  14640
gcagcaacag cagtggcagc ggcgcggaag agaactccaa cgcggcagcc gcggcaatgc  14700
agccggtgga ggacatgaac gatcatgcca ttcgcggcga cacctttgcc acacgggctg  14760
aggagaagcg cgctgaggcc gaagcagcgg ccgaagctgc cgcccccgct gcgcaacccg  14820
aggtcgagaa gcctcagaag aaaccggtga tcaaacccct gacagaggac agcaagaaac  14880
gcagttacaa cctaataagc aatgacagca ccttcaccca gtaccgcagc tggtaccttg  14940
catacaacta cggcgaccct cagaccggaa tccgctcatg gaccctgctt tgcactcctg  15000
acgtaacctg cggctcggag caggtctact ggtcgttgcc agacatgatg caagaccccg  15060
tgaccttccg ctccacgcgc cagatcagca actttccggt ggtgggcgcc gagctgttgc  15120
ccgtgcactc caagagcttc tacaacgacc aggccgtcta ctcccaactc atccgccagt  15180
ttacctctct gacccacgtg ttcaatcgct ttcccgagaa ccagattttg gcgcgcccgc  15240
cagcccccac catcaccacc gtcagtgaaa acgttcctgc tctcacagat cacgggacgc  15300
```

-continued

```
taccgctgcg caacagcatc ggaggagtcc agcgagtgac cattactgac gccagacgcc  15360
gcacctgccc ctacgtttac aaggccctgg gcatagtctc gccgcgcgtc ctatcgagcc  15420
gcactttttg agcaagcatg tccatcctta tatcgcccag caataacaca ggctggggcc  15480
tgcgcttccc aagcaagatg tttggcgggg ccaagaagcg ctccgaccaa cacccagtgc  15540
gcgtgcgcgg gcactaccgc gcgccctggg gcgcgcacaa acgcggccgc actgggcgca  15600
ccaccgtcga tgacgccatc gacgcggtgg tggaggaggc gcgcaactac acgcccacgc  15660
cgccaccagt gtccacagtg gacgcggcca ttcagaccgt ggtgcgcgga gcccggcgct  15720
atgctaaaat gaagagacgg cggaggcgcg tagcacgtcg ccaccgccgc cgacccggca  15780
ctgccgccca acgcgcggcg gcggccctgc ttaaccgcgc acgtcgcacc ggccgacggg  15840
cggccatgcg ggccgctcga aggctggccg cgggtattgt cactgtgccc cccaggtcca  15900
ggcgacgagc ggccgccgca gcagccgcgg ccattagtgc tatgactcag ggtcgcaggg  15960
gcaacgtgta ttgggtgcgc gactcggtta gcggcctgcg cgtgcccgtg cgcacccgcc  16020
ccccgcgcaa ctagattgca agaaaaaact acttagactc gtactgttgt atgtatccag  16080
cggcggcggc gcgcaacgaa gctatgtcca agcgcaaaat caaagaagag atgctccagg  16140
tcatcgcgcc ggagatctat ggccccccga agaaggaaga gcaggattac aagccccgaa  16200
agctaaagcg ggtcaaaaag aaaaagaaag atgatgatga tgaacttgac gacgaggtgg  16260
aactgctgca cgctaccgcg cccaggcgac gggtacagtg gaaaggtcga cgcgtaaaac  16320
gtgttttgcg acccggcacc accgtagtct ttacgcccgg tgagcgctcc acccgcacct  16380
acaagcgcgt gtatgatgag gtgtacggcg acgaggacct gcttgagcag gccaacgagc  16440
gcctcgggga gtttgcctac ggaaagcggc ataaggacat gctggcgttg ccgctggacg  16500
agggcaaccc aacacctagc ctaaagcccg taacactgca gcaggtgctg cccgcgcttg  16560
caccgtccga agaaaagcgc ggcctaaagc gcgagtctgg tgacttggca cccaccgtgc  16620
agctgatggt acccaagcgc cagcgactgg aagatgtctt ggaaaaaatg accgtggaac  16680
ctgggctgga gcccgaggtc cgcgtgcggc caatcaagca ggtggcgccg ggactgggcg  16740
tgcagaccgt ggacgttcag atacccacta ccagtagcac cagtattgcc accgccacag  16800
agggcatgga gacacaaacg tccccggttg cctcagcggt ggcggatgcc gcggtgcagg  16860
cggtcgctgc ggccgcgtcc aagacctcta cggaggtgca aacggacccg tggatgtttc  16920
gcgtttcagc cccccggcgc ccgcgcggtt cgaggaagta cggcgccgcc agcgcgctac  16980
tgcccgaata tgccctacat ccttccattg cgcctacccc cggctatcgt ggctacacct  17040
accgccccag aagacgagca actacccgac gccgaaccac cactggaacc cgccgccgcc  17100
gtcgccgtcg ccagcccgtg ctggccccga tttccgtgcg cagggtggct cgcgaaggag  17160
gcaggaccct ggtgctgcca acagcgcgct accaccccag catcgtttaa aagccggtct  17220
ttgtggttct tgcagatatg gccctcacct gccgcctccg tttcccggtg ccgggattcc  17280
gaggaagaat gcaccgtagg aggggcatgg ccggccacgg cctgacgggc ggcatgcgtc  17340
gtgcgcacca ccggcggcgg cgcgcgtcgc accgtcgcat gcgcggcggt atcctgcccc  17400
tccttattcc actgatcgcc gcggcgattg gcgccgtgcc cggaattgca tccgtggcct  17460
tgcaggcgca gagacactga ttaaaaacaa gttgcatgtg gaaaaatcaa aataaaaagt  17520
ctggactctc acgctcgctt ggtcctgtaa ctattttgta gaatggaaga catcaacttt  17580
gcgtctctgg ccccgcgaca cggctcgcgc ccgttcatgg gaaactggca agatatcggc  17640
```

-continued accagcaata tgagcggtgg cgccttcagc tggggctcgc tgtggagcgg cattaaaaat 17700
ttcggttcca ccgttaagaa ctatggcagc aaggcctgga acagcagcac aggccagatg 17760
ctgagggata agttgaaaga gcaaaatttc caacaaaagg tggtagatgg cctggcctct 17820
ggcattagcg gggtggtgga cctggccaac caggcagtgc aaaataagat taacagtaag 17880
cttgatcccc gccctcccgt agaggagcct ccaccggccg tggagacagt gtctccagag 17940
gggcgtggcg aaaagcgtcc gcgccccgac agggaagaaa ctctggtgac gcaaatagac 18000
gagcctccct cgtacgagga ggcactaaag caaggcctgc ccaccacccg tcccatcgcg 18060
cccatggcta ccggagtgct gggccagcac acacccgtaa cgctggacct gcctcccccc 18120
gccgacaccc agcagaaacc tgtgctgcca ggcccgaccg ccgttgttgt aacccgtcct 18180
agccgcgcgt ccctgcgccg cgccgccagc ggtccgcgat cgttgcggcc cgtagccagt 18240
ggcaactggc aaagcacact gaacagcatc gtgggtctgg gggtgcaatc cctgaagcgc 18300
cgacgatgct tctgaatagc taacgtgtcg tatgtgtgtc atgtatgcgt ccatgtcgcc 18360
gccagaggag ctgctgagcc gccgcgcgcc cgctttccaa gatggctacc ccttcgatga 18420
tgccgcagtg gtcttacatg cacatctcgg gccaggacgc ctcggagtac ctgagccccg 18480
ggctggtgca gtttgcccgc gccaccgaga cgtacttcag cctgaataac aagtttagaa 18540
accccacggt ggcgcctacg cacgacgtga ccacagaccg gtcccagcgt ttgacgctgc 18600
ggttcatccc tgtggaccgt gaggatactg cgtactcgta caaggcgcgg ttcaccctag 18660
ctgtgggtga taaccgtgtg ctggacatgg cttccacgta ctttgacatc cgcggcgtgc 18720
tggacagggg ccctactttt aagccctact ctggcactgc ctacaacgcc ctggctccca 18780
agggtgcccc aaatccttgc gaatgggatg aagctgctac tgctcttgaa ataaacctag 18840
aagaagagga cgatgacaac gaagacgaag tagacgagca agctgagcag caaaaaactc 18900
acgtatttgg gcaggcgcct tattctggta taaatattac aaaggagggt attcaaatag 18960
gtgtcgaagg tcaaacacct aaatatgccg ataaaacatt tcaacctgaa cctcaaatag 19020
gagaatctca gtggtacgaa actgaaatta atcatgcagc tgggagagtc cttaaaaaga 19080
ctaccccaat gaaaccatgt tacggttcat atgcaaaacc cacaaatgaa aatggagggc 19140
aaggcattct tgtaaagcaa caaaatggaa agctagaaag tcaagtggaa atgcaatttt 19200
tctcaactac tgaggcgacc gcaggcaatg gtgataactt gactcctaaa gtggtattgt 19260
acagtgaaga tgtagatata gaaaccccag acactcatat ttcttacatg cccactatta 19320
aggaaggtaa ctcacgagaa ctaatgggcc aacaatctat gcccaacagg cctaattaca 19380
ttgcttttag ggacaatttt attggtctaa tgtattacaa cagcacgggt aatatgggtg 19440
ttctggcggg ccaagcatcg cagttgaatg ctgttgtaga tttgcaagac agaaacacag 19500
agctttcata ccagcttttg cttgattcca ttggtgatag aaccaggtac ttttctatgt 19560
ggaatcaggc tgttgacagc tatgatccag atgttagaat tattgaaaat catggaactg 19620
aagatgaact tccaaattac tgctttccac tgggaggtgt gattaataca gagactctta 19680
ccaaggtaaa acctaaaaca ggtcaggaaa atggatggga aaaagatgct acagaatttt 19740
cagataaaaa tgaaataaga gttggaaata attttgccat ggaaatcaat ctaaatgcca 19800
acctgtggag aaatttcctg tactccaaca tagcgctgta tttgcccgac aagctaaagt 19860
acagtccttc caacgtaaaa atttctgata acccaaacac ctacgactac atgaacaagc 19920
gagtggtggc tcccgggtta gtggactgct acattaacct tggagcacgc tggtcccttg 19980
actatatgga caacgtcaac ccatttaacc accaccgcaa tgctggcctg cgctaccgct 20040
caatgttgct gggcaatggt cgctatgtgc ccttccacat ccaggtgcct cagaagttct 20100
ttgccattaa aaacctcctt ctcctgccgg gctcatacac ctacgagtgg aacttcagga 20160
aggatgttaa catggttctg cagagctccc taggaaatga cctaagggtt gacggagcca 20220
gcattaagtt tgatagcatt tgcctttacg ccaccttctt ccccatggcc cacaacaccg 20280
cctccacgct tgaggccatg cttagaaacg acaccaacga ccagtccttt aacgactatc 20340
tctccgccgc caacatgctc taccctatac ccgccaacgc taccaacgtg cccatatcca 20400
tcccctcccg caactgggcg gctttccgcg gctgggcctt cacgcgcctt aagactaagg 20460
aaaccccatc actgggctcg ggctacgacc cttattacac ctactctggc tctataccct 20520
acctagatgg aacctttac ctcaaccaca cctttaagaa ggtggccatt acctttgact 20580
cttctgtcag ctggcctggc aatgaccgcc tgcttacccc caacgagttt gaaattaagc 20640
gctcagttga cggggagggt tacaacgttg cccagtgtaa catgaccaaa gactggttcc 20700
tggtacaaat gctagctaac tacaacattg gctaccaggg cttctatatc ccagagagct 20760
acaaggaccg catgtactcc ttctttagaa acttccagcc catgagccgt caggtggtgg 20820
atgatactaa atacaaggac taccaacagg tgggcatcct acaccaacac aacaactctg 20880
gatttgttgg ctaccttgcc cccaccatgc gcgaaggaca ggcctaccct gctaacttcc 20940
cctatccgct tataggcaag accgcagttg acagcattac ccagaaaaag tttctttgcg 21000
atcgcaccct ttggcgcatc ccattctcca gtaactttat gtccatgggc gcactcacag 21060
acctgggcca aaaccttctc tacgccaact ccgcccacgc gctagacatg acttttgagg 21120
tggatcccat ggacgagccc acccttcttt atgttttgtt tgaagtcttt gacgtggtcc 21180
gtgtgcaccg gccgcaccgc ggcgtcatcg aaaccgtgta cctgcgcacg cccttctcgg 21240
ccggcaacgc cacaacataa agaagcaagc aacatcaaca acagctgccg ccatgggctc 21300
cagtgagcag gaactgaaag ccattgtcaa agatcttggt tgtgggccat atttttggg 21360 cacctatgac aagcgctttc caggctttgt ttctccacac aagctcgcct gcgccatagt 21420
caatacggcc ggtcgcgaga ctgggggcgt acactggatg gcctttgcct ggaacccgca 21480
ctcaaaaaca tgctacctct ttgagccctt tggcttttct gaccagcgac tcaagcaggt 21540
ttaccagttt gagtacgagt cactcctgcg ccgtagcgcc attgcttctt cccccgaccg 21600
ctgtataacg ctggaaaagt ccacccaaag cgtacagggg cccaactcgg ccgcctgtgg 21660
actattctgc tgcatgtttc tccacgcctt tgccaactgg ccccaaactc ccatggatca 21720
caaccccacc atgaacctta ttaccggggt acccaactcc atgctcaaca gtccccaggt 21780
acagcccacc ctgcgtcgca accaggaaca gctctacagc ttcctggagc gccactcgcc 21840
ctacttccgc agccacagtg cgcagattag gagcgccact tctttttgtc acttgaaaaa 21900
catgtaaaaa taatgtacta gagacacttt caataaaggc aaatgctttt atttgtacac 21960
tctcgggtga ttatttaccc ccacccttgc cgtctgcgcc gtttaaaaat caaaggggtt 22020
ctgccgcgca tcgctatgcg ccactggcag ggacacgttg cgatactggt gtttagtgct 22080
ccacttaaac tcaggcacaa ccatccgcgg cagctcggtg aagttttcac tccacaggct 22140
gcgcaccatc accaacgcgt ttagcaggtc gggcgccgat atcttgaagt cgcagttggg 22200
gcctccgccc tgcgcgcgcg agttgcgata cacagggttg cagcactgga acactatcag 22260
cgccgggtgg tgcacgctgg ccagcacgct cttgtcggag atcagatccg cgtccaggtc 22320
ctccgcgttg ctcagggcga acggagtcaa ctttggtagc tgccttccca aaaagggcgc 22380

-continued

```
gtgcccaggc tttgagttgc actcgcaccg tagtggcatc aaaaggtgac cgtgcccggt  22440
ctgggcgtta ggatacagcg cctgcataaa agccttgatc tgcttaaaag ccacctgagc  22500
ctttgcgcct tcagagaaga acatgccgca agacttgccg gaaaactgat tggccggaca  22560
ggccgcgtcg tgcacgcagc accttgcgtc ggtgttggag atctgcacca catttcggcc  22620
ccaccggttc ttcacgatct tggccttgct agactgctcc ttcagcgcgc gctgcccgtt  22680
ttcgctcgtc acatccattt caatcacgtg ctccttattt atcataatgc ttccgtgtag  22740
acacttaagc tcgccttcga tctcagcgca gcggtgcagc cacaacgcgc agcccgtggg  22800
ctcgtgatgc ttgtaggtca cctctgcaaa cgactgcagg tacgcctgca ggaatcgccc  22860
catcatcgtc acaaaggtct tgttgctggt gaaggtcagc tgcaacccgc ggtgctcctc  22920
gttcagccag gtcttgcata cggccgccag agcttccact tggtcaggca gtagtttgaa  22980
gttcgccttt agatcgttat ccacgtggta cttgtccatc agcgcgcgcg cagcctccat  23040
gcccttctcc cacgcagaca cgatcggcac actcagcggg ttcatcaccg taatttcact  23100
ttccgcttcg ctgggctctt cctcttcctc ttgcgtccgc ataccacgcg ccactgggtc  23160
gtcttcattc agccgccgca ctgtgcgctt acctcctttg ccatgcttga ttagcaccgg  23220
tgggttgctg aaacccacca tttgtagcgc cacatcttct ctttcttcct cgctgtccac  23280
gattacctct ggtgatggcg ggcgctcggg cttgggagaa gggcgcttct ttttcttctt  23340
gggcgcaatg gccaaatccg ccgccgaggt cgatggccgc gggctgggtg tgcgcggcac  23400
cagcgcgtct tgtgatgagt cttcctcgtc ctcggactcg atacgccgcc tcatccgctt  23460
ttttgggggc gcccggggag gcggcggcga cggggacggg gacgacacgt cctccatggt  23520
tgggggacgt cgcgccgcac cgcgtccgcg ctcgggggtg gtttcgcgct gctcctcttc  23580
ccgactggcc atttccttct cctataggca gaaaaagatc atggagtcag tcgagaagaa  23640
ggacagccta accgcccccct ctgagttcgc caccaccgcc tccaccgatg ccgccaacgc  23700
gcctaccacc ttccccgtcg aggcaccccc gcttgaggag gaggaagtga ttatcgagca  23760
ggacccaggt tttgtaagcg aagacgacga ggaccgctca gtaccaacag aggataaaaa  23820
gcaagaccag gacaacgcag aggcaaacga ggaacaagtc gggcgggggg acgaaaggca  23880
tggcgactac ctagatgtgg gagacgacgt gctgttgaag catctgcagc gccagtgcgc  23940
cattatctgc gacgcgttgc aagagcgcag cgatgtgccc ctcgccatag cggatgtcag  24000
ccttgcctac gaacgccacc tattctcacc gcgcgtaccc cccaaacgcc aagaaaacgg  24060
cacatgcgag cccaacccgc gcctcaactt ctaccccgta tttgccgtgc cagaggtgct  24120
tgccacctat cacatctttt tccaaaactg caagataccc ctatcctgcc gtgccaaccg  24180
cagccgagcg gacaagcagc tggccttgcg gcagggcgct gtcatacctg atatcgcctc  24240
gctcaacgaa gtgccaaaaa tctttgaggg tcttggacgc gacgagaagc gcgcggcaaa  24300
cgctctgcaa caggaaaaca gcgaaaatga aagtcactct ggagtgttgg tggaactcga  24360
gggtgacaac gcgcgcctag ccgtactaaa acgcagcatc gaggtcaccc actttgccta  24420
cccggcactt aacctacccc ccaaggtctt gcctaccact ctgacataat ggaagacgtg  24480
agcggtgacg gtctactgga gtgtcactgt cgctgcaacc tatgcacccc gcaccgctcc  24540
ctggtttgca attcgcagct gcttaacgaa agtcaaatta tcggtacctt tgagctgcag  24600
ggtccctcgc ctgacgaaaa gtccgcggct ccggggttga aactcactcc ggggctgtgg  24660
acgtcggctt accttcgcaa atttgtacct gaggactacc acgcccacga gattaggttc  24720
tacgaagacc aatcccgccc gccaaatgcg gagcttaccg cctgcgtcat tacccagggc  24780
```

```
cacattcttg gccaattgca agccatcaac aaagcccgcc aagagtttct gctacgaaag  24840
ggacgggggg tttacttgga cccccagtcc ggcgaggagc tcaacccaat ccccccgccg  24900
ccgcagccct atcagcagca gccgcgggcc cttgcttccc aggatggcac ccaaaaagaa  24960
gctgcagctg ccgccgccac ccacggacga ggaggaatac tgggacagtc aggcagagga  25020
ggttttggac gaggaggagg aggacatgat ggaagactgg gagagcctag acgaggaagc  25080
ttccgaggtc gaagaggtgt cagacgaaac accgtcaccc tcggtcgcat tcccctcgcc  25140
ggcgccccag aaatcggcaa ccggttccag catggctaca acctccgctc ctcaggcgcc  25200
gccggcactg cccgttcgcc gacccaaccg tagatgggac accactggaa ccagggccgg  25260
taagtccaag cagccgccgc cgttagccca agagcaacaa cagcgccaag gctaccgctc  25320
atggcgcggg cacaagaacg ccatagttgc ttgcttgcaa gactgtgggg gcaacatctc  25380
cttcgcccgc cgctttcttc tctaccatca cggcgtggcc ttcccccgta acatcctgca  25440
ttactaccgt catctctaca gcccatactg caccggcggc agcggcagcg gcagcaacag  25500
cagcggccac acagaagcaa aggcgaccgg atagcaagac tctgacaaag cccaagaaat  25560
ccacagcggc ggcagcagca ggaggaggag cgctgcgtct ggcgcccaac gaacccgtat  25620
cgacccgcga gcttagaaac aggatttttc ccactctgta tgctatattt caacagagca  25680
ggggccaaga acaagagctg aaaataaaaa acaggtctct gcgatccctc acccgcagct  25740
gcctgtatca caaaagcgaa gatcagcttc ggcgcacgct ggaagacgcg gaggctctct  25800
tcagtaaata ctgcgcgctg actcttaagg actagtttcg cgccctttct caaatttaag  25860
cgcgaaaact acgtcatctc cagcggccac acccggcgcc agcacctgtc gtcagcgcca  25920
ttatgagcaa ggaaattccc acgccctaca tgtggagtta ccagccacaa atgggacttg  25980
cggctggagc tgcccaagac tactcaaccc gaataaacta catgagcgcg ggaccccaca  26040
tgatatcccg ggtcaacgga atccgcgccc accgaaaccg aattctcttg gaacaggcgg  26100
ctattaccac cacacctcgt aataacctta atccccgtag ttggcccgct gccctggtgt  26160
accaggaaag tcccgctccc accactgtgg tacttcccag agacgcccag gccgaagttc  26220
agatgactaa ctcaggggcg cagcttgcgg gcggctttcg tcacagggtg cggtcgcccg  26280
ggcagggtat aactcacctg acaatcagag ggcgaggtat tcagctcaac gacgagtcgg  26340
tgagctcctc gcttggtctc cgtccggacg ggacatttca gatcggcggc gccggccgtc  26400
cttcattcac gcctcgtcag gcaatcctaa ctctgcagac ctcgtcctct gagccgcgct  26460
ctggaggcat tggaactctg caatttattg aggagtttgt gccatcggtc tactttaacc  26520
ccttctcggg acctcccggc cactatccgg atcaatttat tcctaacttt gacgcggtaa  26580
aggactcggc ggacggctac gactgaatgt taagtggaga ggcagagcaa ctgcgcctga  26640
aacacctggt ccactgtcgc cgccacaagt gctttgcccg cgactccggt gagttttgct  26700
actttgaatt gcccgaggat catatcgagg gcccggcgca cggcgtccgg cttaccgccc  26760
agggagagct tgcccgtagc ctgattcggg agtttaccca gcgcccccctg ctagttgagc  26820
gggacagggg accctgtgtt ctcactgtga tttgcaactg tcctaacctt ggattacatc  26880
aagatctttg ttgccatctc tgtgctgagt ataataaata cagaaattaa aatatactgg  26940
ggctcctatc gccatcctgt aaacgccacc gtcttcaccc gcccaagcaa accaaggcga  27000
accttacctg gtacttttaa catctctccc tctgtgattt acaacagttt caacccagac  27060
ggagtgagtc tacgagagaa cctctccgag ctcagctact ccatcagaaa aaacaccacc  27120
```

-continued ctccttacct gccgggaacg tacgagtgcg tcaccggccg ctgcaccaca cctaccgcct 27180
gaccgtaaac cagacttttt ccggacagac ctcaataact ctgtttacca gaacaggagg 27240
tgagcttaga aaacccttag ggtattaggc caaaggcgca gctactgtgg ggtttatgaa 27300
caattcaagc aactctacgg gctattctaa ttcaggtttc tctagaatcg gggttggggt 27360
tattctctgt cttgtgattc tctttattct tatactaacg cttctctgcc taaggctcgc 27420
cgcctgctgt gtgcacattt gcatttattg tcagcttttt aaacgctggg gtcgccaccc 27480
aagatgatta ggtacataat cctaggttta ctcacccttg cgtcagccca cggtaccacc 27540
caaaaggtgg attttaagga gccagcctgt aatgttacat tcgcagctga agctaatgag 27600
tgcaccactc ttataaaatg caccacagaa catgaaaagc tgcttattcg ccacaaaaac 27660
aaaattggca agtatgctgt ttatgctatt tggcagccag gtgacactac agagtataat 27720
gttacagttt tccagggtaa aagtcataaa acttttatgt atacttttcc attttatgaa 27780
atgtgcgaca ttaccatgta catgagcaaa cagtataagt tgtggccccc acaaaattgt 27840
gtggaaaaca ctggcacttt ctgctgcact gctatgctaa ttacagtgct cgctttggtc 27900
tgtaccctac tctatattaa atacaaaagc agacgcagct ttattgagga aaagaaaatg 27960
ccttaattta ctaagttaca aagctaatgt caccactaac tgctttactc gctgcttgca 28020
aaacaaattc aaaaagttag cattataatt agaataggat ttaaaccccc cggtcatttc 28080
ctgctcaata ccattcccct gaacaattga ctctatgtgg gatatgctcc agcgctacaa 28140
ccttgaagtc aggcttcctg gatgtcagca tctgactttg gccagcacct gtcccgcgga 28200
tttgttccag tccaactaca gcgacccacc ctaacagaga tgaccaacac aaccaacgcg 28260
gccgccgcta ccggacttac atctaccaca aatacacccc aagtttctgc ctttgtcaat 28320
aactgggata acttgggcat gtggtggttc tccatagcgc ttatgtttgt atgccttatt 28380
attatgtggc tcatctgctg cctaaagcgc aaacgcgccc gaccacccat ctatagtccc 28440
atcattgtgc tacacccaaa caatgatgga atccatagat tggacggact gaaacacatg 28500
ttcttttctc ttacagtatg attaaatgag acatgattcc tcgagttttt atattactga 28560
cccttgttgc gctttttttgt gcgtgctcca cattggctgc ggtttctcac atcgaagtag 28620
actgcattcc agccttcaca gtctatttgc tttacggatt tgtcaccctc acgctcatct 28680
gcagcctcat cactgtggtc atcgccttta tccagtgcat tgactgggtc tgtgtgcgct 28740
ttgcatatct cagacaccat ccccagtaca gggacaggac tatagctgag cttcttagaa 28800
ttctttaatt atgaaattta ctgtgacttt tctgctgatt atttgcaccc tatctgcgtt 28860
ttgttccccg acctccaagc ctcaaagaca tatatcatgc agattcactc gtatatggaa 28920
tattccaagt tgctacaatg aaaaaagcga tctttccgaa gcctggttat atgcaatcat 28980
ctctgttatg gtgttctgca gtaccatctt agccctagct atatatccct accttgacat 29040
tggctggaaa cgaatagatg ccatgaacca cccaactttc cccgcgcccg ctatgcttcc 29100
actgcaacaa gttgttgccg gcggctttgt cccagccaat cagcctcgcc ccacttctcc 29160 caccccccact gaaatcagct actttaatct aacaggagga gatgactgac accctagatc 29220
tagaaatgga cggaattatt acagagcagc gcctgctaga aagacgcagg gcagcggccg 29280
agcaacagcg catgaatcaa gagctccaag acatggttaa cttgcaccag tgcaaaaggg 29340
gtatcttttg tctggtaaag caggccaaag tcacctacga cagtaatacc accggacacc 29400
gccttagcta caagttgcca accaagcgtc agaaattggt ggtcatggtg ggagaaaagc 29460
ccattaccat aactcagcac tcggtagaaa ccgaaggctg cattcactca ccttgtcaag 29520

-continued gacctgagga tctctgcacc cttattaaga ccctgtgcgg tctcaaagat cttattccct 29580
ttaactaata aaaaaaaata ataaagcatc acttacttaa aatcagttag caaatttctg 29640
tccagtttat tcagcagcac ctccttgccc tcctcccagc tctggtattg cagcttcctc 29700
ctggctgcaa actttctcca caatctaaat ggaatgtcag tttcctcctg ttcctgtcca 29760
tccgcaccca ctatcttcat gttgttgcag atgaagcgcg caagaccgtc tgaagatacc 29820
ttcaaccccg tgtatccata tgacacggaa accggtcctc caactgtgcc ttttcttact 29880
cctccctttg tatcccccaa tgggtttcaa gagagtcccc ctggggtact ctctttgcgc 29940
ctatccgaac ctctagttac ctccaatggc atgcttgcgc tcaaaatggg caacggcctc 30000
tctctggacg aggccggcaa ccttacctcc caaaatgtaa ccactgtgag cccacctctc 30060
aaaaaaacca agtcaaacat aaacctggaa atatctgcac ccctcacagt tacctcagaa 30120
gccctaactg tggctgccgc cgcacctcta atggtcgcgg gcaacacact caccatgcaa 30180
tcacaggccc cgctaaccgt gcacgactcc aaacttagca ttgccaccca aggacccctc 30240
acagtgtcag aaggaaagct agccctgcaa acatcaggcc ccctcaccac caccgatagc 30300
agtaccctta ctatcactgc ctcacccccct ctaactactg ccactggtag cttgggcatt 30360
gacttgaaag agcccattta tacacaaaat ggaaaactag gactaaagta cggggctcct 30420
ttgcatgtaa cagacgacct aaacactttg accgtagcaa ctggtccagg tgtgactatt 30480
aataatactt ccttgcaaac taaagttact ggagccttgg gttttgattc acaaggcaat 30540
atgcaactta atgtagcagg aggactaagg attgattctc aaaacagacg ccttatactt 30600
gatgttagtt atccgtttga tgctcaaaac caactaaatc taagactagg acagggccct 30660
ctttttataa actcagccca caacttggat attaactaca acaaaggcct ttacttgttt 30720
acagcttcaa acaattccaa aaagcttgag gttaacctaa gcactgccaa ggggttgatg 30780
tttgacgcta cagccatagc cattaatgca ggagatgggc ttgaatttgg ttcacctaat 30840
gcaccaaaca caaatcccct caaaacaaaa attggccatg gcctagaatt tgattcaaac 30900
aaggctatgg ttcctaaact aggaactggc cttagttttg acagcacagg tgccattaca 30960
gtaggaaaca aaaataatga taagctaact ttgtggacca caccagctcc atctcctaac 31020
tgtagactaa atgcagagaa agatgctaaa ctcactttgg tcttaacaaa atgtggcagt 31080
caaatacttg ctacagtttc agttttggct gttaaaggca gtttggctcc aatatctgga 31140
acagttcaaa gtgctcatct tattataaga tttgacgaaa atggagtgct actaaacaat 31200
tccttcctgg acccagaata ttggaacttt agaaatggag atcttactga aggcacagcc 31260
tatacaaacg ctgttggatt tatgcctaac ctatcagctt atccaaaatc tcacggtaaa 31320
actgccaaaa gtaacattgt cagtcaagtt tacttaaacg gagacaaaac taaacctgta 31380
acactaacca ttacactaaa cggtacacag gaaacaggag acacaactcc aagtgcatac 31440
tctatgtcat tttcatggga ctggtctggc cacaactaca ttaatgaaat atttgccaca 31500
tcctcttaca ctttttcata cattgcccaa gaataaagaa tcgtttgtgt tatgtttcaa 31560
cgtgtttatt tttcaattgc agaaaatttc aagtcatttt tcattcagta gtatagcccc 31620
accaccacat agcttataca gatcaccgta ccttaatcaa actcacagaa ccctagtatt 31680
caacctgcca cctccctccc aacacacaga gtacacagtc ctttctcccc ggctggcctt 31740
aaaaagcatc atatcatggg taacagacat attcttaggt gttatattcc acacggtttc 31800
ctgtcgagcc aaacgctcat cagtgatatt aataaactcc ccgggcagct cacttaagtt 31860

-continued catgtcgctg tccagctgct gagccacagg ctgctgtcca acttgcggtt gcttaacggg 31920
cggcgaagga gaagtccacg cctacatggg ggtagagtca taatcgtgca tcaggatagg 31980
gcggtggtgc tgcagcagcg cgcgaataaa ctgctgccgc cgccgctccg tcctgcagga 32040
atacaacatg gcagtggtct cctcagcgat gattcgcacc gcccgcagca taaggcgcct 32100
tgtcctccgg gcacagcagc gcaccctgat ctcacttaaa tcagcacagt aactgcagca 32160
cagcaccaca atattgttca aaatcccaca gtgcaaggcg ctgtatccaa agctcatggc 32220
ggggaccaca gaacccacgt ggccatcata ccacaagcgc aggtagatta agtggcgacc 32280
cctcataaac acgctggaca taaacattac ctcttttggc atgttgtaat tcaccacctc 32340
ccggtaccat ataaacctct gattaaacat ggcgccatcc accaccatcc taaaccagct 32400
ggccaaaacc tgcccgccgg ctatacactg cagggaaccg ggactggaac aatgacagtg 32460
gagagcccag gactcgtaac catggatcat catgctcgtc atgatatcaa tgttggcaca 32520
acacaggcac acgtgcatac acttcctcag gattacaagc tcctcccgcg ttagaaccat 32580
atcccaggga acaacccatt cctgaatcag cgtaaatccc acactgcagg gaagacctcg 32640
cacgtaactc acgttgtgca ttgtcaaagt gttacattcg ggcagcagcg gatgatcctc 32700
cagtatggta gcgcgggttt ctgtctcaaa aggaggtaga cgatccctac tgtacggagt 32760
gcgccgagac aaccgagatc gtgttggtcg tagtgtcatg ccaaatggaa cgccggacgt 32820
agtcatattt cctgaagcaa aaccaggtgc gggcgtgaca aacagatctg cgtctccggt 32880
ctcgccgctt agatcgctct gtgtagtagt tgtagtatat ccactctctc aaagcatcca 32940 ggcgcccct ggcttcgggt tctatgtaaa ctccttcatg cgccgctgcc ctgataacat 33000
ccaccaccgc agaataagcc acacccagcc aacctacaca ttcgttctgc gagtcacaca 33060
cgggaggagc gggaagagct ggaagaacca tgtttttttt tttattccaa aagattatcc 33120
aaaacctcaa aatgaagatc tattaagtga acgcgctccc ctccggtggc gtggtcaaac 33180
tctacagcca aagaacagat aatggcattt gtaagatgtt gcacaatggc ttccaaaagg 33240
caaacggccc tcacgtccaa gtggacgtaa aggctaaacc cttcagggtg aatctcctct 33300
ataaacattc cagcaccttc aaccatgccc aaataattct catctcgcca ccttctcaat 33360
atatctctaa gcaaatcccg aatattaagt ccggccattg taaaaatctg ctccagagcg 33420
ccctccacct tcagcctcaa gcagcgaatc atgattgcaa aaattcaggt tcctcacaga 33480
cctgtataag attcaaaagc ggaacattaa caaaaatacc gcgatcccgt aggtcccttc 33540
gcagggccag ctgaacataa tcgtgcaggt ctgcacggac cagcgcggcc acttccccgc 33600
caggaacctt gacaaaagaa cccacactga ttatgacacg catactcgga gctatgctaa 33660
ccagcgtagc cccgatgtaa gctttgttgc atgggcggcg atataaaatg caaggtgctg 33720
ctcaaaaaat caggcaaagc ctcgcgcaaa aaagaaagca catcgtagtc atgctcatgc 33780
agataaaggc aggtaagctc cggaaccacc acagaaaaag acaccatttt tctctcaaac 33840
atgtctgcgg gtttctgcat aaacacaaaa taaaataaca aaaaaacatt taaacattag 33900
aagcctgtct tacaacagga aaaacaaccc ttataagcat aagacggact acggccatgc 33960
cggcgtgacc gtaaaaaaac tggtcaccgt gattaaaaag caccaccgac agctcctcgg 34020
tcatgtccgg agtcataatg taagactcgg taaacacatc aggttgattc atcggtcagt 34080
gctaaaaagc gaccgaaata gcccggggga atacataccc gcaggcgtag agacaacatt 34140
acagccccca taggaggtat aacaaaatta ataggagaga aaaacacata aacacctgaa 34200
aaaccctcct gcctaggcaa aatagcaccc tcccgctcca gaacaacata cagcgcttca 34260
cagcggcagc ctaacagtca gccttaccag taaaaaagaa aacctattaa aaaaacacca 34320
ctcgacacgg caccagctca atcagtcaca gtgtaaaaaa gggccaagtg cagagcgagt 34380
atatatagga ctaaaaaatg acgtaacggt taaagtccac aaaaaacacc cagaaaaccg 34440
cacgcgaacc tacgcccaga aacgaaagcc aaaaaaccca caacttcctc aaatcgtcac 34500
ttccgttttc ccacgttacg taacttccca ttttaagaaa actacaattc ccaacacata 34560
caagttactc cgccctaaaa cctacgtcac ccgccccgtt cccacgcccc gcgccacgtc 34620
acaaactcca ccccctcatt atcatattgg cttcaatcca aaataaggta tattattgat 34680
gatgatttaa atgccgcagt actgttgtaa ttcattaagc attctgccga catggaagcc 34740
atcacaaacg gcatgatgaa cctgaatcgc cagcggcatc agcaccttgt cgccttgcgt 34800
ataatatttg cccatggtga aaacgggggc gaagaagttg tccatattgg ccacgtttaa 34860
atcaaaactg gtgaaactca cccagggatt ggctgagacg aaaaacatat tctcaataaa 34920
ccctttaggg aaataggcca ggttttcacc gtaacacgcc acatcttgcg aatatatgtg 34980
tagaaactgc cggaaatcgt cgtggtattc actccagagc gatgaaaacg tttcagtttg 35040
ctcatggaaa acggtgtaac aagggtgaac actatcccat atcaccagct caccgtcttt 35100
cattgccata cggaattccg gatgagcatt catcaggcgg gcaagaatgt gaataaaggc 35160
cggataaaac ttgtgcttat ttttctttac ggtctttaaa aaggccgtaa tatccagctg 35220
aacggtctgg ttataggtac attgagcaac tgactgaaat gcctcaaaat gttctttacg 35280
atgccattgg gatatatcaa cggtggtata tccagtgatt tttttctcca ttttagcttc 35340
cttagctcct gaaaatctcg ataactcaaa aaatacgccc ggtagtgatc ttatttcatt 35400
atggtgaaag ttggaacctc ttacgtgccg atcaacgtct cattttcgcc aaaagttggc 35460
ccagggcttc ccggtatcaa cagggacacc aggatttatt tattctgcga agtgatcttc 35520
cgtcacaggt atttattcgc gataagctca tggagcggcg taaccgtcgc acaggaagga 35580
cagagaaagc gcggatctgg gaagtgacgg acagaacggt caggacctgg attggggagg 35640
cggttgccgc cgctgctgct gacggtgtga cgttctctgt tccggtcaca ccacatacgt 35700
tccgccattc ctatgcgatg cacatgctgt atgccggtat accgctgaaa gttctgcaaa 35760
gcctgatggg acataagtcc atcagttcaa cggaagtcta cacgaaggtt tttgcgctgg 35820
atgtggctgc ccggcaccgg gtgcagtttg cgatgccgga gtctgatgcg gttgcgatgc 35880
tgaaacaatt atcctgagaa taaatgcctt ggcctttata tggaaatgtg gaactgagtg 35940
gatatgctgt ttttgtctgt taaacagaga agctggctgt tatccactga gaagcgaacg 36000
aaacagtcgg gaaaatctcc cattatcgta gagatccgca ttattaatct caggagcctg 36060
tgtagcgttt ataggaagta gtgttctgtc atgatgcctg caagcggtaa cgaaaacgat 36120
ttgaatatgc cttcaggaac aatagaaatc ttcgtgcggt gttacgttga agtggagcgg 36180
attatgtcag caatggacag aacaacctaa tgaacacaga accatgatgt ggtctgtcct 36240
tttacagcca gtagtgctcg ccgcagtcga gcgacagggc gaagccctcg agtgagcgag 36300
gaagcaccag ggaacagcac ttatatattc tgcttacaca cgatgcctga aaaaacttcc 36360
cttggggtta tccacttatc cacggggata tttttataat tatttttttt atagttttta 36420
gatcttcttt tttagagcgc cttgtaggcc tttatccatg ctggttctag agaaggtgtt 36480
gtgacaaatt gccctttcag tgtgacaaat caccctcaaa tgacagtcct gtctgtgaca 36540
aattgccctt aaccctgtga caaattgccc tcagaagaag ctgttttttc acaaagttat 36600

-continued

```
ccctgcttat tgactctttt ttatttagtg tgacaatcta aaaacttgtc acacttcaca  36660
tggatctgtc atggcggaaa cagcggttat caatcacaag aaacgtaaaa atagcccgcg  36720
aatcgtccag tcaaacgacc tcactgaggc ggcatatagt ctctcccggg atcaaaaacg  36780
tatgctgtat ctgttcgttg accagatcag aaaatctgat ggcaccctac aggaacatga  36840
cggtatctgc gagatccatg ttgctaaata tgctgaaata ttcggattga cctctgcgga  36900
agccagtaag gatatacggc aggcattgaa gagtttcgcg gggaaggaag tggtttttta  36960
tcgccctgaa gaggatgccg gcgatgaaaa aggctatgaa tcttttcctt ggtttatcaa  37020
acgtgcgcac agtccatcca gagggcttta cagtgtacat atcaacccat atctcattcc  37080
cttctttatc gggttacaga accggtttac gcagtttcgg cttagtgaaa caaaagaaat  37140
caccaatccg tatgccatgc gtttatacga atccctgtgt cagtatcgta agccggatgg  37200
ctcaggcatc gtctctctga aaatcgactg gatcatagag cgttaccagc tgcctcaaag  37260
ttaccagcgt atgcctgact tccgccgccg cttcctgcag gtctgtgtta atgagatcaa  37320
cagcagaact ccaatgcgcc tctcatacat tgagaaaaag aaaggccgcc agacgactca  37380
tatcgtattt tccttccgcg atatcacttc catgacgaca ggatagtctg agggttatct  37440
gtcacagatt tgagggtggt tcgtcacatt tgttctgacc tactgagggt aatttgtcac  37500
agttttgctg tttccttcag cctgcatgga ttttctcata ctttttgaac tgtaattttt  37560
aaggaagcca aatttgaggg cagtttgtca cagttgattt ccttctcttt cccttcgtca  37620
tgtgacctga tatcgggggt tagttcgtca tcattgatga gggttgatta tcacagttta  37680
ttactctgaa ttggctatcc gcgtgtgtac ctctacctgg agtttttccc acggtggata  37740
tttcttcttg cgctgagcgt aagagctatc tgacagaaca gttcttcttt gcttcctcgc  37800
cagttcgctc gctatgctcg gttacacggc tgcggcgagc gctagtgata ataagtgact  37860
gaggtatgtg ctcttcttat ctccttttgt agtgttgctc ttattttaaa caactttgcg  37920
gtttttttgat gactttgcga ttttgttgtt gctttgcagt aaattgcaag atttaataaa  37980
aaaacgcaaa gcaatgatta aaggatgttc agaatgaaac tcatggaaac acttaaccag  38040
tgcataaacg ctggtcatga aatgacgaag gctatcgcca ttgcacagtt taatgatgac  38100
agcccggaag cgaggaaaat aacccggcgc tggagaatag gtgaagcagc ggatttagtt  38160
ggggtttctt ctcaggctat cagagatgcc gagaaagcag ggcgactacc gcacccggat  38220
atggaaattc gaggacgggt tgagcaacgt gttggttata caattgaaca aattaatcat  38280
atgcgtgatg tgtttggtac gcgattgcga cgtgctgaag acgtatttcc accggtgatc  38340
ggggttgctg cccataaagg tggcgtttac aaaacctcag tttctgttca tcttgctcag  38400
gatctggctc tgaaggggct acgtgttttg ctcgtggaag gtaacgaccc ccagggaaca  38460
gcctcaatgt atcacggatg ggtaccagat cttcatattc atgcagaaga cactctcctg  38520
cctttctatc ttggggaaaa ggacgatgtc acttatgcaa taaagcccac ttgctggccg  38580
gggcttgaca ttattccttc ctgtctggct ctgcaccgta ttgaaactga gttaatgggc  38640
aaatttgatg aaggtaaact gcccaccgat ccacacctga tgctccgact ggccattgaa  38700
actgttgctc atgactatga tgtcatagtt attgacagcg cgcctaacct gggtatcggc  38760
acgattaatg tcgtatgtgc tgctgatgtg ctgattgttc ccacgcctgc tgagttgttt  38820
gactacacct ccgcactgca gtttttcgat atgcttcgtg atctgctcaa gaacgttgat  38880
cttaaagggt tcgagcctga tgtacgtatt ttgcttacca aatacagcaa tagtaatggc  38940
tctcagtccc cgtggatgga ggagcaaatt cgggatgcct ggggaagcat ggttctaaaa  39000
```

```
aatgttgtac gtgaaacgga tgaagttggt aaaggtcaga tccggatgag aactgttttt  39060
gaacaggcca ttgatcaacg ctcttcaact ggtgcctgga gaaatgctct ttctatttgg  39120
gaacctgtct gcaatgaaat tttcgatcgt ctgattaaac cacgctggga gattagataa  39180
tgaagcgtgc gcctgttatt ccaaaacata cgctcaatac tcaaccggtt gaagatactt  39240
cgttatcgac accagctgcc ccgatggtgg attcgttaat tgcgcgcgta ggagtaatgg  39300
ctcgcggtaa tgccattact ttgcctgtat gtggtcggga tgtgaagttt actcttgaag  39360
tgctccgggg tgatagtgtt gagaagacct ctcgggtatg gtcaggtaat gaacgtgacc  39420
aggagctgct tactgaggac gcactggatg atctcatccc ttcttttcta ctgactggtc  39480
aacagacacc ggcgttcggt cgaagagtat ctggtgtcat agaaattgcc gatgggagtc  39540
gccgtcgtaa agctgctgca cttaccgaaa gtgattatcg tgttctggtt ggcgagctgg  39600
atgatgagca gatggctgca ttatccagat tgggtaacga ttatcgccca acaagtgctt  39660
atgaacgtgg tcagcgttat gcaagccgat tgcagaatga atttgctgga aatatttctg  39720
cgctggctga tgcggaaaat atttcacgta agattattac ccgctgtatc aacaccgcca  39780
aattgcctaa atcagttgtt gctctttttt ctcaccccgg tgaactatct gcccggtcag  39840
gtgatgcact tcaaaaagcc tttacagata aagaggaatt acttaagcag caggcatcta  39900
accttcatga gcagaaaaaa gctggggtga tatttgaagc tgaagaagtt atcactcttt  39960
taacttctgt gcttaaaacg tcatctgcat caagaactag tttaagctca cgacatcagt  40020
ttgctcctgg agcgacagta ttgtataagg gcgataaaat ggtgcttaac ctggacaggt  40080
ctcgtgttcc aactgagtgt atagagaaaa ttgaggccat tcttaaggaa cttgaaaagc  40140
cagcaccctg atgcgaccac gttttagtct acgtttatct gtctttactt aatgtccttt  40200
gttacaggcc agaaagcata actggcctga atattctctc tgggcccact gttccacttg  40260
tatcgtcggt ctgataatca gactgggacc acggtcccac tcgtatcgtc ggtctgatta  40320
ttagtctggg accacggtcc cactcgtatc gtcggtctga ttattagtct gggaccacgg  40380
tcccactcgt atcgtcggtc tgataatcag actgggacca cggtcccact cgtatcgtcg  40440
gtctgattat tagtctggga ccatggtccc actcgtatcg tcggtctgat tattagtctg  40500
ggaccacggt cccactcgta tcgtcggtct gattattagt ctggaaccac ggtcccactc  40560
gtatcgtcgg tctgattatt agtctgggac cacggtccca ctcgtatcgt cggtctgatt  40620
attagtctgg gaccacgatc ccactcgtgt tgtcggtctg attatcggtc tgggaccacg  40680
gtcccacttg tattgtcgat cagactatca gcgtgagact acgattccat caatgcctgt  40740
caagggcaag tattgacatg tcgtcgtaac ctgtagaacg gagtaacctc ggtgtgcggt  40800
tgtatgcctg ctgtggattg ctgctgtgtc ctgcttatcc acaacatttt gcgcacggtt  40860
atgtggacaa aatacctgtt accatttcca tttaaatcat catcaataat ataccttatt  40920
ttggattgaa gccaatatga taatgagggg gtggagtttg tgacgtggcg cggggcgtgg  40980
gaacggggcg ggtgacgtag tagtgtggcg gaagtgtgat gttgcaagtg tggcggaaca  41040
catgtaagcg acggatgtgg caaaagtgac gtttttggtg tgcgccggtg tacacaggaa  41100
gtgacaattt tcgcgcggtt ttaggcggat gttgtagtaa atttgggcgt aaccgagtaa  41160
gatttggcca ttttcgcggg aaaactgaat aagaggaagt gaaatctgaa taattttgtg  41220
ttactcatag cgcgtaatat ttgtctaggg ccgcggggac tttgaccgtt tacgtggaga  41280
ctcgcccagg tgtttttctc aggtgttttc cgcgttccgg gtcaaagttg gcgtttt     41337
```

<210> SEQ ID NO 8
<211> LENGTH: 100
<212> TYPE: DNA
<213> ORGANISM: Artificial sequence
<220> FEATURE:
<223> OTHER INFORMATION: Sequence of the L4-100K deletion

<400> SEQUENCE: 8
tcgaggtcac ccactttgcc tacccggcac ttaacctacc ccccaaggtc ttgcctacca 60
ctctgacata atggaagacg tgagcggtga cggtctactg 100

<210> SEQ ID NO 9
<211> LENGTH: 74
<212> TYPE: DNA
<213> ORGANISM: Artificial sequence
<220> FEATURE:
<223> OTHER INFORMATION: Primer sequence for the RED?/ET? recombination (L4-100K)

<400> SEQUENCE: 9
tcgaggtcac ccactttgcc tacccggcac ttaacctacc ccccaaggtc ggcctggtga 60
tgatggcggg atcg 74

<210> SEQ ID NO 10
<211> LENGTH: 74
<212> TYPE: DNA
<213> ORGANISM: Artificial sequence
<220> FEATURE:
<223> OTHER INFORMATION: Primer sequence for the RED?/ET? recombination (L4-100K)

<400> SEQUENCE: 10
cagtagaccg tcaccgctca cgtcttccat tatgtcagag tggtaggcaa tcagaagaac 60
tcgtcaagaa ggcg 74

<210> SEQ ID NO 11
<211> LENGTH: 100
<212> TYPE: DNA
<213> ORGANISM: Artificial sequence
<220> FEATURE:
<223> OTHER INFORMATION: Primer sequence for the RED?/ET? recombination (L4-100K)

<400> SEQUENCE: 11
tcgaggtcac ccactttgcc tacccggcac ttaacctacc ccccaaggtc ttgcctacca 60
ctctgacata atggaagacg tgagcggtga cggtctactg 100

<210> SEQ ID NO 12
<211> LENGTH: 33
<212> TYPE: DNA
<213> ORGANISM: Artificial sequence
<220> FEATURE:
<223> OTHER INFORMATION: Forward amplification primer with Kozak sequence (L4-100K)

<400> SEQUENCE: 12
tgcggccgcg accatggagt cagtcgagaa gaa 33

<210> SEQ ID NO 13
<211> LENGTH: 28
<212> TYPE: DNA
<213> ORGANISM: Artificial sequence
<220> FEATURE:
<223> OTHER INFORMATION: Reverse amplification primer (L4-100K)

<400> SEQUENCE: 13
attcccgggc tacggttggg tcggcgaa 28

<210> SEQ ID NO 14
<211> LENGTH: 21
<212> TYPE: DNA
<213> ORGANISM: Artificial sequence
<220> FEATURE:
<223> OTHER INFORMATION: Amplification forward primer (L4-100K)

<400> SEQUENCE: 14
ggaaccccta gtgatggagt t 21

<210> SEQ ID NO 15
<211> LENGTH: 16
<212> TYPE: DNA
<213> ORGANISM: Artificial sequence
<220> FEATURE:
<223> OTHER INFORMATION: Amplification reverse primer (L4-100K)

<400> SEQUENCE: 15
cggcctcagt gagcga 16

<210> SEQ ID NO 16
<211> LENGTH: 21
<212> TYPE: DNA
<213> ORGANISM: Artificial sequence
<220> FEATURE:
<223> OTHER INFORMATION: Amplification forward primer (L4-100K)

<400> SEQUENCE: 16
ggaaccccta gtgatggagt t 21

<210> SEQ ID NO 17
<211> LENGTH: 16
<212> TYPE: DNA
<213> ORGANISM: Artificial sequence
<220> FEATURE:
<223> OTHER INFORMATION: Amplification reverse primer (L4-100K)

<400> SEQUENCE: 17
cggcctcagt gagcga 16

<210> SEQ ID NO 18
<211> LENGTH: 100
<212> TYPE: DNA
<213> ORGANISM: Artificial sequence
<220> FEATURE:
<223> OTHER INFORMATION: Sequence of the L1-52/55K deletion

<400> SEQUENCE: 18
ttgcaaattc ctccggaaac agggacgagc ccctttttg cttttcccag cagctggggc 60
cggacctggg ctggcggtgg cacccgcgcg cgctggcaac 100

<210> SEQ ID NO 19
<211> LENGTH: 74
<212> TYPE: DNA
<213> ORGANISM: Artificial sequence
<220> FEATURE:
<223> OTHER INFORMATION: Primer sequence for the RED?/ET? recombination (L1-52/55K)

<400> SEQUENCE: 19
ttgcaaattc ctccggaaac agggacgagc ccctttttg cttttcccag ggcctggtga 60
tgatggcggg atcg 74

<210> SEQ ID NO 20
<211> LENGTH: 74
<212> TYPE: DNA
<213> ORGANISM: Artificial sequence
<220> FEATURE:
<223> OTHER INFORMATION: Primer sequence for the RED?/ET? recombination (L1-52/55K)

<400> SEQUENCE: 20
gttgccagcg cgcgcgggtg ccaccgccag cccaggtccg gccccagctg tcagaagaac 60
tcgtcaagaa ggcg 74

<210> SEQ ID NO 21
<211> LENGTH: 100
<212> TYPE: DNA
<213> ORGANISM: Artificial sequence
<220> FEATURE:
<223> OTHER INFORMATION: Primer sequence for the RED?/ET? recombination (L1-52/55K)

<400> SEQUENCE: 21
ttgcaaattc ctccggaaac agggacgagc cccttttttg cttttcccag cagctggggc 60
cggacctggg ctggcggtgg cacccgcgcg cgctggcaac 100

<210> SEQ ID NO 22
<211> LENGTH: 36
<212> TYPE: DNA
<213> ORGANISM: Artificial sequence
<220> FEATURE:
<223> OTHER INFORMATION: Forward amplification primer with Kozak sequence (L1-52/55K)

<400> SEQUENCE: 22
atagctagcg accatgcatc cggtgctgcg gcagat 36

<210> SEQ ID NO 23
<211> LENGTH: 39
<212> TYPE: DNA
<213> ORGANISM: Artificial sequence
<220> FEATURE:
<223> OTHER INFORMATION: Reverse amplification primer (L1-52/55K)

<400> SEQUENCE: 23
agtctgatat cttagtactc gccgtcctct ggctcgtac 39

<210> SEQ ID NO 24
<211> LENGTH: 19
<212> TYPE: DNA
<213> ORGANISM: Artificial sequence
<220> FEATURE:
<223> OTHER INFORMATION: Amplification forward primer (L1-52/55K)

<400> SEQUENCE: 24
atgcatccgg tgctgcggc 19

<210> SEQ ID NO 25
<211> LENGTH: 21
<212> TYPE: DNA
<213> ORGANISM: Artificial sequence
<220> FEATURE:
<223> OTHER INFORMATION: Amplification reverse primer (L1-52/55K)

<400> SEQUENCE: 25
ttagtactcg ccgtcctctg g 21

<210> SEQ ID NO 26
<211> LENGTH: 100
<212> TYPE: DNA
<213> ORGANISM: Artificial sequence
<220> FEATURE:
<223> OTHER INFORMATION: Sequence of the pTP deletion

<400> SEQUENCE: 26
ccatgtcctt gggtccggcc tgctgaatgc gcagggggtc ggccatgccc ctagaccgtg 60
caaaaggaga gcgtgtaagc gggcactctt ccgtggtctg 100

<210> SEQ ID NO 27
<211> LENGTH: 74
<212> TYPE: DNA
<213> ORGANISM: Artificial sequence
<220> FEATURE:
<223> OTHER INFORMATION: Primer sequence for the RED?/ET? recombination
(deltapTP)

<400> SEQUENCE: 27
ccatgtcctt gggtccggcc tgctgaatgc gcaggcggtc ggccatgccc ggcctggtga 60
tgatggcggg atcg 74

<210> SEQ ID NO 28
<211> LENGTH: 74
<212> TYPE: DNA
<213> ORGANISM: Artificial sequence
<220> FEATURE:
<223> OTHER INFORMATION: Primer sequence for the RED?/ET? recombination
(deltapTP)

<400> SEQUENCE: 28
cagaccacgg aagagtgccc gcttacaggc tctccttttg cacggtctag tcagaagaac 60
tcgtcaagaa ggcg 74

<210> SEQ ID NO 29
<211> LENGTH: 100
<212> TYPE: DNA
<213> ORGANISM: Artificial sequence
<220> FEATURE:
<223> OTHER INFORMATION: Primer sequence for the RED?/ET? recombination
(deltapTP)

<400> SEQUENCE: 29
ccatgtcctt gggtccggcc tgctgaatgc gcaggcggtc ggccatgccc ctagaccgtg 60
caaaaggaga gcctgtaagc cggcactctt ccgtggtctg 100

<210> SEQ ID NO 30
<211> LENGTH: 39
<212> TYPE: DNA
<213> ORGANISM: Artificial sequence
<220> FEATURE:
<223> OTHER INFORMATION: Forward amplification primer with Kozak
sequence (deltapTP)

<400> SEQUENCE: 30
attgctagca ccatggcctt gagcgtcaac gattgcgcg 39

<210> SEQ ID NO 31
<211> LENGTH: 29
<212> TYPE: DNA

```
<213> ORGANISM: Artificial sequence
<220> FEATURE:
<223> OTHER INFORMATION: Reverse amplification primer (deltapTP)

<400> SEQUENCE: 31

agcggccgcc taaaagcggt gacgcgggc                                29

<210> SEQ ID NO 32
<211> LENGTH: 18
<212> TYPE: DNA
<213> ORGANISM: Artificial sequence
<220> FEATURE:
<223> OTHER INFORMATION: Amplification forward primer (deltapTP)

<400> SEQUENCE: 32

tgtagccttt gagcgcga                                            18

<210> SEQ ID NO 33
<211> LENGTH: 20
<212> TYPE: DNA
<213> ORGANISM: Artificial sequence
<220> FEATURE:
<223> OTHER INFORMATION: Amplification reverse primer (deltapTP)

<400> SEQUENCE: 33

accatgatta cgccaagctc                                          20

<210> SEQ ID NO 34
<211> LENGTH: 21
<212> TYPE: DNA
<213> ORGANISM: Artificial sequence
<220> FEATURE:
<223> OTHER INFORMATION: Amplification forward primer (deltapTP)

<400> SEQUENCE: 34

ggaaccccta gtgatggagt t                                        21

<210> SEQ ID NO 35
<211> LENGTH: 16
<212> TYPE: DNA
<213> ORGANISM: Artificial sequence
<220> FEATURE:
<223> OTHER INFORMATION: Amplification reverse primer (deltapTP)

<400> SEQUENCE: 35

cggcctcagt gagcga                                              16

<210> SEQ ID NO 36
<211> LENGTH: 21
<212> TYPE: DNA
<213> ORGANISM: Artificial sequence
<220> FEATURE:
<223> OTHER INFORMATION: Amplification forward primer (deltapTP)

<400> SEQUENCE: 36

ggaaccccta gtgatggagt t                                        21

<210> SEQ ID NO 37
<211> LENGTH: 16
<212> TYPE: DNA
<213> ORGANISM: Artificial sequence
<220> FEATURE:
<223> OTHER INFORMATION: Amplification reverse primer (deltapTP)

<400> SEQUENCE: 37

cggcctcagt gagcga                                              16
```

<210> SEQ ID NO 38
<211> LENGTH: 74
<212> TYPE: DNA
<213> ORGANISM: Artificial sequence
<220> FEATURE:
<223> OTHER INFORMATION: Primer sequence for the RED?/ET? recombination (ts100K)

<400> SEQUENCE: 38
aactgctaaa gcaaaacttg aaggacctat ggacggcctt caacgagcgc ggcctggtga 60
tgatggcggg atcg 74

<210> SEQ ID NO 39
<211> LENGTH: 74
<212> TYPE: DNA
<213> ORGANISM: Artificial sequence
<220> FEATURE:
<223> OTHER INFORMATION: Primer sequence for the RED?/ET? recombination (ts100K)

<400> SEQUENCE: 39
gttttaagca ggcgttcggg gaaaatgatg tccgccaggt gcgcggccac tcagaagaac 60
tcgtcaagaa ggcg 74

<210> SEQ ID NO 40
<211> LENGTH: 102
<212> TYPE: DNA
<213> ORGANISM: Artificial sequence
<220> FEATURE:
<223> OTHER INFORMATION: Primer sequence for the RED?/ET? recombination (ts100K)

<400> SEQUENCE: 40
aactgctaaa gcaaaacttg aaggacctat ggacggcctt caacgagcgc cccgtggccg 60
cgcacctggc ggacatcatt ttccccgaac gcctgcttaa aa 102

<210> SEQ ID NO 41
<211> LENGTH: 74
<212> TYPE: DNA
<213> ORGANISM: Artificial sequence
<220> FEATURE:
<223> OTHER INFORMATION: Primer sequence for the RED?/ET? recombination (double ts)

<400> SEQUENCE: 41
acatgaccaa agactggttc ctggtacaaa tgctagctaa ctacaacatt ggcctggtga 60
tgatggcggg atcg 74

<210> SEQ ID NO 42
<211> LENGTH: 74
<212> TYPE: DNA
<213> ORGANISM: Artificial sequence
<220> FEATURE:
<223> OTHER INFORMATION: Primer sequence for the RED?/ET? recombination (double ts)

<400> SEQUENCE: 42
aaggagtaca tgcggtcctt gtagctctct gggatataga agccctggta tcagaagaac 60
tcgtcaagaa ggcg 74

<210> SEQ ID NO 43
<211> LENGTH: 103

<212> TYPE: DNA
<213> ORGANISM: Artificial sequence
<220> FEATURE:
<223> OTHER INFORMATION: Primer sequence for the RED?/ET? recombination (double ts)

<400> SEQUENCE: 43
acatgaccaa agactggttc ctggtacaaa tgctagctaa ctacaacatt gattaccagg 60
gcttctatat cccagagagc tacaaggacc gcatgtactc ctt 103

<210> SEQ ID NO 44
<211> LENGTH: 21
<212> TYPE: DNA
<213> ORGANISM: Artificial sequence
<220> FEATURE:
<223> OTHER INFORMATION: Amplification forward primer (double ts)

<400> SEQUENCE: 44
ggaaccccta gtgatggagt t 21

<210> SEQ ID NO 45
<211> LENGTH: 16
<212> TYPE: DNA
<213> ORGANISM: Artificial sequence
<220> FEATURE:
<223> OTHER INFORMATION: Amplification reverse primer (double ts)

<400> SEQUENCE: 45
cggcctcagt gagcga 16

<210> SEQ ID NO 46
<211> LENGTH: 35938
<212> TYPE: DNA
<213> ORGANISM: Adenovirus type 5

<400> SEQUENCE: 46
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tatttgtcta gggccgcggg 360
gactttgacc gtttacgtgg agactcgccc aggtgttttt ctcaggtgtt ttccgcgttc 420
cgggtcaaag ttggcgtttt attattatag tcagctgacg tgtagtgtat ttatacccgg 480
tgagttcctc aagaggccac tcttgagtgc cagcgagtag agttttctcc tccgagccgc 540
tccgacaccg ggactgaaaa tgagacatat tatctgccac ggaggtgtta ttaccgaaga 600
aatggccgcc agtcttttgg accagctgat cgaagaggta ctggctgata atcttccacc 660
tcctagccat tttgaaccac ctacccttca cgaactgtat gatttagacg tgacggcccc 720
cgaagatccc aacgaggagg cggtttcgca gatttttccc gactctgtaa tgttggcggt 780
gcaggaaggg attgacttac tcacttttcc gccggcgccc ggttctccgg agccgcctca 840
cctttcccgg cagcccgagc agccggagca gagagccttg ggtccggttt ctatgccaaa 900
ccttgtaccg gaggtgatcg atcttacctg ccacgaggct ggctttccac ccagtgacga 960
cgaggatgaa gagggtgagg agtttgtgtt agattatgtg gagcaccccg ggcacggttg 1020
caggtcttgt cattatcacc ggaggaatac gggggaccca gatattatgt gttcgctttg 1080
ctatatgagg acctgtggca tgtttgtcta cagtaagtga aaattatggg cagtgggtga 1140
tagagtggtg ggtttggtgt ggtaattttt tttttaattt ttacagtttt gtggtttaaa 1200
gaattttgta ttgtgatttt tttaaaaggt cctgtgtctg aacctgagcc tgagcccgag 1260
ccagaaccgg agcctgcaag acctacccgc cgtcctaaaa tggcgcctgc tatcctgaga 1320
cgcccgacat cacctgtgtc tagagaatgc aatagtagta cggatagctg tgactccggt 1380
ccttctaaca cacctcctga gatacacccg gtggtcccgc tgtgccccat taaaccagtt 1440
gccgtgagag ttggtgggcg tcgccaggct gtggaatgta tcgaggactt gcttaacgag 1500
cctgggcaac ctttggactt gagctgtaaa cgccccaggc cataaggtgt aaacctgtga 1560
ttgcgtgtgt ggttaacgcc tttgtttgct gaatgagttg atgtaagttt aataaagggt 1620
gagataatgt ttaacttgca tggcgtgtta aatggggcgg ggcttaaagg gtatataatg 1680
cgccgtgggc taatcttggt tacatctgac ctcatggagg cttgggagtg tttggaagat 1740
ttttctgctg tgcgtaactt gctggaacag agctctaaca gtacctcttg gttttggagg 1800
tttctgtggg gctcatccca ggcaaagtta gtctgcagaa ttaaggagga ttacaagtgg 1860
gaatttgaag agcttttgaa atcctgtggt gagctgtttg attctttgaa tctgggtcac 1920
caggcgcttt tccaagagaa ggtcatcaag actttggatt tttccacacc ggggcgcgct 1980
gcggctgctg ttgctttttt gagttttata aaggataaat ggagcgaaga aacccatctg 2040
agcggggggt acctgctgga ttttctggcc atgcatctgt ggagagcggt tgtgagacac 2100
aagaatcgcc tgctactgtt gtcttccgtc cgcccggcga taataccgac ggaggagcag 2160
cagcagcagc aggaggaagc caggcggcgg cggcaggagc agagcccatg gaacccgaga 2220
gccggcctgg accctcggga atgaatgttg tacaggtggc tgaactgtat ccagaactga 2280
gacgcatttt gacaattaca gaggatgggc aggggctaaa gggggtaaag agggagcggg 2340
gggcttgtga ggctacagag gaggctagga atctagcttt tagcttaatg accagacacc 2400
gtcctgagtg tattactttt caacagatca aggataattg cgctaatgag cttgatctgc 2460
tggcgcagaa gtattccata gagcagctga ccacttactg gctgcagcca ggggatgatt 2520
ttgaggaggc tattagggta tatgcaaagg tggcacttag gccagattgc aagtacaaga 2580
tcagcaaact tgtaaatatc aggaattgtt gctacatttc tgggaacggg gccgaggtgg 2640
agatagatac ggaggatagg gtggccttta gatgtagcat gataaatatg tggccggggg 2700
tgcttggcat ggacggggtg gttattatga atgtaaggtt tactggcccc aattttagcg 2760
gtacggtttt cctggccaat accaacctta tcctacacgg tgtaagcttc tatgggttta 2820
acaatacctg tgtggaagcc tggaccgatg taagggttcg ggctgtgcc ttttactgct 2880
gctggaaggg ggtggtgtgt cgccccaaaa gcagggcttc aattaagaaa tgcctctttg 2940
aaaggtgtac cttgggtatc ctgtctgagg gtaactccag ggtgcgccac aatgtggcct 3000
ccgactgtgg ttgcttcatg ctagtgaaaa gcgtggctgt gattaagcat aacatggtat 3060
gtggcaactg cgaggacagg gcctctcaga tgctgacctg ctcggacggc aactgtcacc 3120
tgctgaagac cattcacgta gccagccact ctcgcaaggc ctggccagtg tttgagcata 3180
acatactgac ccgctgttcc ttgcatttgg gtaacaggag gggggtgttc ctaccttacc 3240
aatgcaattt gagtcacact aagatattgc ttgagcccga gagcatgtcc aaggtgaacc 3300
tgaacggggt gtttgacatg accatgaaga tctggaaggt gctgaggtac gatgagaccc 3360
gcaccaggtg cagaccctgc gagtgtggcg gtaaacatat taggaaccag cctgtgatgc 3420

-continued

```
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
```

```
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
tttccagtac tcttggatcg gaaacccgtc ggcctccgaa cggtaagagc ctagcatgta   7200
gaactggttg acggcctggt aggcgcagca tccctttttct acgggtagcg cgtatgcctg   7260
cgcggccttc cggagcgagg tgtgggtgag cgcaaaggtg tccctgacca tgactttgag   7320
gtactggtat ttgaagtcag tgtcgtcgca tccgccctgc tcccagagca aaaagtccgt   7380
gcgctttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat tttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
```

-continued

```
cacaaggaag cagagtggga atttgagccc ctcgcctggc gggtttggct ggtggtcttc   8220

tacttcggct gcttgtcctt gaccgtctgg ctgctcgagg ggagttacgg tggatcggac   8280

caccacgccg cgcgagccca aagtccagat gtccgcgcgc ggcggtcgga gcttgatgac   8340

aacatcgcgc agatgggagc tgtccatggt ctggagctcc cgcggcgtca ggtcaggcgg   8400

gagctcctgc aggtttacct cgcatagacg ggtcagggcg cgggctagat ccaggtgata   8460

cctaatttcc aggggctggt tggtggcggc gtcgatggct tgcaagaggc cgcatccccg   8520

cggcgcgact acggtaccgc gcggcgggcg gtgggccgcg ggggtgtcct tggatgatgc   8580

atctaaaagc ggtgacgcgg gcgagccccc ggaggtaggg ggggctccgg acccgccggg   8640

agagggggca ggggcacgtc ggcgccgcgc gcgggcagga gctggtgctg cgcgcgtagg   8700

ttgctggcga acgcgacgac gcggcggttg atctcctgaa tctggcgcct ctgcgtgaag   8760

acgacgggcc cggtgagctt gagcctgaaa gagagttcga cagaatcaat ttcggtgtcg   8820

ttgacggcgg cctggcgcaa aatctcctgc acgtctcctg agttgtcttg ataggcgatc   8880

tcggccatga actgctcgat ctcttcctcc tggagatctc cgcgtccggc tcgctccacg   8940

gtggcggcga ggtcgttgga aatgcgggcc atgagctgcg agaaggcgtt gaggcctccc   9000

tcgttccaga cgcggctgta gaccacgccc ccttcggcat cgcgggcgcg catgaccacc   9060

tgcgcgagat tgagctccac gtgccgggcg aagacggcgt agtttcgcag gcgctgaaag   9120

aggtagttga gggtggtggc ggtgtgttct gccacgaaga agtacataac ccagcgtcgc   9180

aacgtggatt cgttgatatc ccccaaggcc tcaaggcgct ccatggcctc gtagaagtcc   9240

acggcgaagt tgaaaaactg ggagttgcgc gccgacacgg ttaactcctc ctccagaaga   9300

cggatgagct cggcgacagt gtcgcgcacc tcgcgctcaa aggctacagg ggcctcttct   9360

tcttcttcaa tctcctcttc cataagggcc tccccttctt cttcttctgg cggcggtggg   9420

ggagggggga cacggcggcg acgacggcgc accgggaggc ggtcgacaaa gcgctcgatc   9480

atctccccgc ggcgacggcg catggtctcg gtgacggcgc ggccgttctc gcgggggcgc   9540

agttggaaga cgccgcccgt catgtcccgg ttatgggttg gcggggggct gccatgcggc   9600

agggatacgg cgctaacgat gcatctcaac aattgttgtg taggtactcc gccgccgagg   9660

gacctgagcg agtccgcatc gaccggatcg gaaaacctct cgagaaaggc gtctaaccag   9720

tcacagtcgc aaggtaggct gagcaccgtg gcgggcggca gcgggcggcg gtcggggttg   9780

tttctggcgg aggtgctgct gatgatgtaa ttaaagtagg cggtcttgag acggcggatg   9840

gtcgacagaa gcaccatgtc cttgggtccg gcctgctgaa tgcgcaggcg gtcggccatg   9900

ccccaggctt cgttttgaca tcggcgcagg tctttgtagt agtcttgcat gagcctttct   9960

accggcactt cttcttctcc ttcctcttgt cctgcatctc ttgcatctat cgctgcggcg  10020

gcggcggagt ttggccgtag gtggcgccct cttcctccca tgcgtgtgac cccgaagccc  10080

ctcatcggct gaagcagggc taggtcggcg acaacgcgct cggctaatat ggcctgctgc  10140

acctgcgtga gggtagactg gaagtcatcc atgtccacaa agcggtggta tgcgcccgtg  10200

ttgatggtgt aagtgcagtt ggccataacg gaccagttaa cggtctggtg acccggctgc  10260

gagagctcgg tgtacctgag acgcgagtaa gccctcgagt caaatacgta gtcgttgcaa  10320

gtccgcacca ggtactggta tcccaccaaa aagtgcggcg gcggctggcg gtagaggggc  10380

cagcgtaggg tggccggggc tccgggggcg agatcttcca acataaggcg atgatatccg  10440

tagatgtacc tggacatcca ggtgatgccg gcggcggtgg tggaggcgcg cggaaagtcg  10500

cggacgcggt tccagatgtt gcgcagcggc aaaaagtgct ccatggtcgg gacgctctgg  10560
```

```
ccggtcaggc gcgcgcaatc gttgacgctc tagaccgtgc aaaaggagag cctgtaagcg  10620
ggcactcttc cgtggtctgg tggataaatt cgcaagggta tcatggcgga cgaccggggt  10680
tcgagccccg tatccggccg tccgccgtga tccatgcggt taccgcccgc gtgtcgaacc  10740
caggtgtgcg acgtcagaca acgggggagt gctccttttg gcttccttcc aggcgcggcg  10800
gctgctgcgc tagctttttt ggccactggc cgcgcgcagc gtaagcggtt aggctggaaa  10860
gcgaaagcat taagtggctc gctccctgta gccggagggt tattttccaa gggttgagtc  10920
gcgggacccc cggttcgagt ctcggaccgg ccggactgcg gcgaacgggg gtttgcctcc  10980
ccgtcatgca agaccccgct tgcaaattcc tccggaaaca gggacgagcc ccttttttgc  11040
ttttcccaga tgcatccggt gctgcggcag atgcgccccc ctcctcagca gcggcaagag  11100
caagagcagc ggcagacatg cagggcaccc tcccctcctc ctaccgcgtc aggaggggcg  11160
acatccgcgg ttgacgcggc agcagatggt gattacgaac cccgcggcg ccgggcccgg   11220
cactacctgg acttggagga gggcgagggc ctggcgcggc taggagcgcc ctctcctgag  11280
cggtacccaa gggtgcagct gaagcgtgat acgcgtgagg cgtacgtgcc gcggcagaac  11340
ctgtttcgcg accgcgaggg agaggagccc gaggagatgc gggatcgaaa gttccacgca  11400
gggcgcgagc tgcggcatgg cctgaatcgc gagcggttgc tgcgcgagga ggactttgag  11460
cccgacgcgc gaaccgggat tagtcccgcg cgcgcacacg tggcggccgc cgacctggta  11520
accgcatacg agcagacggt gaaccaggag attaactttc aaaaaagctt taacaaccac  11580
gtgcgtacgc ttgtggcgcg cgaggaggtg gctataggac tgatgcatct gtgggacttt  11640
gtaagcgcgc tggagcaaaa cccaaatagc aagccgctca tggcgcagct gttccttata  11700
gtgcagcaca gcagggacaa cgaggcattc agggatgcgc tgctaaacat agtagagccc  11760
gagggccgct ggctgctcga tttgataaac atcctgcaga gcatagtggt gcaggagcgc  11820
agcttgagcc tggctgacaa ggtggccgcc atcaactatt ccatgcttag cctgggcaag  11880
ttttacgccc gcaagatata ccatacccct tacgttccca tagacaagga ggtaaagatc  11940
gaggggttct acatgcgcat ggcgctgaag gtgcttacct tgagcgacga cctgggcgtt  12000
tatcgcaacg agcgcatcca caaggccgtg agcgtgagcc ggcggcgcga gctcagcgac  12060
cgcgagctga tgcacagcct gcaaagggcc ctggctggca cgggcagcgg cgatagagag  12120
gccgagtcct actttgacgc gggcgctgac ctgcgctggg ccccaagccg acgcgccctg  12180
gaggcagctg gggccggacc tgggctggcg gtggcacccg cgcgcgctgg caacgtcggc  12240
ggcgtggagg aatatgacga ggacgatgag tacgagccag aggacggcga gtactaagcg  12300
gtgatgtttc tgatcagatg atgcaagacg caacggaccc ggcggtgcgg gcggcgctgc  12360
agagccagcc gtccggcctt aactccacgg acgactggcg ccaggtcatg gaccgcatca  12420
tgtcgctgac tgcgcgcaat cctgacgcgt tccggcagca gccgcaggcc aaccggctct  12480
ccgcaattct ggaagcggtg gtcccggcgc gcgcaaaccc cacgcacgag aaggtgctgg  12540
cgatcgtaaa cgcgctggcc gaaaacaggg ccatccggcc cgacgaggcc ggcctggtct  12600
acgacgcgct gcttcagcgc gtggctcgtt acaacagcgg caacgtgcag accaacctgg  12660
accggctggt gggggatgtg cgcgaggccg tggcgcagcg tgagcgcgcg cagcagcagg  12720
gcaacctggg ctccatggtt gcactaaacg ccttcctgag tacacagccc gccaacgtgc  12780
cgcggggaca ggaggactac accaactttg tgagcgcact gcggctaatg gtgactgaga  12840
caccgcaaag tgaggtgtac cagtctgggc cagactattt tttccagacc agtagacaag  12900
```

gcctgcagac cgtaaacctg agccaggctt tcaaaaactt gcaggggctg tggggggtgc 12960
gggctcccac aggcgaccgc gcgaccgtgt ctagcttgct gacgcccaac tcgcgcctgt 13020
tgctgctgct aatagcgccc ttcacggaca gtggcagcgt gtcccgggac acatacctag 13080
gtcacttgct gacactgtac cgcgaggcca taggtcaggc gcatgtggac gagcatactt 13140
tccaggagat tacaagtgtc agccgcgcgc tggggcagga ggacacgggc agcctggagg 13200
caaccctaaa ctacctgctg accaaccggc ggcagaagat cccctcgttg cacagtttaa 13260
acagcgagga ggagcgcatt ttgcgctacg tgcagcagag cgtgagcctt aacctgatgc 13320
gcgacggggt aacgcccagc gtggcgctgg acatgaccgc gcgcaacatg gaaccgggca 13380
tgtatgcctc aaaccggccg tttatcaacc gcctaatgga ctacttgcat cgcgcggccg 13440
ccgtgaaccc cgagtatttc accaatgcca tcttgaaccc gcactggcta ccgccccctg 13500
gtttctacac cgggggattc gaggtgcccg agggtaacga tggattcctc tgggacgaca 13560
tagacgacag cgtgttttcc ccgcaaccgc agaccctgct agagttgcaa cagcgcgagc 13620
aggcagaggc ggcgctgcga aaggaaagct tccgcaggcc aagcagcttg tccgatctag 13680
gcgctgcggc cccgcggtca gatgctagta gcccatttcc aagcttgata gggtctctta 13740
ccagcactcg caccacccgc ccgcgcctgc tgggcgagga ggagtaccta aacaactcgc 13800
tgctgcagcc gcagcgcgaa aaaaacctgc ctccggcatt tcccaacaac gggatagaga 13860
gcctagtgga caagatgagt agatggaaga cgtacgcgca ggagcacagg gacgtgccag 13920
gcccgcgccc gcccacccgt cgtcaaaggc acgaccgtca gcggggtctg gtgtgggagg 13980
acgatgactc ggcagacgac agcagcgtcc tggatttggg agggagtggc aacccgtttg 14040
cgcaccttcg ccccaggctg gggagaatgt tttaaaaaaa aaaaagcatg atgcaaaata 14100
aaaaactcac caaggccatg gcaccgagcg ttggttttct tgtattcccc ttagtatgcg 14160
gcgcgcggcg atgtatgagg aaggtcctcc tccctcctac gagagtgtgg tgagcgcggc 14220
gccagtggcg gcggcgctgg gttctccctt cgatgctccc ctggacccgc cgtttgtgcc 14280
tccgcggtac ctgcggccta ccggggggag aaacagcatc cgttactctg agttggcacc 14340
cctattcgac accacccgtg tgtacctggt ggacaacaag tcaacggatg tggcatccct 14400
gaactaccag aacgaccaca gcaactttct gaccacggtc attcaaaaca atgactacag 14460
cccgggggag gcaagcacac agaccatcaa tcttgacgac cggtcgcact ggggcggcga 14520
cctgaaaacc atcctgcata ccaacatgcc aaatgtgaac gagttcatgt ttaccaataa 14580
gtttaaggcg cgggtgatgg tgtcgcgctt gcctactaag gacaatcagg tggagctgaa 14640
atacgagtgg gtggagttca cgctgcccga gggcaactac tccgagacca tgaccataga 14700
ccttatgaac aacgcgatcg tggagcacta cttgaaagtg ggcagacaga acggggttct 14760
ggaaagcgac atcggggtaa agtttgacac ccgcaacttc agactggggt ttgaccccgt 14820
cactggtctt gtcatgcctg ggtatatac aaacgaagcc ttccatccag acatcatttt 14880
gctgccagga tgcggggtgg acttcaccca cagccgcctg agcaacttgt tgggcatccg 14940
caagcggcaa cccttccagg agggctttag gatcacctac gatgatctgg agggtggtaa 15000
cattcccgca ctgttggatg tggacgccta ccaggcgagc ttgaaagatg acaccgaaca 15060
gggcgggggt ggcgcaggcg gcagcaacag cagtggcagc ggcgcggaag agaactccaa 15120
cgcggcagcc gcggcaatgc agccggtgga ggacatgaac gatcatgcca ttcgcggcga 15180
cacctttgcc acacgggctg aggagaagcg cgctgaggcc gaagcagcgg ccgaagctgc 15240
cgcccccgct gcgcaacccg aggtcgagaa gcctcagaag aaaccggtga tcaaacccct 15300

-continued

```
gacagaggac agcaagaaac gcagttacaa cctaataagc aatgacagca ccttcaccca  15360
gtaccgcagc tggtaccttg catacaacta cggcgaccct cagaccggaa tccgctcatg  15420
gaccctgctt tgcactcctg acgtaacctg cggctcggag caggtctact ggtcgttgcc  15480
agacatgatg caagaccccg tgaccttccg ctccacgcgc cagatcagca actttccggt  15540
ggtgggcgcc gagctgttgc ccgtgcactc caagagcttc tacaacgacc aggccgtcta  15600
ctcccaactc atccgccagt ttacctctct gacccacgtg ttcaatcgct ttcccgagaa  15660
ccagattttg gcgcgcccgc cagcccccac catcaccacc gtcagtgaaa acgttcctgc  15720
tctcacagat cacgggacgc taccgctgcg caacagcatc ggaggagtcc agcgagtgac  15780
cattactgac gccagacgcc gcacctgccc ctacgtttac aaggccctgg gcatagtctc  15840
gccgcgcgtc ctatcgagcc gcactttttg agcaagcatg tccatcctta tatcgcccag  15900
caataacaca ggctggggcc tgcgcttccc aagcaagatg tttggcgggg ccaagaagcg  15960
ctccgaccaa cacccagtgc gcgtgcgcgg gcactaccgc gcgccctggg gcgcgcacaa  16020
acgcggccgc actgggcgca ccaccgtcga tgacgccatc gacgcggtgg tggaggaggc  16080
gcgcaactac acgcccacgc cgccaccagt gtccacagtg gacgcggcca ttcagaccgt  16140
ggtgcgcgga gcccggcgct atgctaaaat gaagagacgg cggaggcgcg tagcacgtcg  16200
ccaccgccgc cgacccggca ctgccgccca acgcgcggcg gcggccctgc ttaaccgcgc  16260
acgtcgcacc ggccgacggg cggccatgcg ggccgctcga aggctggccg cgggtattgt  16320
cactgtgccc cccaggtcca ggcgacgagc ggccgccgca gcagccgcgg ccattagtgc  16380
tatgactcag ggtcgcaggg gcaacgtgta ttgggtgcgc gactcggtta gcggcctgcg  16440
cgtgcccgtg cgcacccgcc ccccgcgcaa ctagattgca agaaaaaact acttagactc  16500
gtactgttgt atgtatccag cggcggcggc gcgcaacgaa gctatgtcca agcgcaaaat  16560
caaagaagag atgctccagg tcatcgcgcc ggagatctat ggccccccga agaaggaaga  16620
gcaggattac aagccccgaa agctaaagcg ggtcaaaaag aaaaagaaag atgatgatga  16680
tgaacttgac gacgaggtgg aactgctgca cgctaccgcg cccaggcgac gggtacagtg  16740
gaaaggtcga cgcgtaaaac gtgttttgcg acccggcacc accgtagtct ttacgcccgg  16800
tgagcgctcc acccgcacct acaagcgcgt gtatgatgag gtgtacggcg acgaggacct  16860
gcttgagcag gccaacgagc gcctcgggga gtttgcctac ggaaagcggc ataaggacat  16920
gctggcgttg ccgctggacg agggcaaccc aacacctagc ctaaagcccg taacactgca  16980
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
```

-continued

```
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag gggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
```

```
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aaccttttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat atttttgggc cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
```

aaatgctttt atttgtacac tctcgggtga ttatttaccc ccacccttgc cgtctgcgcc 22440
gtttaaaaat caaaggggtt ctgccgcgca tcgctatgcg ccactggcag ggacacgttg 22500
cgatactggt gtttagtgct ccacttaaac tcaggcacaa ccatccgcgg cagctcggtg 22560
aagttttcac tccacaggct gcgcaccatc accaacgcgt ttagcaggtc gggcgccgat 22620
atcttgaagt cgcagttggg gcctccgccc tgcgcgcgcg agttgcgata cacagggttg 22680
cagcactgga acactatcag cgccgggtgg tgcacgctgg ccagcacgct cttgtcggag 22740
atcagatccg cgtccaggtc ctccgcgttg ctcagggcga acggagtcaa ctttggtagc 22800
tgccttccca aaaagggcgc gtgcccaggc tttgagttgc actcgcaccg tagtggcatc 22860
aaaaggtgac cgtgcccggt ctgggcgtta ggatacagcg cctgcataaa agccttgatc 22920
tgcttaaaag ccacctgagc ctttgcgcct tcagagaaga acatgccgca agacttgccg 22980
gaaaactgat tggccggaca ggccgcgtcg tgcacgcagc accttgcgtc ggtgttggag 23040
atctgcacca catttcggcc ccaccggttc ttcacgatct tggccttgct agactgctcc 23100
ttcagcgcgc gctgcccgtt ttcgctcgtc acatccattt caatcacgtg ctccttattt 23160
atcataatgc ttccgtgtag acacttaagc tcgccttcga tctcagcgca gcggtgcagc 23220
cacaacgcgc agcccgtggg ctcgtgatgc ttgtaggtca cctctgcaaa cgactgcagg 23280
tacgcctgca ggaatcgccc catcatcgtc acaaaggtct tgttgctggt gaaggtcagc 23340
tgcaacccgc ggtgctcctc gttcagccag gtcttgcata cggccgccag agcttccact 23400
tggtcaggca gtagtttgaa gttcgccttt agatcgttat ccacgtggta cttgtccatc 23460
agcgcgcgcg cagcctccat gcccttctcc cacgcagaca cgatcggcac actcagcggg 23520
ttcatcaccg taatttcact ttccgcttcg ctgggctctt cctcttcctc ttgcgtccgc 23580
ataccacgcg ccactgggtc gtcttcattc agccgccgca ctgtgcgctt acctcctttg 23640
ccatgcttga ttagcaccgg tgggttgctg aaacccacca tttgtagcgc cacatcttct 23700
ctttcttcct cgctgtccac gattacctct ggtgatggcg ggcgctcggg cttgggagaa 23760
gggcgcttct ttttcttctt gggcgcaatg gccaaatccg ccgccgaggt cgatggccgc 23820
gggctgggtg tgcgcggcac cagcgcgtct tgtgatgagt cttcctcgtc ctcggactcg 23880
atacgccgcc tcatccgctt ttttgggggc gcccggggag gcggcggcga cggggacggg 23940
gacgacacgt cctccatggt tgggggacgt cgcgccgcac cgcgtccgcg ctcgggggtg 24000
gtttcgcgct gctcctcttc ccgactggcc atttccttct cctataggca gaaaaagatc 24060
atggagtcag tcgagaagaa ggacagccta accgcccccct ctgagttcgc caccaccgcc 24120
tccaccgatg ccgccaacgc gcctaccacc ttccccgtcg aggcaccccc gcttgaggag 24180
gaggaagtga ttatcgagca ggacccaggt tttgtaagcg aagacgacga ggaccgctca 24240
gtaccaacag aggataaaaa gcaagaccag gacaacgcag aggcaaacga ggaacaagtc 24300
gggcgggggg acgaaaggca tggcgactac ctagatgtgg gagacgacgt gctgttgaag 24360
catctgcagc gccagtgcgc cattatctgc gacgcgttgc aagagcgcag cgatgtgccc 24420
ctcgccatag cggatgtcag ccttgcctac gaacgccacc tattctcacc gcgcgtaccc 24480
cccaaacgcc aagaaaacgg cacatgcgag cccaacccgc gcctcaactt ctaccccgta 24540
tttgccgtgc cagaggtgct tgccacctat cacatctttt tccaaaactg caagataccc 24600
ctatcctgcc gtgccaaccg cagccgagcg gacaagcagc tggccttgcg gcagggcgct 24660
gtcatacctg atatcgcctc gctcaacgaa gtgccaaaaa tctttgaggg tcttggacgc 24720
gacgagaagc gcgcggcaaa cgctctgcaa caggaaaaca gcgaaaatga aagtcactct 24780
ggagtgttgg tggaactcga gggtgacaac gcgcgcctag ccgtactaaa acgcagcatc 24840
gaggtcaccc actttgccta cccggcactt aacctacccc ccaaggtcat gagcacagtc 24900
atgagtgagc tgatcgtgcg ccgtgcgcag cccctggaga gggatgcaaa tttgcaagaa 24960
caaacagagg agggcctacc cgcagttggc gacgagcagc tagcgcgctg gcttcaaacg 25020
cgcgagcctg ccgacttgga ggagcgacgc aaactaatga tggccgcagt gctcgttacc 25080
gtggagcttg agtgcatgca gcggttcttt gctgacccgg agatgcagcg caagctagag 25140
gaaacattgc actacacctt tcgacagggc tacgtacgcc aggcctgcaa gatctccaac 25200
gtggagctct gcaacctggt ctcctacctt ggaattttgc acgaaaaccg ccttgggcaa 25260
aacgtgcttc attccacgct caagggcgag gcgcgccgcg actacgtccg cgactgcgtt 25320
tacttatttc tatgctacac ctggcagacg gccatgggcg tttggcagca gtgcttggag 25380
gagtgcaacc tcaaggagct gcagaaactg ctaaagcaaa acttgaagga cctatggacg 25440
gccttcaacg agcgctccgt ggccgcgcac ctggcggaca tcattttccc cgaacgcctg 25500
cttaaaaccc tgcaacaggg tctgccagac ttcaccagtc aaagcatgtt gcagaacttt 25560
aggaacttta tcctagagcg ctcaggaatc ttgcccgcca cctgctgtgc acttcctagc 25620
gactttgtgc ccattaagta ccgcgaatgc cctccgccgc tttggggcca ctgctacctt 25680
ctgcagctag ccaactacct tgcctaccac tctgacataa tggaagacgt gagcggtgac 25740
ggtctactgg agtgtcactg tcgctgcaac ctatgcaccc cgcaccgctc cctggtttgc 25800
aattcgcagc tgcttaacga aagtcaaatt atcggtacct ttgagctgca gggtccctcg 25860
cctgacgaaa agtccgcggc tccggggttg aaactcactc cggggctgtg gacgtcggct 25920
taccttcgca aatttgtacc tgaggactac cacgcccacg agattaggtt ctacgaagac 25980
caatcccgcc cgccaaatgc ggagcttacc gcctgcgtca ttacccaggg ccacattctt 26040
ggccaattgc aagccatcaa caaagcccgc caagagtttc tgctacgaaa gggacggggg 26100
gtttacttgg acccccagtc cggcgaggag ctcaacccaa tcccccgcc gccgcagccc 26160
tatcagcagc agccgcgggc ccttgcttcc caggatggca cccaaaaaga agctgcagct 26220
gccgccgcca cccacggacg aggaggaata ctgggacagt caggcagagg aggttttgga 26280
cgaggaggag gaggacatga tggaagactg ggagagccta gacgaggaag cttccgaggt 26340
cgaagaggtg tcagacgaaa caccgtcacc ctcggtcgca ttcccctcgc cggcgcccca 26400
gaaatcggca accggttcca gcatggctac aacctccgct cctcaggcgc cgccggcact 26460
gcccgttcgc cgacccaacc gtagatggga caccactgga accagggccg gtaagtccaa 26520
gcagccgccg ccgttagccc aagagcaaca acagcgccaa ggctaccgct catggcgcgg 26580
gcacaagaac gccatagttg cttgcttgca agactgtggg ggcaacatct ccttcgcccg 26640
ccgctttctt ctctaccatc acggcgtggc cttcccccgt aacatcctgc attactaccg 26700
tcatctctac agcccatact gcaccggcgg cagcggcagc ggcagcaaca gcagcggcca 26760
cacagaagca aaggcgaccg gatagcaaga ctctgacaaa gcccaagaaa tccacagcgg 26820
cggcagcagc aggaggagga gcgctgcgtc tggcgcccaa cgaacccgta tcgacccgcg 26880
agcttagaaa caggattttt cccactctgt atgctatatt tcaacagagc aggggccaag 26940
aacaagagct gaaaataaaa aacaggtctc tgcgatccct cacccgcagc tgcctgtatc 27000
acaaaagcga agatcagctt cggcgcacgc tggaagacgc ggaggctctc ttcagtaaat 27060
actgcgcgct gactcttaag gactagtttc gcgccctttc tcaaatttaa gcgcgaaaac 27120

-continued

```
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgcccccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggctcctat  28200
cgccatcctg taaacgccac cgtcttcacc cgcccaagca aaccaaggcg aaccttacct  28260
ggtactttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500
aaaaccctta gggtattagg ccaaaggcgc agctactgtg gggtttatga acaattcaag  28560
caactctacg ggctattcta attcaggttt ctctagaatc ggggttgggg ttattctctg  28620
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acggtaccac ccaaaaggtg  28800
gattttaagg agccagcctg taatgttaca ttcgcagctg aagctaatga gtgcaccact  28860
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aacttttatg tatactttc cattttatga aatgtgcgac  29040
attaccatgt acatgagcaa acagtataag ttgtggcccc cacaaaattg tgtggaaaac  29100
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca accttgaagt  29400
caggcttcct ggatgtcagc atctgacttt ggccagcacc tgtcccgcgg atttgttcca  29460
gtccaactac agcgacccac cctaacagag atgaccaaca caaccaacgc ggccgccgct  29520
```

-continued

```
accggactta catctaccac aaatacaccc caagtttctg cctttgtcaa taactgggat  29580
aacttgggca tgtggtggtt ctccatagcg cttatgtttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg acccttgttg  29820
cgcttttttg tgcgtgctcc acattggctg cggtttctca catcgaagta gactgcattc  29880
cagccttcac agtctatttg ctttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttcccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc acccaacttt ccccgcgccc gctatgcttc cactgcaaca  30360
agttgttgcc ggcggctttg tcccagccaa tcagcctcgc cccacttctc ccaccccccac  30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
actatcttca tgttgttgca gatgaagcgc gcaagaccgt ctgaagatac cttcaacccc  31080
gtgtatccat atgacacgga aaccggtcct ccaactgtgc cttttcttac tcctcccttt  31140
gtatcccccca atgggtttca agagagtccc cctggggtac tctctttgcg cctatccgaa  31200
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga agccctaact  31380
gtggctgccg ccgcacctct aatggtcgcg ggcaacacac tcaccatgca atcacaggcc  31440
ccgctaaccg tgcacgactc caaacttagc attgccaccc aaggacccct cacagtgtca  31500
gaaggaaagc tagccctgca aacatcaggc cccctcacca ccaccgatag cagtaccctt  31560
actatcactg cctcaccccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
```

-continued

```
tatccgtttg atgctcaaaa ccaactaaat ctaagactag gacagggccc tctttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760
actttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
tggcttcggg ttctatgtaa actccttcat gcgccgctgc cctgataaca tccaccaccg  34260
```

```
cagaataagc cacacccagc caacctacac attcgttctg cgagtcacac acgggaggag  34320
cgggaagagc tggaagaacc atgttttttt ttttattcca aaagattatc caaaacctca  34380
aaatgaagat ctattaagtg aacgcgctcc cctccggtgg cgtggtcaaa ctctacagcc  34440
aaagaacaga taatggcatt tgtaagatgt tgcacaatgg cttccaaaag gcaaacggcc  34500
ctcacgtcca agtggacgta aaggctaaac ccttcagggt gaatctcctc tataaacatt  34560
ccagcacctt caaccatgcc caaataattc tcatctcgcc accttctcaa tatatctcta  34620
agcaaatccc gaatattaag tccggccatt gtaaaaatct gctccagagc gccctccacc  34680
ttcagcctca agcagcgaat catgattgca aaaattcagg ttcctcacag acctgtataa  34740
gattcaaaag cggaacatta acaaaaatac cgcgatcccg taggtccctt cgcagggcca  34800
gctgaacata atcgtgcagg tctgcacgga ccagcgcggc cacttccccg ccaggaacca  34860
tgacaaaaga acccacactg attatgacac gcatactcgg agctatgcta accagcgtag  34920
ccccgatgta agcttgttgc atgggcggcg atataaaatg caaggtgctg ctcaaaaaat  34980
caggcaaagc ctcgcgcaaa aaagaaagca catcgtagtc atgctcatgc agataaaggc  35040
aggtaagctc cggaaccacc acagaaaaag acaccatttt tctctcaaac atgtctgcgg  35100
gtttctgcat aaacacaaaa taaaataaca aaaaaacatt taaacattag aagcctgtct  35160
tacaacagga aaaacaaccc ttataagcat aagacggact acggccatgc cggcgtgacc  35220
gtaaaaaaac tggtcaccgt gattaaaaag caccaccgac agctcctcgg tcatgtccgg  35280
agtcataatg taagactcgg taaacacatc aggttgattc acatcggtca gtgctaaaaa  35340
gcgaccgaaa tagcccgggg gaatacatac ccgcaggcgt agagacaaca ttacagcccc  35400
cataggaggt ataacaaaat taataggaga gaaaaacaca taaacacctg aaaaaccctc  35460
ctgcctaggc aaaatagcac cctcccgctc cagaacaaca tacagcgctt ccacagcggc  35520
agccataaca gtcagcctta ccagtaaaaa agaaaaccta ttaaaaaaac accactcgac  35580
acggcaccag ctcaatcagt cacagtgtaa aaaagggcca agtgcagagc gagtatatat  35640
aggactaaaa aatgacgtaa cggttaaagt ccacaaaaaa cacccagaaa accgcacgcg  35700
aacctacgcc cagaaacgaa agccaaaaaa cccacaactt cctcaaatcg tcacttccgt  35760
tttcccacgt tacgtaactt cccattttaa gaaaactaca attcccaaca catacaagtt  35820
actccgccct aaaacctacg tcacccgccc cgttcccacg ccccgcgcca cgtcacaaac  35880
tccacccccct cattatcata ttggcttcaa tccaaaataa ggtatattat tgatgatg   35938
```

<210> SEQ ID NO 47
<211> LENGTH: 2424
<212> TYPE: DNA
<213> ORGANISM: Adenovirus type 5

<400> SEQUENCE: 47

```
atggagtcag tcgagaagaa ggacagccta accgcccccct ctgagttcgc caccaccgcc     60
tccaccgatg ccgccaacgc gcctaccacc ttccccgtcg aggcaccccc gcttgaggag    120
gaggaagtga ttatcgagca ggacccaggt tttgtaagcg aagacgacga ggaccgctca    180
gtaccaacag aggataaaaa gcaagaccag gacaacgcag aggcaaacga ggaacaagtc    240
gggcgggggg acgaaaggca tggcgactac ctagatgtgg gagacgacgt gctgttgaag    300
catctgcagc gccagtgcgc cattatctgc gacgcgttgc aagagcgcag cgatgtgccc    360
ctcgccatag cggatgtcag ccttgcctac gaacgccacc tattctcacc gcgcgtaccc    420
```

-continued cccaaacgcc aagaaaacgg cacatgcgag cccaacccgc gcctcaactt ctaccccgta 480
tttgccgtgc cagaggtgct tgccacctat cacatctttt tccaaaactg caagataccc 540
ctatcctgcc gtgccaaccg cagccgagcg gacaagcagc tggccttgcg gcagggcgct 600
gtcatacctg atatcgcctc gctcaacgaa gtgccaaaaa tctttgaggg tcttggacgc 660
gacgagaagc gcgcggcaaa cgctctgcaa caggaaaaca gcgaaaatga aagtcactct 720
ggagtgttgg tggaactcga gggtgacaac gcgcgcctag ccgtactaaa acgcagcatc 780
gaggtcaccc actttgccta cccggcactt aacctacccc ccaaggtcat gagcacagtc 840
atgagtgagc tgatcgtgcg ccgtgcgcag cccctggaga gggatgcaaa tttgcaagaa 900
caaacagagg agggcctacc cgcagttggc gacgagcagc tagcgcgctg gcttcaaacg 960
cgcgagcctg ccgacttgga ggagcgacgc aaactaatga tggccgcagt gctcgttacc 1020
gtggagcttg agtgcatgca gcggttcttt gctgacccgg agatgcagcg caagctagag 1080
gaaacattgc actacacctt tcgacagggc tacgtacgcc aggcctgcaa gatctccaac 1140
gtggagctct gcaacctggt ctcctacctt ggaattttgc acgaaaaccg ccttgggcaa 1200
aacgtgcttc attccacgct caagggcgag gcgcgccgcg actacgtccg cgactgcgtt 1260
tacttatttc tatgctacac ctggcagacg gccatgggcg tttggcagca gtgcttggag 1320
gagtgcaacc tcaaggagct gcagaaactg ctaaagcaaa acttgaagga cctatggacg 1380
gccttcaacg agcgctccgt ggccgcgcac ctggcggaca tcattttccc cgaacgcctg 1440
cttaaaaccc tgcaacaggg tctgccagac ttcaccagtc aaagcatgtt gcagaacttt 1500
aggaacttta tcctagagcg ctcaggaatc ttgcccgcca cctgctgtgc acttcctagc 1560
gactttgtgc ccattaagta ccgcgaatgc cctccgccgc tttggggcca ctgctacctt 1620
ctgcagctag ccaactacct tgcctaccac tctgacataa tggaagacgt gagcggtgac 1680
ggtctactgg agtgtcactg tcgctgcaac ctatgcaccc cgcaccgctc cctggtttgc 1740
aattcgcagc tgcttaacga aagtcaaatt atcggtacct ttgagctgca gggtccctcg 1800
cctgacgaaa agtccgcggc tccggggttg aaactcactc cggggctgtg gacgtcggct 1860
taccttcgca aatttgtacc tgaggactac cacgcccacg agattaggtt ctacgaagac 1920
caatcccgcc cgccaaatgc ggagcttacc gcctgcgtca ttacccaggg ccacattctt 1980
ggccaattgc aagccatcaa caaagcccgc caagagtttc tgctacgaaa gggacggggg 2040
gtttacttgg acccccagtc cggcgaggag ctcaacccaa tccccccgcc gccgcagccc 2100
tatcagcagc agccgcgggc ccttgcttcc caggatggca cccaaaaaga agctgcagct 2160
gccgccgcca cccacggacg aggaggaata ctgggacagt caggcagagg aggttttgga 2220
cgaggaggag gaggacatga tggaagactg ggagagccta gacgaggaag cttccgaggt 2280
cgaagaggtg tcagacgaaa caccgtcacc ctcggtcgca ttcccctcgc cggcgcccca 2340
gaaatcggca accggttcca gcatggctac aacctccgct cctcaggcgc cgccggcact 2400
gcccgttcgc cgacccaacc gtag 2424

<210> SEQ ID NO 48
<211> LENGTH: 1248
<212> TYPE: DNA
<213> ORGANISM: Adenovirus type 5

<400> SEQUENCE: 48
atgcatccgg tgctgcggca gatgcgcccc cctcctcagc agcggcaaga gcaagagcag 60
cggcagacat gcagggcacc ctcccctcct cctaccgcgt caggaggggc gacatccgcg 120

```
gttgacgcgg cagcagatgg tgattacgaa cccccgcggc gccgggcccg gcactacctg    180

gacttggagg agggcgaggg cctggcgcgg ctaggagcgc cctctcctga gcggcaccca    240

agggtgcagc tgaagcgtga tacgcgtgag gcgtacgtgc cgcggcagaa cctgtttcgc    300

gaccgcgagg gagaggagcc cgaggagatg cgggatcgaa agttccacgc agggcgcgag    360

ctgcggcatg gcctgaatcg cgagcggttg ctgcgcgagg aggactttga gcccgacgcg    420

cgaaccggga ttagtcccgc gcgcgcacac gtggcggccg ccgacctggt aaccgcatac    480

gagcagacgg tgaaccagga gattaacttt caaaaaagct ttaacaacca cgtgcgtacg    540

cttgtggcgc gcgaggaggt ggctatagga ctgatgcatc tgtgggactt tgtaagcgcg    600

ctggagcaaa acccaaatag caagccgctc atggcgcagc tgttccttat agtgcagcac    660

agcagggaca acgaggcatt cagggatgcg ctgctaaaca tagtagagcc cgagggccgc    720

tggctgctcg atttgataaa catcctgcag agcatagtgg tgcaggagcg cagcttgagc    780

ctggctgaca aggtggccgc catcaactat tccatgctta gcctgggcaa gttttacgcc    840

cgcaagatat accatacccc ttacgttccc atagacaagg aggtaaagat cgaggggttc    900

tacatgcgca tggcgctgaa ggtgcttacc ttgagcgacg acctgggcgt ttatcgcaac    960

gagcgcatcc acaaggccgt gagcgtgagc cggcggcgcg agctcagcga ccgcgagctg   1020

atgcacagcc tgcaaagggc cctggctggc acgggcagcg gcgatagaga ggccgagtcc   1080

tactttgacg cgggcgctga cctgcgctgg gccccaagcc gacgcgccct ggaggcagct   1140

ggggccggac ctgggctggc ggtggcaccc gcgcgcgctg gcaacgtcgg cggcgtggag   1200

gaatatgacg aggacgatga gtacgagcca gaggacggcg agtactaa                1248
```

<210> SEQ ID NO 49
<211> LENGTH: 2016
<212> TYPE: DNA
<213> ORGANISM: Adenovirus type 5

<400> SEQUENCE: 49

```
atggccttga gcgtcaacga ttgcgcgcgc ctgaccggcc agagcgtccc gaccatggag     60

cactttttgc cgctgcgcaa catctggaac cgcgtccgcg actttccgcg cgcctccacc    120

accgccgccg gcatcacctg gatgtccagg tacatctacg gatatcatcg ccttatgttg    180

gaagatctcg cccccggagc ccccggccacc ctacgctggc ccctctaccg ccagccgccg    240

ccgcactttt tggtgggata ccagtacctg gtgcggactt gcaacgacta cgtatttgac    300

tcgagggctt actcgcgtct caggtacacc gagctctcgc agccgggtca ccagaccgtt    360

aactggtccg ttatggccaa ctgcacttac accatcaaca cgggcgcata ccaccgcttt    420

gtggacatgg atgacttcca gtctaccctc acgcaggtgc agcaggccat attagccgag    480

cgcgttgtcg ccgacctagc cctgcttcag ccgatgaggg gcttcggggt cacacgcatg    540

ggaggaagag ggcgccacct acggccaaac tccgccgccg ccgcagcgat agatgcaaga    600

gatgcaggac aagaggaagg agaagaagaa gtgccggtag aaaggctcat gcaagactac    660

tacaaagacc tgcgccgatg tcaaaacgaa gcctggggca tggccgaccg cctgcgcatt    720

cagcaggccg gacccaagga catggtgctt ctgtcgacca tccgccgtct caagaccgcc    780

tactttaatt acatcatcag cagcacctcc gccagaaaca accccgaccg ccgcccgctg    840

ccgcccgcca cggtgctcag cctaccttgc gactgtgact ggttagacgc ctttctcgag    900

aggttttccg atccggtcga tgcggactcg ctcaggtccc tcggcggcgg agtacctaca    960
```

-continued

```
caacaattgt tgagatgcat cgttagcgcc gtatccctgc cgcatggcag ccccccgcca   1020

acccataacc gggacatgac gggcggcgtc ttccaactgc gcccccgcga gaacggccgc   1080

gccgtcaccg agaccatgcg ccgtcgccgc ggggagatga tcgagcgctt tgtcgaccgc   1140

ctcccggtgc gccgtcgtcg ccgccgtgtc cccccctcccc caccgccgcc agaagaagaa   1200

gaaggggagg cccttatgga agaggagatt gaagaagaag aagaggcccc tgtagccttt   1260

gagcgcgagg tgcgcgacac tgtcgccgag ctcatccgtc ttctggagga ggagttaacc   1320

gtgtcggcgc gcaactccca gtttttcaac ttcgccgtgg acttctacga ggccatggag   1380

cgccttgagg ccttgggggga tatcaacgaa tccacgttgc gacgctgggt tatgtacttc   1440

ttcgtggcag aacacaccgc caccaccctc aactacctct ttcagcgcct gcgaaactac   1500

gccgtcttcg cccggcacgt ggagctcaat ctcgcgcagg tggtcatgcg cgcccgcgat   1560

gccgaagggg gcgtggtcta cagccgcgtc tggaacgagg gaggcctcaa cgccttctcg   1620

cagctcatgg cccgcatttc caacgacctc gccgccaccg tggagcgagc cggacgcgga   1680

gatctccagg aggaagagat cgagcagttc atggccgaga tcgcctatca agacaactca   1740

ggagacgtgc aggagatttt gcgccaggcc gccgtcaacg acaccgaaat tgattctgtc   1800

gaactctctt tcaggctcaa gctcaccggg cccgtcgtct tcacgcagag gcgccagatt   1860

caggagatca accgccgcgt cgtcgcgttc gccagcaacc tacgcgcgca gcaccagctc   1920

ctgcccgcgc gcggcgccga cgtgcccctg ccccctctcc cggcgggtcc ggagcccccc   1980

ctacctccgg gggctcgccc gcgtcaccgc ttttag                            2016
```

LIFE-CYCLE-DEFECTIVE ADENOVIRUS HELPER VIRUSES, THEIR PRODUCTION AND USE FOR PRODUCING rAAV

SUMMARY

The present invention generally concerns the production of life-cycle-defective Adenovirus helper viruses for producing a recombinant adeno-associated virus (rAAV), wherein the Adenovirus helper virus contains at least one mutation selected from (a) an inactivating mutation in the transcription unit coding for the L4-100K protein; (b) an inactivating mutation in the transcription unit coding for the L1-52/55K protein; (c) an inactivating mutation in the transcription unit coding for the preterminal protein (pTP); (d) a mutation in the L4-100K protein in order to render it temperature-sensitive (ts); (e) a mutation in the hexon protein in order to render it temperature-sensitive (ts); and/or (f) a mutation in the L4-100K protein and a mutation in the hexon protein in order to render it temperature-sensitive (ts).

INCORPORATION OF ELECTRONIC SEQUENCE LISTING

The electronic sequence listing, submitted herewith as an ASCII text file named 110272-01_ST25.txt (247,118 bytes), created on Oct. 10, 2023, is herein incorporated by reference in its entirety.

BACKGROUND

Adeno-associated virus (AAV) vectors have considerable potential for gene therapy due to their promising safety profile and their ability to transduce many tissues in vivo. However, production is still quite difficult and complex and scale-up of production at an industrial scale has been accomplished only to a limited degree. One reason is that AAV virus production depends on a co-infection with a helper virus to propagate and establish a productive life-cycle. Infection of cells with a replication competent helper virus, e.g. an adenovirus, for the production of recombinant AAV vectors harbors the disadvantage that rAAV stocks are contaminated with helper virus, requiring validated virus removal steps in the down-stream purification process. Using life-cycle-defective adenovirus mutants to provide the helper functions would allow for an infection-based production system for rAAV, reducing subsequent down-stream processes and therefore increasing suitability for large-scale biopharmaceutical production by enhancing safety and efficiency, as well as avoiding the production cost of plasmids otherwise required to supply helper virus functions.

BRIEF DESCRIPTION OF THE INVENTION

One subject-matter of the present invention concerns a method for producing a recombinant adeno-associated virus (rAAV), said method comprising the steps of:

(1) providing a suitable host cell containing at least one rAAV construct, (2) infecting said host cell with a life-cycle-defective Adenovirus helper virus selected from (a) an Adenovirus helper virus containing an inactivating mutation in the transcription unit coding for the L4-100K protein;

(b) an Adenovirus helper virus containing an inactivating mutation in the transcription unit coding for the L1-52/55K protein;

(c) an Adenovirus helper virus containing only an inactivating N-terminal deletion in the transcription unit coding for the preterminal protein (pTP) in order to render it non-functional;

(d) an Adenovirus helper virus containing a mutation in the L4-100K protein in order to render it temperature-sensitive (ts);

(e) an Adenovirus helper virus containing a mutation in the hexon protein in order to render it temperature-sensitive; and/or (f) an Adenovirus helper virus containing a mutation in the L4-100K protein and a mutation in the hexon protein in order to render it temperature-sensitive, and (3) incubating said cell until rAAV is produced. The above-described steps also constitute a method for reducing or eliminating Adenoviral helper virus contamination in rAAV preparations produced by infection-based provision of Adenoviral helper functions.

An "inactivating mutation" means a mutation in the transcription unit which renders the gene or protein encoded by the gene non-functional. The mutation can be a deletion, substitution or addition of nucleotides which either destroys the expression of the gene or leads to the expression of a non-functional, i.e. inactive protein product. In particular, the L4-100K protein mutant and the ts mutants are capsid defective, i.e. no capsids can be formed; the L1-52/55K protein mutant is packaging deficient, i.e. no encapsidation of the nucleic acid can occur, and the pTP protein mutant is replication defective, i.e. no DNA replication can occur. Consequently, such mutants are life-cycle-defective mutants of the Adenovirus helper virus, hereinafter also referred to as "life-cycle-defective Adenovirus helper virus".

According to the present invention, "life-cycle-defective" generally means that new helper virus, i.e. progeny, infection competent virus can essentially not be produced in a non-complementing cell or at high temperature, i.e. in case of is mutations, as shown below.

Preferred examples of inactivating mutations are as follows.

In a specific embodiment the mutation in the transcription unit coding for the L4-100K protein is a deletion mutant, in particular wherein the hexon-binding element, the elF4G-binding element, the nuclear-export signal and/or the RNA-recognition motif (RRN) are rendered non-functional, preferably wherein the deletion corresponds to at least nucleotides 25200-25400 of SEQ ID NO: 46 (NCBI Ref. No. AC_000008.1), in particular nucleotides 25000-25600 of SEQ ID NO: 46, more in particular nucleotides 24889-25699 of SEQ ID NO: 46, or nucleotides 24773-25887 of SEQ ID NO: 46, or nucleotides 24061-24665 of SEQ ID NO: 46, or nucleotides 24061-24665 plus nucleotides 24889-25699 of SEQ ID NO: 46, or nucleotides 24061-24665 plus nucleotides 24889-25887 of SEQ ID NO: 46, especially wherein the remaining L4-100K coding sequence consists of SEQ ID NO: 1 (FIG. 3). Adenovirus serotype 5 also serves as a reference virus with respect to the nucleic acid positions for all other Adenoviruses recited herein. Corresponding nucleic acid positions of other Adenoviruses or serotypes can be identified by routine sequence alignment.

In another specific embodiment the mutation in the transcription unit coding for the L1-52/55K protein is a deletion mutant, in particular wherein the deletion corresponds to at least nucleotides 11500-12000 of SEQ ID NO: 46, more in particular nucleotides 11050-12184 of SEQ ID NO: 46, or nucleotides 11050-12297 of SEQ ID NO: 46 (FIG. 7).

In another specific embodiment the N-terminal deletion in the transcription unit coding for pTP corresponds to at least nucleotides 10100-10300 of SEQ ID NO: 46, in particular nucleotides 9904-10589 of SEQ ID NO: 46, or nucleotides 9734-10589 of SEQ ID NO: 46, especially wherein the remaining pTP coding sequence consists of the sequence of SEQ ID NO: 3 (FIG. 11).

In another specific embodiment the mutation in the L4-100K protein is a mutation at position 25456, in particular a TCC to CCC mutation located at positions 25456-25458 of SEQ ID NO: 46, or a TCC to CCA mutation located at positions 25456-25458 of SEQ ID NO: 46, or a TCC to CCG mutation located at positions 25456-25458 of SEQ ID NO: 46, or a TCC to CCT mutation located at positions 25456-25458 of SEQ ID NO: 46, preferably a TCC to CCC mutation located at positions 25456-25458 of SEQ ID NO: 46.

In another specific embodiment the mutation in the hexon protein is a point mutation at positions 21171-21172, in particular a GGC to GAT mutation located at positions 21170-21172 of SEQ ID NO: 46, or a GGC to GAO mutation located at positions 21170-21172 of SEQ ID NO: 46, preferably a GGC to GAT mutation located at positions 21170-21172 of SEQ ID NO: 46.

The rAAV construct preferably comprises (a) a construct expressing at least one AAV Rep protein and at least one AAV Cap protein and a construct containing a pair of ITR sequences flanking (i) a heterologous nucleic acid coding for a nucleic acid of interest, or (ii) a unique cloning site for cloning a heterologous nucleic acid coding for a nucleic acid of interest, (b) a construct expressing at least one AAV Rep protein, a construct expressing at least one AAV Cap protein and a construct containing a pair of ITR sequences flanking (i) a heterologous nucleic acid coding for a nucleic acid of interest, or (ii) a unique cloning site for cloning a heterologous nucleic acid coding for a nucleic acid of interest, or (c) a construct expressing at least one AAV Rep protein, at least one AAV Cap protein and containing a pair of ITR sequences flanking (i) a heterologous nucleic acid coding for a nucleic acid of interest, or (ii) a unique cloning site for cloning a heterologous nucleic acid coding for a nucleic acid of interest.

Generally it is preferred that the life-cycle-defective Adenovirus helper virus codes for a functional viral associated (VA) RNA I and II, a functional E2A protein and a functional E4ORF6/7 protein, and optionally also for a functional E1A protein and/or a functional E1B protein, in particular a functional E1B 55K protein.

Generally, the Adenovirus helper virus is selected or derived from a serotype of subgroup A, B, C, D, E, F and/or G, in particular the Adenovirus is selected or derived from at least one of adenovirus type 1 to 57, preferably the Adenovirus is selected or derived from Adenovirus type 2 (Ad2) or Adenovirus type 5 (Ad5), more preferably from human Ad2 (hAd2) or human Ad5 (hAd5). As noted above, Adenovirus type 5 serves as a reference Adenovirus for the sequences recited herein. Starting from this reference Adenovirus, engineered mutations can be made in other Adenoviruses by sequence alignments.

Preferably the suitable host cell is infected with the life-cycle-defective Adenovirus helper virus at a multiplicity of infection (MOI) of at least 1, preferably at least 10, more preferably at least 100, even more preferably at least 500, and most preferably at least 1000. For example, a MOI of 500 worked well.

Generally, the at least one AAV Rep protein is selected from Rep protein 40 (Rep40), Rep protein 52 (Rep52), Rep protein 68 (Rep68) and/or Rep protein 78 (Rep78) and/or the at least one AAV Cap protein is selected from the VP1, VP2 and/or VP3 capsid proteins, the AAV Cap protein is derived from at least one serotype of a dependoparvovirus, in particular from at least one of the serotypes AAV1, AAV2, AAV3, AAV3A, AAV3B, AAV4, AAV5, AAV6, AAV7, AAV8, AAV9, AAV10, AAV11, AAV12, AAV13, AAV-Go1, AAVS3, AAV-LKO3 avian AAV, bat AAV, bovine AAV, Californian sea lion AAV, canine AAV, caprine AAV, equine AAV, mAAV-EVE, mouse AAV1, ovine AAV, porcine AAV po1-6, rat AAV1, ancestral AAVs, natural AAV isolates from human or animals, barbarie duck parvovirus, bearded dragon parvovirus, corn snake parvovirus, duck parvovirus, goose parvovirus, hamster parvovirus, Muscovy duck parvovirus, pig-tailed macaques parvovirus, pygmy chameleon parvovirus, Raccoon parvovirus, rhesus macaque parvoviruses, or capsid variants or hybrids thereof, and/or the nucleic acid of interest is selected from a nucleic acid coding for an enzyme, a metabolic protein, a signaling protein, an antibody, an antibody fragment, an antibody-like protein, an antigen, or an RNA such as an miRNA, siRNA or snRNA.

Advantageously, the host cell is incubated in a serum-free medium.

The produced rAAV can further be purified, in particular by means of at least one CsCl gradient centrifugation, at least one filtration step, at least one ion exchange chromatography, at least one size exclusion chromatography, at least one affinity chromatography, at least one hydrophobic interaction chromatography or combinations thereof, and/or further concentrated, preferably by means of ultrafiltration.

In addition, the produced rAAV can further be formulated with one or more pharmaceutically acceptable excipients into a pharmaceutical preparation.

Generally, the at least one rAAV construct can be either episomally maintained in the host cell, or chromosomally integrated in the host cell.

The host cell can be selected from a BHK cell, a COS cell, a Vero cell, a EB66 cell, a Hela cell, a A549 cell, a SF9 cell, a SF plus cell, a Hi5 cell or a S2 cell.

In case, wherein the host cell already codes for a functional Adenovirus E1A protein and a functional Adenovirus E1B protein or a functional Adenovirus E1B 55K protein, the host cell is preferably selected from a HEK293 cell, a HEK293T cell, a HEK293EBNA cell, a C139 cell, a CAP cell, a CAPT cell, a PERC6 cell or a AGE1 cell.

In case the life-cycle-defective Adenovirus helper virus contains a ts mutation selected from a temperature-sensitive (ts) point mutation in the L4-100K protein or a temperature-sensitive point mutation in the hexon protein, the cell is advantageously incubated at a temperature ≥39° C.

In case the life-cycle-defective Adenovirus helper virus contains a ts mutation selected from a ts point mutation in the L4-100K protein and also a ts point mutation in the hexon protein, the cell is advantageously incubated at a temperature ≥37° C.

An advantage of the above-described method is that the generation of progeny Adenovirus (AdV) is reduced or even eliminated, and/or the produced rAAV is substantially free of Adenovirus. As a result, rAAV preparations may advantageously be produced in which are substantially free, or have low levels, of contaminating Adenovirus. Absence of progeny Adenovirus generation can be shown by infection of the respective complementing cell (e.g. pTP cell line infected with rAAV produced with pTP Adenovirus mutant) or a cell at the permissive temperature for the respective ts mutant with at least 3 repeated rounds of infections. If progeny tsAdV/AdV mutant is produced during rAAV manufacturing, it will be detected by e.g. qPCR on AdV-specific sequences etc.

A further embodiment of the present invention is a rAAV produced according to a method as described herein.

Generally, as described above, said life-cycle-defective Adenovirus helper virus can be used for producing rAAV.

Another subject-matter of the present invention concerns a life-cycle-defective Adenovirus helper vector construct containing a mutation selected from (a) a deletion mutant in the transcription unit coding for the L4-100K protein, wherein the deletion corresponds to nucleotides 25200-25400 of SEQ ID NO: 46, in particular nucleotides 25000-25600 of SEQ ID NO: 46, more in particular nucleotides 24889-25699 of SEQ ID NO: 46, or nucleotides 24773-25887 of SEQ ID NO: 46, or nucleotides 24061-24665 of SEQ ID NO: 46, or nucleotides 24061-24665 plus nucleotides 24889-25699 of SEQ ID NO: 46, or nucleotides 24061-24665 plus nucleotides 24889-25887 of SEQ ID NO: 46, especially wherein the remaining L4-100K coding sequence consists of SEQ ID NO: 1;
(b) a deletion mutant in the transcription unit coding for the L1-52/55K protein, wherein the deletion corresponds to nucleotides 11500-12000 of SEQ ID NO: 46, more in particular nucleotides 11050-12184 of SEQ ID NO: 46, or nucleotides 11050-12297 of SEQ ID NO: 46, especially wherein the remaining L1-52/55K coding sequence consists of the sequence of SEQ ID NO: 2;
(c) a deletion mutant in the transcription unit coding for pTP, wherein the deletion corresponds to nucleotides 10100-10300 of SEQ ID NO: 46, in particular nucleotides 9904-10589 of SEQ ID NO: 46, or nucleotides 9734-10589 of SEQ ID NO: 46, especially wherein the remaining pTP coding sequence consists of the sequence of SEQ ID NO: 3; and/or
(d) a ts mutation in the L4-100K protein and a ts mutation in the hexon protein, wherein
  (i) the ts mutation in the L4-100K protein is a TCC to CCC mutation located at positions 25456-25458 of SEQ ID NO: 46, or a TCC to CCA mutation located at positions 25456-25458 of SEQ ID NO: 46, or a TCC to CCG mutation located at positions 25456-25458 of SEQ ID NO: 46, or a TCC to CCT mutation located at positions 25456-25458 of SEQ ID NO: 46, preferably a TCC to CCC mutation located at positions 25456-25458 of SEQ ID NO: 46; and
  (ii) the ts mutation in the hexon protein is a GGC to GAT mutation located at positions 21170-21172 of SEQ ID NO: 46, or a GGC to GAO mutation located at positions 21170-21172 of SEQ ID NO: 46, preferably a GGC to GAT mutation located at positions 21170-21172 of SEQ ID NO: 46.

Generally, it is preferred that the helper vector construct codes for a functional viral associated (VA) RNA I and II, a functional E2A protein and a functional E4ORF6/7 protein, and optionally further for a functional E1A protein and/or a functional E1B protein, in particular a functional E1B 55K protein.

Generally, the Adenovirus is selected from a serotype of subgroup A, B, C, D, E, F and/or G, in particular the Adenovirus is selected from at least one of adenovirus type 1 to 57, preferably the Adenovirus is selected from Adenovirus type 2 (Ad5) or Adenovirus type 5 (Ad5), more preferably from human Ad2 (hAd2) or human Ad5 (hAd5).

Another subject-matter of the present invention concerns a method for making the above-described life-cycle-defective Adenovirus helper vector construct, wherein said method comprises the steps:

(a) deleting nucleotides corresponding to nucleotides 25200-25400 of SEQ ID NO: 46, in particular nucleotides 25000-25600 of SEQ ID NO: 46, more in particular nucleotides 24889-25699 of SEQ ID NO: 46, or nucleotides 24773-25887 of SEQ ID NO: 46, or nucleotides 24061-24665 of SEQ ID NO: 46, or nucleotides 24061-24665 plus nucleotides 24889-25699 of SEQ ID NO: 46, or nucleotides 24061-24665 plus nucleotides 24889-25887 of SEQ ID NO: 46 in the transcription unit coding for the L4-100K protein;
(b) deleting nucleotides corresponding to nucleotides 11500-12000 of SEQ ID NO: 46, more in particular nucleotides 11050-12184 of SEQ ID NO: 46, or nucleotides 11050-12297 of SEQ ID NO: 46 in the transcription unit coding for the L1-52/55K protein;
(c) deleting nucleotides corresponding to nucleotides 10100-10300 of SEQ ID NO: 46, in particular nucleotides 9904-10589 of SEQ ID NO: 46, or nucleotides 9734-10589 of SEQ ID NO: 46 in the transcription unit coding for pTP; and/or
(d) preparing ts point mutations in the L4-100K protein and in the hexon protein, wherein
  (i) the ts mutation in the L4-100K protein is a TCC to CCC mutation located at positions 25456-25458 of SEQ ID NO: 46, or a TCC to CCA mutation located at positions 25456-25458 of SEQ ID NO: 46, or a TCC to CCG mutation located at positions 25456-25458 of SEQ ID NO: 46, or a TCC to CCT mutation located at positions 25456-25458 of SEQ ID NO: 46, preferably a TCC to CCC mutation located at positions 25456-25458 of SEQ ID NO: 46; and
  (ii) the ts mutation in the hexon protein is a GGC to GAT mutation located at positions 21170-21172 of SEQ ID NO: 46, or a GGC to GAO mutation located at positions 21170-21172 of SEQ ID NO: 46, preferably a GGC to GAT mutation located at positions 21170-21172 of SEQ ID NO: 46.

Another subject-matter of the present invention concerns a method for producing a life-cycle-defective Adenovirus helper virus, said method comprising introducing a life-cycle-defective Adenovirus helper vector construct as described or made as described above into a suitable host cell, and incubating the cell until the life-cycle-defective Adenovirus helper virus is produced, wherein the suitable host cell is a cell containing at least one Adenovirus complementing gene, in particular an Adenovirus L4-100K complementing cell, an Adenovirus L1-52/55K complementing cell and/or an Adenovirus pTP complementing cell, and optionally further an Adenovirus E1A and/or E1B complementing cell.

Generally, the host cell is transiently transfected with or has stably integrated at least one Adenovirus complementing gene, in particular an Adenovirus L4-100K complementing gene, an Adenovirus L1-52/55K complementing gene and/or an Adenovirus pTP complementing gene, and optionally further an Adenovirus E1A and/or E1B complementing gene.

Advantageously, the Adenovirus complementing cell (host cell) expresses the Adenovirus L4-100K protein, the Adenovirus L1-52/55K protein and/or Adenovirus pTP.

Generally, the L4-100K protein and/or pTP can be expressed under the control of a constitutive promoter, preferably under the control of a CMV promoter. However it is preferred that the L4-100K protein, the L1-52/55K protein and/or pTP are expressed under the control of an inducible promotor, preferably under the control of a tetracycline-inducible promoter.

Advantageously, the host cell is incubated in a serum-free medium. For example, the host cell is incubated at least transiently in the presence of a suitable inducer, preferably tetracycline or doxycycline, e.g. in case the expression is under the control of a tetracycline-inducible promoter.

The host cell can be incubated at a temperature below 37° C., in particular between 28° C. and 36° C., preferably between 30° C. and 34° C., more preferably at about 32° C.

The produced life-cycle-defective Adenovirus helper virus can further be harvested and optionally further purified, in particular by means of at least one CsCl gradient centrifugation, at least one filtration, at least one ion exchange chromatography, at least one size exclusion chromatography, at least one affinity chromatography, at least one hydrophobic interaction chromatography or combinations thereof, and/or further concentrated, preferably by means of ultrafiltration.

According to the present invention the produced life-cycle-defective Adenovirus helper virus has advantageously a titer of at least 1×10E5 i.u./μL, preferably 1×10E7 i.u./μL, more preferably 1×10E9 i.u./μL, and most preferably at least 1×10E10 i.u./μL, or alternatively between 10E6 and 10E11 particles/μL, in particular between 10E8 and 10E10 particles/μL.

Generally, as described above, the life-cycle-defective Adenovirus helper vector construct can be used for producing a life-cycle-defective Adenovirus helper virus.

Therefore, a further embodiment of the present invention is an Adenovirus helper virus produced according to a method as described herein, and/or with the features as described herein.

Another subject-matter of the present invention concerns a complementing cell for producing a life-cycle-defective Adenovirus helper virus, wherein the virus contains a deletion in the transcription unit coding for the L4-100K protein, wherein the deletion corresponds to at least nucleotides 25200-25400 of SEQ ID NO: 46, in particular nucleotides 25000-25600 of SEQ ID NO: 46, more in particular nucleotides 24889-25699 of SEQ ID NO: 46, or nucleotides 24773-25887 of SEQ ID NO: 46, or nucleotides 24061-24665 of SEQ ID NO: 46, or nucleotides 24061-24665 plus nucleotides 24889-25699 of SEQ ID NO: 46, or nucleotides 24061-24665 plus nucleotides 24889-25887 of SEQ ID NO: 46, and/or wherein the complementing cell is transiently transfected with or has stably integrated a nucleic acid comprising the sequence of SEQ ID NO: 1.

A further subject-matter of the present invention concerns a complementing cell for producing a life-cycle-defective Adenovirus helper virus containing a deletion in the transcription unit coding for the L1-52/55K protein, wherein the deletion corresponds to at least nucleotides 11500-12000 of SEQ ID NO: 46, more in particular nucleotides 11050-12184 of SEQ ID NO: 46, or nucleotides 11050-12297 of SEQ ID NO: 46, and/or wherein the complementing cell is transiently transfected with or has stably integrated a nucleic acid comprising the sequence of SEQ ID NO: 2, optionally under the control of an inducible promotor, preferably under a tetracycline-inducible promoter.

An additional subject-matter of the present invention concerns a complementing cell for producing a life-cycle-defective Adenovirus helper virus containing a N-terminal deletion in the transcription unit coding for pTP, wherein the deletion corresponds to at least nucleotides 10100-10300 of SEQ ID NO: 46, in particular nucleotides 9904-10589 of SEQ ID NO: 46, or nucleotides 9734-10589 of SEQ ID NO: 46, and/or wherein the complementing cell is transiently transfected with or has stably integrated a nucleic acid comprising the sequence of SEQ ID NO: 3, optionally under the control of an inducible promoter, such as a tetracycline-inducible promoter, or a promotor which drives less strong expression relative to the cytomegalovirus (CMV) promoter, preferably the human phosphoglycerate kinase (hPGK) promoter.

A suitable complementing cell can be selected from a HEK293 cell, a HEK293T cell, a HEK293EBNA cell, a HeLa cell, a A549 cell, a EB66 cell, a PerC6 cell, or a CAP cell.

Generally, the complementing cell as described above can be used for producing a life-cycle-defective Adenovirus helper virus selected from (a) an Adenovirus helper virus containing an inactivating mutation in the transcription unit coding for the L4-100K protein;
(b) an Adenovirus helper virus containing an inactivating mutation in the transcription unit coding for the L1-52/55K protein;
(c) an Adenovirus helper virus containing an inactivating N-terminal deletion in the transcription unit coding for the preterminal protein (pTP), wherein said transcription unit contains no C-terminal deletion.

Advantages of the Invention

The above-described life-cycle-defective Adenovirus helper viruses were successfully designed and produced to contain as much sequence deletions as possible in the L4-100K protein, the L1-52/55K protein or the preterminal protein pTP while ensuring the necessary functionality of the other partially overlapping Adenovirus helper genes which are required for efficient rAAV manufacturing.

In addition, as also experimentally shown, essentially no generation of wildtype Adenovirus revertants were obtained via recombination between the Adenovirus mutant genomes and the complementing L4-100K, L1-52/55K and pTP gene sequences of the complementing cell lines.

The life-cycle-defective Adenovirus helper viruses could also be obtained in sufficient amounts for the production of rAAV. In the case of the pTP replication-life-cycle-defective mutant of the present invention it is particularly surprising that, while only having a 685 bp N-terminal deletion, it surprisingly supports rAAV manufacturing with an efficiency which is comparable to wildtype Adenovirus. Furthermore, despite a small deletion in the pTP transcription unit, no revertants were generated via recombination between the Adenovirus mutant genome and the complementing gene sequence of the complementing cell line.

It was also surprisingly and advantageously found that an Adenovirus helper virus containing a temperature-sensitive (ts) mutation in the L4-100K protein as well as a ts mutation in the hexon protein was non-permissive for packaging at 37° C.

DESCRIPTION OF THE FIGURES

FIG. 3 shows the remaining coding sequence (1613 bp) of the L4-100K protein mutant at position nucleotides 24061 . . . 24888, 25700 . . . 26484 according to NCBI Ref. No. AC_000008.1. Deletion inserted from position 24889-25699, position marked by two flanking nucleotides each, black bold, inserted deletion between C|T marked by underlining.

FIG. 8 B shows a Western blot analysis of the 52/55K protein.

FIGS. 11A-11B show the remaining sequence (1309 bp plus 9 bp) of the pTP protein mutant at position nucleotides join (8583 . . . 9903, 14111 . . . 14119) according to NCBI Ref. No. AC_000008.1 (complement strand); transcript is getting spliced (non-coding sequence marked in grey), remaining coding sequence for pTP marked in black bold and underlined).

DESCRIPTION OF THE SEQUENCES

Figure 1:
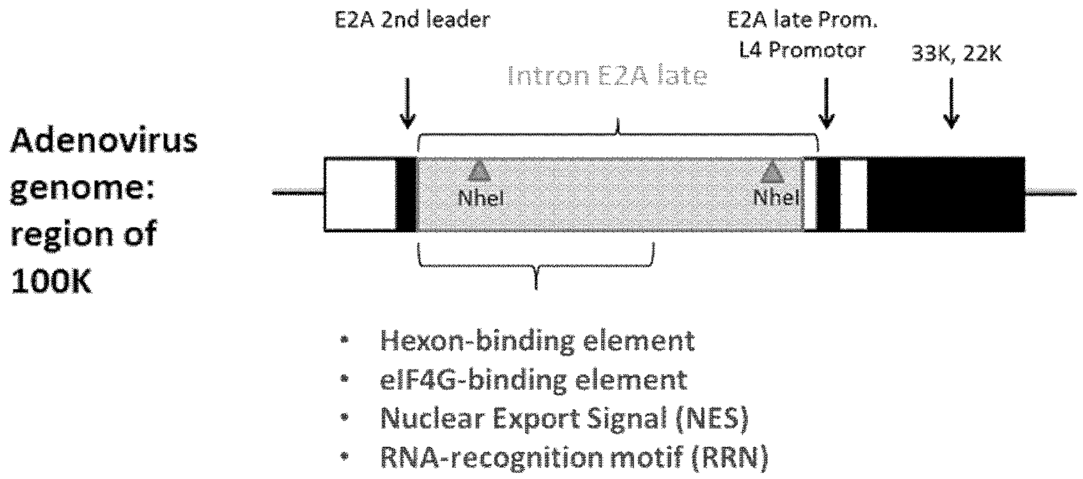
FIG. 1 shows the region of the L4-100K in the Adenovirus genome.

SEQ ID NO: 1 nucleic acid encoding the L4-100K mutant

SEQ ID NO: 2 nucleic acid encoding the L1-52/55K mutant

SEQ ID NO: 3 nucleic acid encoding the pTP mutant

SEQ ID NO: 4 sequence pBELO66 Ad5 wt (42148 bp)

SEQ ID NO: 5 sequence pGS66 (35789 bp)

SEQ ID NO: 6 sequence pBSK-CMV-TPLIn-100K (6690 bp)

SEQ ID NO: 7 bacmid sequence Ad5Δ100K (41337 bp)

SEQ ID NO: 8 sequence of the L4-100K deletion

SEQ ID NO: 9 primer sequence for the RED®/ET® recombination (L4-100K)

SEQ ID NO: 10 primer sequence for the RED®/ET® recombination (L4-100K)

SEQ ID NO: 11 primer sequence for the RED®/ET® recombination (L4-100K)

SEQ ID NO: 12 forward amplification primer with Kozak sequence (L4-100K)

SEQ ID NO: 13 reverse amplification primer (L4-100K)

SEQ ID NO: 14 amplification forward primer (L4-100K)

SEQ ID NO: 15 amplification reverse primer (L4-100K)

SEQ ID NO: 16 amplification forward primer (L4-100K)

SEQ ID NO: 17 amplification reverse primer (L4-100K)

SEQ ID NO: 18 sequence of the L1-52/55K deletion

SEQ ID NO: 19 primer sequence for the RED®/ET® recombination (L1-52/55K)

SEQ ID NO: 20 primer sequence for the RED®/ET® recombination (L1-52/55K)

SEQ ID NO: 21 primer sequence for the RED®/ET® recombination (L1-52/55K)

SEQ ID NO: 22 forward amplification primer with Kozak sequence (L1-52/55K)

SEQ ID NO: 23 reverse amplification primer (L1-52/55K)

SEQ ID NO: 24 amplification forward primer (L1-52/55K)

SEQ ID NO: 25 amplification reverse primer (L1-52/55K)

SEQ ID NO: 26 sequence of the pTP deletion

SEQ ID NO: 27 primer sequence for the RED®/ET® recombination (ΔpTP)

SEQ ID NO: 28 primer sequence for the RED®/ET® recombination (ΔpTP)

SEQ ID NO: 29 primer sequence for the RED®/ET® recombination (ΔpTP)

SEQ ID NO: 30 forward amplification primer with Kozak sequence (ΔpTP)

SEQ ID NO: 31 reverse amplification primer (ΔpTP)

SEQ ID NO: 32 amplification forward primer (ΔpTP)

SEQ ID NO: 33 amplification reverse primer (ΔpTP)

SEQ ID NO: 34 amplification forward primer (ΔpTP)

SEQ ID NO: 35 amplification reverse primer (ΔpTP)

SEQ ID NO: 36 amplification forward primer (ΔpTP)

SEQ ID NO: 37 amplification reverse primer (ΔpTP)

SEQ ID NO: 38 primer sequence for the RED®/ET® recombination (ts100K)

SEQ ID NO: 39 primer sequence for the RED®/ET® recombination (ts100K)

SEQ ID NO: 40 primer sequence for the RED®/ET® recombination (ts100K)

SEQ ID NO: 41 primer sequence for the RED®/ET® recombination (double ts)

SEQ ID NO: 42 primer sequence for the RED®/ET® recombination (double ts)

SEQ ID NO: 43 primer sequence for the RED®/ET® recombination (double ts)

SEQ ID NO: 44 amplification forward primer (double ts)

SEQ ID NO: 45 amplification reverse primer (double ts)

SEQ ID NO: 46 human Adenovirus 5 genome according to NCBI database reference AC000008.1 (coding sequence nt 24061-26484)

SEQ ID NO: 47 nucleic acid encoding the L4-100K protein

SEQ ID NO: 48 nucleic acid encoding the 52/55K protein

SEQ ID NO: 49 nucleic acid encoding the pTP protein

DETAILED DESCRIPTION OF THE INVENTION

A. Replication-Deficient Ad5 Mutant Deleted in L4-100K Protein

I. Generation of Adenovirus 5 Deletion Mutant Δ100K on DNA Level

I.1 Rationale Ad5 Δ100K Deletion Mutant

The L4-100K is a multifunctional protein, which is expressed late during the adenovirus life cycle. When viral DNA replication has begun and all late mRNA transcripts have been synthesized, cellular mRNA translation is blocked by inhibition of mRNA export from the nucleus to the cytoplasm. In counterpart, the export of viral mRNA from the nucleus is facilitated and preferentially translated leading to synthesis of structural polypeptides. One responsible protein is the 100K protein. It dephosphorylates eIF4E, which is a translation initiation factor. By dephosphorylation cap-dependent translation of cellular mRNA is reduced.

Furthermore, binding of eIF4E to viral mRNA is enhanced and translation of viral mRNAs is stimulated by ribosome shunting. Additional to having an impact on viral protein synthesis, 100K plays an essential role in the assembly of hexon monomers to trimeric hexon capsomers. It acts both as a chaperone, facilitating folding of hexon proteins, and as a scaffold promoting assembly of trimers. In case of a deletion of 100K, the AdV life-cycle is interrupted in a late phase of the infectious cycle, similar to the 52/55K-mutant. Yet, in this case, adenoviral DNA is replicated but viral particles should not be assembled. Furthermore, no inhibition of cellular RNA translation should take place, probably positively influencing yield during rAAV production. Therefore, one objective of the present invention is to delete essential functional elements of the 100K, such as the hexon-binding element, eIF4G-binding element, the nuclear-export signal and/or the RNA-recognition motif (RRN), to prevent hexon trimerization and inhibition of cellular RNA translation (FIG. 1).

Figure 2:
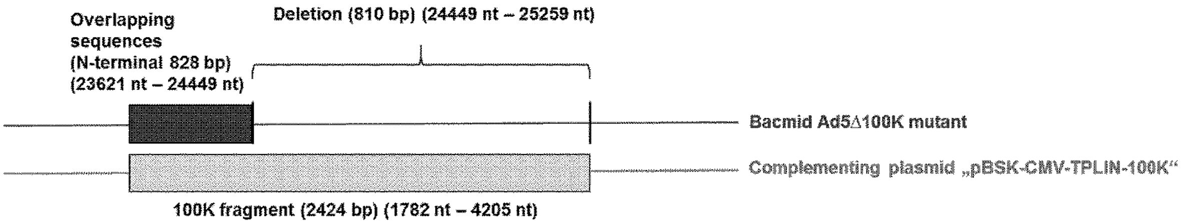
FIG. 2 shows overlapping sequences between the complementing plasmid pBSK-CMV-TPLIN-100K and the Ad5Δ100K mutant (L4-100K). The numbering at the upper part of the figure corresponds to the bacmid sequence BacAd5Delta100K (SEQ ID NO: 7) and the numbering at the lower part of the figure corresponds to the sequence of the construct pBSK-CMV-TPLIN-100K (SEQ ID NO: 6).

Exemplarily, the N-terminal 810 bp within the 100K encoding sequence of 2424 bp length, representing nearly the entire E2A late intron, were deleted from position nt 24889-nt 25699 according to the NCBI database reference AC_000008.1 of the human Adenovirus 5 complete genome (coding sequence nt 24061-nt 26484; SEQ ID NO: 46). This deletion preserved essential coding sequences on the complementary strand, resulting in some sequence overlap between the virus mutant and the 100K encoding sequence to be provided in a complementing cell line. (FIG. 2).

TABLE 1

| L4-100K deletion in the human Adenovirus 5 NCBI AC_000008.1 complete genome: |
|---|
| . . . TCGAGGTCACCCACTTTGCCTACCCGGCACTTAACCTACCCCCC<br>AAGGTC_[Δnt24889--nt25699]_TTGCCTACCACTCTGACATAATG<br>GAAGACGTGAGCGGTGACGGTCTACTG . . . (SEQ ID NO: 8) |

1.2 Cloning of Ad5 Δ100K

The adenovirus deletion mutant Δ100K was generated using Homologous Recombination Gene Bridges Counter Selection Bac Modification Kit by RED®/ET® Recombination according to manufacturer's instructions. The template DNA for insertion of the deletion defect was a pBELO66, a bacmid containing the adenovirus type 5 wild-type genome. Bacteria used for bacmid modifications were *E. coli* DH10Beta. Deletion region within the bacmid was located from nt 24449 to nt 25259 of pBELO66 (SEQ ID NO: 4) which corresponds to nt 24889-25699 of human Adenovirus 5 (NCBI AC_000008.1; SEQ ID NO: 46).

For the first and second RED®/ET® recombination step following primers were designed:

TABLE 2

| Ad5 mutant 100K (intermediate): 50 bp (24838-24888) 100K left of deletion + 24 bp rpSLneo for integration into rpSLneo cassette: |
|---|
| TCGAGGTCACCCACTTTGCCTACCCGGCACTTAACCTACCCCCCAAGGTC<br>*GGCCTGGTGATGATGGCGGGATCG*<br>(SEQ ID NO: 9) |
| **Ad5 mutant 100K (intermediate): 50 bp (25700-25749) 100K left of deletion + 24 bp rpSLneo for integration into rpSLneo cassette:** |
| CAGTAGACCGTCACCGCTCACGTCTTCCATTATGTCAGAGTGGTAGGCAA<br>*TCAGAAGAACTCGTCAAGAAGGCG*<br>(SEQ ID NO: 10) |
| **M3: Ad5 mutant 100K, deletion No. 24889-25699:** |
| TCGAGGTCACCCACTTTGCCTACCCGGCACTTAACCTACCCCCCAAGGTC<br>TTGCCTACCACTCTGACATAATGGAAGACGTGAGCGGTGACGGTCTACTG<br>(SEQ ID NO: 11) |

Bacterial amplification of accomplished bacmid was done in DH10Beta and purified via Qiagen Large Construct Bacmid Preparation Kit according to manufacturer's protocol including the deviation that no exonuclease digestion was performed.

II. Cloning of Plasmid DNA Encoding Ad5 "L4-100K" for the Complementing Cell Line To produce life-cycle-defective Adenovirus mutants that carry a deletion in a crucial gene during life-cycle as virus particles, a complementing cell line expressing that deleted gene is necessary to get virus amplification and progeny. These produced virus particles are then life-cycle-defective on non-complementing cell lines.

II.1 Amplification of the Target Gene "L4-100K" as Insert for the Complementing Plasmid The complementing gene for the Adenovirus deletion mutant Δ100K was extracted from the bacmid pGS66 encoding the Ad5 genome sequence w/o E1 via Polymerase-Chain-Reaction (PCR) using primers additionally encoding endonuclease-restriction sites NotI and SmaI for further cloning steps. The forward primer additionally encoded for a Kozak sequence which was planned to be inserted in front of the 100K coding sequence.

TABLE 3

| Ad5 100K NotI Kozak forward |
|---|
| tGCGGCCGCgaccATGGAGTCAGTCGAGAAGAA (SEQ ID NO: 12) |
| **Ad5 100K SmaI reverse** |
| attCCCGGGCTACGGTTGGGTCGGCGAA (SEQ ID NO: 13) |

The amplified fragment was digested with NotI and SmaI. This fragment represented the insert encoding 100K (FIG. 1; SEQ ID NO: 3) to be introduced into intermediate cloning vectors for subsequent bacterial amplification and introduction of the complementing gene into cells.

II.2 Preparation of Final Complementing Plasmid "pBSK-CMV-TPLIn-100K"

The generated PCR fragment (2424 bp) encoding the 100K produced in 11.1 was introduced into the backbone vector pBSK-CMV-TPLIn (4248 bp), containing CMV promoter and a tripartite leader (TPL) sequence flanked by an intron, which had been prepared previously.

II.3 Analysis of cloned "pBSK-CMV-TPLIn-100K"

Successfully cloned "pBSK-CMV-TPLIn-100K" was amplified in *E. coli* XL-2 Blue to obtain material sufficient both for characterization and stable transfection. Transient transfection was performed to analyze expression of 100K via Western blotting. Therefore, 1E6 HeLa cells were seeded on 6 cm dishes and transfected 24 h post seeding under following conditions: transfection reactions of 250 μl NaCl containing either 5 μg DNA or 60 μl 7.5 mM PEI were prepared, mixed, incubated for 10-15 min at room temperature and transferred onto the cells after medium change. Cells were harvested 48 h post transfection and processed for Western blot analysis. 50 μg protein were loaded on 8% SDS-Tris gels for electrophoresis in Tris-Glycin buffer. Transfer was performed via tank blotting on nitrocellulose 0.45 μm membrane in Towbin buffer containing 20% methanol. Subsequently, membranes were blocked in 5% milk powder in 0.1% Tween-TBS over night at 4° C. Afterwards, membranes were incubated for 2 h with $1^{st}$ antibody 100K rabbit 2a #136-148 diluted 1:100 in said blocking buffer. After three rounds of washing, membranes were treated at room temperature for 1 h with $2^{nd}$ antibody Anti-Rabbit IgG-Peroxidase Antibody produced in goat (Sigma) diluted 1:20000 in 0.1% Tween-TBS. Detection was done at AGFA CP 1000 via Pierce West Pico Chemoluminescence Substrate using GE Healthcare Amersham Hyperfilms.

III. Generation of Complementing Cell Line for Δ100K Mutant Virus Production

III.1 Generation and selection of stable cell clones expressing the complementing gene L4-100K For stable and random transfection, the complementing plasmid pBSK-CMV-TPLIn-100K and a selection marker encoding the puromycin resistance gene were linearized. Therefore, 30 μg of pBSK-CMV-TPLIn-100K was restriction digested using SmaI, a double cutter resulting in fragments of 3821 bp and 2869 bp, to remove backbone sequences.

HeLa-t cells (passage 6) were seeded 24 h prior transfection on 6 cm dishes at a density of 1E6 cells/dish. In total 6 μg linearized DNA in a molar ratio of 15:1 target vector to selection marker was transfected using calcium phosphate transfection method as followed: DNA was mixed with 150 μl 270 mM $CaCl_2$, 150 μl 2×HEBS (50 mM Hepes, 280 mM NaCl, 1.5 mM $Na_2HPO_4$, pH 7.1) were added, reaction mix was incubated for 20 min at room temperature and then added slowly onto the cells. Cells were incubated for 20 h at 35° C., 3% $CO_2$ and then shifted to 37° C., 5% $CO_2$. 24-30 h post transfection cells from one 6 cm dish were expanded to two 15 cm-dishes. Selection pressure using complemented culture media containing 0.25 μg puromycin was started 24 h post expansion. Medium change was performed once in every two days. 10 days after selection start, 36 cell clones were picked and transferred to 24-Well plates, cultivated in 0.5 ml/well selection medium. Clones were kept under selection pressure and expanded sequentially over 6-Well plates to 6 cm dishes, once they reached 80% confluency on the plates.

III.2 Expression Analysis of Integrated 100K

Gene expression of stably integrated 100K by positive transfectants was analyzed via Western blot. Therefore, cells were seeded in 6-Well plates and harvested at confluency of about 80% using TrypLE and prepared as protein samples. 50 μg protein were loaded on 10% BIS-Tris gels for PAGE in MOPS buffer additionally containing 0.98% sodium-bisulfite. Proteins were transferred on PVDF membrane 0.45 μm via tank blotting using Towbin buffer comprising 20% methanol. Membranes were blocked in 5% milk powder dissolved in 0.1% Tween-TBS, over night at 4° C. Subsequently, membranes were incubated with $1^{st}$ antibody diluted 1:100 in said blocking buffer at 4° C. over night. After three rounds of washing, membranes were treated with $2^{nd}$ antibody Anti-Rabbit IgG peroxidase HRP produced in goat (Sigma) diluted 1:10000 in 5% milk powder in 0.1 Tween-TBS. Detection was done at AGFA CP 1000 via Pierce West Pico Chemoluminescence Substrate using GE Healthcare Amersham Hyperfilms. One clone, designated HeLa-t 6.11, showed definite 100K expression and would be used for complementation of the adenovirus mutant deleted in L4-100K.

Furthermore, this cell clone was tested for stability by long-term experiments using concentrations of the selection agent puromycin 0.0 μg/ml, 0.25 μg/ml, 0.5 μg/ml and 1 μg/ml, to which cells were exposed over 35 passages and afterwards would be tested for 100K expression.

IV. Adenovirus Deletion Mutant Δ100K Virus Production

IV.1 Virus Rescue/Production after Bacmid Transfection

HeLa-t 6.11 cells were seeded on 6 cm dishes at a density of 1E6 cells/dish in selection medium. Bacmid DNA encoding the adenovirus deletion mutant Δ100K was linearized via SwaI restriction digestion, removing the vector backbone from the DNA fragment containing the mutant virus DNA with free adenoviral terminal repeats. After restriction digestion, 60 μg of DNA were purified via phenol/chlorophorm extraction with subsequent ethanol/sodium acetate precipitation. Cells were transfected 24 h post seeding using laboratory's PEI in a ratio of 60 μl 7.5 mM PEI per 5 μg DNA. Transfection mixes were prepared in 150 mM NaCl as total volumes of 250 μl per DNA-reaction mix and PEI-reaction mix, each. 24 h post transfection medium change was performed. Cells were cultivated in medium without selection pressure during virus amplification and expanded into larger culture formats to avoid overgrowing. At day 7 post transfection, cells did not show cytopathic effect (CPE) but severe viability loss was observed. Therefore, cells were harvested completely (medium+cells) by scraping and lysed by three freeze and thaw cycles to re-infect HeLa-t 6.11 cells seeded in a 6 cm dish (=$1^{st}$ amplification step). 72 h post re-infection, those cells showed CPE and were harvested for the $2^{nd}$ amplification step in the same manner as previously, but only half of the lysate was used to re-infect two 15 cm dishes of HeLa-t 6.11 cells. For the $3^{rd}$ amplification step 2×15 cm dishes a 3E6 cells/dish were infected with 250 μl lysate obtained from the $2^{nd}$ amplification step.

Furthermore, virus mutant analysis was performed during amplification using Adeno-X™ Rapid Titer Kit (Clontech), Dot blot analysis and multiple re-infections of non-complementing cells, to characterize produced virus and possible revertants.

IV.2 Adenovirus Deletion Mutant Δ100K Preparation/Purification

For final preparation, the virus lysates from the second and third amplification step were pooled and used to re-infect 11×15 cm dishes of HeLa-t 6.11, seeded at a density of 5E6 cells/dish. Previously, on 24-Well plate format, the optimal amount of virus lysate had been titrated to obtain optimal CPE 48 h post infection. According to that titration experiment, 150 μl virus lysate per 15 cm dish were sufficient to obtain CPE 48 h post infection. Cells were cultivated in medium without selection pressure and incubated at 37° C., 5% $CO_2$, for 48 h. After that time, cells showed complete CPE and were harvested completely together with the supernatant and centrifuged at 400×g, 4° C. for 10 min. Pellet was resolved in 3 ml HEPES pH 8 (50 mM Hepes, 150 mM NaCl). Virus was released via three freeze and thaw cycles (liquid nitrogen, water bath 37° C.) and cell debris removed by subsequent centrifugation at 4400 rpm for 10 min.

CsCl step gradient ultracentrifugation purification was performed to obtain purified virus stocks. For the first discontinous CsCl-gradient, virus lysate solution was layered on two CsCl-buffers comprising the densities 1.41 g/ml and 1.27 g/ml, and centrifuged for 2 h at 32 000 rpm at 4° C., using a Sorvall Discovery 90SE Hitachi Ultracentrifuge.

Subsequently, concentrated virus was extracted from the gradient and applied for the second continuous CsCl gradient ultracentrifugation for further purification. Therefore, extracted virus was mixed with CsCl-buffer pH 7.5 comprising a density of 1.34 g/ml and centrifuged for 20 h at 32 000 rpm at 4° C. After centrifugation, virus was extracted and added to HEPES pH 8.0. Virus was desalted via size exclusion chromatography using PD-10 columns (GE Healthcare). Purified vector particles were supplemented with 10% glycerol and stored in aliquots at −80° C.

IV.3 Adenovirus Deletion Mutant Δ100K Characterization

Produced adenovirus deletion mutant Δ100K was verified by several analyses during amplification steps and subsequent to virus purification.

Viral DNA was isolated from virus lysates from re-infected cells during the amplification steps and from purified virus using Qiagen QIAmp DNA Mini Kit. Isolated DNA was controlled via restriction digestion with subsequent agarose gel electrophoresis.

Since virus progeny of the mutant should only be possible on cells complementing the deletion defect, no virus amplification and thus no cytopathic effect (CPE) should occur in cells not carrying the complementing gene. Therefore, three rounds of re-infections on non-complementing HeLa and A549 cells using different amounts of non-purified virus lysates and different MOIs of virus stock were done to exclude possible reversion of deletion and to confirm replication-deficiency. All validation steps showed no CPE.

Photometric analysis was performed to determine physical titer, purity and to some extend integrity. Additionally, to evaluate potency and quality of produced virus, complementing cells were analyzed via Slot Blot to determine the infectious titer.

V. Adenovirus Deletion Mutant Δ100K as Helper Virus for rAAV Production

V.1 Transient rAAV Production Cells Using Adenovirus Deletion Mutant Δ100K as Helper Virus A549 cells were seeded in 6 cm-dishes at a density of 4E4 cells/cm$^2$ and transfected 24 h post seeding via single-plasmid transfection with one plasmid, designated “All-in-One”, encoding for rAAV vector+rep+cap. Directly after transfection, cells were infected with helper virus Ad5Δ100K pMOI 500 and as a reference with Adenovirus type 5 wildtype pMOI 500. Cells were incubated at 37° C., 5% $CO_2$ for 48 h. Microscopy of cells revealed CPE (=cytopathic effect) on cells infected with Adwt. As expected, little CPE was observed on cells infected with Ad5Δ100K, too. Since L4-100K is a very late protein, the naturally occurring life cycle of adenovirus was not interrupted until maturation and virus assembly, thus most viral proteins were already expressed leading to the cytopathic effect in cells.

Cells were harvested via scraping and lysed by three freeze and thaw cycles (liquid nitrogen, water bath 37° C.) with subsequent centrifugation at 3700×g for 10 min to remove cell debris. In case of Adwt infection, helper virus was inactivated by incubation at 56° C. for 30 min. Non-purified rAAV lysates were analyzed via qPCR to evaluate the genomic titer.

For qPCR 30 μl diluted $10^{-2}$ rAAV lysate was treated with 10 U recombinant DNase I (Roche) for 3 hours at 37° C. water bath to remove genomic and non-packaged vector DNA. Afterwards, 30 μl 400 mM NaOH was added for 45 min at 65° C. to inactivate DNase and denature vector particles. For efficient PCR, sample pH was neutralized by adding 30 μl 400 mM HCl and were finally diluted $12.5^{-1}$ in nuclease-free water.

Amplification was performed in a total volume of 25 μl using 2×QUANTIFAST™ SYBR®Green PCR Mix, 100 nM forward primer 5'-GGAACCCCTAGTGATGGAGTT-3' (SEQ ID NO: 14), 300 nM reverse primer 5'-CGGCCTCAGTGAGCGA-3' (SEQ ID NO: 15)

and 5 μl template. PCR conditions were as followed: initial heat activation of polymerase at 95° C. for 5 min; 39 cycles of denaturation at 95° C. for 10 s and annealing/extension at 60° C. for 30 s; followed by a temperature gradient of 1° C. $s^{-1}$ from 65 to 95° C.

Figure 4:
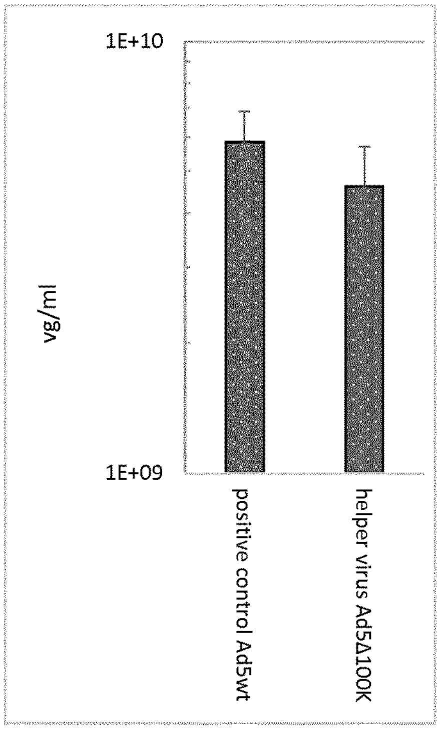
FIG. 4 shows the results that the Ad5Δ100K deletion mutant provides helper functions for rAAV production.
Figure 5:
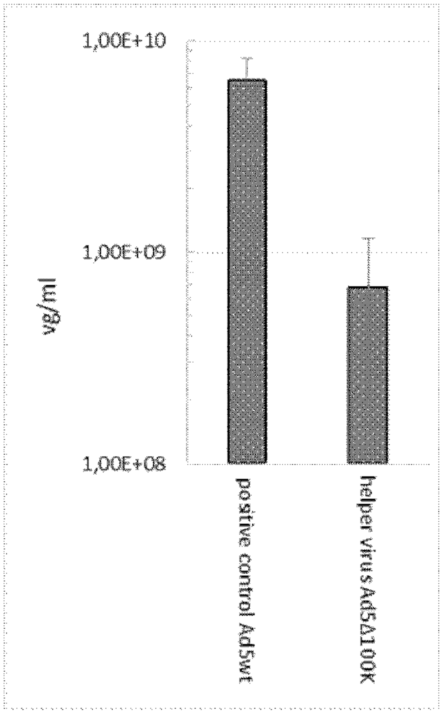
FIG. 5 shows additional results that Ad5Δ100K deletion mutant provides helper functions for rAAV production.

Results showed that Ad5Δ100K deletion mutant efficiently provided helper functions for rAAV production. Transiently produced rAAV in A549 led to titers around $5\times10^{09}$ vector genomes per ml (vg/ml), indicating a helper efficiency comparable to Adenovirus wildtype (FIG. 4). Calculations revealed yields of about $1.7\times10^4$ rAAV vectors per cell.

V.2 rAAV Production on Stable Producer Cell Using Adenovirus Deletion Mutant Δ100K as Helper Virus In contrast to transient rAAV production where the components for rAAV packaging are introduced to the cell via co-transfection of three or two plasmids encoding the required elements for replicase (rep genes) and structure proteins (cap genes) and the vector transgene cassette itself with subsequent delivery of helper functions via infection, a stable producer cell line harbors the entire set of components, stably integrated into its genome. Therefore, rAAV production is initiated after super-infection of this cell by a helper virus.

For rAAV production stable producer cells were seeded in 6 cm-dishes at a density of 4E4 cells/cm$^2$ and 24 h post seeding, cells were infected with helper virus Ad5Δ100K pMOI 500 and as a reference with Adenovirus type 5 wildtype pMOI 500. Cells were incubated at 37° C., 5% $CO_2$ for 48 h. Microscopy of cells revealed CPE on cells infected with Adwt but no cytopathic effect was observed on cells infected with Ad5Δ100K.

Cells were harvested via scraping and lysed by three freeze and thaw cycles (liquid nitrogen, water bath 37° C.) with subsequent centrifugation at 3700×g for 10 min to remove cell debris. In case of Adwt infection, helper virus was inactivated by incubation at 56° C. for 30 min. Non-purified rAAV lysates were analyzed via qPCR to evaluate the genomic titer.

For qPCR 30 μl diluted $10^{-2}$ rAAV lysate was treated with 10 U recombinant DNase I (Roche) for 3 hours at 37° C. water bath to remove genomic and non-packaged vector DNA. Afterwards, 30 μl 400 mM NaOH was added for 45 min at 65° C. to inactivate DNase and denature vector particles. For efficient PCR, sample pH was neutralized by adding 30 μl 400 mM HCl and were finally diluted $12.5^{-1}$ in nuclease-free water.

Amplification was performed in a total volume of 25 μl using 2×QUANTIFAST™ SYBR®Green PCR Mix, 100 nM forward primer 5'-GGAACCCCTAGTGATG-GAGTT-3'(SEQ ID NO: 16), 300 nM reverse primer 5'-CGGCCTCAGTGAGCGA-3' (SEQ ID NO: 17)

and 5 μl template. PCR conditions were as followed: initial heat activation of polymerase at 95° C. for 5 min; 39 cycles of denaturation at 95° C. for 10 s and annealing/extension at 60° C. for 30 s; followed by a temperature gradient of 1° C. $s^{-1}$ from 65 to 95° C.

Results showed that Ad5Δ100K deletion mutant provided helper functions for rAAV production. rAAV produced in stable A549 producer cells after super-infection with helper virus led to titers of about $5\times10^{08}$ vector genomes per ml (vg/ml), around 1 log lower compared to yields obtained with Adenovirus wildtype. Calculations revealed yields of about $2\times10^{3}$ rAAV vectors per cell.

B. Life-Cycle-Defective Ad5 Mutant Deleted in the 52/55K Protein

I. Generation of Adenovirus 5 Deletion Mutant Δ52/55K on DNA Level

I.1 Rationale for the Ad5 Δ52/55K Deletion Mutant

The L1-52/55-kDa proteins are known to be essential for the encapsidation of viral DNA into pre-formed virions.

Figures 6, 7:
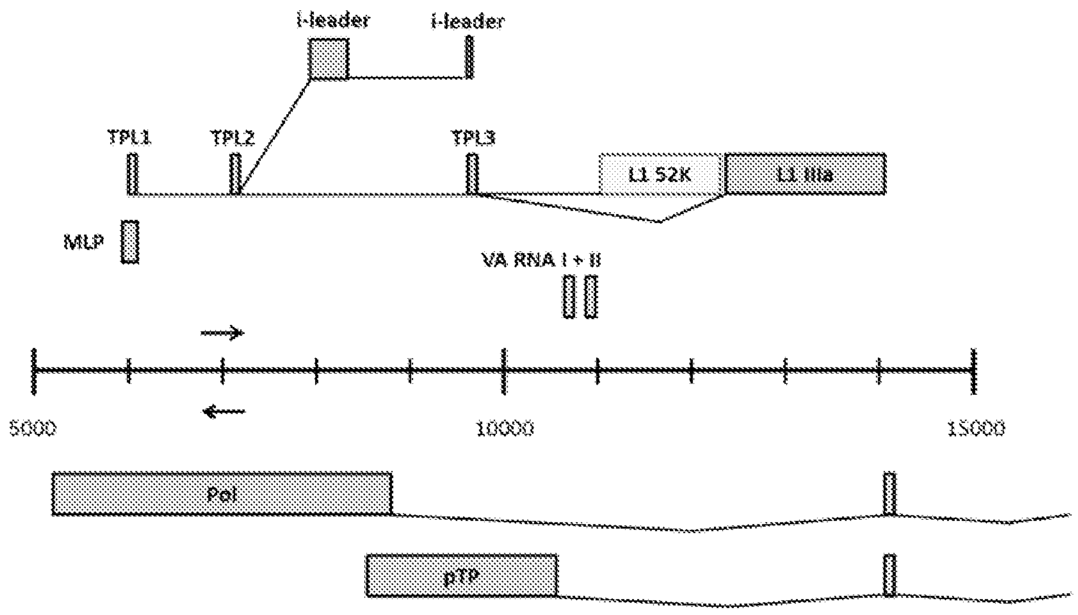
FIG. 6 shows the region of the L1 52/55K protein in the Adenovirus genome.
FIG. 7 shows the remaining coding sequence (113 bp) of the 52/55K protein mutant at position nucleotides 12185 . . . 12297 according to NCBI Ref. No. AC_000008.1.

Therefore, one objective of the present invention is to delete nearly the entire sequence encoding for the L1-52/55 kDa-protein to use it as helper virus for rAAV production (FIG. 6).

The N-terminal 1134 bp within the 52/55 kDa encoding sequence of 1248 bp length were deleted from position 11050 nt to 12184 nt according to the NCBI database reference AC_000008.1 Human Adenovirus 5 complete genome (coding sequence 52/55K: nt 11050-nt 12297; SEQ ID NO: 46).

TABLE 4

| deletion according to Human Adenovirus 5 NCBI AC_000008.1 complete genome |
|---|
| . . . TTGCAAATTCCTCCGGAAACAGGGACGAGCCCCTTTTTTGCTTT |
| TCCCAG_[Δnt11050--12184]_CAGCTGGGGCCGGACCTGGGCTGGC |
| GGTGGCACCCGCGCGCGCTGGCAAC . . . (SEQ ID NO: 18) |

According to this deletion region, overlapping homologous sequences with the gene encoding the 52/55 kDa within the complementing cell line, for virus production, were avoided, thus reducing the risk of homologous recombination between cell and virus, which could lead to revertants.

I.2 Cloning of Ad5 Δ52/55 kDa

The adenovirus deletion mutant Δ52/55 kDa was generated using Homologous Recombination Gene Bridges Counter Selection Bac Modification Kit by RED®/ET® Recombination according to manufacturer's instructions.

The template DNA for insertion of the deletion defect was an adenovirus wildtype encoding bacmid pBELO66. Bacteria used for bacmid modifications were *E. coli* DH10Beta. Deletion region within the bacmid was located from nt 10610 to nt 11744.

For the first and second RED®/ET® recombination step following primers were designed:

TABLE 5

| Ad5 mutant 52/55K (intermediate): 50 bp (11000-11049) 52/55K left to deletion + 24 bp rpSLneo for integration into rpSLneo cassette (italics) |
|---|
| TTGCAAATTCCTCCGGAAACAGGGACGAGCCCCTTTTTTGCTTTTCCCAG *GGCCTGGTGATGATGGCGGGATCG* (SEQ ID NO: 19) |
| **Ad5 mutant 52/55K (intermediate): 50 bp (12185-12234) 52/55K right to deletion + 24 bp rpSLneo for integration into rpSLneo cassette (italics)** |
| GTTGCCAGCGCGCGCGGGTGCCACCGCCAGCCCAGGTCCGGCCCCAGCTG *TCAGAAGAACTCGTCAAGAAGGCG* (SEQ ID NO: 20) |
| **M2: Ad5 mutant 52/55K, deletion No. 11050-12184** |
| TTGCAAATTCCTCCGGAAACAGGGACGAGCCCCTTTTTTGCTTTTCCCAG CAGCTGGGGCCGGACCTGGGCTGGCGGTGGCACCCGCGCGCGCTGGCAAC (SEQ ID NO: 21) |

Bacterial amplification of accomplished bacmid was done in *E. coli* DH10Beta and purified via Qiagen Large Construct Bacmid Preparation Kit according to manufacturer's protocol including the deviation that no exonuclease digestion was performed.

II. Cloning of Plasmid DNA Encoding Ad5 "L1-52/55K" for the Complementing Cell Line To produce life-cycle-defective Adenovirus mutants that carry a deletion in a crucial gene during life-cycle as virus particles, a complementing cell line expressing that deleted gene is necessary to get virus amplification and progeny. These produced virus particles are then life-cycle-defective on non-complementing cell lines.

II.1 Amplification of the Target Gene "L1-52/55K" as Insert for the Complementing Plasmid The complementing gene for the Adenovirus deletion mutant Δ52/55K was extracted from the bacmid pGS66 encoding the Ad5 genome sequence w/o E1 via Polymerase-Chain-Reaction (PCR) using primers additionally encoding endonuclease-restriction sites NheI and EcoRV for further cloning steps (underlined).

TABLE 6

| Ad5 52K NheI Kozak forward |
|---|
| ataGCTAGCgaccATGCATCCGGTGCTGCGGCAGAT (SEQ ID NO: 22) |
| **Ad5 52K EcoRV reverse** |
| agtctGATATCTTAGTACTCGCCGTCCTCTGGCTCGTAC (SEQ ID NO: 23) |

The amplified fragment was restriction-digested using NheI and EcoRV. is transiently transfected with or has stably integrated a nucleic acid comprising the sequence of SEQ ID NO: 3, optionally under the control of an inducible promoter, such as a tetracycline-inducible promoter, or a promotor which drives less strong expression relative to the cytomegalovirus (CMV) promoter, preferably the human phosphoglycerate kinase (hPGK) promoter.

This fragment represented the insert encoding 52/55 kDa (FIG. 7; SEQ ID NO: 2) to be introduced into a plasmid vector for subsequent bacterial amplification and introduction of the complementing gene into cells.

II.2 Preparation of Complementing Plasmid "pTRE-Tight-BI-AcGFP1-52/55K"

The generated fragment encoding 52/55K obtained from pGS66 via PCR amplification was used in several approaches to create a complementing cell line. Therefore, the fragment was first cloned in intermediate plasmids either carrying a strong cytomegalovirus derived promoter (CMV) or a weaker human phosphoglycerate kinase promotor (hPGK) for constitutive gene expression with subsequent introduction into A549 cells either via two-plasmid co-transfection of selection marker and expressing vector or via single-plasmid transfection after additional cloning procedures to obtain plasmids encoding both selection marker and target gene. However, these approaches did not result in cell clones expressing the 52/55K gene due to presumed epigenetic silencing. The inability to create cells constitutively expressing the 52/55K gene indicated some cytotoxicity of that protein and therefore possibly causing a negative selection pressure on positively expressing cells. The next approach focused on an inducible 52/55K gene expression in stable cell clones. An inducible expression system would lead to the possibility to solely express the gene of interest for the time of mutant production hopefully reducing the risk of silencing and increasing cell viability, cell line stability and steady expression levels after induction. The generation of the double-stable cell line was based on Hek293TetON (Clontech). The target gene 52/55K was integrated into the MCS of the second generation vector pTRE-Tight-BI-AcGFP1 (#631066). According to Clontech Vector Information, PR083616; published Aug. 20, 2010: "pTRE-Tight-BI-AcGFP1 is a bidirectional TRE-Tight plasmid that can be used to inducibly express a reporter green fluorescent protein (AcGFP1) along with a gene of interest with our Tet-On and Tet-Off Gene Expression Systems and Cell Lines. pTRE-Tight-BI-AcGFP1 contains a modified Tet response element, which consists of seven direct repeats of a 36 bp sequence that contains the 19 bp tet operator sequence (tetO). The two mini CMV promoters, which lack the enhancer that is part of the complete CMV promoter, flank the TREmod. pTRE-Tight-BI-AcGFP1 encodes a variant of wild-type *Aqueorea coerulescens* green fluorescent protein (AcGFP1). pTRE-Tight-BI-AcGFP1 contains a multiple cloning site (MCS) downstream of the BI-Tet-responsive Ptight promoters".

The Hek293TetON cell line was cultured in MEMα complemented with 10% FCS (heat-inactivated, Hyclone), 1× GlutaMax (gibco) and 100 μg/ml geneticin.

The 52/55 kDa-encoding fragment was introduced into the MCS of the tetracycline-inducible TetON vector pTRE-Tight-BI-AcGFP1 via NheI and EcoRV.

II.3 Analysis and Characterization of Cloned "pTRE-Tight-BI-AcGFP1-52/55K"

Prior to stable transfection into Hek293TetON cells to generate a double-stable TetON inducible cell line expression 52/55K, the cloned plasmid was transiently analyzed for gene expression. Therefore, Hek293TetON were seeded on 6-Well plates in a density of 1E5 cells/$cm^2$ and transfected 24 h post seeding using Polyplus PEIPro 1 mg/ml in a ratio of 2:1 to DNA. For transfection in 6-Well plate format, 3 μg total DNA were transfected, preparing transfection reaction mixes in non-complemented MEMα (gibco) in a total volume of 200 μl (100 μl DNA-mix, 100 μl PEI-mix). About 4-6 h after transfection, medium was exchanged to induction-medium consisting of previously described culture medium, additionally containing 1 μg/ml doxycycline. Cells were harvested 24 h and 48 h after induction using TrypLE and centrifuged at 200×g for 5-10 min. Pellets were used for cDNA analysis and Western blotting.

For cDNA analysis total RNA was isolated via Qiagen RNeasy Plus Mini Kit according to manufacturer's protocol, using Qiagen QIA shredder to homogenize cells, and eluted in 50 μl nuclease-free water. cDNA was synthesized from 1 μl of isolated RNA using Qiagen Omniscript Reverse Transcriptase Kit according to manufacturer's instructions. PCR priming 52/55K gene was performed in a total volume of 50 μl using Qiagen HotStar Taq Polymerase Kit as followed: 1×PCR buffer, 1×Q-solution, 200 μM dNTPs (each), 200 nM forward primer 5'-ATGCATCCGGTGCTGCGGC-3' (SEQ ID NO: 24), 200 nM reverse primer 5'-TTAGTACTCGCCGTCCTCTGG-3' (SEQ ID NO: 25) and 5 μl of cDNA sample. Amplification was performed under following conditions:

initial heat activation at 95° C. for 15 min, 35 cycles of denaturation at 94° C. for 30 sec, annealing at 58° C. for 30 sec, elongation at 72° C. for 3 min, followed by a final extension step at 72° C. for 5 min. Products were visualized via 1% agarose gel electrophoresis, showing positive signals at 1.25 kb (FIG. 8 A).

For Western blotting, pelleted samples were lyzed in 50 μl lysis buffer (50 mM Tris pH 7,5; 250 mM sucrose; 1 mM EDTA; 1 mM EGTA; 1% Triton-X, 1 protease-inhibitor cocktail tablet (Roche)) for 1-3 h on ice, vortexing once in a while, and then centrifuged at 14 000 rpm, 4° C. for 30 min to remove cell debris. Supernatant was complemented with SDS loading buffer containing β-mercaptoethanol. Determination of protein concentration and normalization was not performed due to focusing solely on a qualitative answer towards the question of gene expression. For western blot analysis, 25 μl sample were loaded on BioRad Mini-PROTEAN® Gels TGX for gel electrophoresis at 120 V for 1-3 h using Tris-Glycin buffer. Proteins were transferred on PVDF 0.2 μm membrane via tank blotting at 100 V for 1 h using Towbin buffer containing 20% methanol. Positive transfer was confirmed via Ponceau-S staining. Membranes were blocked for 1 h at RT using Roth ROTI®Block blocking reagent. After blocking, membranes were incubated over night at 4° C., 50 rpm, with 1st antibody αL115K 52/55K Rabbit 414 diluted 1:1000 in 5% milk powder dissolved in 0.1% PBS-Tween. Next day, subsequent to three rounds of washing using 0.1% PBS-Tween, membranes were treated with 2nd Anti-Rabbit IgG-peroxidase HRP-labelled antibody (Sigma) diluted 1:5000 in 5% milk powder dissolved in 0.1% PBS-Tween, for 3 h at RT. Detection was performed via AGFA CP 1000 using Pierce West Pico ECL Chemiluminescence Substrate Kit and GE Healthcare Amersham Hyperfilms.

Figure 8A:
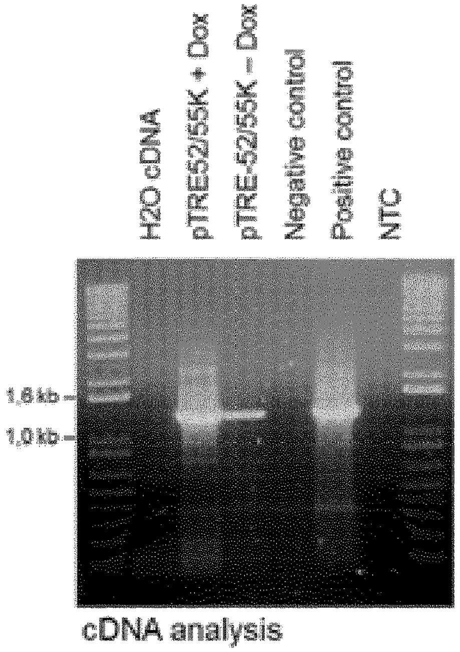
FIG. 8 A shows a cDNA analysis of the 52/55K gene on a agarose gel.
Figure 8B:
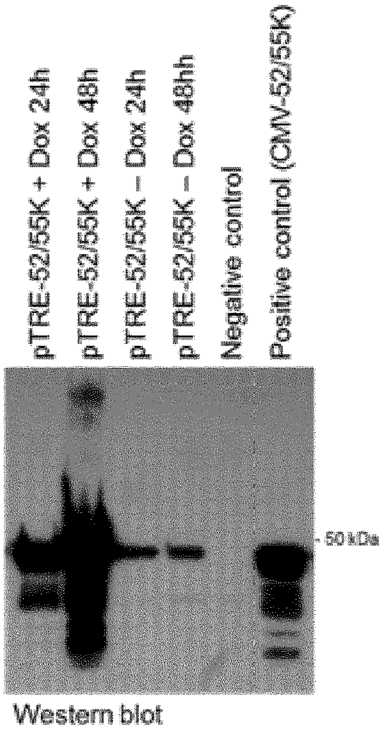

Both assays revealed strong gene expression of 52/55K after induction, however additionally showed some leakiness of the pTRE-Tight promoter due to detectable signals in non-induced cells (FIG. 8 B). This leakiness should be reduced in stably transfected cells, since the amount of DNA is much higher when transiently introduced than genomically integrated.

III. Generation of Inducible Complementing Cell Line for ΔL1-52/55k Mutant Virus Production III.1 Generation and Selection of Stable Cell Clones Expressing L1-52/55K Subsequent to Induction For stable and random transfection, the complementing plasmid pTRE-Tight-BI-AcGFP1-52/55K and a selection marker encoding the puromycin resistance gene were linearized. Therefore, pTRE-Tight-BI-AcGFP1-52/55K was restriction digested using PvuI, a single cutter linearizing the plasmid within the ampicillin resistance gene cassette and for that reason leaving extended overhanging sequences on both ends to reduce loss of information due to DNA breaks during transfection and genomic integration.

Hek293TetON cells (passage 11) were seeded 24 h prior transfection on 6 cm dishes in a density of 1E5 cells/$cm^2$ and cultivated in MEMα+10% FCS+1× GlutaMax+100 μg/ml geneticin. In total 6 μg linearized DNA in a molar ratio of 20:1 target vector to selection marker were transfected using PEIPro Polyplus in a concentration of 2 μg PEI per 1 μg DNA. 24-48 h post transfection cells from one 6 cm dish were expanded to two 15 cm-dishes. Selection pressure using complemented culture media containing 1 μg puromycin was started 96 h post expansion, when cells grew adherently again and showed viable morphology. Medium change was performed once in every two days. 19 days after selection start, 5 cell clones were picked and transferred to 24-Well plates, cultivated in 1 ml/well selection medium. Clones were kept under selection pressure and cultivated up to 6 cm dishes.

III.2 Expression Analysis of Integrated TetON 52/55K

Gene expression of stably integrated inducible TetON 52/55K vector (=pTRE-Tight-BI-AcGFP1-52/55K) was analyzed via Western blotting. Therefore, cell clones were seeded in duplicates in 6-Well plates in a density of 2E5 cells/$cm^2$. 24 h post seeding cell were induced using complemented MEMα medium without selection agent but containing 1 μg/ml doxycycline for induction. Cells were analyzed via GFP-based fluorescence microscopy 48 h after induction and then harvested for Western blot analysis. Homogenous GFP-fluorescence was observed in induced cells and low to no GFP signal was observed in non-induced cells.

Figure 9:
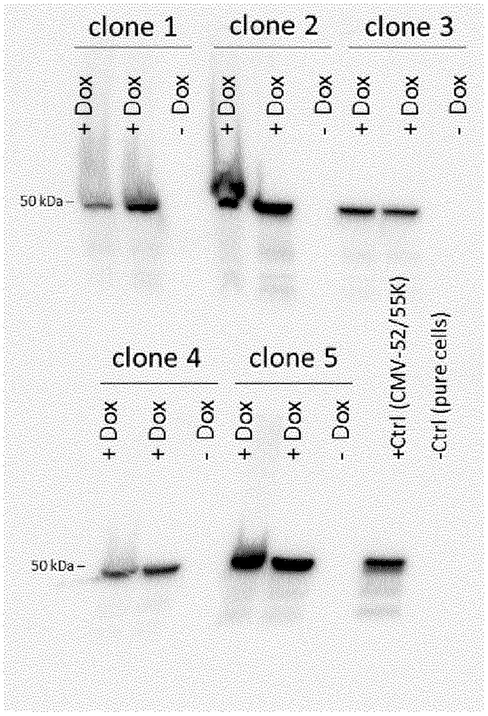
FIG. 9 shows a Western blot analysis of gene expression of stably integrated inducible TetON 52/55K vector (=pTRE-Tight-BI-AcGFP1-52/55K).

Western blot was performed according to the transient expression analysis done previously on the cloned plasmid (see above). Here, strong 52/55K gene expression was detectable from induced cells (=+Dox), but leakiness of the promoter was not shown by non-induced cells (=−Dox). The selected five cell clones showed comparable potency in 52/55K expression to complement the deletion defect of the adenovirus mutant to rescue virus particle production (FIG. 9).

C. Life-Cycle-Defective Ad5 Mutant Deleted in the Pre-Terminal Protein

I. Generation of Adenovirus 5 Deletion Mutant ΔpTP on DNA Level

I.1 Rationale Ad5 ΔpTP Deletion Mutant

Figure 10:
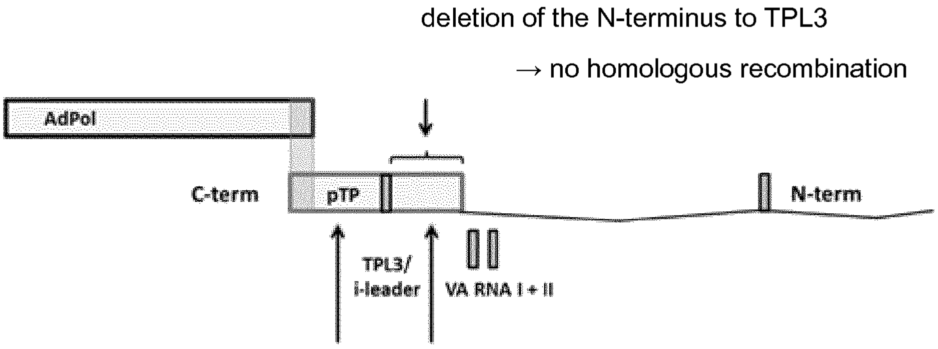
FIG. 10 shows the region of the pTP in the Adenovirus genome.

The terminal protein (TP) has its crucial role during initiation of adenoviral replication. As pre-terminal protein (pTP) it recognizes the terminus of the adenovirus DNA serving as a primer for DNA synthesis and forms a complex together with the adenoviral polymerase (AdPol) to enable replication of the viral genome. Deletion of essential gene sequences within the pTP should interrupt adenoviral life cycle at a very early phase—prior to genome replication. Almost the entire N-terminal coding sequence of 685 bp was deleted up to the beginning of the tripartite leader sequence (TPL) located from nt 9904 to 10589 according to the reference in the database NCBI AC_000008.1 Ad5 complete genome (FIG. 10).

TABLE 7

| pTP deletion in the human Adenovirus 5 NCBI AC_000008.1 complete genome: |
|---|
| . . . CCATGTCCTTGGGTCCGGCCTGCTGAATGCGCAGGGGGTCGGCC |
| ATGCCC_[Δnt9904--10589]_CTAGACCGTGCAAAAGGAGAGCGTGT |
| AAGCGGGCACTCTTCCGTGGTCTG . . . SEQ ID NO: 26) |

"The adenovirus tripartite leader is a 200-nucleotide-long 5' noncoding region which facilitates translation of viral mRNAs at late times after infection" (Dolph et al., 1990). According to this deletion region, overlapping homologous sequences with the gene encoding the pTP within the complementing cell line, for virus production, were avoided, thus reducing the risk of homologous recombination between cell and virus, which could lead to revertants.

Therefore, one object of the present invention is to prepare a ΔpTP deletion mutation and to test its efficiency to support rAAV production.

I.2 Cloning of Ad5 ΔpTP

The adenovirus deletion mutant ΔpTP was generated using Homologous Recombination Gene Bridges Counter Selection Bac Modification Kit by RED®/ET® Recombination according to manufacturer's instructions.

The template DNA for insertion of the deletion defect was an adenovirus wildtype encoding bacmid pBELO66. Bacteria used for bacmid modifications were *E. coli* DH10Beta. Deletion region within the bacmid was located from nt 9464 to nt 10149.

For the first and second RED®/ET® recombination step following primers were designed:

TABLE 8

| Ad5 mutant pTP (intermediate): 50 bp (9853-9903) pTP left to deletion + 24 bp rpSLneo for integration into rpSLneo cassette (italics) |
|---|
| CCATGTCCTTGGGTCCGGCCTGCTGAATGCGCAGGCGGTCGGCCATGCCC *GGCCTGGTGATGATGGCGGGATCG* (SEQ ID NO: 27) |
| **Ad5 mutant pTP (intermediat): 50 bp (10590-10640) pTP right to deletion + 24 bp rpSLneo for integration into rpSLneo cassette (italics)** |
| CAGACCACGGAAGAGTGCCCGCTTACAGGCTCTCCTTTTGCACGGTCTAG *TCAGAAGAACTCGTCAAGAAGGCG* (SEQ ID NO: 28) |
| **M1: Ad5 mutant pTP, deletion No. 9904-10589** |
| CCATGTCCTTGGGTCCGGCCTGCTGAATGCGCAGGCGGTCGGCCATGCCC CTAGACCGTGCAAAAGGAGAGCCTGTAAGCCGGCACTCTTCCGTGGTCTG (SEQ ID NO: 29) |

Bacterial amplification of accomplished bacmid was done in DH10Beta and purified via Qiagen Large Construct Bacmid Preparation Kit according to manufacturer's protocol including the deviation that no exonuclease digestion was performed.

II. Cloning of Plasmid DNA Encoding Ad5 Terminal Protein (pTP) for the Complementing Cell Line To produce Adenovirus mutants that carry a deletion in a crucial gene during life-cycle as virus particles, a complementing cell line expressing that deleted gene is necessary to get virus amplification and progeny. These produced virus particles are then replication-deficient on non-complementing cell lines.

II.1 Amplification of the Target Gene Terminal Protein (pTP) as Insert for the Complementing Plasmid The complementing gene for the Adenovirus deletion mutant ΔpTP was extracted from the bacmid pGS66 encoding the Ad5 genome sequence w/o E1 via Polymerase-Chain-Reaction (PCR) using primers additionally encoding endonuclease-restriction sites NheI and NotI for further cloning steps. The forward primer additionally encoded for a Kozak sequence which was planned to be inserted ahead of the pTP.

TABLE 9

| |
|---|
| Ad5 terminal protein NheI Kozak + 3AS 5'pTP forward |
| attGCTAGCaccATGGCCTTGAGCGTCAACGATTGCGCG (SEQ ID NO: 30) |
| Ad5 terminal protein NotI reverse |
| aGCGGCCGCCTAAAAGCGGTGACGCGGGC (SEQ ID NO: 31) |

The amplified fragment was digested using NheI and NotI. This fragment represented the insert encoding pTP to be introduced into a plasmid vector for subsequent bacterial amplification and introduction of the complementing gene into cells.

II.2 Preparation of Final Complementing Plasmid "pBSK-hPGK-pTP"—Cloning of Target Gene pTP into Backbone Vector pBSK-hPGK The generated PCT fragment encoding the pTP (SEQ ID NO: 3) produced in 11.1 was introduced into backbone vector pBSK-hPGK, containing the hPGK promoter, which had been prepared previously. The hPGK promoter was chosen due to its 'weaker' activity relative to e.g. CMV promoter, on the basis that high expression levels of pTP were assumed to have a cytotoxic effect. Successfully cloned "pBSK-hPGK-pTP" was amplified in *E. coli* XL-2 Blue to obtain material sufficient both for characterization and stable transfection.

III. Generation of Complementing Cell Line for ATP Mutant Virus Production

III.1 Generation and Selection of Stable Cell Clones Expressing pTP

For stable and random transfection, the complementing plasmid pBSK-hPGK-pTP and a selection marker encoding the puromycin resistance gene were linearized. Therefore, pBSK-hPGK-pTP was restriction digested using XmnI, a single cutter linearizing the plasmid within the ampicillin resistance gene cassette and for that reason leaving extended overhanging sequences on both ends to reduce loss of information due to DNA breaks during transfection and genomic integration.

A549 cells (passage 94) were seeded 24 h prior transfection on 6 cm dishes in a density of 1E6 cells/dish. In total 6 μg linearized DNA in a molar ratio of 10:1 target vector to selection marker were transfected using PEIPro Polyplus in a concentration of 1 μg PEI per 1 μg DNA. 48 h post transfection cells from one 6 cm dish were expanded to two 15 cm-dishes. Selection pressure using complemented culture media containing 0.5 μg puromycin was started 24 post expansion. Medium change was performed once in every two days. 10 days after selection start, 30 cell clones were picked and transferred to 6-Well plates, cultivated in 3 ml/well selection medium. Clones were kept under selection pressure and cultivated up to 6 cm dishes.

III.2 Expression analysis of integrated pTP

Gene expression of stably integrated pTP by positive transfectants was analyzed via PCR. Therefore, 3E5 cells were harvested using Trypsin and pelleted for total gDNA isolation using Qiagen QIAmp DNA Mini Kit according to manufacturer's instructions (Appendix A: Protocol for cultured cells).

PCR reactions were performed in a total volume of 25 μl using 600 ng gDNA, primer concentrations of 200 nM each, 600 μM dNTP, 1×Thermo Pol Buffer and 1 U Taq DNA polymerase. Following primers were used: 5'-TGTAGCCTTTGAGCGCGA-3' (forward) (SEQ ID NO: 32); 5'-ACCATGATTACGCCAAGCTC-3' (reverse) (SEQ ID NO: 33). Amplification was performed under following conditions: initial heat activation at 95° C. for 2 min, 28 cycles of denaturation at 95° C. for 30 sec, annealing at 49° C. for 30 sec, elongation at 68° C. for 1:25 min, followed by a final extension step at 68° C. for 5 min. Molecular mass was calculated to 6.60E-09 ng/fragment and amount of template applied corresponded to 6 μg/genome. As a reference circular plasmid DNA of pBSK-hPGK-pTP was used as serial $10^{-1}$ dilution in concentrations from 6E6 to 6E3. In case of correct amplification products, PCR fragments in size of 1113 bp were available on agarose gel electrophoresis. According to the calculation of 6 μg template DNA per genome, selected stable cell clones indicated all to express the complementing gene pTP, leading to the assumption of a homogenous cell population. Selected cell clone A549 42.9 was cryoconserved as MCB and WCB. Maintenance cell culture was further done without selection pressure.

IV. Adenovirus Deletion Mutant ATP Virus Production

IV.1 Virus Rescue/Production after Bacmid Transfection

A549 42.9 cells were seeded on 6 cm dishes at a density of 1E6 cells/dish in selection medium. Bacmid DNA encoding the adenovirus deletion mutant ΔpTP was linearized via SwaI restriction digestion, extracting the vector backbone from the sequence encoding the mutant to release adenoviral terminal repeats. After restriction digestion, 5 μg of DNA was purified via phenol/chlorophorm extraction with subsequent ethanol/sodium acetate precipitation. Cells were transfected 24 h post seeding using laboratory's PEI in a ratio of 60 μl PEI per 5 μg DNA. Transfection mixes were prepared in 150 mM NaCl as total volumes of 250 μl per DNA-reaction mix and PEI-reaction mix, each. 24 h post transfection medium change was performed. Cells were kept in selection medium during virus amplification and expanded into larger culture formats to avoid overgrowing. At day 7 post transfection, cells showed cytopathic effect (CPE), indicating virus mutant rescue and virus amplification. Therefore, cells were harvested completely (medium+cells) by scraping and lysed by three freeze and thaw cycles to re-infect A549 42.9 cells seeded in a 15 cm dish (=1$^{st}$ amplification step). 48 h post re-infection, those cells showed CPE and were harvested for the 2$^{nd}$ amplification step in the same manner as previously, but only half of the lysate was used to re-infect two 15 cm dishes of A549 42.9 cells. In total three amplification steps were performed with 2×15 cm dishes a 7E6 cells/dish to obtain enough adenovirus for virus preparation.

IV.2 Adenovirus Deletion Mutant ΔpTP Preparation/Purification

For final preparation, the virus lysates from the second and third amplification step were pooled and used to re-infect 12×15 cm dishes of A549 42.9 cells. Previously, on 24-Well plate format, the optimal amount of virus lysate had been titrated to obtain optimal CPE 48 h post infection. According to that titration experiment, the entire virus lysate from the amplification steps had been sufficient for 12 dishes of cells seeded to 70-80% growth confluency. Cells were kept in selection medium containing 0.5 μg/ml puromycin, and incubated at 37° C., 5% $CO_2$, for 48 h. After that time, cells showed complete CPE and were harvested completely together with the supernatant and centrifuged at 400×g, 4° C. for 10 min. Pellet was resolved in 3 ml HEPES pH 7.5 (50 mM Hepes, 150 mM NaCl) Control plate showed no CPE. Virus was released via three freeze and thaw cycles (liquid nitrogen, water bath 37° C.) and cell debris removed by subsequent centrifugation at 3000 rpm for 10 min.

CsCl step gradient ultracentrifugation purification was performed to obtain purified virus stocks. For the first discontinous CsCl-gradient, virus lysate solution was layered on two CsCl-buffers comprising the densities 1.41 g/ml and 1.27 g/ml, and centrifuged for 2 h at 32 000 rpm at 4° C., using a Sorvall Discovery 90SE Hitachi Ultracentrifuge.

Subsequently, concentrated virus was extracted from the gradient and applied for the second continuous CsCl gradient ultracentrifugation for further purification. Therefore, extracted virus was mixed with CsCl-buffer pH 7.5 comprising a density of 1.34 g/ml and centrifuged for 24 h at 32 000 rpm at 4° C. After centrifugation, virus was extracted and desalted via size exclusion chromatography using PD-10 columns (GE Healthcare). Purified vector particles were supplemented with 10% glycerol and stored in aliquots at −80° C.

IV.3 Adenovirus Deletion Mutant ΔpTP Characterization

Produced adenovirus deletion mutant ΔpTP was verified by several analyses during amplification steps and subsequent to virus purification.

Viral DNA was isolated from virus lysates from reinfected cells during the amplification steps and from purified virus using Qiagen QIAmp DNA Mini Kit. Isolated DNA was controlled via restriction digestion using HindIII with subsequent agarose gel electrophoresis.

Since virus progeny of the mutant should only be possible on cells complementing the deletion defect, no virus amplification and thus no cytopathic effect (CPE) should occur in cells not carrying the complementing gene. Therefore, three rounds of re-infections on non-complementing A549 cells using different amounts of non-purified virus lysates and different MOIs of virus stock were done to exclude possible reversion of deletion and to confirm replication-deficiency. All validation steps showed no CPE.

Photometric analysis was performed to determine physical titer, purity and to some extend integrity. Additionally, to evaluate potency and quality of produced virus, complementing cells were titrated using different ratios of infectivity (MOI) and observed for optimal CPE 48 h p.i.

V. Adenovirus Deletion Mutant ΔTP as Helper Virus for rAAV Production

V.1 Transient rAAV Production on A549 Cells Using Adenovirus Deletion Mutant ΔpTP as Helper Virus A549 cells were seeded in 6 cm-dishes at a density of 4E4 cells/$cm^2$ and transfected 24 h post seeding via co-transfection of the three plasmids rAAV vector+rep+cap. Directly after transfection, cells were infected with helper virus Ad5ΔpTP pMOI 500 and as a reference with Adenovirus type 5 wildtype pMOI 500. Cells were incubated at 37° C., 5% $CO_2$ for 48 h. Microscopy of cells revealed CPE on cells infected with Adwt but no cytopathic effect was observed on cells infected with Ad5ΔpTP.

Cells were harvested via scraping and lysed by three freeze and thaw cycles (liquid nitrogen, water bath 37° C.) with subsequent centrifugation at 3700×g for 10 min to remove cell debris. In case of Adwt infection, helper virus was inactivated by incubation at 56° C. for 30 min. Non-purified rAAV lysates were analyzed via qPCR to evaluate the genomic titer.

For qPCR 30 μl diluted $10^{-2}$ rAAV lysate was treated with 10 U recombinant DNase I (Roche) for 3 hours at 37° C. water bath to remove genomic and non-packaged vector DNA. Afterwards, 30 μl 400 mM NaOH was added for 45 min at 65° C. to inactivate DNase and denature vector particles. For efficient PCR, sample pH was neutralized by adding 30 μl 400 mM HCl and were finally diluted $12.5^{-1}$ in nuclease-free water.

Amplification was performed in a total volume of 25 μl using 2×QUANTIFAST™ SYBR®Green PCR Mix, 100 nM forward primer 5'-GGAACCCCTAGTGATGGAGTT-3' (SEQ ID NO: 34), 300 nM reverse primer 5'-CGGCCTCAGTGAGCGA-3' (SEQ ID NO: 35) and 5 μl template. PCR conditions were as followed: initial heat activation of polymerase at 95° C. for 5 min; 39 cycles of denaturation at 95° C. for 10 s and annealing/extension at 60° C. for 30 s; followed by a temperature gradient of 1° C. $s^{-1}$ from 65 to 95° C.

Figure 12:
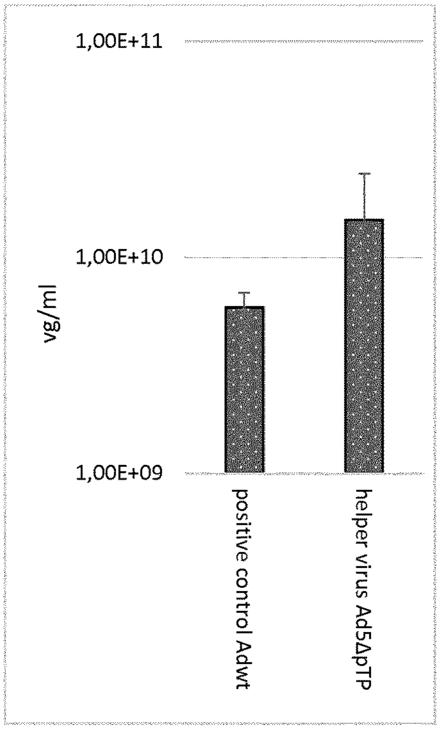
FIG. 12 shows the results that the Ad5ΔpTP deletion mutant provides helper functions for rAAV production.

Results showed that Ad5ΔpTP deletion mutant efficiently provided helper functions for rAAV production (FIG. 12). Transiently produced rAAV in A549 via co-transfection and subsequent helper virus infection led to titers of about $10^{10}$ vector genomes per ml (vg/ml), indicating a helper efficiency comparable to Adenovirus wildtype. Calculations revealed yields of about $5\times10^4$ rAAV vectors per cell.

V.2 rAAV Production on Stable Producer Cell Using Adenovirus Deletion Mutant ΔpTP as Helper Virus In contrast to transient rAAV production where the components for rAAV packaging are introduced to the cell via co-transfection of three or two plasmids encoding the required elements for replicase (rep genes) and structure proteins (cap genes) and the vector transgene cassette itself with subsequent delivery of helper functions via infection, a stable producer cell line harbors the entire set of components, stably integrated into its genome. Therefore, rAAV production is initiated after super-infection of this cell by a helper virus.

For rAAV production stable producer cells were seeded in 6 cm-dishes at a density of 4E4 cells/$cm^2$ and 24 h post seeding, cells were infected with helper virus Ad5ΔpTP pMOI 500 and as a reference with Adenovirus type 5 wildtype pMOI 500. Cells were incubated at 37° C., 5% $CO_2$ for 48 h. Microscopy of cells revealed CPE on cells infected with Adwt but no cytopathic effect was observed on cells infected with Ad5ΔpTP.

Cells were harvested via scraping and lysed by three freeze and thaw cycles (liquid nitrogen, water bath 37° C.) with subsequent centrifugation at 3700×g for 10 min to remove cell debris. In case of Adwt infection, helper virus was inactivated by incubation at 56° C. for 30 min. Non-purified rAAV lysates were analyzed via qPCR to evaluate the genomic titer.

For qPCR 30 μl diluted $10^{-2}$ rAAV lysate was treated with 10 U recombinant DNase I (Roche) for 3 hours at 37° C. water bath to remove genomic and non-packaged vector DNA. Afterwards, 30 μl 400 mM NaOH was added for 45 min at 65° C. to inactivate DNase and denature vector particles. For efficient PCR, sample pH was neutralized by adding 30 μl 400 mM HCl and were finally diluted $12.5^{-1}$ in nuclease-free water.

Amplification was performed in a total volume of 25 μl using 2×QUANTIFAST™ SYBR®Green PCR Mix, 100 nM forward primer 5'-GGAACCCCTAGTGATGGAGTT-3' (SEQ ID NO: 36), 300 nM reverse primer 5'-CGGCCTCAGTGAGCGA-3' (SEQ ID NO: 37) and 5 μl template. PCR conditions were as followed: initial heat activation of polymerase at 95° C. for 5 min; 39 cycles of denaturation at 95° C. for 10 s and annealing/extension at 60° C. for 30 s; followed by a temperature gradient of 1° C. $s^{-1}$ from 65 to 95° C.

Figure 13:
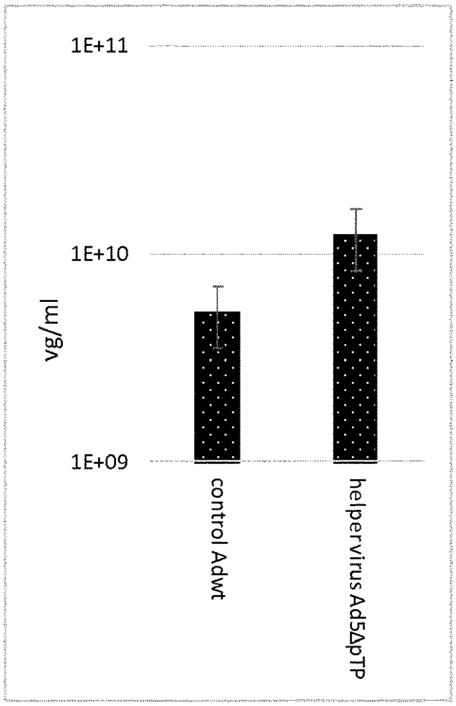
FIG. 13 shows additional results that the Ad5ΔpTP deletion mutant provides helper functions for rAAV production.

Results showed that Ad5ΔpTP deletion mutant efficiently provided helper functions for rAAV production (FIG. 13). rAAV produced in stable A549 producer cells after super-infection with helper virus led to titers of about $10^{10}$ vector genomes per ml (vg/ml), indicating a helper efficiency comparable to Adenovirus wildtype. Calculations revealed yields of about $2\times10^4$ rAAV vectors per cell.

D. Temperature-Sensitive Ad5 Mutant Point-Mutated in the L4-100K and Hexon Protein I. Generation of Adenovirus 5 Temperature-Sensitive Double-Mutant with Mutations in 100K and Hexon on DNA Level 1.1 Rationale Ad5 temperature-sensitive mutant ts100KtsHexon A double-mutant carrying temperature-sensitive mutations in the L4-100k and hexon genes has not previously been generated. Since both genes do not function as adenoviral helper genes for a productive rAAV life-cycle, a virus having ts mutations in these genes would have the potency to be used as helper virus. In addition, the two ts mutations would essentially eliminate a reversion of the ts phenotype. Typical reversion frequencies of Adenovirus ts mutants are between $10^{-6}$ to $10^{-7}$. Combining two ts mutants on one virus reduced the likelihood of reversion to $10^{-12}$ to $10^{14}$, which means to a completely non-ts phenotype. Adenovirus wild-type infection for rAAV production results in contaminated stocks of rAAV by adenovirus due to simultaneous adenovirus production. By rAAV production at non-permissive temperature, no adenovirus progeny should be formed, thus not contaminating the rAAV stocks produced.

Therefore, one object of the present invention is to prepare a double-mutant carrying both mutations and to test for its efficiency to support rAAV production.

I.2 Cloning of Ad5 ts100KtsHexon

The adenovirus temperature-sensitive mutant ts100KtsHexon was generated in two consecutive alteration steps using Homologous Recombination Gene Bridges Counter Selection Bac Modification by RED®/ET® Recombination according to manufacturer's instructions. First, an adenovirus mutant carrying the point-mutation for the ts100K was generated. Second, the temperature-sensitive point mutation for the hexon protein was additionally inserted into the mutant to obtain the temperature-sensitive double-mutant ts100KtsHexon, carrying the mutations TCC to CCC and GGC to GAT, located at positions nt 25456-nt 25458 and nt 21170-nt 21172 according to the reference NCBI AC_000008.1 Human Adenovirus type 5 complete genome.

1.2.1 Generation of Intermediate Temperature-Sensitive Mutant ts100K

The template DNA for insertion of the ts100K defect was an adenovirus wildtype encoding bacmid pBELO66. Bacteria used for bacmid modifications were *E. coli* DH10Beta. Region mutated on the bacmid comprised an exchange from TCC to CCC, representing the alteration from Serine (Ser466) to Proline (Pro466), and was located from nt 25016 to nt 25018.

For the first and second RED®/ET® recombination step to obtain the mutant carrying the temperature-sensitive mutation within the 100K, following primers were designed:

TABLE 10

| Ad5 mutant H5ts1B 100K (intermediate): 50 bp (25406-25455) 100K left from mutation + 24 bp rpSLneo for integration of rpSLneo cassette (italics) |
|---|
| AACTGCTAAAGCAAAACTTGAAGGACCTATGGACGGCCTTCAACGAGCGC *GGCCTGGTGATGATGGCGGGATCG* (SEQ ID NO: 38) |
| Ad5 mutant H5ts1B 100K (intermediate): 50 bp (25459-25508) 100K right from mutation + 24 bp rpSLneo for integration of rpSLneo cassette (italics) |
| GTTTTAAGCAGGCGTTCGGGGAAAATGATGTCCGCCAGGTGCGCGGCCAC *TCAGAAGAACTCGTCAAGAAGGCG* (SEQ ID NO: 39) |
| M4: Ad5 H5ts1B Mutant ts100K, mutation nt 25456-nt 25458 (TCC (Ser466) to CCC (Pro466) mutated) |
| AACTGCTAAAGCAAAACTTGAAGGACCTATGGACGGCCTTCAACGAGCGC **CCC**GTGGCCGCGCACCTGGCGGACATCATTTTCCCCGAACGCCTGCTTAA AA (SEQ ID NO: 40) |

Bacterial amplification of accomplished bacmid was done in *E. coli* DH10Beta and purified via Qiagen Large Construct Bacmid Preparation Kit according to manufacturer's protocol including the deviation that no exonuclease digestion was performed.

1.2.2 Generation of Final Temperature-Sensitive Mutant ts100KtsHexon

The previously generated mutant Ad5ts100K represented the template DNA for the second round of bacmid modification using RED®/ET® recombination to additionally insert the tsHexon defect to obtain the temperature-sensitive double mutant Ad5ts100KtsHexon. Bacteria used for bacmid modifications were *E. coli* DH10Beta. Region mutated on the bacmid comprised an exchange from GGC to GAT, representing the alteration from Glycin (Gly) to Aspartic acid (Asp), and was located from nt 20730 to nt 220732.

For the first and second RED®/ET® recombination step to obtain the double-mutant additionally carrying the temperature-sensitive mutation within Hexon, following primers were designed:

TABLE 11

| Ad5ts147 Hexon ts intermediate: 50 bp left from nt 20730 (Hexon) + 24 bp rpSLneo for integration of rpSLneo cassette (italics) |
|---|
| acatgaccaaagactggttcctggtacaaatgctagctaactacaacatt *GGCCTGGTGATGATGGCGGGATCG* (SEQ ID NO: 41) |
| Ad5ts147 Hexon ts intermediate: 50 bp right from nt 20732 (Hexon) + 24 bp rpSLneo for integration of rpSLneo cassette (italics) |
| aaggagtacatgcggtccttgtagctctctgggatatagaagccctggta *TCAGAAGAACTCGTCAAGAAGGCG* (SEQ ID NO: 42) |
| Ad5ts147 Hexon ts: Hexon nt 2329 = AS 776: Gly (GGC) => Asp (GAT) 20730-20732 in pBEL066 = Mutation |
| acatgaccaaagactggttcctggtacaaatgctagctaactacaacatt **GAT**taccagggcttctatatcccagagagctacaaggaccgcatgtactc ctt (SEQ ID NO: 43) |

Bacterial amplification of accomplished bacmid was done in *E. coli* DH10Beta and purified via Qiagen Large Construct Bacmid Preparation Kit according to manufacturer's protocol including the deviation that no exonuclease digestion was performed.

II. Adenovirus Temperature-Sensitive Mutant ts100KtsHexon Virus Production

II.1 Virus Rescue/Amplification after Bacmid Transfection

The production of Adenovirus mutants carrying a temperature-sensitive point-mutation is not limited to a cell line complementing the defect, but to production at permissive temperatures. Therefore, A549 cells were seeded on 6 cm dishes in a density of 5E5 cells/dish in a total volume of 5.5 ml DMEM medium (gibco #10938) complemented with 10% FCS and 1× GlutaMax medium. Bacmid DNA encoding the adenovirus deletion mutant ts100KtsHexon was linearized via SwaI restriction digestion at 25° C. for 15 h, extracting the vector backbone of 6205 bp from the sequence encoding the mutant to release adenoviral terminal repeats. After restriction digestion, 60 μg of DNA were purified via phenol/chlorophorm extraction with subsequent ethanol/sodium acetate precipitation, and 100 ng controlled via agarose gel electrophoresis. Cells were transfected 24 h post seeding using laboratory's PEI in a ratio of 62.5 μl 7.5 mM PEI per 5 μg DNA. Transfection mixes were prepared in 150 mM NaCl as total volumes of 250 μl per DNA-reaction mix and PEI-reaction mix, each, united and added to the cells after 10 min of incubation. In case of virus rescue, cells would show cytopathic effect several days after transfection, due to viral protein expression and amplification. 24 h post transfection medium change was performed. About 7-9 days after transfection, cells were harvested via TrypLE, and ⅓ was seeded on one 10 cm dish, whereas ⅔ were lyzed via three freeze and thaw cycles (liquid nitrogen, water bath 37° C.) to re-infect A549 cells seeded on a 15 cm dish (=1 amplification). Cells were incubated at 32° C., 5% $CO_2$. Three days later, cells showed CPE and were harvested for the $2^{nd}$ amplification step in the same manner as previously and the lysate for used to re-infect 4×15 cm dishes of A549 cells. During amplification steps, temperature-sensitivity was controlled additionally by using the lysate from amplification at 32° C. to re-infect A549 cells seeded in 6 cm dishes and cultivated at the non-permissive temperature of 39° C. Furthermore, possible revertants were analyzed by several amplification rounds, continuously performed at 39° C. In those controls, no virus should be observed.

After three days of $2^{nd}$ amplification, cells were harvested completely, centrifuged at 300×g for 5 min and the pellet dissolved in 4 ml PBS and lyzed via three freeze and thaw cycles with subsequent centrifugation at 4400 rpm for 10 min, to remove cell debris. The supernatant was the lysate for the infection of A549 cells for virus preparation.

II.2 Adenovirus is Mutant Ts100KtsHexon Preparation/Purification

For final preparation, the virus lysate from the second amplification step were used to re-infect 20×15 cm dishes of A549 cells, seeded to a confluency of about 80%. Cells were incubated at 32° C., 5% $CO_2$, for 72 h. After that time, cells showed CPE and were harvested completely via scraping, together with the supernatant and centrifuged at 400×g, 4° C. for 10 min. Pellet was resolved in 6 ml PBS. Virus was released via three freeze and thaw cycles (liquid nitrogen, water bath 37° C.) and cell debris removed by subsequent centrifugation at 4400 rpm for 10 min.

CsCl step gradient ultracentrifugation purification was performed to obtain purified virus stocks. For the first discontinuous CsCl-gradient, virus lysate solution was layered on two CsCl-buffers comprising the densities 1.41 g/ml and 1.27 g/ml, and centrifuged for 2 h at 32 000 rpm at 4° C., using a Sorvall Discovery 90SE Hitachi Ultracentrifuge.

Subsequently, concentrated virus was extracted from the gradient and applied for the second continuous CsCl gradient ultracentrifugation for further purification.

Therefore, extracted virus was mixed with CsCl-buffer pH 7.5 comprising a density of 1.34 g/ml and centrifuged for 20 h at 32 000 rpm at 4° C. After centrifugation, virus was extracted and added to HEPES buffer pH 7.1 (150 mM NaCl, 50 mM HEPES). Virus was desalted via size exclusion chromatography using PD-10 columns (GE Healthcare), which previously were equilibrated five times with 5 ml HEPES buffer. Subsequently, previously extracted vector sample was loaded onto the columns and eluted with 5 ml HEPES buffer, collected in five fractions of 1 ml volume, wherein fraction two and three contained the vector. Purified vector particles were supplemented with 10% glycerol and stored in aliquots at −80° C.

II.3 Adenovirus Temperature-Sensitive Mutant ts100KtsHexon Characterization

Produced adenovirus mutant ts100KtsHexon was verified by several analyses subsequent to virus purification.

Viral DNA was isolated from purified virus using Qiagen QIAmp DNA Mini Kit and controlled via restriction digestion of 150 ng DNA with subsequent agarose gel electrophoresis.

Photometric analysis was performed to determine physical titer, purity and to some extend integrity. Since virus progeny of the mutant should only be possible at permissive temperature, no virus amplification and thus no cytopathic effect (CPE) should occur in cells incubated at the non-permissive temperature of 39° C. Therefore, A549 cells were infected with purified virus using different ratios of infection and incubated at 37° C., 32° C. and 39° C. to analyze temperature-sensitivity of the virus mutant. As control, cells were infected with Ad5 wt, respectively. Cytopathic effect occurred at all incubation temperatures, but was not observed in cells infected with mutant virus at temperatures of 37° C. and 39° C., thus indicating, that the double-mutant carrying both ts100K and tsHexon mutations had a higher temperature-sensitivity than mutants carrying only one of both mutations which were known to be permissive at 37° C. Furthermore, stability was controlled by three rounds of re-infection at non-permissive temperature to analyze possible virus revertants during amplification.

Furthermore, quantitative analysis of temperature-sensitivity and determination of infectious particles were analyzed via Plaque Assay. Therefore, A549 cells were seeded in 6-Well plates in a density of $3.5\times10^5$ cells/well and incubated at 32° C., 5% $CO_2$ at 32° C. Cells were infected with Ad5ts100KtsHexon and Ad5 wt as reference using infection rates of 1E3, 1E2 and 1E1 particles/cell. Infected cells were incubated at 32° C. for 4 hours, then an 0.75% agarose gel overlay was prepared in culture medium and subsequently cells were further kept at 32° C. or shifted to 37° C. and 39° C., respectively. Next day a second overlay was performed onto the first agarose gel overlay to provide enough nutrition during the time of assay. Cells were incubated for 15 days and analyzed via microscopy once every two to three days. In cells infected with Ad5 wt plaques emerged at day seven and showed complete CPE till day 9, independently to infection rate and incubation temperature. In cells infected with the double-mutant Ad5ts100KtsHexon plaques, thus CPE, was observed from day 7 till reaching complete CPE till day nine, at incubation temperature at 32° C. and an infection rate of 1E3 particles/cell. Infection rates of 1E2 and 1E1 reached complete CPE 13 days after infection. Cells incubated at 39° C. did not develop plaques during all 15 days, confirming temperature-sensitivity. However, most striking was the observation that cells infected with Ad5ts100KtsHexon and incubated at temperatures of 37° C. did not develop plaques at all, indicating that 37° C. represents a non-permissive temperature for that double-mutant.

III. Transient rAAV Production on A549 Cells Using Ad5 ts100KtsHexon as Helper Virus A549 cells were seeded in 6 cm-dishes at a density of 4E4 cells/cm2 and transfected 24 h post seeding either via single-plasmid transfection with one plasmid, designated "All-in-One", encoding for rAAV vector+rep+cap, or via co-transfection of three plasmids each encoding rAAV vector, rep, and cap in a molar ratio of 4:3:9. Directly after transfection, cells were infected with helper virus Ad5ts100KtsHexon pMOI 500 and as a reference with Adenovirus type 5 wildtype pMOI 500. rAAV production was performed at 37° C. and 39° C., respectively, due to previous investigations indicating even 37° C. to be non-permissive to the double-mutant. For rAAV production at 39° C., cells were incubated at 37° C., 5% $CO_2$ for 1 h and then shifted to 39° C., 5%$00_2$ for 48 h. Microscopy of cells revealed CPE (=cytopathic effect) on cells infected with Adwt. As expected, little CPE was observed on cells infected with Ad5ts100KtsHexon, too. Since L4-100K is a very late protein playing a role in virion assembly and the hexon mutation results in a transport deficiency of hexon capsid proteins from cytoplasm to nucleus, the naturally occurring life cycle of adenovirus is not interrupted until maturation and virus assembly, thus most viral proteins are already expressed leading to the cytopathic effect in cells.

Cells were harvested via scraping and lysed by three freeze and thaw cycles (liquid nitrogen, water bath 37° C.) with subsequent centrifugation at 3700×g for 10 min to remove cell debris. In case of Adwt infection, helper virus was inactivated by incubation at 56° C. for 30 min. Non-purified rAAV lysates were analyzed via qPCR to evaluate the genomic titer.

For qPCR 30 μl diluted 10-2 rAAV lysate was treated with 10 U recombinant DNase I (Roche) for 3 hours at 37° C. water bath to remove genomic and non-packaged vector DNA. Afterwards, 30 μl 400 mM NaOH was added for 45 min at 65° C. to inactivate DNase and denature vector particles. For efficient PCR, sample pH was neutralized by adding 30 μl 400 mM HCl and were finally diluted 12.5-1 in nuclease-free water.

Amplification was performed in a total volume of 25 μl using 2×QUANTIFAST™ SYBR®Green PCR Mix, 100 nM forward primer 5'-GGAACCCCTAGTGATGGAGTT-3' (SEQ ID NO: 44), 300 nM reverse primer 5'-CGGCCTCAGTGAGCGA-3' (SEQ ID NO: 45) and 5 μl template. PCR conditions were as followed: initial heat activation of polymerase at 95° C. for 5 min; 39 cycles of denaturation at 95° C. for 10 s and annealing/extension at 60° C. for 30 s; followed by a temperature gradient of 1° C. s−1 from 65 to 95° C.

Figure 14:
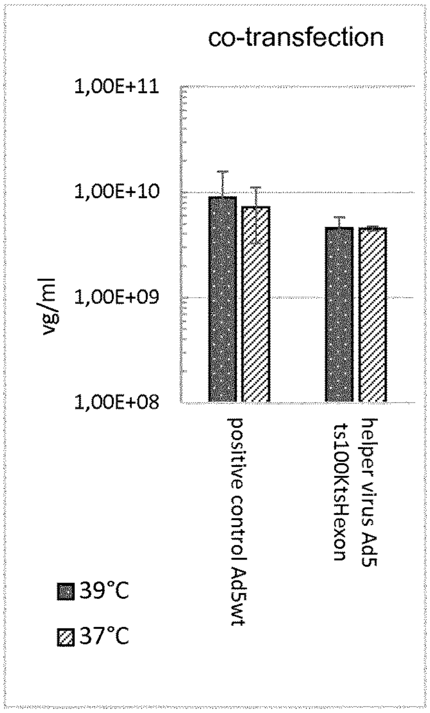
FIG. 14 shows the results of a co-transfection experiment of three plasmids each encoding rAAV vector, rep and cap.
Figure 15:
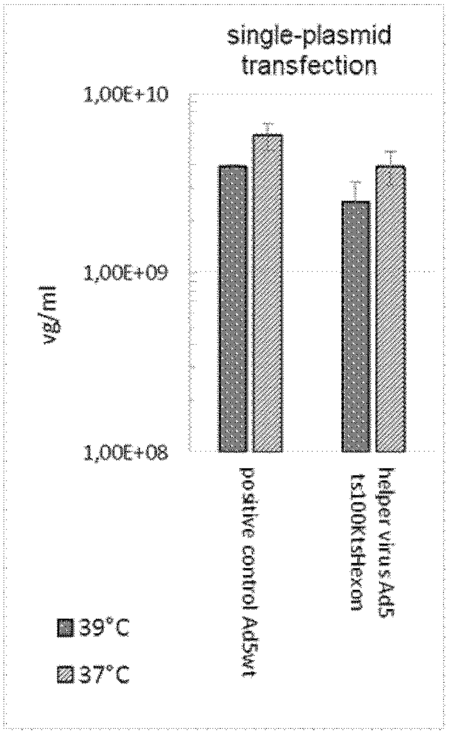
FIG. 15 shows the results of a single "All-in-One" transfection experiment with one plasmid encoding rAAV vector plus rep plus cap.

Results showed that Ad5Ad5Δts100KtsHexon mutant efficiently provided helper functions for rAAV production. Transiently produced rAAV in A549 via co-transfection led to titers of about $5\times10^{09}$ vector genomes per ml (vg/ml) and of about $2\times10^{04}$ vectors per cell (vg/cell) (FIG. 14). Production via single-plasmid transfection led to lower titers of about $2.5\times10^{9}$ vg/ml and about $9.5\times10^{93}$ vg/cell (FIG. 15). In comparison to Ad5 wt both production methods showed about ½-fold lower yields using the Ad5ts100KtsHexon mutant.

LITERATURE

Dolph, P. J., J. T. Huang, und R. J. Schneider. "Translation by the Adenovirus Tripartite Leader: Elements Which Determine Independence from Cap-Binding Protein Complex". Journal of Virology 64, Nr. 6 (Juni 1990): 2669-77.

Gustin, K. E., und M. J. Imperiale. "Encapsidation of Viral DNA Requires the Adenovirus L1 52/55-Kilodalton Protein". Journal of Virology 72, Nr. 10 (Oktober 1998): 7860-70.

Hasson, T. B., P. D. Soloway, D. A. Ornelles, W. Doerfler, und T. Shenk. "Adenovirus L1 52- and 55-Kilodalton Proteins Are Required for Assembly of Virions". Journal of Virology 63, Nr. 9 (September 1989): 3612-21.

Hodges, B. L., H. K. Evans, R. S. Everett, E. Y. Ding, D. Serra, und A. Amalfitano. "Adenovirus Vectors with the 100K Gene Deleted and Their Potential for Multiple Gene Therapy Applications". Journal of Virology 75, Nr. 13 (Juli 2001): 5913-20. doi:10.1128/JVI.75.13.5913-5920.2001.

Kauffman, R. S., und H. S. Ginsberg. "Characterization of a Temperature-Sensitive, Hexon Transport Mutant of Type 5 Adenovirus". Journal of Virology 19, Nr. 2 (August 1976): 643-58.

Maxwell, I. H., F. Maxwell, und J. Schaack. "An Adenovirus Type 5 Mutant with the Preterminal Protein Gene Deleted Efficiently Provides Helper Functions for the Production of Recombinant Adeno-Associated Virus". Journal of Virology 72, Nr. 10 (Oktober 1998): 8371-73.

Oosterom-Dragon, E A, und H S Ginsberg. "Characterization of two temperature-sensitive mutants of type 5 adenovirus with mutations in the 100,000-dalton protein gene." Journal of Virology 40, Nr. 2 (November 1981): 491-500.

Perez-Romero, Pilar, Kurt E. Gustin, und Michael J. Imperiale. "Dependence of the Encapsidation Function of the Adenovirus L1 52/55-Kilodalton Protein on Its Ability to Bind the Packaging Sequence". Journal of Virology 80, Nr. 4 (Februar 2006): 1965-71. doi:10.1128/JVI.80.4.1965-1971.2006.

Schaack, J., X. Guo, und S. J. Langer. "Characterization of a Replication-Incompetent Adenovirus Type 5 Mutant Deleted for the Preterminal Protein Gene". Proceedings of the National Academy of Sciences of the United States of America 93, Nr. 25 (10. December 1996): 14686-91.

Schaack, J., X. Guo, W. Y. Ho, M. Karlok, C. Chen, und D. Ornelles. "Adenovirus Type 5 Precursor Terminal Protein-Expressing 293 and HeLa Cell Lines". Journal of Virology 69, Nr. 7 (Juli 1995): 4079-85.

Williams, J. F., Meera Gharpure, S. Ustacelebi, und Sylvia McDonald. "Isolation of Temperature-sensitive Mutants of Adenovirus Type 5". Journal of General Virology 11, Nr. 2 (1971): 95-101. doi:10.1099/0022-1317-11-2-95.

Wodrich, Harald, Tinglu Guan, Gino Cingolani, Dan Von Seggern, Glen Nemerow, und Larry Gerace. "Switch from Capsid Protein Import to Adenovirus Assembly by Cleavage of Nuclear Transport Signals". The EMBO Journal 22, Nr. 23 (1, Dec. 2003): 6245-55. doi:10.1093/emboj/cdg614.

ADDITIONAL SEQUENCES (L4-100K mutant)

SEQ ID NO: 1

ATGGAGTCAGTCGAGAAGAAGGACAGCCTAACCGCCCCCTCTGAGTTCGCCACCACCGCCTCCACCGATGCCGCCAACGC

GCCTACCACCTTCCCCGTCGAGGCACCCCCGCTTGAGGAGGAGGAAGTGATTATCGAGCAGGACCCAGGTTTTGTAAGCG

AAGACGACGAGGACCGCTCAGTACCAACAGAGGATAAAAAGCAAGACCAGGACAACGCAGAGGCAAACGAGGAACAAGTC

GGGCGGGGGGACGAAAGGCATGGCGACTACCTAGATGTGGGAGACGACGTGCTGTTGAAGCATCTGCAGCGCCAGTGCGC

CATTATCTGCGACGCGTTGCAAGAGCGCAGCGATGTGCCCCTCGCCATAGCGGATGTCAGCCTTGCCTACGAACGCCACC

TATTCTCACCGCGCGTACCCCCCAAACGCCAAGAAAACGGCACATGCGAGCCCAACCCGCGCCTCAACTTCTACCCCGTA

TTTGCCGTGCCAGAGGTGCTTGCCACCTATCACATCTTTTTCCAAAACTGCAAGATACCCCTATCCTGCCGTGCCAACCG

CAGCCGAGCGGACAAGCAGCTGGCCTTGCGGCAGGGCGCTGTCATACCTGATATCGCCTCGCTCAACGAAGTGCCAAAAA

TCTTTGAGGGTCTTGGACGCGACGAGAAGCGCGCGGCAAACGCTCTGCAACAGGAAAACAGCGAAAATGAAAGTCACTCT

GGAGTGTTGGTGGAACTCGAGGGTGACAACGCGCGCCTAGCCGTACTAAAACGCAGCATCGAGGTCACCCACTTTGCCTA

CCCGGCACTTAACCTACCCCCCAAGGTCTTGCCTACCACTCTGACATAATGGAAGACGTGAGCGGTGACGGTCTACTGGA

GTGTCACTGTCGCTGCAACCTATGCACCCCGCACCGCTCCCTGGTTTGCAATTCGCAGCTGCTTAACGAAAGTCAAATTA

TCGGTACCTTTGAGCTGCAGGGTCCCTCGCCTGACGAAAAGTCCGCGGCTCCGGGGTTGAAACTCACTCCGGGGCTGTGG

ACGTCGGCTTACCTTCGCAAATTTGTACCTGAGGACTACCACGCCCACGAGATTAGGTTCTACGAAGACCAATCCCGCCC

GCCAAATGCGGAGCTTACCGCCTGCGTCATTACCCAGGGCCACATTCTTGGCCAATTGCAAGCCATCAACAAAGCCCGCC

AAGAGTTTCTGCTACGAAAGGGACGGGGGGTTTACTTGGACCCCCAGTCCGGCGAGGAGCTCAACCCAATCCCCCCGCCG

CCGCAGCCCTATCAGCAGCAGCCGCGGGCCCTTGCTTCCCAGGATGGCACCCAAAAAGAAGCTGCAGCTGCCGCCGCCAC

CCACGGACGAGGAGGAATACTGGGACAGTCAGGCAGAGGAGGTTTTGGACGAGGAGGAGGAGGACATGATGGAAGACTGG

GAGAGCCTAGACGAGGAAGCTTCCGAGGTCGAAGAGGTGTCAGACGAAACACCGTCACCCTCGGTCGCATTCCCCTCGCC

GGCGCCCCAGAAATCGGCAACCGGTTCCAGCATGGCTACAACCTCCGCTCCTCAGGCGCCGCCGGCACTGCCCGTTCGCC

GACCCAACCGTAG (L1-52/55K mutant)

SEQ ID NO: 2

CAGCTGGGGCCGGACCTGGGCTGGCGGTGGCACCCGCGCGCGCTGGCAACGTCGGCGGCGTGGAGGAATATGACGAGGAC

GATGAGTACGAGCCAGAGGACGGCGAGTACTAA (pTP mutant)

SEQ ID NO: 3

CTAAAAGCGGTGACGCGGGCGAGCCCCCGGAGGTAGGGGGGGCTCCGGACCCGCCGGGAGAGGGGGCAGGGGC

ACGTCGGCGCCGCGCGCGGGCAGGAGCTGGTGCTGCGCGCGTAGGTTGCTGGCGAACGCGACGACGCGGCGGT

TGATCTCCTGAATCTGGCGCCTCTGCGTGAAGACGACGGGCCCGGTGAGCTTGAGCCTGAAAGAGAGTTCGAC

AGAATCAATTTCGGTGTCGTTGACGGCGGCCTGGCGCAAAATCTCCTGCACGTCTCCTGAGTTGTCTTGATAG

GCGATCTCGGCCATGAACTGCTCGATCTCTTCCTCCTGGAGATCTCCGCGTCCGGCTCGCTCCACGGTGGCGG

CGAGGTCGTTGGAAATGCGGGCCATGAGCTGCGAGAAGGCGTTGAGGCCTCCCTCGTTCCAGACGCGGCTGTA

GACCACGCCCCCTTCGGCATCGCGGGCGCGCATGACCACCTGCGCGAGATTGAGCTCCACGTGCCGGGCGAAG

ACGGCGTAGTTTCGCAGGCGCTGAAAGAGGTAGTTGAGGGTGGTGGCGGTGTGTTCTGCCACGAAGAAGTACA

TAACCCAGCGTCGCAACGTGGATTCGTTGATATCCCCCAAGGCCTCAAGGCGCTCCATGGCCTCGTAGAAGTC

CACGGCGAAGTTGAAAAACTGGGAGTTGCGCGCCGACACGGTTAACTCCTCCTCCAGAAGACGGATGAGCTCG

GCGACAGTGTCGCGCACCTCGCGCTCAAAGGCTACAGGGGCCTCTTCTTCTTCTTCAATCTCCTCTTCCATAA

GGGCCTCCCCTTCTTCTTCTTCTGGCGGCGGTGGGGGAGGGGGGACACGGCGGCGACGACGGCGCACCGGGAG

GCGGTCGACAAAGCGCTCGATCATCTCCCCGCGGCGACGGCGCATGGTCTCGGTGACGGCGCGGCCGTTCTCG

-continued

CGGGGGCGCAGTTGGAAGACGCCGCCCGTCATGTCCCGGTTATGGGTTGGCGGGGGGCTGCCATGCGGCAGGG

ATACGGCGCTAACGATGCATCTCAACAATTGTTGTGTAGGTACTCCGCCGCCGAGGGACCTGAGCGAGTCCGC

ATCGACCGGATCGGAAAACCTCTCGAGAAAGGCGTCTAACCAGTCACAGTCGCAAGGTAGGCTGAGCACCGTG

GCGGGCGGCAGCGGGCGGCGGTCGGGGTTGTTTCTGGCGGAGGTGCTGCTGATGATGTAATTAAAGTAGGCGG

TCTTGAGACGGCGGATGGTCGACAGAAGCACCATGTCCTTGGGTCCGGCCTGCTGAATGCGCAGGCGGTCGGC

CATGCCCCTAGACCGTGCAAAAGGAGAGCCTGTAAGCGGGCACTCTTCCGTGGTCTGGTGGATAAATTCGCAA

GGGTATCATGGCGGACGACCGGGGTTCGAGCCCCGTATCCGGCCGTCCGCCGTGATCCATGCGGTTACCGCCC

GCGTGTCGAACCCAGGTGTGCGACGTCAGACAACGGGGGAGTGCTCCTTTTGGCTTCCTTCCAGGCGCGGCGG

CTGCTGCGCTAGCTTTTTTGGCCACTGGCCGCGCGCAGCGTAAGCGGTTAGGCTGGAAAGCGAAAGCATTAAG

TGGCTCGCTCCCTGTAGCCGGAGGGTTATTTTCCAAGGGTTGAGTCGCGGGACCCCCGGTTCGAGTCTCGGAC

CGGCCGGACTGCGGCGAACGGGGGTTTGCCTCCCCGTCATGCAAGACCCCGCTTGCAAATTCCTCCGGAAACA

GGGACGAGCCCCTTTTTTGCTTTTCCCAGATGCATCCGGTGCTGCGGCAGATGCGCCCCCCTCCTCAGCAGCG

GCAAGAGCAAGAGCAGCGGCAGACATGCAGGGCACCCTCCCCTCCTCCTACCGCGTCAGGAGGGGCGACATCC

GCGGTTGACGCGGCAGCAGATGGTGATTACGAACCCCCGCGGCGCCGGGCCCGGCACTACCTGGACTTGGAGG

AGGGCGAGGGCCTGGCGCGGCTAGGAGCGCCCTCTCCTGAGCGGTACCCAAGGGTGCAGCTGAAGCGTGATAC

GCGTGAGGCGTACGTGCCGCGGCAGAACCTGTTTCGCGACCGCGAGGGAGAGGAGCCCGAGGAGATGCGGGAT

CGAAAGTTCCACGCAGGGCGCGAGCTGCGGCATGGCCTGAATCGCGAGCGGTTGCTGCGCGAGGAGGACTTTG

AGCCCGACGCGCGAACCGGGATTAGTCCCCGTGGCGGCCGCCGACCTGGTAACCGCATACGAGCAGACGGTGA

ACCAGGAGATTAACTTTCAAGCGCGCGCACAAAAAGCTTTAACAACCACGTGCGTACGCTTGTGGCGCGCGAG

GAGGTGGCTATAGGACTGATGCATCTGTGGGACTTTGTAAGCGCGCTGGAGCAAAACCCAAATAGCAAGCCGC

TCATGGCGCAGCTGTTCCTTATAGTGCAGCACAGCAGGGACAACGAGGCATTCAGGGATGCGCTGCTAAACAT

AGTAGAGCCCGAGGGCCGCTGGCTGCTCGATTTGATAAACATCCTGCAGAGCATAGTGGTGCAGGAGCGCAGC

TTGAGCCTGGCTGACAAGGTGGCCGCCATCAACTATTCCATGCTTAGCCTGGGCAAGTTTTACGCCCGCAAGA

TATACCATACCCCTTACGTTCCCATAGACAAGGAGGTAAAGATCGAGGGGTTCTACATGCGCATGGCGCTGAA

GGTGCTTACCTTGAGCGACGACCTGGGCGTTTATCGCAACGAGCGCATCCACAAGGCCGTGAGCGTGAGCCGG

CGGCGCGAGCTCAGCGACCGCGAGCTGATGCACAGCCTGCAAAGGGCCCTGGCTGGCACGGGCAGCGGCGATA

GAGAGGCCGAGTCCTACTTTGACGCGGGCGCTGACCTGCGCTGGGCCCCAAGCCGACGCGCCCTGGAGGCAGC

TGGGGCCGGACCTGGGCTGGCGGTGGCACCCGCGCGCGCTGGCAACGTCGGCGGCGTGGAGGAATATGACGAG

GACGATGAGTACGAGCCAGAGGACGGCGAGTACTAAGCGGTGATGTTTCTGATCAGATGATGCAAGACGCAAC

GGACCCGGCGGTGCGGGCGGCGCTGCAGAGCCAGCCGTCCGGCCTTAACTCCACGGACGACTGGCGCCAGGTC

ATGGACCGCATCATGTCGCTGACTGCGCGCAATCCTGACGCGTTCCGGCAGCAGCCGCAGGCCAACCGGCTCT

CCGCAATTCTGGAAGCGGTGGTCCCGGCGCGCGCAAACCCCACGCACGAGAAGGTGCTGGCGATCGTAAACGC

GCTGGCCGAAAACAGGGCCATCCGGCCCGACGAGGCCGGCCTGGTCTACGACGCGCTGCTTCAGCGCGTGGCT

CGTTACAACAGCGGCAACGTGCAGACCAACCTGGACCGGCTGGTGGGGGATGTGCGCGAGGCCGTGGCGCAGC

GTGAGCGCGCGCAGCAGCAGGGCAACCTGGGCTCCATGGTTGCACTAAACGCCTTCCTGAGTACACAGCCCGC

CAACGTGCCGCGGGGACAGGAGGACTACACCAACTTTGTGAGCGCACTGCGGCTAATGGTGACTGAGACACCG

CAAAGTGAGGTGTACCAGTCTGGGCCAGACTATTTTTTCCAGACCAGTAGACAAGGCCTGCAGACCGTAAACC

TGAGCCAGGCTTTCAAAAACTTGCAGGGGCTGTGGGGGGTGCGGGCTCCCACAGGCGACCGCGCGACCGTGTC

TAGCTTGCTGACGCCCAACTCGCGCCTGTTGCTGCTGCTAATAGCGCCCTTCACGGACAGTGGCAGCGTGTCC

CGGGACACATACCTAGGTCACTTGCTGACACTGTACCGCGAGGCCATAGGTCAGGCGCATGTGGACGAGCATA

CTTTCCAGGAGATTACAAGTGTCAGCCGCGCGCTGGGGCAGGAGGACACGGGCAGCCTGGAGGCAACCCTAAA

-continued

CTACCTGCTGACCAACCGGCGGCAGAAGATCCCCTCGTTGCACAGTTTAAACAGCGAGGAGGAGCGCATTTTG

CGCTACGTGCAGCAGAGCGTGAGCCTTAACCTGATGCGCGACGGGGTAACGCCCAGCGTGGCGCTGGACATGA

CCGCGCGCAACATGGAACCGGGCATGTATGCCTCAAACCGGCCGTTTATCAACCGCCTAATGGACTACTTGCA

TCGCGCGGCCGCCGTGAACCCCGAGTATTTCACCAATGCCATCTTGAACCCGCACTGGCTACCGCCCCCTGGT

TTCTACACCGGGGGATTCGAGGTGCCCGAGGGTAACGATGGATTCCTCTGGGACGACATAGACGACAGCGTGT

TTTCCCCGCAACCGCAGACCCTGCTAGAGTTGCAACAGCGCGAGCAGGCAGAGGCGGCGCTGCGAAAGGAAAG

CTTCCGCAGGCCAAGCAGCTTGTCCGATCTAGGCGCTGCGGCCCCGCGGTCAGATGCTAGTAGCCCATTTCCA

AGCTTGATAGGGTCTCTTACCAGCACTCGCACCACCCGCCCGCGCCTGCTGGGCGAGGAGGAGTACCTAAACA

ACTCGCTGCTGCAGCCGCAGCGCGAAAAAAACCTGCCTCCGGCATTTCCCAACAACGGGATAGAGAGCCTAGT

GGACAAGATGAGTAGATGGAAGACGTACGCGCAGGAGCACAGGGACGTGCCAGGCCCGCGCCCGCCCACCCGT

CGTCAAAGGCACGACCGTCAGCGGGGTCTGGTGTGGGAGGACGATGACTCGGCAGACGACAGCAGCGTCCTGG

ATTTGGGAGGGAGTGGCAACCCGTTTGCGCACCTTCGCCCCAGGCTGGGGAGAATGTTTTG

CATGATGCAAAATAAAAAACTCACCAAGGCCAT (pBELO66 Ad5 wt)

SEQ ID NO: 4

ATTATTATAGTCAGCTGACGTGTAGTGTATTTATACCCGGTGAGTTCCTCAAGAGGCCAC

TCTTGAGTGCCAGCGAGTAGAGTTTTCTCCTCCGAGCCGCTCCGACACCGGGACTGAAAA

TGAGACATATTATCTGCCACGGAGGTGTTATTACCGAAGAAATGGCCGCCAGTCTTTTGG

ACCAGCTGATCGAAGAGGTACTGGCTGATAATCTTCCACCTCCTAGCCATTTTGAACCAC

CTACCCTTCACGAACTGTATGATTTAGACGTGACGGCCCCCGAAGATCCCAACGAGGAGG

CGGTTTCGCAGATTTTTCCCGACTCTGTAATGTTGGCGGTGCAGGAAGGGATTGACTTAC

TCACTTTTCCGCCGGCGCCCGGTTCTCCGGAGCCGCCTCACCTTTCCCGGCAGCCCGAGC

AGCCGGAGCAGAGAGCCTTGGGTCCGGTTTCTATGCCAAACCTTGTACCGGAGGTGATCG

ATCTTACCTGCCACGAGGCTGGCTTTCCACCCAGTGACGACGAGGATGAAGAGGGTGAGG

AGTTTGTGTTAGATTATGTGGAGCACCCCGGGCACGGTTGCAGGTCTTGTCATTATCACC

GGAGGAATACGGGGGACCCAGATATTATGTGTTCGCTTTGCTATATGAGGACCTGTGGCA

TGTTTGTCTACAGTAAGTGAAAATTATGGGCAGTGGGTGATAGAGTGGTGGGTTTGGTGT

GGTAATTTTTTTTTTAATTTTTACAGTTTTGTGGTTTAAAGAATTTTGTATTGTGATTTT

TTTAAAAGGTCCTGTGTCTGAACCTGAGCCTGAGCCCGAGCCAGAACCGGAGCCTGCAAG

ACCTACCCGCCGTCCTAAAATGGCGCCTGCTATCCTGAGACGCCCGACATCACCTGTGTC

TAGAGAATGCAATAGTAGTACGGATAGCTGTGACTCCGGTCCTTCTAACACACCTCCTGA

GATACACCCGGTGGTCCCGCTGTGCCCCATTAAACCAGTTGCCGTGAGAGTTGGTGGGCG

TCGCCAGGCTGTGGAATGTATCGAGGACTTGCTTAACGAGCCTGGGCAACCTTTGGACTT

GAGCTGTAAACGCCCCAGGCCATAAGGTGTAAACCTGTGATTGCGTGTGTGGTTAACGCC

TTTGTTTGCTGAATGAGTTGATGTAAGTTTAATAAAGGGTGAGATAATGTTTAACTTGCA

TGGCGTGTTAAATGGGGCGGGGCTTAAAGGGTATATAATGCGCCGTGGGCTAATCTTGGT

TACATCTGACCTCATGGAGGCTTGGGAGTGTTTGGAAGATTTTTCTGCTGTGCGTAACTT

GCTGGAACAGAGCTCTAACAGTACCTCTTGGTTTTGGAGGTTTCTGTGGGGCTCATCCCA

GGCAAAGTTAGTCTGCAGAATTAAGGAGGATTACAAGTGGGAATTTGAAGAGCTTTTGAA

ATCCTGTGGTGAGCTGTTTGATTCTTTGAATCTGGGTCACCAGGCGCTTTTCCAAGAGAA

GGTCATCAAGACTTTGGATTTTTCCACACCGGGGCGCGCTGCGGCTGCTGTTGCTTTTTT

-continued

GAGTTTTATAAAGGATAAATGGAGCGAAGAAACCCATCTGAGCGGGGGGTACCTGCTGGA

TTTTCTGGCCATGCATCTGTGGAGAGCGGTTGTGAGACACAAGAATCGCCTGCTACTGTT

GTCTTCCGTCCGCCCGGCGATAATACCGACGGAGGAGCAGCAGCAGCAGCAGGAGGAAGC

CAGGCGGCGGCGGCAGGAGCAGAGCCCATGGAACCCGAGAGCCGGCCTGGACCCTCGGGA

ATGAATGTTGTACAGGTGGCTGAACTGTATCCAGAACTGAGACGCATTTTGACAATTACA

GAGGATGGGCAGGGGCTAAAGGGGGTAAAGAGGGAGCGGGGGGCTTGTGAGGCTACAGAG

GAGGCTAGGAATCTAGCTTTTAGCTTAATGACCAGACACCGTCCTGAGTGTATTACTTTT

CAACAGATCAAGGATAATTGCGCTAATGAGCTTGATCTGCTGGCGCAGAAGTATTCCATA

GAGCAGCTGACCACTTACTGGCTGCAGCCAGGGGATGATTTTGAGGAGGCTATTAGGGTA

TATGCAAAGGTGGCACTTAGGCCAGATTGCAAGTACAAGATCAGCAAACTTGTAAATATC

AGGAATTGTTGCTACATTTCTGGGAACGGGGCCGAGGTGGAGATAGATACGGAGGATAGG

GTGGCCTTTAGATGTAGCATGATAAATATGTGGCCGGGGGTGCTTGGCATGGACGGGGTG

GTTATTATGAATGTAAGGTTTACTGGCCCCAATTTTAGCGGTACGGTTTTCCTGGCCAAT

ACCAACCTTATCCTACACGGTGTAAGCTTCTATGGGTTTAACAATACCTGTGTGGAAGCC

TGGACCGATGTAAGGGTTCGGGGCTGTGCCTTTTACTGCTGCTGGAAGGGGGTGGTGTGT

CGCCCCAAAAGCAGGGCTTCAATTAAGAAATGCCTCTTTGAAAGGTGTACCTTGGGTATC

CTGTCTGAGGGTAACTCCAGGGTGCGCCACAATGTGGCCTCCGACTGTGGTTGCTTCATG

CTAGTGAAAAGCGTGGCTGTGATTAAGCATAACATGGTATGTGGCAACTGCGAGGACAGG

GCCTCTCAGATGCTGACCTGCTCGGACGGCAACTGTCACCTGCTGAAGACCATTCACGTA

GCCAGCCACTCTCGCAAGGCCTGGCCAGTGTTTGAGCATAACATACTGACCCGCTGTTCC

TTGCATTTGGGTAACAGGAGGGGGGTGTTCCTACCTTACCAATGCAATTTGAGTCACACT

AAGATATTGCTTGAGCCCGAGAGCATGTCCAAGGTGAACCTGAACGGGGTGTTTGACATG

ACCATGAAGATCTGGAAGGTGCTGAGGTACGATGAGACCCGCACCAGGTGCAGACCCTGC

GAGTGTGGCGGTAAACATATTAGGAACCAGCCTGTGATGCTGGATGTGACCGAGGAGCTG

AGGCCCGATCACTTGGTGCTGGCCTGCACCCGCGCTGAGTTTGGCTCTAGCGATGAAGAT

ACAGATTGAGGTACTGAAATGTGtgggcgtggCttaagggtgggaaagaatatataaggt gggggtcttatgtagttttgtatctgttttgcagcagccgccgccgccatgagcaccaac tcgtttgatggaagcattgtgagctcatatttgacaacgcgcatgcccccatgggccggg gtgcgtcagaatgtgatgggctccagcattgatggtcgccccgtcctgcccgcaaactct actaccttgacctacgagaccgtgtctggaacgccgttggagactgcagcctccgccgcc gcttcagccgctgcagccaccgcccgcgggattgtgactgactttgctttcctgagcccg cttgcaagcagtgcagcttcccgttcatccgcccgcgatgacaagttgacggctcttttg gcacaattggattctttgacccgggaacttaatgtcgtttctcagcagctgttggatctg cgccagcaggtttctgccctgaaggcttcctcccctcccaatgcggtttaaaacataaat aaaaaaccagactctgtttggatttggatcaagcaagtgtcttgctgtctttatttaggg gttttgcgcgcgcggtaggcccgggaccagcggtctcggtcgttgagggtcctgtgtatt ttttccaggacgtggtaaaggtgactctggatgttcagatacatgggcataagcccgtct ctggggtggaggtagcaccactgcagagcttcatgctgcggggtggtgttgtagatgatc cagtcgtagcaggagcgctgggcgtggtgcctaaaaatgtctttcagtagcaagctgatt gccaggggcaggcccttggtgtaagtgtttacaaagcggttaagctgggatgggtgcata cgtggggatatgagatgcatcttggactgtatttttaggttggctatgttcccagccata -continued tccctccggggattcatgttgtgcagaaccaccagcacagtgtatccggtgcacttggga aatttgtcatgtagcttagaaggaaatgcgtggaagaacttggagacgcccttgtgacct ccaagattttccatgcattcgtccataatgatggcaatgggcccacgggcggcggcctgg gcgaagatatttctgggatcactaacgtcatagttgtgttccaggatgagatcgtcatag gccatttttacaaagcgcgggcggagggtgccagactgcggtataatggttccatccggc ccaggggcgtagttaccctcacagatttgcatttcccacgctttgagttcagatgggggg atcatgtctacctgcggggcgatgaagaaaacggtttccggggtaggggagatcagctgg gaagaaagcaggttcctgagcagctgcgacttaccgcagccggtgggcccgtaaatcaca cctattaccgggtgcaactggtagttaagagagctgcagctgccgtcatccctgagcagg ggggccacttcgttaagcatgtccctgactcgcatgttttccctgaccaaatccgccaga aggcgctcgccgcccagcgatagcagttcttgcaaggaagcaaagtttttcaacggtttg agaccgtccgccgtaggcatgcttttgagcgtttgaccaagcagttccaggcggtcccac agctcggtcacctgctctacggcatctcgatccagcatatctcctcgtttcgcgggttgg ggcggctttcgctgtacggcagtagtcggtgctcgtccagacgggccagggtcatgtctt tccacgggcgcagggtcctcgtcagcgtagtctgggtcacggtgaaggggtgcgctccgg gctgcgcgctggccagggtgcgcttgaggctggtcctgctggtgctgaagcgctgccggt cttcgccctgcgcgtcggccaggtagcatttgaccatggtgtcatagtccagcccctccg cggcgtggcccttggcgcgcagcttgcccttggaggaggcgccgcacgaggggcagtgca gacttttgagggcgtagagcttgggcgcgagaaataccgattccggggagtaggcatccg cgccgcaggccccgcagacggtctcgcattccacgagccaggtgagctctggccgttcgg ggtcaaaaaccaggtttcccccatgctttttgatgcgtttcttacctctggtttccatga gccggtgtccacgctcggtgacgaaaaggctgtccgtgtccccgtatacagacttgagag gcctgtcctcgagcggtgttccgcggtcctcctcgtatagaaactcggaccactctgaga caaaggctcgcgtccaggccagcacgaaggaggctaagtgggaggggtagcggtcgttgt ccactagggggtccactcgctccagggtgtgaagacacatgtcgccctcttcggcatcaa ggaaggtgattggtttgtaggtgtaggccacgtgaccgggtgttcctgaaggggggctat aaaagggggtgggggcgcgttcgtcctcactctcttccgcatcgctgtctgcgagggcca gctgttggggtgagtactccctctgaaaagcgggcatgacttctgcgctaagattgtcag tttccaaaaacgaggaggatttgatattcacctggcccgcggtgatgcctttgagggtgg ccgcatccatctggtcagaaaagacaatctttttgttgtcaagcttggtggcaaacgacc cgtagagggcgttggacagcaacttggcgatggagcgcagggtttggtttttgtcgcgat cggcgcgctccttggccgcgatgtttagctgcacgtattcgcgcgcaacgcaccgccatt cgggaaagacggtggtgcgctcgtcgggcaccaggtgcacgcgccaaccgcggttgtgca gggtgacaaggtcaacgctggtggctacctctccgcgtaggcgctcgttggtccagcaga ggcggccgcccttgcgcgagcagaatggcggtagggggtctagctgcgtctcgtccgggg ggtctgcgtccacggtaaagaccccgggcagcaggcgcgcgtcgaagtagtctatcttgc atccttgcaagtctagcgcctgctgccatgcgcgggcggcaagcgcgcgctcgtatgggt tgagtgggggaccccatggcatggggtgggtgagcgcggaggcgtacatgccgcaaatgt cgtaaacgtagaggggctctctgagtattccaagatatgtagggtagcatcttccaccgc ggatgctggcgcgcacgtaatcgtatagttcgtgcgagggagcgaggaggtcgggaccga -continued ggttgctacgggcgggctgctctgctcggaagactatctgcctgaagatggcatgtgagt tggatgatatggttggacgctggaagacgttgaagctggcgtctgtgagacctaccgcgt cacgcacgaaggaggcgtaggagtcgcgcagcttgttgaccagctcggcggtgacctgca cgtctagggcgcagtagtccagggtttccttgatgatgtcatacttatcctgtccctttt ttttccacagctcgcggttgaggacaaactcttcgcggtctttccagtactcttggatcg gaaacccgtcggcctccgaacggtaagagcctagcatgtagaactggttgacggcctggt aggcgcagcatcccttttctacgggtagcgcgtatgcctgcgcggccttccggagcgagg tgtgggtgagcgcaaaggtgtccctgaccatgactttgaggtactggtatttgaagtcag tgtcgtcgcatccgccctgctcccagagcaaaaagtccgtgcgctttttggaacgcggat ttggcagggcgaaggtgacatcgttgaagagtatctttcccgcgcgaggcataaagttgc gtgtgatgcggaagggtcccggcacctcggaacggttgttaattacctgggcggcgagca cgatctcgtcaaagccgttgatgttgtggcccacaatgtaaagttccaagaagcgcggga tgcccttgatggaaggcaattttttaagttcctcgtaggtgagctcttcaggggagctga gcccgtgctctgaaagggcccagtctgcaagatgagggttggaagcgacgaatgagctcc acaggtcacgggccattagcatttgcaggtggtcgcgaaaggtcctaaactggcgaccta tggccatttttctggggtgatgcagtagaaggtaagcgggtcttgttcccagcggtccc atccaaggttcgcggctaggtctcgcgcggcagtcactagaggctcatctccgccgaact tcatgaccagcatgaagggcacgagctgcttcccaaaggcccccatccaagtataggtct ctacatcgtaggtgacaaagagacgctcggtgcgaggatgcgagccgatcgggaagaact ggatctcccgccaccaattggaggagtggctattgatgtggtgaaagtagaagtccctgc gacgggccgaacactcgtgctggcttttgtaaaaacgtgcgcagtactggcagcggtgca cgggctgtacatcctgcacgaggttgacctgacgaccgcgcacaaggaagcagagtggga atttgagcccctcgcctggcgggtttggctggtggtcttctacttcggctgcttgtcctt gaccgtctggctgctcgaggggagttacggtggatcggaccaccacgccgcgcgagccca aagtccagatgtccgcgcgcggcggtcggagcttgatgacaacatcgcgcagatgggagc tgtccatggtctggagctcccgcggcgtcaggtcaggcgggagctcctgcaggtttacct cgcatagacgggtcagggcgcgggctagatccaggtgatacctaatttccaggggctggt tggtggcggcgtcgatggcttgcaagaggccgcatccccgcggcgcgactacggtaccgc gcggcgggcggtgggccgcgggggtgtccttggatgatgcatctaaaagcggtgacgcgg gcgagcccccggaggtagggggggctccggacccgccgggagagggggcaggggcacgtc ggcgccgcgcgcgggcaggagctggtgctgcgcgcgtaggttgctggcgaacgcgacgac gcggcggttgatctcctgaatctggcgcctctgcgtgaagacgacgggcccggtgagctt gagcctgaaagagagttcgacagaatcaatttcggtgtcgttgacggcggcctggcgcaa aatctcctgcacgtctcctgagttgtcttgataggcgatctcggccatgaactgctcgat ctcttcctcctggagatctccgcgtccggctcgctccacggtggcggcgaggtcgttgga aatgcgggccatgagctgcgagaaggcgttgaggcctccctcgttccagacgcggctgta gaccacgcccccttcggcatcgcgggcgcgcatgaccacctgcgcgagattgagctccac gtgccgggcgaagacggcgtagtttcgcaggcgctgaaagaggtagttgagggtggtggc ggtgtgttctgccacgaagaagtacataacccagcgtcgcaacgtggattcgttgatatc ccccaaggcctcaaggcgctccatggcctcgtagaagtccacggcgaagttgaaaaactg ggagttgcgcgccgacacggttaactcctcctccagaagacggatgagctcggcgacagt -continued gtcgcgcacctcgcgctcaaaggctacaggggcctcttcttcttcttcaatctcctcttc cataagggcctccccttcttcttcttctggcggcggtgggggagggggacacggcggcg acgacggcgcaccgggaggcggtcgacaaagcgctcgatcatctccccgcggcgacggcg catggtctcggtgacggcgcggccgttctcgcgggggcgcagttggaagacgccgcccgt catgtcccggttatgggttggcggggggctgccatgcggcagggatacggcgctaacgat gcatctcaacaattgttgtgtaggtactccgccgccgagggacctgagcgagtccgcatc gaccggatcggaaaacctctcgagaaaggcgtctaaccagtcacagtcgcaaggtaggct gagcaccgtggcgggcggcagcgggcggcggtcggggttgtttctggcggaggtgctgct gatgatgtaattaaagtaggcggtcttgagacggcggatggtcgacagaagcaccatgtc cttgggtccggcctgctgaatgcgcaggcggtcggccatgccccaggcttcgttttgaca tcggcgcaggtctttgtagtagtcttgcatgagcctttctaccggcacttcttcttctcc ttcctcttgtcctgcatctcttgcatctatcgctgcggcggcggcggagtttggccgtag gtggcgccctcttcctcccatgcgtgtgaccccgaagcccctcatcggctgaagcagggc taggtcggcgacaacgcgctcggctaatatggcctgctgcacctgcgtgagggtagactg gaagtcatccatgtccacaaagcggtggtatgcgcccgtgttgatggtgtaagtgcagtt ggccataacggaccagttaacggtctggtgacccggctgcgagagctcggtgtacctgag acgcgagtaagccctcgagtcaaatacgtagtcgttgcaagtccgcaccaggtactggta tcccaccaaaaagtgcggcggcggctggcggtagaggggccagcgtagggtggccggggc tccgggggcgagatcttccaacataaggcgatgatatccgtagatgtacctggacatcca ggtgatgccggcggcggtggtggaggcgcgcggaaagtcgcggacgcggttccagatgtt gcgcagcggcaaaaagtgctccatggtcgggacgctctggccggtcaggcgcgcgcaatc gttgacgctctagaccgtgcaaaaggagagcctgtaagcgggcactcttccgtggtctgg tggataaattcgcaagggtatcatggcggacgaccggggttcgagccccgtatccggccg tccgccgtgatccatgcggttaccgcccgcgtgtcgaacccaggtgtgcgacgtcagaca acgggggagtgctccttttggcttccttccaggcgcggcggctgctgcgctagcttttttt ggccactggccgcgcgcagcgtaagcggttaggctggaaagcgaaagcattaagtggctc gctccctgtagccggagggttattttccaagggttgagtcgcgggacccccggttcgagt ctcggaccggccggactgcggcgaacgggggtttgcctccccgtcatgcaagaccccgct tgcaaattcctccggaaacagggacgagcccctttttttgcttttcccagatgcatccggt gctgcggcagatgcgcccccctcctcagcagcggcaagagcaagagcagcggcagacatg cagggcaccctcccctcctcctaccgcgtcaggaggggcgacatccgcggttgacgcggc agcagatggtgattacgaacccccgcggcgccgggcccggcactacctggacttggagga gggcgagggcctggcgcggctaggagcgccctctcctgagcggtacccaagggtgcagct gaagcgtgatacgcgtgaggcgtacgtgccgcggcagaacctgtttcgcgaccgcgaggg agaggagcccgaggagatgcgggatcgaaagttccacgcagggcgcgagctgcggcatgg cctgaatcgcgagcggttgctgcgcgaggaggactttgagcccgacgcgcgaaccgggat tagtccccgtggcggccgccgacctggtaaccgcatacgagcagacggtgaaccaggaga ttaactttcaagcgcgcgcacaaaaagctttaacaaccacgtgcgtacgcttgtggcgcg cgaggaggtggctataggactgatgcatctgtgggactttgtaagcgcgctggagcaaaa cccaaatagcaagccgctcatggcgcagctgttccttatagtgcagcacagcagggacaa -continued cgaggcattcagggatgcgctgctaaacatagtagagcccgagggccgctggctgctcga tttgataaacatcctgcagagcatagtggtgcaggagcgcagcttgagcctggctgacaa ggtggccgccatcaactattccatgcttagcctgggcaagttttacgcccgcaagatata ccataccccttacgttcccatagacaaggaggtaaagatcgaggggttctacatgcgcat ggcgctgaaggtgcttaccttgagcgacgacctgggcgtttatcgcaacgagcgcatcca caaggccgtgagcgtgagccggcggcgcgagctcagcgaccgcgagctgatgcacagcct gcaaagggccctggctggcacgggcagcggcgatagagaggccgagtcctactttgacgc gggcgctgacctgcgctgggccccaagccgacgcgccctggaggcagctggggccggacc tgggctggcggtggcacccgcgcgcgctggcaacgtcggcggcgtggaggaatatgacga ggacgatgagtacgagccagaggacggcgagtactaagcggtgatgtttctgatcagatg atgcaagacgcaacggacccggcggtgcgggcggcgctgcagagccagccgtccggcctt aactccacggacgactggcgccaggtcatggaccgcatcatgtcgctgactgcgcgcaat cctgacgcgttccggcagcagccgcaggccaaccggctctccgcaattctggaagcggtg gtcccggcgcgcgcaaaccccacgcacgagaaggtgctggcgatcgtaaacgcgctggcc gaaaacagggccatccggcccgacgaggccggcctggtctacgacgcgctgcttcagcgc gtggctcgttacaacagcggcaacgtgcagaccaacctggaccggctggtgggggatgtg cgcgaggccgtggcgcagcgtgagcgcgcgcagcagcagggcaacctgggctccatggtt gcactaaacgccttcctgagtacacagcccgccaacgtgccgcggggacaggaggactac accaactttgtgagcgcactgcggctaatggtgactgagacaccgcaaagtgaggtgtac cagtctgggccagactatttttccagaccagtagacaaggcctgcagaccgtaaacctg agccaggctttcaaaaacttgcaggggctgtgggggtgcgggctcccacaggcgaccgc gcgaccgtgtctagcttgctgacgcccaactcgcgcctgttgctgctgctaatagcgccc ttcacggacagtggcagcgtgtcccgggacacatacctaggtcacttgctgacactgtac cgcgaggccataggtcaggcgcatgtggacgagcatactttccaggagattacaagtgtc agccgcgcgctggggcaggaggacacgggcagcctggaggcaaccctaaactacctgctg accaaccggcggcagaagatcccctcgttgcacagtttaaacagcgaggaggagcgcatt ttgcgctacgtgcagcagagcgtgagccttaacctgatgcgcgacggggtaacgcccagc gtggcgctggacatgaccgcgcgcaacatggaaccgggcatgtatgcctcaaaccggccg tttatcaaccgcctaatggactacttgcatcgcgcggccgccgtgaaccccgagtatttc accaatgccatcttgaacccgcactggctaccgccccctggtttctacaccgggggattc gaggtgcccgagggtaacgatggattcctctgggacgacatagacgacagcgtgttttcc ccgcaaccgcagaccctgctagagttgcaacagcgcgagcaggcagaggcggcgctgcga aaggaaagcttccgcaggccaagcagcttgtccgatctaggcgctgcggccccgcggtca gatgctagtagcccatttccaagcttgatagggtctcttaccagcactcgcaccacccgc ccgcgcctgctgggcgaggaggagtacctaaacaactcgctgctgcagccgcagcgcgaa aaaaacctgcctccggcatttcccaacaacgggatagagagcctagtggacaagatgagt agatggaagacgtacgcgcaggagcacagggacgtgccaggcccgcgcccgcccacccgt cgtcaaaggcacgaccgtcagcggggtctggtgtgggaggacgatgactcggcagacgac agcagcgtcctggatttgggagggagtggcaacccgtttgcgcaccttcgccccaggctg gggagaatgttttaaaaaaaaaaaagcatgatgcaaaataaaaaactcaccaaggccatg gcaccgagcgttggttttcttgtattccccttagtatgcggcgcgcggcgatgtatgagg -continued aaggtcctcctccctcctacgagagtgtggtgagcgcggcgccagtggcggcggcgctgg gttctcccttcgatgctcccctggacccgccgtttgtgcctccgcggtacctgcggccta ccgggggggagaaacagcatccgttactctgagttggcacccctattcgacaccacccgtg tgtacctggtggacaacaagtcaacggatgtggcatccctgaactaccagaacgaccaca gcaactttctgaccacggtcattcaaaacaatgactacagcccgggggaggcaagcacac agaccatcaatcttgacgaccggtcgcactggggcggcgacctgaaaaccatcctgcata ccaacatgccaaatgtgaacgagttcatgtttaccaataagtttaaggcgcgggtgatgg tgtcgcgcttgcctactaaggacaatcaggtggagctgaaatacgagtgggtggagttca cgctgcccgagggcaactactccgagaccatgaccatagaccttatgaacaacgcgatcg tggagcactacttgaaagtgggcagacagaacggggttctggaaagcgacatcggggtaa agtttgacacccgcaacttcagactggggtttgaccccgtcactggtcttgtcatgcctg gggtatatacaaacgaagccttccatccagacatcattttgctgccaggatgcggggtgg acttcacccacagccgcctgagcaacttgttgggcatccgcaagcggcaacccttccagg agggctttaggatcacctacgatgatctggagggtggtaacattcccgcactgttggatg tggacgcctaccaggcgagcttgaaagatgacaccgaacagggcgggggtggcgcaggcg gcagcaacagcagtggcagcggcgcggaagagaactccaacgcggcagccgcggcaatgc agccggtggaggacatgaacgatcatgccattcgcggcgacacctttgccacacgggctg aggagaagcgcgctgaggccgaagcagcggccgaagctgccgcccccgctgcgcaacccg aggtcgagaagcctcagaagaaaccggtgatcaaacccctgacagaggacagcaagaaac gcagttacaacctaataagcaatgacagcaccttcacccagtaccgcagctggtaccttg catacaactacggcgaccctcagaccggaatccgctcatggaccctgctttgcactcctg acgtaacctgcggctcggagcaggtctactggtcgttgccagacatgatgcaagaccccg tgaccttccgctccacgcgccagatcagcaactttccggtggtgggcgccgagctgttgc ccgtgcactccaagagcttctacaacgaccaggccgtctactcccaactcatccgccagt ttacctctctgacccacgtgttcaatcgctttcccgagaaccagattttggcgcgcccgc cagcccccaccatcaccaccgtcagtgaaaacgttcctgctctcacagatcacgggacgc taccgctgcgcaacagcatcggaggagtccagcgagtgaccattactgacgccagacgcc gcacctgcccctacgtttacaaggccctgggcatagtctcgccgcgcgtcctatcgagcc gcactttttgagcaagcatgtccatccttatatcgcccagcaataacacaggctggggcc tgcgcttcccaagcaagatgtttggcggggccaagaagcgctccgaccaacacccagtgc gcgtgcgcgggcactaccgcgcgccctggggcgcgcacaaacgcggccgcactgggcgca ccaccgtcgatgacgccatcgacgcggtggtggaggaggcgcgcaactacacgcccacgc cgccaccagtgtccacagtggacgcggccattcagaccgtggtgcgcggagcccggcgct atgctaaaatgaagagacggcggaggcgcgtagcacgtcgccaccgccgccgacccggca ctgccgcccaacgcgcggcggcggccctgcttaaccgcgcacgtcgcaccggccgacggg cggccatgcgggccgctcgaaggctggccgcgggtattgtcactgtgccccccaggtcca ggcgacgagcggccgccgcagcagccgcggccattagtgctatgactcagggtcgcaggg gcaacgtgtattgggtgcgcgactcggttagcggcctgcgcgtgcccgtgcgcacccgcc ccccgcgcaactagattgcaagaaaaaactacttagactcgtactgttgtatgtatccag cggcggcggcgcgcaacgaagctatgtccaagcgcaaaatcaaagaagagatgctccagg -continued tcatcgcgccggagatctatggcccccgaagaaggaagagcaggattacaagccccgaa agctaaagcgggtcaaaaagaaaaagaaagatgatgatgatgaacttgacgacgaggtgg aactgctgcacgctaccgcgcccaggcgacgggtacagtggaaaggtcgacgcgtaaaac gtgttttgcgacccggcaccaccgtagtctttacgcccggtgagcgctccacccgcacct acaagcgcgtgtatgatgaggtgtacggcgacgaggacctgcttgagcaggccaacgagc gcctcggggagtttgcctacggaaagcggcataaggacatgctggcgttgccgctggacg agggcaacccaacacctagcctaaagcccgtaacactgcagcaggtgctgcccgcgcttg caccgtccgaagaaaagcgcggcctaaagcgcgagtctggtgacttggcacccaccgtgc agctgatggtacccaagcgccagcgactggaagatgtcttggaaaaaatgaccgtggaac ctgggctggagcccgaggtccgcgtgcggccaatcaagcaggtggcgccgggactgggcg tgcagaccgtggacgttcagatacccactaccagtagcaccagtattgccaccgccacag agggcatggagacacaaacgtccccggttgcctcagcggtggcggatgccgcggtgcagg cggtcgctgcggccgcgtccaagacctctacggaggtgcaaacggacccgtggatgtttc gcgtttcagcccccggcgcccgcgcggttcgaggaagtacggcgccgccagcgcgctac tgcccgaatatgccctacatccttccattgcgcctacccccggctatcgtggctacacct accgccccagaagacgagcaactacccgacgccgaaccaccactggaacccgccgccgcc gtcgccgtcgccagcccgtgctggccccgatttccgtgcgcagggtggctcgcgaaggag gcaggaccctggtgctgccaacagcgcgctaccaccccagcatcgtttaaaagccggtct ttgtggttcttgcagatatggccctcacctgccgcctccgtttcccggtgccgggattcc gaggaagaatgcaccgtaggaggggcatggccggccacggcctgacgggcggcatgcgtc gtgcgcaccaccggcggcggcgcgcgtcgcaccgtcgcatgcgcggcggtatcctgcccc tccttattccactgatcgccgcggcgattggcgccgtgcccggaattgcatccgtggcct tgcaggcgcagagacactgattaaaaacaagttgcatgtggaaaaatcaaaataaaaagt ctggactctcacgctcgcttggtcctgtaactattttgtagaatggaagacatcaacttt gcgtctctggccccgcgacacggctcgcgcccgttcatgggaaactggcaagatatcggc accagcaatatgagcggtggcgccttcagctggggctcgctgtggagcggcattaaaaat ttcggttccaccgttaagaactatggcagcaaggcctggaacagcagcacaggccagatg ctgagggataagttgaaagagcaaaatttccaacaaaaggtggtagatggcctggcctct ggcattagcggggtggtggacctggccaaccaggcagtgcaaaataagattaacagtaag cttgatccccgccctcccgtagaggagcctccaccggccgtggagacagtgtctccagag gggcgtggcgaaaagcgtccgcgccccgacagggaagaaactctggtgacgcaaatagac gagcctccctcgtacgaggaggcactaaagcaaggcctgcccaccacccgtcccatcgcg cccatggctaccggagtgctgggccagcacacacccgtaacgctggacctgcctcccccc gccgacacccagcagaaacctgtgctgccaggcccgaccgccgttgttgtaacccgtcct agccgcgcgtccctgcgccgcgccgccagcggtccgcgatcgttgcggcccgtagccagt ggcaactggcaaagcacactgaacagcatcgtgggtctgggggtgcaatccctgaagcgc cgacgatgcttctgaatagctaacgtgtcgtatgtgtgtcatgtatgcgtccatgtcgcc gccagaggagctgctgagccgccgcgcgcccgctttccaagatggctaccccttcgatga tgccgcagtggtcttacatgcacatctcgggccaggacgcctcggagtacctgagccccg ggctggtgcagtttgcccgcgccaccgagacgtacttcagcctgaataacaagtttagaa accccacggtggcgcctacgcacgacgtgaccacagaccggtcccagcgtttgacgctgc -continued ggttcatccctgtggaccgtgaggatactgcgtactcgtacaaggcgcggttcaccctag
ctgtgggtgataaccgtgtgctggacatggcttccacgtactttgacatccgcggcgtgc
tggacaggggccctacttttaagccctactctggcactgcctacaacgccctggctccca
agggtgccccaaatccttgcgaatgggatgaagctgctactgctcttgaaataaacctag
aagaagaggacgatgacaacgaagacgaagtagacgagcaagctgagcagcaaaaaactc
acgtatttgggcaggcgccttattctggtataaatattacaaaggagggtattcaaatag
gtgtcgaaggtcaaacacctaaatatgccgataaaacatttcaacctgaacctcaaatag
gagaatctcagtggtacgaaactgaaattaatcatgcagctgggagagtccttaaaaaga
ctaccccaatgaaaccatgttacggttcatatgcaaaacccacaaatgaaaatggagggc
aaggcattcttgtaaagcaacaaaatggaaagctagaaagtcaagtggaaatgcaatttt
tctcaactactgaggcgaccgcaggcaatggtgataacttgactcctaaagtggtattgt
acagtgaagatgtagatatagaaaccccagacactcatatttcttacatgcccactatta
aggaaggtaactcacgagaactaatgggccaacaatctatgcccaacaggcctaattaca
ttgcttttagggacaattttattggtctaatgtattacaacagcacgggtaatatgggtg
ttctggcgggccaagcatcgcagttgaatgctgttgtagatttgcaagacagaaacacag
agctttcataccagcttttgcttgattccattggtgatagaaccaggtacttttctatgt
ggaatcaggctgttgacagctatgatccagatgttagaattattgaaaatcatggaactg
aagatgaacttccaaattactgctttccactgggaggtgtgattaatacagagactctta
ccaaggtaaaacctaaaacaggtcaggaaaatggatgggaaaaagatgctacagaatttt
cagataaaaatgaaataagagttggaaataattttgccatggaaatcaatctaaatgcca
acctgtggagaaatttcctgtactccaacatagcgctgtatttgcccgacaagctaaagt
acagtccttccaacgtaaaaatttctgataacccaaacacctacgactacatgaacaagc
gagtggtggctcccgggttagtggactgctacattaaccttggagcacgctggtcccttg
actatatggacaacgtcaacccatttaaccaccaccgcaatgctggcctgcgctaccgct
caatgttgctgggcaatggtcgctatgtgcccttccacatccaggtgcctcagaagttct
ttgccattaaaaacctccttctcctgccgggctcatacacctacgagtggaacttcagga
aggatgttaacatggttctgcagagctccctaggaaatgacctaagggttgacggagcca
gcattaagtttgatagcatttgcctttacgccaccttcttccccatggcccacaacaccg
cctccacgcttgaggccatgcttagaaacgacaccaacgaccagtcctttaacgactatc
tctccgccgccaacatgctctaccctatacccgccaacgctaccaacgtgcccatatcca
tcccctcccgcaactgggcggctttccgcggctgggccttcacgcgccttaagactaagg
aaaccccatcactgggctcgggctacgacccttattacacctactctggctctataccct
acctagatggaaccttttacctcaaccacacctttaagaaggtggccattacctttgact
cttctgtcagctggcctggcaatgaccgcctgcttacccccaacgagtttgaaattaagc
gctcagttgacggggagggttacaacgttgcccagtgtaacatgaccaaagactggttcc
tggtacaaatgctagctaactacaacattggctaccagggcttctatatcccagagagct
acaaggaccgcatgtactccttctttagaaacttccagcccatgagccgtcaggtggtgg
atgatactaaatacaaggactaccaacaggtgggcatcctacaccaacacaacaactctg
gatttgttggctaccttgcccccaccatgcgcgaaggacaggcctaccctgctaacttcc
cctatccgcttataggcaagaccgcagttgacagcattacccagaaaaagtttctttgcg -continued atcgcaccctttggcgcatcccattctccagtaactttatgtccatgggcgcactcacag acctgggccaaaaccttctctacgccaactccgcccacgcgctagacatgacttttgagg tggatcccatggacgagcccacccttctttatgttttgtttgaagtctttgacgtggtcc gtgtgcaccggccgcaccgcggcgtcatcgaaaccgtgtacctgcgcacgcccttctcgg ccggcaacgccacaacataaagaagcaagcaacatcaacaacagctgccgccatgggctc cagtgagcaggaactgaaagccattgtcaaagatcttggttgtgggccatatttttttggg cacctatgacaagcgctttccaggctttgtttctccacacaagctcgcctgcgccatagt caatacggccggtcgcgagactgggggcgtacactggatggcctttgcctggaacccgca ctcaaaaacatgctacctctttgagccctttggcttttctgaccagcgactcaagcaggt ttaccagtttgagtacgagtcactcctgcgccgtagcgccattgcttcttcccccgaccg ctgtataacgctggaaaagtccacccaaagcgtacaggggcccaactcggccgcctgtgg actattctgctgcatgtttctccacgcctttgccaactggccccaaactcccatggatca caaccccaccatgaaccttattaccggggtacccaactccatgctcaacagtccccaggt acagcccaccctgcgtcgcaaccaggaacagctctacagcttcctggagcgccactcgcc ctacttccgcagccacagtgcgcagattaggagcgccacttctttttgtcacttgaaaaa catgtaaaaataatgtactagagacactttcaataaaggcaaatgcttttatttgtacac tctcgggtgattatttacccccacccttgccgtctgcgccgtttaaaaatcaaaggggtt ctgccgcgcatcgctatgcgccactggcagggacacgttgcgatactggtgtttagtgct ccacttaaactcaggcacaaccatccgcggcagctcggtgaagttttcactccacaggct gcgcaccatcaccaacgcgtttagcaggtcgggcgccgatatcttgaagtcgcagttggg gcctccgccctgcgcgcgcgagttgcgatacacagggttgcagcactggaacactatcag cgccgggtggtgcacgctggccagcacgctcttgtcggagatcagatccgcgtccaggtc ctccgcgttgctcagggcgaacggagtcaactttggtagctgccttcccaaaaagggcgc gtgcccaggctttgagttgcactcgcaccgtagtggcatcaaaaggtgaccgtgcccggt ctgggcgttaggatacagcgcctgcataaaagccttgatctgcttaaaagccacctgagc ctttgcgccttcagagaagaacatgccgcaagacttgccggaaaactgattggccggaca ggccgcgtcgtgcacgcagcaccttgcgtcggtgttggagatctgcaccacatttcggcc ccaccggttcttcacgatcttggccttgctagactgctccttcagcgcgcgctgcccgtt ttcgctcgtcacatccatttcaatcacgtgctccttatttatcataatgcttccgtgtag acacttaagctcgccttcgatctcagcgcagcggtgcagccacaacgcgcagcccgtggg ctcgtgatgcttgtaggtcacctctgcaaacgactgcaggtacgcctgcaggaatcgccc catcatcgtcacaaaggtcttgttgctggtgaaggtcagctgcaacccgcggtgctcctc gttcagccaggtcttgcatacggccgccagagcttccacttggtcaggcagtagtttgaa gttcgcctttagatcgttatccacgtggtacttgtccatcagcgcgcgcgcagcctccat gcccttctcccacgcagacacgatcggcacactcagcgggttcatcaccgtaatttcact ttccgcttcgctgggctcttcctcttcctcttgcgtccgcataccacgcgccactgggtc gtcttcattcagccgccgcactgtgcgcttacctcctttgccatgcttgattagcaccgg tgggttgctgaaacccaccatttgtagcgccacatcttctctttcttcctcgctgtccac gattacctctggtgatggcgggcgctcgggcttgggagaagggcgcttctttttcttctt gggcgcaatggccaaatccgccgccgaggtcgatggccgcgggctgggtgtgcgcggcac cagcgcgtcttgtgatgagtcttcctcgtcctcggactcgatacgccgcctcatccgctt -continued ttttgggggcgcccggggaggcggcggcgacggggacggggacgacacgtcctccatggt
tgggggacgtcgcgccgcaccgcgtccgcgctcgggggtggtttcgcgctgctcctcttc
ccgactggccatttccttctcctataggcagaaaaagatcatggagtcagtcgagaagaa
ggacagcctaaccgccccctctgagttcgccaccaccgcctccaccgatgccgccaacgc
gcctaccaccttccccgtcgaggcacccccgcttgaggaggaggaagtgattatcgagca
ggacccaggttttgtaagcgaagacgacgaggaccgctcagtaccaacagaggataaaaa
gcaagaccaggacaacgcagaggcaaacgaggaacaagtcgggcgggggggacgaaaggca
tggcgactacctagatgtgggagacgacgtgctgttgaagcatctgcagcgccagtgcgc
cattatctgcgacgcgttgcaagagcgcagcgatgtgcccctcgccatagcggatgtcag
ccttgcctacgaacgccacctattctcaccgcgcgtacccccccaaacgccaagaaaacgg
cacatgcgagcccaacccgcgcctcaacttctaccccgtatttgccgtgccagaggtgct
tgccacctatcacatctttttccaaaactgcaagatacccctatcctgccgtgccaaccg
cagccgagcggacaagcagctggccttgcggcagggcgctgtcatacctgatatcgcctc
gctcaacgaagtgccaaaaatctttgagggtcttggacgcgacgagaagcgcgcggcaaa
cgctctgcaacaggaaaacagcgaaaatgaaagtcactctggagtgttggtggaactcga
gggtgacaacgcgcgcctagccgtactaaaacgcagcatcgaggtcacccactttgccta
cccggcacttaacctacccccccaaggtcatgagcacagtcatgagtgagctgatcgtgcg
ccgtgcgcagcccctggagagggatgcaaatttgcaagaacaaacagaggagggcctacc
cgcagttggcgacgagcagctagcgcgctggcttcaaacgcgcgagcctgccgacttgga
ggagcgacgcaaactaatgatggccgcagtgctcgttaccgtggagcttgagtgcatgca
gcggttctttgctgacccggagatgcagcgcaagctagaggaaacattgcactacacctt
tcgacagggctacgtacgccaggcctgcaagatctccaacgtggagctctgcaacctggt
ctcctaccttggaattttgcacgaaaaccgccttgggcaaaacgtgcttcattccacgct
caagggcgaggcgcgccgcgactacgtccgcgactgcgtttacttatttctatgctacac
ctggcagacggccatgggcgtttggcagcagtgcttggaggagtgcaacctcaaggagct
gcagaaactgctaaagcaaaacttgaaggacctatggacggccttcaacgagcgctccgt
ggccgcgcacctggcggacatcattttccccgaacgcctgcttaaaaccctgcaacaggg
tctgccagacttcaccagtcaaagcatgttgcagaactttaggaactttatcctagagcg
ctcaggaatcttgcccgccacctgctgtgcacttcctagcgactttgtgcccattaagta
ccgcgaatgccctccgccgctttggggccactgctaccttctgcagctagccaactacct
tgcctaccactctgacataatggaagacgtgagcggtgacggtctactggagtgtcactg
tcgctgcaacctatgcaccccgcaccgctccctggtttgcaattcgcagctgcttaacga
aagtcaaattatcggtacctttgagctgcagggtccctcgcctgacgaaaagtccgcggc
tccggggttgaaactcactccggggctgtggacgtcggcttaccttcgcaaatttgtacc
tgaggactaccacgcccacgagattaggttctacgaagaccaatcccgcccgccaaatgc
ggagcttaccgcctgcgtcattacccagggccacattcttggccaattgcaagccatcaa
caaagcccgccaagagtttctgctacgaaagggacgggggggtttacttggacccccagtc
cggcgaggagctcaacccaatccccccgccgccgcagccctatcagcagcagccgcgggc
ccttgcttcccaggatggcacccaaaaagaagctgcagctgccgccgccacccacggacg
aggaggaatactgggacagtcaggcagaggaggttttggacgaggaggaggaggacatga -continued tggaagactgggagagcctagacgaggaagcttccgaggtcgaagaggtgtcagacgaaa caccgtcaccctcggtcgcattcccctcgccggcgccccagaaatcggcaaccggttcca gcatggctacaacctccgctcctcaggcgccgccggcactgcccgttcgccgacccaacc gtagatgggacaccactggaaccagggccggtaagtccaagcagccgccgccgttagccc aagagcaacaacagcgccaaggctaccgctcatggcgcgggcacaagaacgccatagttg cttgcttgcaagactgtgggggcaacatctccttcgcccgccgctttcttctctaccatc acggcgtggccttcccccgtaacatcctgcattactaccgtcatctctacagcccatact gcaccggcggcagcggcagcggcagcaacagcagcggccacacagaagcaaaggcgaccg gatagcaagactctgacaaagcccaagaaatccacagcggcggcagcagcaggaggagga gcgctgcgtctggcgcccaacgaacccgtatcgacccgcgagcttagaaacaggattttt cccactctgtatgctatatttcaacagagcaggggccaagaacaagagctgaaaataaaa aacaggtctctgcgatccctcacccgcagctgcctgtatcacaaaagcgaagatcagctt cggcgcacgctggaagacgcggaggctctcttcagtaaatactgcgcgctgactcttaag gactagtttcgcgccctttctcaaatttaagcgcgaaaactacgtcatctccagcggcca cacccggcgccagcacctgtcgtcagcgccattatgagcaaggaaattcccacgccctac atgtggagttaccagccacaaatgggacttgcggctggagctgcccaagactactcaacc cgaataaactacatgagcgcgggaccccacatgatatcccgggtcaacggaatccgcgcc caccgaaaccgaattctcttggaacaggcggctattaccaccacacctcgtaataacctt aatccccgtagttggcccgctgccctggtgtaccaggaaagtcccgctcccaccactgtg gtacttcccagagacgcccaggccgaagttcagatgactaactcaggggcgcagcttgcg ggcggctttcgtcacagggtgcggtcgcccgggcagggtataactcacctgacaatcaga gggcgaggtattcagctcaacgacgagtcggtgagctcctcgcttggtctccgtccggac gggacatttcagatcggcggcgccggccgtccttcattcacgcctcgtcaggcaatccta actctgcagacctcgtcctctgagccgcgctctggaggcattggaactctgcaatttatt gaggagtttgtgccatcggtctactttaaccccttctcgggacctcccggccactatccg gatcaatttattcctaactttgacgcggtaaaggactcggcggacggctacgactgaatg ttaagtggagaggcagagcaactgcgcctgaaacacctggtccactgtcgccgccacaag tgctttgcccgcgactccggtgagttttgctactttgaattgcccgaggatcatatcgag ggcccggcgcacggcgtccggcttaccgcccagggagagcttgcccgtagcctgattcgg gagtttacccagcgcccccctgctagttgagcgggacaggggaccctgtgttctcactgtg atttgcaactgtcctaaccttggattacatcaagatctttgttgccatctctgtgctgag tataataaatacagaaattaaaatatactggggctcctatcgccatcctgtaaacgccac cgtcttcacccgcccaagcaaaccaaggcgaaccttacctggtacttttaacatctctcc ctctgtgatttacaacagtttcaacccagacggagtgagtctacgagagaacctctccga gctcagctactccatcagaaaaaacaccaccctccttacctgccgggaacgtacgagtgc gtcaccggccgctgcaccacacctaccgcctgaccgtaaaccagactttttccggacaga cctcaataactctgtttaccagaacaggaggtgagcttagaaaacccttagggtattagg ccaaaggcgcagctactgtggggtttatgaacaattcaagcaactctacgggctattcta attcaggtttctctagaatcggggttggggttattctctgtcttgtgattctctttattc ttatactaacgcttctctgcctaaggctcgccgcctgctgtgtgcacatttgcatttatt gtcagctttttaaacgctggggtcgccacccaagatgattaggtacataatcctaggttt -continued actcacccttgcgtcagcccacggtaccacccaaaaggtggattttaaggagccagcctg
taatgttacattcgcagctgaagctaatgagtgcaccactcttataaaatgcaccacaga
acatgaaaagctgcttattcgccacaaaaacaaaattggcaagtatgctgtttatgctat
ttggcagccaggtgacactacagagtataatgttacagttttccagggtaaaagtcataa
aacttttatgtatacttttccattttatgaaatgtgcgacattaccatgtacatgagcaa
acagtataagttgtggccccccacaaaattgtgtggaaaacactggcactttctgctgcac
tgctatgctaattacagtgctcgctttggtctgtaccctactctatattaaatacaaaag
cagacgcagctttattgaggaaaagaaaatgccttaatttactaagttacaaagctaatg
tcaccactaactgctttactcgctgcttgcaaaacaaattcaaaaagttagcattataat
tagaataggatttaaaccccccggtcatttcctgctcaataccattcccctgaacaattg
actctatgtgggatatgctccagcgctacaaccttgaagtcaggcttcctggatgtcagc
atctgactttggccagcacctgtcccgcggatttgttccagtccaactacagcgacccac
cctaacagagatgaccaacacaaccaacgcggccgccgctaccggacttacatctaccac
aaatacaccccaagtttctgcctttgtcaataactgggataacttgggcatgtggtggtt
ctccatagcgcttatgtttgtatgccttattattatgtggctcatctgctgcctaaagcg
caaacgcgcccgaccacccatctatagtcccatcattgtgctacacccaaacaatgatgg
aatccatagattggacggactgaaacacatgttcttttctcttacagtatgattaaatga
gacatgattcctcgagtttttatattactgacccttgttgcgctttttttgtgcgtgctcc
acattggctgcggtttctcacatcgaagtagactgcattccagccttcacagtctatttg
ctttacggatttgtcaccctcacgctcatctgcagcctcatcactgtggtcatcgccttt
atccagtgcattgactgggtctgtgtgcgctttgcatatctcagacaccatccccagtac
agggacaggactatagctgagcttcttagaattctttaattatgaaatttactgtgactt
ttctgctgattatttgcaccctatctgcgttttgttccccgacctccaagcctcaaagac
atatatcatgcagattcactcgtatatggaatattccaagttgctacaatgaaaaaagcg
atctttccgaagcctggttatatgcaatcatctctgttatggtgttctgcagtaccatct
tagccctagctatatatccctaccttgacattggctggaaacgaatagatgccatgaacc
acccaactttccccgcgcccgctatgcttccactgcaacaagttgttgccggcggctttg
tcccagccaatcagcctcgccccacttctcccacccccactgaaatcagctactttaatc
taacaggaggagatgactgacaccctagatctagaaatggacggaattattacagagcag
cgcctgctagaaagacgcagggcagcggccgagcaacagcgcatgaatcaagagctccaa
gacatggttaacttgcaccagtgcaaaaggggtatcttttgtctggtaaagcaggccaaa
gtcacctacgacagtaataccaccggacaccgccttagctacaagttgccaaccaagcgt
cagaaattggtggtcatggtgggagaaaagcccattaccataactcagcactcggtagaa
accgaaggctgcattcactcaccttgtcaaggacctgaggatctctgcacccttattaag
accctgtgcggtctcaaagatcttattccctttaactaataaaaaaaaataataaagcat
cacttacttaaaatcagttagcaaatttctgtccagtttattcagcagcacctccttgcc
ctcctcccagctctggtattgcagcttcctcctggctgcaaactttctccacaatctaaa
tggaatgtcagtttcctcctgttcctgtccatccgcacccactatcttcatgttgttgca
gatgaagcgcgcaagaccgtctgaagataccttcaaccccgtgtatccatatgacacgga
aaccggtcctccaactgtgccttttcttactcctccctttgtatcccccaatgggtttca -continued agagagtcccccctggggtactctctttgcgcctatccgaacctctagttacctccaatgg catgcttgcgctcaaaatgggcaacggcctctctctggacgaggccggcaaccttacctc ccaaaatgtaaccactgtgagcccacctctcaaaaaaaccaagtcaaacataaacctgga aatatctgcacccctcacagttacctcagaagccctaactgtggctgccgccgcacctct aatggtcgcgggcaacacactcaccatgcaatcacaggccccgctaaccgtgcacgactc caaacttagcattgccacccaaggacccctcacagtgtcagaaggaaagctagccctgca aacatcaggcccccctcaccaccaccgatagcagtacccttactatcactgcctcaccccc tctaactactgccactggtagcttgggcattgacttgaaagagcccatttatacacaaaa tggaaaactaggactaaagtacggggctcctttgcatgtaacagacgacctaaacacttt gaccgtagcaactggtccaggtgtgactattaataatacttccttgcaaactaaagttac tggagccttgggttttgattcacaaggcaatatgcaacttaatgtagcaggaggactaag gattgattctcaaaacagacgccttatacttgatgttagttatccgtttgatgctcaaaa ccaactaaatctaagactaggacagggccctctttttataaactcagcccacaacttgga tattaactacaacaaaggcctttacttgtttacagcttcaaacaattccaaaaagcttga ggttaacctaagcactgccaaggggttgatgtttgacgctacagccatagccattaatgc aggagatgggcttgaatttggttcacctaatgcaccaaacacaaatcccctcaaaacaaa aattggccatggcctagaatttgattcaaacaaggctatggttcctaaactaggaactgg ccttagttttgacagcacaggtgccattacagtaggaaacaaaaataatgataagctaac tttgtggaccacaccagctccatctcctaactgtagactaaatgcagagaaagatgctaa actcactttggtcttaacaaaatgtggcagtcaaatacttgctacagtttcagttttggc tgttaaaggcagtttggctccaatatctggaacagttcaaagtgctcatcttattataag atttgacgaaaatggagtgctactaaacaattccttcctggacccagaatattggaactt tagaaatggagatcttactgaaggcacagcctatacaaacgctgttggatttatgcctaa cctatcagcttatccaaaatctcacggtaaaactgccaaaagtaacattgtcagtcaagt ttacttaaacggagacaaaactaaacctgtaacactaaccattacactaaacggtacaca ggaaacaggagacacaactccaagtgcatactctatgtcattttcatgggactggtctgg ccacaactacattaatgaaatatttgccacatcctcttacacttttttcatacattgccca agaataaagaatcgtttgtgttatgtttcaacgtgtttatttttcaattgcagaaaattt caagtcatttttcattcagtagtatagccccaccaccacatagcttatacagatcaccgt accttaatcaaactcacagaaccctagtattcaacctgccacctccctcccaacacacag agtacacagtcctttctccccggctggccttaaaaagcatcatatcatgggtaacagaca tattcttaggtgttatattccacacggtttcctgtcgagccaaacgctcatcagtgatat taataaactccccgggcagctcacttaagttcatgtcgctgtccagctgctgagccacag gctgctgtccaacttgcggttgcttaacgggcggcgaaggagaagtccacgcctacatgg gggtagagtcataatcgtgcatcaggatagggcggtggtgctgcagcagcgcgcgaataa actgctgccgccgccgctccgtcctgcaggaatacaacatggcagtggtctcctcagcga tgattcgcaccgcccgcagcataaggcgccttgtcctccgggcacagcagcgcaccctga tctcacttaaatcagcacagtaactgcagcacagcaccacaatattgttcaaaatcccac agtgcaaggcgctgtatccaaagctcatggcggggaccacagaacccacgtggccatcat accacaagcgcaggtagattaagtggcgacccctcataaacacgctggacataaacatta cctcttttggcatgttgtaattcaccacctcccggtaccatataaacctctgattaaaca -continued tggcgccatccaccaccatcctaaaccagctggccaaaacctgcccgccggctatacact gcagggaaccgggactggaacaatgacagtggagagcccaggactcgtaaccatggatca tcatgctcgtcatgatatcaatgttggcacaacacaggcacacgtgcatacacttcctca ggattacaagctcctcccgcgttagaaccatatcccagggaacaacccattcctgaatca gcgtaaatcccacactgcagggaagacctcgcacgtaactcacgttgtgcattgtcaaag tgttacattcgggcagcagcggatgatcctccagtatggtagcgcgggtttctgtctcaa aaggaggtagacgatccctactgtacggagtgcgccgagacaaccgagatcgtgttggtc gtagtgtcatgccaaatggaacgccggacgtagtcatatttcctgaagcaaaaccaggtg cgggcgtgacaaacagatctgcgtctccggtctcgccgcttagatcgctctgtgtagtag ttgtagtatatccactctctcaaagcatccaggcgccccctggcttcgggttctatgtaa actccttcatgcgccgctgccctgataacatccaccaccgcagaataagccacacccagc caacctacacattcgttctgcgagtcacacacgggaggagcgggaagagctggaagaacc atgtttttttttttattccaaaagattatccaaaacctcaaaatgaagatctattaagtg aacgcgctcccctccggtggcgtggtcaaactctacagccaaagaacagataatggcatt tgtaagatgttgcacaatggcttccaaaaggcaaacggccctcacgtccaagtggacgta aaggctaaacccttcagggtgaatctcctctataaacattccagcaccttcaaccatgcc caaataattctcatctcgccaccttctcaatatatctctaagcaaatcccgaatattaag tccggccattgtaaaaatctgctccagagcgccctccaccttcagcctcaagcagcgaat catgattgcaaaaattcaggttcctcacagacctgtataagattcaaaagcggaacatta acaaaaataccgcgatcccgtaggtcccttcgcagggccagctgaacataatcgtgcagg tctgcacggaccagcgcggccacttccccgccaggaaccttgacaaaagaacccacactg attatgacacgcatactcggagctatgctaaccagcgtagccccgatgtaagctttgttg catgggcggcgatataaaatgcaaggtgctgctcaaaaaatcaggcaaagcctcgcgcaa aaaagaaagcacatcgtagtcatgctcatgcagataaaggcaggtaagctccggaaccac cacagaaaaagacaccatttttctctcaaacatgtctgcgggtttctgcataaacacaaa ataaaataacaaaaaaacatttaaacattagaagcctgtcttacaacaggaaaaacaacc cttataagcataagacggactacggccatgccggcgtgaccgtaaaaaaactggtcaccg tgattaaaaagcaccaccgacagctcctcggtcatgtccggagtcataatgtaagactcg gtaaacacatcaggttgattcatcggtcagtgctaaaaagcgaccgaaatagcccggggg aatacatacccgcaggcgtagagacaacattacagcccccataggaggtataacaaaatt aataggagagaaaaacacataaacacctgaaaaaccctcctgcctaggcaaaatagcacc ctcccgctccagaacaacatacagcgcttcacagcggcagcctaacagtcagccttacca gtaaaaaagaaaacctattaaaaaaacaccactcgacacggcaccagctcaatcagtcac agtgtaaaaaagggccaagtgcagagcgagtatatataggactaaaaaatgacgtaacgg ttaaagtccacaaaaaacacccagaaaaccgcacgcgaacctacgcccagaaacgaaagc caaaaaacccacaacttcctcaaatcgtcacttccgttttcccacgttacgtaacttccc attttaagaaaactacaattcccaacacatacaagttactccgccctaaaacctacgtca cccgccccgttcccacgccccgcgccacgtcacaaactccaccccctcattatcatattg gcttcaatccaaaataaggtatattattgatgatgatttaaatgccgcagtactgttgta attcattaagcattctgccgacatggaagccatcacaaacggcatgatgaacctgaatcg -continued ccagcggcatcagcaccttgtcgccttgcgtataatatttgcccatggtgaaaacggggg cgaagaagttgtccatattggccacgtttaaatcaaaactggtgaaactcacccagggat tggctgagacgaaaaacatattctcaataaaccctttagggaaataggccaggttttcac cgtaacacgccacatcttgcgaatatatgtgtagaaactgccggaaatcgtcgtggtatt cactccagagcgatgaaaacgtttcagtttgctcatggaaaacggtgtaacaagggtgaa cactatcccatatcaccagctcaccgtctttcattgccatacggaattccggatgagcat tcatcaggcgggcaagaatgtgaataaaggccggataaaacttgtgcttatttttcttta cggtctttaaaaaggccgtaatatccagctgaacggtctggttataggtacattgagcaa ctgactgaaatgcctcaaaatgttctttacgatgccattgggatatatcaacggtggtat atccagtgatttttttctccattttagcttccttagctcctgaaaatctcgataactcaa aaaatacgcccggtagtgatcttatttcattatggtgaaagttggaacctcttacgtgcc gatcaacgtctcattttcgccaaaagttggcccagggcttcccggtatcaacagggacac caggatttatttattctgcgaagtgatcttccgtcacaggtatttattcgcgataagctc atggagcggcgtaaccgtcgcacaggaaggacagagaaagcgcggatctgggaagtgacg gacagaacggtcaggacctggattggggaggcggttgccgccgctgctgctgacggtgtg acgttctctgttccggtcacaccacatacgttccgccattcctatgcgatgcacatgctg tatgccggtataccgctgaaagttctgcaaagcctgatgggacataagtccatcagttca acggaagtctacacgaaggtttttgcgctggatgtggctgcccggcaccgggtgcagttt gcgatgccggagtctgatgcggttgcgatgctgaaacaattatcctgagaataaatgcct tggcctttatatggaaatgtggaactgagtggatatgctgtttttgtctgttaaacagag aagctggctgttatccactgagaagcgaacgaaacagtcgggaaaatctcccattatcgt agagatccgcattattaatctcaggagcctgtgtagcgtttataggaagtagtgttctgt catgatgcctgcaagcggtaacgaaaacgatttgaatatgccttcaggaacaatagaaat cttcgtgcggtgttacgttgaagtggagcggattatgtcagcaatggacagaacaaccta atgaacacagaaccatgatgtggtctgtccttttacagccagtagtgctcgccgcagtcg agcgacagggcgaagccctcgagtgagcgaggaagcaccagggaacagcacttatatatt ctgcttacacacgatgcctgaaaaacttcccttggggttatccacttatccacggggat atttttataattatttttttatagtttttagatcttctttttttagagcgccttgtaggc ctttatccatgctggttctagagaaggtgttgtgacaaattgccctttcagtgtgacaaa tcaccctcaaatgacagtcctgtctgtgacaaattgcccttaaccctgtgacaaattgcc ctcagaagaagctgtttttttcacaaagttatccctgcttattgactctttttttatttagt gtgacaatctaaaaacttgtcacacttcacatggatctgtcatggcggaaacagcggtta tcaatcacaagaaacgtaaaaatagcccgcgaatcgtccagtcaaacgacctcactgagg cggcatatagtctctcccgggatcaaaaacgtatgctgtatctgttcgttgaccagatca gaaaatctgatggcaccctacaggaacatgacggtatctgcgagatccatgttgctaaat atgctgaaatattcggattgacctctgcggaagccagtaaggatatacggcaggcattga agagtttcgcggggaaggaagtggtttttttatcgccctgaagaggatgccggcgatgaaa aaggctatgaatcttttccttggtttatcaaacgtgcgcacagtccatccagagggcttt acagtgtacatatcaacccatatctcattcccttctttatcgggttacagaaccggttta cgcagtttcggcttagtgaaacaaaagaaatcaccaatccgtatgccatgcgtttatacg aatccctgtgtcagtatcgtaagccggatggctcaggcatcgtctctctgaaaatcgact -continued ggatcatagagcgttaccagctgcctcaaagttaccagcgtatgcctgacttccgccgcc gcttcctgcaggtctgtgttaatgagatcaacagcagaactccaatgcgcctctcataca ttgagaaaaagaaaggccgccagacgactcatatcgtattttccttccgcgatatcactt ccatgacgacaggatagtctgagggttatctgtcacagatttgagggtggttcgtcacat ttgttctgacctactgagggtaatttgtcacagttttgctgtttccttcagcctgcatgg attttctcatactttttgaactgtaatttttaaggaagccaaatttgagggcagtttgtc acagttgatttccttctctttcccttcgtcatgtgacctgatatcggggggttagttcgtc atcattgatgagggttgattatcacagtttattactctgaattggctatccgcgtgtgta cctctacctggagtttttcccacggtggatatttcttcttgcgctgagcgtaagagctat ctgacagaacagttcttctttgcttcctcgccagttcgctcgctatgctcggttacacgg ctgcggcgagcgctagtgataataagtgactgaggtatgtgctcttcttatctcctttg tagtgttgctcttattttaaacaactttgcggtttttttgatgactttgcgattttgttgt tgctttgcagtaaattgcaagatttaataaaaaaacgcaaagcaatgattaaaggatgtt cagaatgaaactcatggaaacacttaaccagtgcataaacgctggtcatgaaatgacgaa ggctatcgccattgcacagtttaatgatgacagcccggaagcgaggaaaataacccggcg ctggagaataggtgaagcagcggatttagttggggtttcttctcaggctatcagagatgc cgagaaagcagggcgactaccgcacccggatatggaaattcgaggacgggttgagcaacg tgttggttatacaattgaacaaattaatcatatgcgtgatgtgtttggtacgcgattgcg acgtgctgaagacgtatttccaccggtgatcggggttgctgcccataaaggtggcgttta caaaacctcagtttctgttcatcttgctcaggatctggctctgaaggggctacgtgtttt gctcgtggaaggtaacgacccccagggaacagcctcaatgtatcacggatgggtaccaga tcttcatattcatgcagaagacactctcctgcctttctatcttggggaaaaggacgatgt cacttatgcaataaagcccacttgctggccggggcttgacattattccttcctgtctggc tctgcaccgtattgaaactgagttaatgggcaaatttgatgaaggtaaactgcccaccga tccacacctgatgctccgactggccattgaaactgttgctcatgactatgatgtcatagt tattgacagcgcgcctaacctgggtatcggcacgattaatgtcgtatgtgctgctgatgt gctgattgttcccacgcctgctgagttgtttgactacacctccgcactgcagtttttcga tatgcttcgtgatctgctcaagaacgttgatcttaaagggttcgagcctgatgtacgtat tttgcttaccaaatacagcaatagtaatggctctcagtccccgtggatggaggagcaaat tcgggatgcctggggaagcatggttctaaaaaatgttgtacgtgaaacggatgaagttgg taaaggtcagatccggatgagaactgtttttgaacaggccattgatcaacgctcttcaac tggtgcctggagaaatgctctttctatttgggaacctgtctgcaatgaaattttcgatcg tctgattaaaccacgctgggagattagataatgaagcgtgcgcctgttattccaaaacat acgctcaatactcaaccggttgaagatacttcgttatcgacaccagctgccccgatggtg gattcgttaattgcgcgcgtaggagtaatggctcgcggtaatgccattactttgcctgta tgtggtcgggatgtgaagtttactcttgaagtgctccggggtgatagtgttgagaagacc tctcgggtatggtcaggtaatgaacgtgaccaggagctgcttactgaggacgcactggat gatctcatcccttcttttctactgactggtcaacagacaccggcgttcggtcgaagagta tctggtgtcatagaaattgccgatgggagtcgccgtcgtaaagctgctgcacttaccgaa agtgattatcgtgttctggttggcgagctggatgatgagcagatggctgcattatccaga -continued ttgggtaacgattatcgcccaacaagtgcttatgaacgtggtcagcgttatgcaagccga ttgcagaatgaatttgctggaaatatttctgcgctggctgatgcggaaaatatttcacgt aagattattacccgctgtatcaacaccgccaaattgcctaaatcagttgttgctcttttt tctcaccccggtgaactatctgcccggtcaggtgatgcacttcaaaaagcctttacagat aaagaggaattacttaagcagcaggcatctaaccttcatgagcagaaaaaagctggggtg atatttgaagctgaagaagttatcactcttttaacttctgtgcttaaaacgtcatctgca tcaagaactagtttaagctcacgacatcagtttgctcctggagcgacagtattgtataag ggcgataaaatggtgcttaacctggacaggtctcgtgttccaactgagtgtatagagaaa attgaggccattcttaaggaacttgaaaagccagcaccctgatgcgaccacgttttagtc tacgtttatctgtctttacttaatgtcctttgttacaggccagaaagcataactggcctg aatattctctctgggcccactgttccacttgtatcgtcggtctgataatcagactgggac cacggtcccactcgtatcgtcggtctgattattagtctgggaccacggtcccactcgtat cgtcggtctgattattagtctgggaccacggtcccactcgtatcgtcggtctgataatca gactgggaccacggtcccactcgtatcgtcggtctgattattagtctgggaccatggtcc cactcgtatcgtcggtctgattattagtctgggaccacggtcccactcgtatcgtcggtc tgattattagtctggaaccacggtcccactcgtatcgtcggtctgattattagtctggga ccacggtcccactcgtatcgtcggtctgattattagtctgggaccacgatcccactcgtg ttgtcggtctgattatcggtctgggaccacggtcccacttgtattgtcgatcagactatc agcgtgagactacgattccatcaatgcctgtcaagggcaagtattgacatgtcgtcgtaa cctgtagaacggagtaacctcggtgtgcggttgtatgcctgctgtggattgctgctgtgt cctgcttatccacaacattttgcgcacggttatgtggacaaaatacctgttaccatttcc atttaaatcatcatcaataatataccttattttggattgaagccaatatgataatgaggg ggtggagtttgtgacgtggcgcggggcgtgggaacggggcgggtgacgtagtagtgtggc ggaagtgtgatgttgcaagtgtggcggaacacatgtaagcgacggatgtggcaaaagtga cgtttttggtgtgcgccggtgtacacaggaagtgacaattttcgcgcggttttaggcgga tgttgtagtaaatttgggcgtaaccgagtaagatttggccattttcgcgggaaaactgaa taagaggaagtgaaatctgaataattttgtgttactcatagcgcgtaatatttgtctagg gccgcggggactttgaccgtttacgtggagactcgcccaggtgtttttctcaggtgtttt ccgcgttccgggtcaaagttggcgtttt (pGS66)

SEQ ID NO: 5

TTCGAAATTTAAATCATCATCAATAATATACCTTATTTTGGATTGAAGCCAATATGATAATGAGGGGGTGGAG

TTTGTGACGTGGCGCGGGGCGTGGGAACGGGGCGGGTGACGTAGTAGTGTGGCGGAAGTGTGATGTTGCAAGT

GTGGCGGAACACATGTAAGCGACGGATGTGGCAAAAGTGACGTTTTTGGTGTGCGCCGGTGTACACAGGAAGT

GACAATTTTCGCGCGGTTTTAGGCGGATGTTGTAGTAAATTTGGGCGTAACCGAGTAAGATTTGGCCATTTTC

GCGGGAAAACTGAATAAGAGGAAGTGAAATCTGAATAATTTTGTGTTACTCATAGCGCGTAATATTTGTCTAG

GGCCGCGGGGACTTTGACCGTTTACGTGGAGACTCGCCCAGGTGTTTTTCTCAGGTGTTTTCCGCGTTCCGGG

TCAAAGTTGGCGTTTTGATGGCGTCCCTTAATTAAGGATCCAGATCTGTGGGCGTGGCTTAAGGGTGGGAAAG

AATATATAAGGTGGGGGTCTTATGTAGTTTTGTATCTGTTTTGCAGCAGCCGCCGCCGCCATGAGCACCAACT

CGTTTGATGGAAGCATTGTGAGCTCATATTTGACAACGCGCATGCCCCCATGGGCCGGGGTGCGTCAGAATGT

GATGGGCTCCAGCATTGATGGTCGCCCCGTCCTGCCCGCAAACTCTACTACCTTGACCTACGAGACCGTGTCT

GGAACGCCGTTGGAGACTGCAGCCTCCGCCGCCGCTTCAGCCGCTGCAGCCACCGCCCGCGGGATTGTGACTG

-continued

ACTTTGCTTTCCTGAGCCCGCTTGCAAGCAGTGCAGCTTCCCGTTCATCCGCCCGCGATGACAAGTTGACGGC

TCTTTTGGCACAATTGGATTCTTTGACCCGGGAACTTAATGTCGTTTCTCAGCAGCTGTTGGATCTGCGCCAG

CAGGTTTCTGCCCTGAAGGCTTCCTCCCCTCCCAATGCGGTTTAAAACATAAATAAAAAACCAGACTCTGTTT

GGATTTGGATCAAGCAAGTGTCTTGCTGTCTTTATTTAGGGGTTTTGCGCGCGCGGTAGGCCCGGGACCAGCG

GTCTCGGTCGTTGAGGGTCCTGTGTATTTTTTCCAGGACGTGGTAAAGGTGACTCTGGATGTTCAGATACATG

GGCATAAGCCCGTCTCTGGGGTGGAGGTAGCACCACTGCAGAGCTTCATGCTGCGGGGTGGTGTTGTAGATGA

TCCAGTCGTAGCAGGAGCGCTGGGCGTGGTGCCTAAAAATGTCTTTCAGTAGCAAGCTGATTGCCAGGGGCAG

GCCCTTGGTGTAAGTGTTTACAAAGCGGTTAAGCTGGGATGGGTGCATACGTGGGGATATGAGATGCATCTTG

GACTGTATTTTTAGGTTGGCTATGTTCCCAGCCATATCCCTCCGGGGATTCATGTTGTGCAGAACCACCAGCA

CAGTGTATCCGGTGCACTTGGGAAATTTGTCATGTAGCTTAGAAGGAAATGCGTGGAAGAACTTGGAGACGCC

CTTGTGACCTCCAAGATTTTCCATGCATTCGTCCATAATGATGGCAATGGGCCCACGGGCGGCGGCCTGGGCG

AAGATATTTCTGGGATCACTAACGTCATAGTTGTGTTCCAGGATGAGATCGTCATAGGCCATTTTTACAAAGC

GCGGGCGGAGGGTGCCAGACTGCGGTATAATGGTTCCATCCGGCCCAGGGGCGTAGTTACCCTCACAGATTTG

CATTTCCCACGCTTTGAGTTCAGATGGGGGGATCATGTCTACCTGCGGGGCGATGAAGAAAACGGTTTCCGGG

GTAGGGGAGATCAGCTGGGAAGAAAGCAGGTTCCTGAGCAGCTGCGACTTACCGCAGCCGGTGGGCCCGTAAA

TCACACCTATTACCGGGTGCAACTGGTAGTTAAGAGAGCTGCAGCTGCCGTCATCCCTGAGCAGGGGGGCCAC

TTCGTTAAGCATGTCCCTGACTCGCATGTTTTCCCTGACCAAATCCGCCAGAAGGCGCTCGCCGCCCAGCGAT

AGCAGTTCTTGCAAGGAAGCAAAGTTTTTCAACGGTTTGAGACCGTCCGCCGTAGGCATGCTTTTGAGCGTTT

GACCAAGCAGTTCCAGGCGGTCCCACAGCTCGGTCACCTGCTCTACGGCATCTCGATCCAGCATATCTCCTCG

TTTCGCGGGTTGGGGCGGCTTTCGCTGTACGGCAGTAGTCGGTGCTCGTCCAGACGGGCCAGGGTCATGTCTT

TCCACGGGCGCAGGGTCCTCGTCAGCGTAGTCTGGGTCACGGTGAAGGGGTGCGCTCCGGGCTGCGCGCTGGC

CAGGGTGCGCTTGAGGCTGGTCCTGCTGGTGCTGAAGCGCTGCCGGTCTTCGCCCTGCGCGTCGGCCAGGTAG

CATTTGACCATGGTGTCATAGTCCAGCCCCTCCGCGGCGTGGCCCTTGGCGCGCAGCTTGCCCTTGGAGGAGG

CGCCGCACGAGGGGCAGTGCAGACTTTTGAGGGCGTAGAGCTTGGGCGCGAGAAATACCGATTCCGGGGAGTA

GGCATCCGCGCCGCAGGCCCCGCAGACGGTCTCGCATTCCACGAGCCAGGTGAGCTCTGGCCGTTCGGGGTCA

AAAACCAGGTTTCCCCCATGCTTTTTGATGCGTTTCTTACCTCTGGTTTCCATGAGCCGGTGTCCACGCTCGG

TGACGAAAAGGCTGTCCGTGTCCCCGTATACAGACTTGAGAGGCCTGTCCTCGAGCGGTGTTCCGCGGTCCTC

CTCGTATAGAAACTCGGACCACTCTGAGACAAAGGCTCGCGTCCAGGCCAGCACGAAGGAGGCTAAGTGGGAG

GGGTAGCGGTCGTTGTCCACTAGGGGGTCCACTCGCTCCAGGGTGTGAAGACACATGTCGCCCTCTTCGGCAT

CAAGGAAGGTGATTGGTTTGTAGGTGTAGGCCACGTGACCGGGTGTTCCTGAAGGGGGGCTATAAAAGGGGGT

GGGGGCGCGTTCGTCCTCACTCTCTTCCGCATCGCTGTCTGCGAGGGCCAGCTGTTGGGGTGAGTACTCCCTC

TGAAAAGCGGGCATGACTTCTGCGCTAAGATTGTCAGTTTCCAAAAACGAGGAGGATTTGATATTCACCTGGC

CCGCGGTGATGCCTTTGAGGGTGGCCGCATCCATCTGGTCAGAAAAGACAATCTTTTTGTTGTCAAGCTTGGT

GGCAAACGACCCGTAGAGGGCGTTGGACAGCAACTTGGCGATGGAGCGCAGGGTTTGGTTTTTGTCGCGATCG

GCGCGCTCCTTGGCCGCGATGTTTAGCTGCACGTATTCGCGCGCAACGCACCGCCATTCGGGAAAGACGGTGG

TGCGCTCGTCGGGCACCAGGTGCACGCGCCAACCGCGGTTGTGCAGGGTGACAAGGTCAACGCTGGTGGCTAC

CTCTCCGCGTAGGCGCTCGTTGGTCCAGCAGAGGCGGCCGCCCTTGCGCGAGCAGAATGGCGGTAGGGGGTCT

AGCTGCGTCTCGTCCGGGGGGTCTGCGTCCACGGTAAAGACCCCGGGCAGCAGGCGCGCGTCGAAGTAGTCTA

TCTTGCATCCTTGCAAGTCTAGCGCCTGCTGCCATGCGCGGGCGGCAAGCGCGCGCTCGTATGGGTTGAGTGG

GGGACCCCATGGCATGGGGTGGGTGAGCGCGGAGGCGTACATGCCGCAAATGTCGTAAACGTAGAGGGGCTCT

-continued

CTGAGTATTCCAAGATATGTAGGGTAGCATCTTCCACCGCGGATGCTGGCGCGCACGTAATCGTATAGTTCGT

GCGAGGGAGCGAGGAGGTCGGGACCGAGGTTGCTACGGGCGGGCTGCTCTGCTCGGAAGACTATCTGCCTGAA

GATGGCATGTGAGTTGGATGATATGGTTGGACGCTGGAAGACGTTGAAGCTGGCGTCTGTGAGACCTACCGCG

TCACGCACGAAGGAGGCGTAGGAGTCGCGCAGCTTGTTGACCAGCTCGGCGGTGACCTGCACGTCTAGGGCGC

AGTAGTCCAGGGTTTCCTTGATGATGTCATACTTATCCTGTCCCTTTTTTTTCCACAGCTCGCGGTTGAGGAC

AAACTCTTCGCGGTCTTTCCAGTACTCTTGGATCGGAAACCCGTCGGCCTCCGAACGGTAAGAGCCTAGCATG

TAGAACTGGTTGACGGCCTGGTAGGCGCAGCATCCCTTTTCTACGGGTAGCGCGTATGCCTGCGCGGCCTTCC

GGAGCGAGGTGTGGGTGAGCGCAAAGGTGTCCCTGACCATGACTTTGAGGTACTGGTATTTGAAGTCAGTGTC

GTCGCATCCGCCCTGCTCCCAGAGCAAAAAGTCCGTGCGCTTTTTGGAACGCGGATTTGGCAGGGCGAAGGTG

ACATCGTTGAAGAGTATCTTTCCCGCGCGAGGCATAAAGTTGCGTGTGATGCGGAAGGGTCCCGGCACCTCGG

AACGGTTGTTAATTACCTGGGCGGCGAGCACGATCTCGTCAAAGCCGTTGATGTTGTGGCCCACAATGTAAAG

TTCCAAGAAGCGCGGGATGCCCTTGATGGAAGGCAATTTTTTAAGTTCCTCGTAGGTGAGCTCTTCAGGGGAG

CTGAGCCCGTGCTCTGAAAGGGCCCAGTCTGCAAGATGAGGGTTGGAAGCGACGAATGAGCTCCACAGGTCAC

GGGCCATTAGCATTTGCAGGTGGTCGCGAAAGGTCCTAAACTGGCGACCTATGGCCATTTTTTCTGGGGTGAT

GCAGTAGAAGGTAAGCGGGTCTTGTTCCCAGCGGTCCCATCCAAGGTTCGCGGCTAGGTCTCGCGCGGCAGTC

ACTAGAGGCTCATCTCCGCCGAACTTCATGACCAGCATGAAGGGCACGAGCTGCTTCCCAAAGGCCCCCATCC

AAGTATAGGTCTCTACATCGTAGGTGACAAAGAGACGCTCGGTGCGAGGATGCGAGCCGATCGGGAAGAACTG

GATCTCCCGCCACCAATTGGAGGAGTGGCTATTGATGTGGTGAAAGTAGAAGTCCCTGCGACGGGCCGAACAC

TCGTGCTGGCTTTTGTAAAAACGTGCGCAGTACTGGCAGCGGTGCACGGGCTGTACATCCTGCACGAGGTTGA

CCTGACGACCGCGCACAAGGAAGCAGAGTGGGAATTTGAGCCCCTCGCCTGGCGGGTTTGGCTGGTGGTCTTC

TACTTCGGCTGCTTGTCCTTGACCGTCTGGCTGCTCGAGGGGAGTTACGGTGGATCGGACCACCACGCCGCGC

GAGCCCAAAGTCCAGATGTCCGCGCGCGGCGGTCGGAGCTTGATGACAACATCGCGCAGATGGGAGCTGTCCA

TGGTCTGGAGCTCCCGCGGCGTCAGGTCAGGCGGGAGCTCCTGCAGGTTTACCTCGCATAGACGGGTCAGGGC

GCGGGCTAGATCCAGGTGATACCTAATTTCCAGGGGCTGGTTGGTGGCGGCGTCGATGGCTTGCAAGAGGCCG

CATCCCCGCGGCGCGACTACGGTACCGCGCGGCGGGCGGTGGGCCGCGGGGGTGTCCTTGGATGATGCATCTA

AAAGCGGTGACGCGGGCGAGCCCCCGGAGGTAGGGGGGGCTCCGGACCCGCCGGGAGAGGGGGCAGGGGCACG

TCGGCGCCGCGCGCGGGCAGGAGCTGGTGCTGCGCGCGTAGGTTGCTGGCGAACGCGACGACGCGGCGGTTGA

TCTCCTGAATCTGGCGCCTCTGCGTGAAGACGACGGGCCCGGTGAGCTTGAGCCTGAAAGAGAGTTCGACAGA

ATCAATTTCGGTGTCGTTGACGGCGGCCTGGCGCAAAATCTCCTGCACGTCTCCTGAGTTGTCTTGATAGGCG

ATCTCGGCCATGAACTGCTCGATCTCTTCCTCCTGGAGATCTCCGCGTCCGGCTCGCTCCACGGTGGCGGCGA

GGTCGTTGGAAATGCGGGCCATGAGCTGCGAGAAGGCGTTGAGGCCTCCCTCGTTCCAGACGCGGCTGTAGAC

CACGCCCCCTTCGGCATCGCGGGCGCGCATGACCACCTGCGCGAGATTGAGCTCCACGTGCCGGGCGAAGACG

GCGTAGTTTCGCAGGCGCTGAAAGAGGTAGTTGAGGGTGGTGGCGGTGTGTTCTGCCACGAAGAAGTACATAA

CCCAGCGTCGCAACGTGGATTCGTTGATATCCCCCAAGGCCTCAAGGCGCTCCATGGCCTCGTAGAAGTCCAC

GGCGAAGTTGAAAAACTGGGAGTTGCGCGCCGACACGGTTAACTCCTCCTCCAGAAGACGGATGAGCTCGGCG

ACAGTGTCGCGCACCTCGCGCTCAAAGGCTACAGGGGCCTCTTCTTCTTCTTCAATCTCCTCTTCCATAAGGG

CCTCCCCTTCTTCTTCTTCTGGCGGCGGTGGGGGAGGGGGGACACGGCGGCGACGACGGCGCACCGGGAGGCG

GTCGACAAAGCGCTCGATCATCTCCCCGCGGCGACGGCGCATGGTCTCGGTGACGGCGCGGCCGTTCTCGCGG

GGGCGCAGTTGGAAGACGCCGCCCGTCATGTCCCGGTTATGGGTTGGCGGGGGGCTGCCATGCGGCAGGGATA

CGGCGCTAACGATGCATCTCAACAATTGTTGTGTAGGTACTCCGCCGCCGAGGGACCTGAGCGAGTCCGCATC

GACCGGATCGGAAAACCTCTCGAGAAAGGCGTCTAACCAGTCACAGTCGCAAGGTAGGCTGAGCACCGTGGCG

-continued

GGCGGCAGCGGGCGGCGGTCGGGGTTGTTTCTGGCGGAGGTGCTGCTGATGATGTAATTAAAGTAGGCGGTCT

TGAGACGGCGGATGGTCGACAGAAGCACCATGTCCTTGGGTCCGGCCTGCTGAATGCGCAGGCGGTCGGCCAT

GCCCCAGGCTTCGTTTTGACATCGGCGCAGGTCTTTGTAGTAGTCTTGCATGAGCCTTTCTACCGGCACTTCT

TCTTCTCCTTCCTCTTGTCCTGCATCTCTTGCATCTATCGCTGCGGCGGCGGCGGAGTTTGGCCGTAGGTGGC

GCCCTCTTCCTCCCATGCGTGTGACCCCGAAGCCCCTCATCGGCTGAAGCAGGGCTAGGTCGGCGACAACGCG

CTCGGCTAATATGGCCTGCTGCACCTGCGTGAGGGTAGACTGGAAGTCATCCATGTCCACAAAGCGGTGGTAT

GCGCCCGTGTTGATGGTGTAAGTGCAGTTGGCCATAACGGACCAGTTAACGGTCTGGTGACCCGGCTGCGAGA

GCTCGGTGTACCTGAGACGCGAGTAAGCCCTCGAGTCAAATACGTAGTCGTTGCAAGTCCGCACCAGGTACTG

GTATCCCACCAAAAAGTGCGGCGGCGGCTGGCGGTAGAGGGGCCAGCGTAGGGTGGCCGGGGCTCCGGGGGCG

AGATCTTCCAACATAAGGCGATGATATCCGTAGATGTACCTGGACATCCAGGTGATGCCGGCGGCGGTGGTGG

AGGCGCGCGGAAAGTCGCGGACGCGGTTCCAGATGTTGCGCAGCGGCAAAAAGTGCTCCATGGTCGGGACGCT

CTGGCCGGTCAGGCGCGCGCAATCGTTGACGCTCTAGACCGTGCAAAAGGAGAGCCTGTAAGCGGGCACTCTT

CCGTGGTCTGGTGGATAAATTCGCAAGGGTATCATGGCGGACGACCGGGGTTCGAGCCCCGTATCCGGCCGTC

CGCCGTGATCCATGCGGTTACCGCCCGCGTGTCGAACCCAGGTGTGCGACGTCAGACAACGGGGGAGTGCTCC

TTTTGGCTTCCTTCCAGGCGCGGCGGCTGCTGCGCTAGCTTTTTTGGCCACTGGCCGCGCGCAGCGTAAGCGG

TTAGGCTGGAAAGCGAAAGCATTAAGTGGCTCGCTCCCTGTAGCCGGAGGGTTATTTTCCAAGGGTTGAGTCG

CGGGACCCCCGGTTCGAGTCTCGGACCGGCCGGACTGCGGCGAACGGGGGTTTGCCTCCCCGTCATGCAAGAC

CCCGCTTGCAAATTCCTCCGGAAACAGGGACGAGCCCCTTTTTTGCTTTTCCCAGATGCATCCGGTGCTGCGG

CAGATGCGCCCCCCTCCTCAGCAGCGGCAAGAGCAAGAGCAGCGGCAGACATGCAGGGCACCCTCCCCTCCTC

CTACCGCGTCAGGAGGGGCGACATCCGCGGTTGACGCGGCAGCAGATGGTGATTACGAACCCCCGCGGCGCCG

GGCCCGGCACTACCTGGACTTGGAGGAGGGCGAGGGCCTGGCGCGGCTAGGAGCGCCCTCTCCTGAGCGGCAC

CCAAGGGTGCAGCTGAAGCGTGATACGCGTGAGGCGTACGTGCCGCGGCAGAACCTGTTTCGCGACCGCGAGG

GAGAGGAGCCCGAGGAGATGCGGGATCGAAAGTTCCACGCAGGGCGCGAGCTGCGGCATGGCCTGAATCGCGA

GCGGTTGCTGCGCGAGGAGGACTTTGAGCCCGACGCGCGAACCGGGATTAGTCCCGCGCGCGCACACGTGGCG

GCCGCCGACCTGGTAACCGCATACGAGCAGACGGTGAACCAGGAGATTAACTTTCAAAAAAGCTTTAACAACC

ACGTGCGTACGCTTGTGGCGCGCGAGGAGGTGGCTATAGGACTGATGCATCTGTGGGACTTTGTAAGCGCGCT

GGAGCAAAACCCAAATAGCAAGCCGCTCATGGCGCAGCTGTTCCTTATAGTGCAGCACAGCAGGGACAACGAG

GCATTCAGGGATGCGCTGCTAAACATAGTAGAGCCCGAGGGCCGCTGGCTGCTCGATTTGATAAACATCCTGC

AGAGCATAGTGGTGCAGGAGCGCAGCTTGAGCCTGGCTGACAAGGTGGCCGCCATCAACTATTCCATGCTTAG

CCTGGGCAAGTTTTACGCCCGCAAGATATACCATACCCCTTACGTTCCCATAGACAAGGAGGTAAAGATCGAG

GGGTTCTACATGCGCATGGCGCTGAAGGTGCTTACCTTGAGCGACGACCTGGGCGTTTATCGCAACGAGCGCA

TCCACAAGGCCGTGAGCGTGAGCCGGCGGCGCGAGCTCAGCGACCGCGAGCTGATGCACAGCCTGCAAAGGGC

CCTGGCTGGCACGGGCAGCGGCGATAGAGAGGCCGAGTCCTACTTTGACGCGGGCGCTGACCTGCGCTGGGCC

CCAAGCCGACGCGCCCTGGAGGCAGCTGGGGCCGGACCTGGGCTGGCGGTGGCACCCGCGCGCGCTGGCAACG

TCGGCGGCGTGGAGGAATATGACGAGGACGATGAGTACGAGCCAGAGGACGGCGAGTACTAAGCGGTGATGTT

TCTGATCAGATGATGCAAGACGCAACGGACCCGGCGGTGCGGGCGGCGCTGCAGAGCCAGCCGTCCGGCCTTA

ACTCCACGGACGACTGGCGCCAGGTCATGGACCGCATCATGTCGCTGACTGCGCGCAATCCTGACGCGTTCCG

GCAGCAGCCGCAGGCCAACCGGCTCTCCGCAATTCTGGAAGCGGTGGTCCCGGCGCGCGCAAACCCCACGCAC

GAGAAGGTGCTGGCGATCGTAAACGCGCTGGCCGAAAACAGGGCCATCCGGCCCGACGAGGCCGGCCTGGTCT

ACGACGCGCTGCTTCAGCGCGTGGCTCGTTACAACAGCGGCAACGTGCAGACCAACCTGGACCGGCTGGTGGG

-continued

GGATGTGCGCGAGGCCGTGGCGCAGCGTGAGCGCGCGCAGCAGCAGGGCAACCTGGGCTCCATGGTTGCACTA

AACGCCTTCCTGAGTACACAGCCCGCCAACGTGCCGCGGGGACAGGAGGACTACACCAACTTTGTGAGCGCAC

TGCGGCTAATGGTGACTGAGACACCGCAAAGTGAGGTGTACCAGTCTGGGCCAGACTATTTTTTCCAGACCAG

TAGACAAGGCCTGCAGACCGTAAACCTGAGCCAGGCTTTCAAAAACTTGCAGGGGCTGTGGGGGGTGCGGGCT

CCCACAGGCGACCGCGCGACCGTGTCTAGCTTGCTGACGCCCAACTCGCGCCTGTTGCTGCTGCTAATAGCGC

CCTTCACGGACAGTGGCAGCGTGTCCCGGGACACATACCTAGGTCACTTGCTGACACTGTACCGCGAGGCCAT

AGGTCAGGCGCATGTGGACGAGCATACTTTCCAGGAGATTACAAGTGTCAGCCGCGCGCTGGGGCAGGAGGAC

ACGGGCAGCCTGGAGGCAACCCTAAACTACCTGCTGACCAACCGGCGGCAGAAGATCCCCTCGTTGCACAGTT

TAAACAGCGAGGAGGAGCGCATTTTGCGCTACGTGCAGCAGAGCGTGAGCCTTAACCTGATGCGCGACGGGGT

AACGCCCAGCGTGGCGCTGGACATGACCGCGCGCAACATGGAACCGGGCATGTATGCCTCAAACCGGCCGTTT

ATCAACCGCCTAATGGACTACTTGCATCGCGCGGCCGCCGTGAACCCCGAGTATTTCACCAATGCCATCTTGA

ACCCGCACTGGCTACCGCCCCCTGGTTTCTACACCGGGGGATTCGAGGTGCCCGAGGGTAACGATGGATTCCT

CTGGGACGACATAGACGACAGCGTGTTTTCCCCGCAACCGCAGACCCTGCTAGAGTTGCAACAGCGCGAGCAG

GCAGAGGCGGCGCTGCGAAAGGAAAGCTTCCGCAGGCCAAGCAGCTTGTCCGATCTAGGCGCTGCGGCCCCGC

GGTCAGATGCTAGTAGCCCATTTCCAAGCTTGATAGGGTCTCTTACCAGCACTCGCACCACCCGCCCGCGCCT

GCTGGGCGAGGAGGAGTACCTAAACAACTCGCTGCTGCAGCCGCAGCGCGAAAAAAACCTGCCTCCGGCATTT

CCCAACAACGGGATAGAGAGCCTAGTGGACAAGATGAGTAGATGGAAGACGTACGCGCAGGAGCACAGGGACG

TGCCAGGCCCGCGCCCGCCCACCCGTCGTCAAAGGCACGACCGTCAGCGGGGTCTGGTGTGGGAGGACGATGA

CTCGGCAGACGACAGCAGCGTCCTGGATTTGGGAGGGAGTGGCAACCCGTTTGCGCACCTTCGCCCCAGGCTG

GGGAGAATGTTTTAAAAAAAAAAAAGCATGATGCAAAATAAAAAACTCACCAAGGCCATGGCACCGAGCGTTG

GTTTTCTTGTATTCCCCTTAGTATGCGGCGCGCGGCGATGTATGAGGAAGGTCCTCCTCCCTCCTACGAGAGT

GTGGTGAGCGCGGCGCCAGTGGCGGCGGCGCTGGGTTCTCCCTTCGATGCTCCCCTGGACCCGCCGTTTGTGC

CTCCGCGGTACCTGCGGCCTACCGGGGGGAGAAACAGCATCCGTTACTCTGAGTTGGCACCCCTATTCGACAC

CACCCGTGTGTACCTGGTGGACAACAAGTCAACGGATGTGGCATCCCTGAACTACCAGAACGACCACAGCAAC

TTTCTGACCACGGTCATTCAAAACAATGACTACAGCCCGGGGGAGGCAAGCACACAGACCATCAATCTTGACG

ACCGGTCGCACTGGGGCGGCGACCTGAAAACCATCCTGCATACCAACATGCCAAATGTGAACGAGTTCATGTT

TACCAATAAGTTTAAGGCGCGGGTGATGGTGTCGCGCTTGCCTACTAAGGACAATCAGGTGGAGCTGAAATAC

GAGTGGGTGGAGTTCACGCTGCCCGAGGGCAACTACTCCGAGACCATGACCATAGACCTTATGAACAACGCGA

TCGTGGAGCACTACTTGAAAGTGGGCAGACAGAACGGGGTTCTGGAAAGCGACATCGGGGTAAAGTTTGACAC

CCGCAACTTCAGACTGGGGTTTGACCCCGTCACTGGTCTTGTCATGCCTGGGGTATATACAAACGAAGCCTTC

CATCCAGACATCATTTTGCTGCCAGGATGCGGGGTGGACTTCACCCACAGCCGCCTGAGCAACTTGTTGGGCA

TCCGCAAGCGGCAACCCTTCCAGGAGGGCTTTAGGATCACCTACGATGATCTGGAGGGTGGTAACATTCCCGC

ACTGTTGGATGTGGACGCCTACCAGGCGAGCTTGAAAGATGACACCGAACAGGGCGGGGGTGGCGCAGGCGGC

AGCAACAGCAGTGGCAGCGGCGCGGAAGAGAACTCCAACGCGGCAGCCGCGGCAATGCAGCCGGTGGAGGACA

TGAACGATCATGCCATTCGCGGCGACACCTTTGCCACACGGGCTGAGGAGAAGCGCGCTGAGGCCGAAGCAGC

GGCCGAAGCTGCCGCCCCCGCTGCGCAACCCGAGGTCGAGAAGCCTCAGAAGAAACCGGTGATCAAACCCCTG

ACAGAGGACAGCAAGAAACGCAGTTACAACCTAATAAGCAATGACAGCACCTTCACCCAGTACCGCAGCTGGT

ACCTTGCATACAACTACGGCGACCCTCAGACCGGAATCCGCTCATGGACCCTGCTTTGCACTCCTGACGTAAC

CTGCGGCTCGGAGCAGGTCTACTGGTCGTTGCCAGACATGATGCAAGACCCCGTGACCTTCCGCTCCACGCGC

CAGATCAGCAACTTTCCGGTGGTGGGCGCCGAGCTGTTGCCCGTGCACTCCAAGAGCTTCTACAACGACCAGG

CCGTCTACTCCCAACTCATCCGCCAGTTTACCTCTCTGACCCACGTGTTCAATCGCTTTCCCGAGAACCAGAT

-continued

TTTGGCGCGCCCGCCAGCCCCCACCATCACCACCGTCAGTGAAAACGTTCCTGCTCTCACAGATCACGGGACG

CTACCGCTGCGCAACAGCATCGGAGGAGTCCAGCGAGTGACCATTACTGACGCCAGACGCCGCACCTGCCCCT

ACGTTTACAAGGCCCTGGGCATAGTCTCGCCGCGCGTCCTATCGAGCCGCACTTTTTGAGCAAGCATGTCCAT

CCTTATATCGCCCAGCAATAACACAGGCTGGGGCCTGCGCTTCCCAAGCAAGATGTTTGGCGGGGCCAAGAAG

CGCTCCGACCAACACCCAGTGCGCGTGCGCGGGCACTACCGCGCGCCCTGGGGCGCGCACAAACGCGGCCGCA

CTGGGCGCACCACCGTCGATGACGCCATCGACGCGGTGGTGGAGGAGGCGCGCAACTACACGCCCACGCCGCC

ACCAGTGTCCACAGTGGACGCGGCCATTCAGACCGTGGTGCGCGGAGCCCGGCGCTATGCTAAAATGAAGAGA

CGGCGGAGGCGCGTAGCACGTCGCCACCGCCGCCGACCCGGCACTGCCGCCCAACGCGCGGCGGCGGCCCTGC

TTAACCGCGCACGTCGCACCGGCCGACGGGCGGCCATGCGGGCCGCTCGAAGGCTGGCCGCGGGTATTGTCAC

TGTGCCCCCCAGGTCCAGGCGACGAGCGGCCGCCGCAGCAGCCGCGGCCATTAGTGCTATGACTCAGGGTCGC

AGGGGCAACGTGTATTGGGTGCGCGACTCGGTTAGCGGCCTGCGCGTGCCCGTGCGCACCCGCCCCCCGCGCA

ACTAGATTGCAAGAAAAAACTACTTAGACTCGTACTGTTGTATGTATCCAGCGGCGGCGGCGCGCAACGAAGC

TATGTCCAAGCGCAAAATCAAAGAAGAGATGCTCCAGGTCATCGCGCCGGAGATCTATGGCCCCCCGAAGAAG

GAAGAGCAGGATTACAAGCCCCGAAAGCTAAAGCGGGTCAAAAAGAAAAAGAAAGATGATGATGATGAACTTG

ACGACGAGGTGGAACTGCTGCACGCTACCGCGCCCAGGCGACGGGTACAGTGGAAAGGTCGACGCGTAAAACG

TGTTTTGCGACCCGGCACCACCGTAGTCTTTACGCCCGGTGAGCGCTCCACCCGCACCTACAAGCGCGTGTAT

GATGAGGTGTACGGCGACGAGGACCTGCTTGAGCAGGCCAACGAGCGCCTCGGGGAGTTTGCCTACGGAAAGC

GGCATAAGGACATGCTGGCGTTGCCGCTGGACGAGGGCAACCCAACACCTAGCCTAAAGCCCGTAACACTGCA

GCAGGTGCTGCCCGCGCTTGCACCGTCCGAAGAAAAGCGCGGCCTAAAGCGCGAGTCTGGTGACTTGGCACCC

ACCGTGCAGCTGATGGTACCCAAGCGCCAGCGACTGGAAGATGTCTTGGAAAAAATGACCGTGGAACCTGGGC

TGGAGCCCGAGGTCCGCGTGCGGCCAATCAAGCAGGTGGCGCCGGGACTGGGCGTGCAGACCGTGGACGTTCA

GATACCCACTACCAGTAGCACCAGTATTGCCACCGCCACAGAGGGCATGGAGACACAAACGTCCCCGGTTGCC

TCAGCGGTGGCGGATGCCGCGGTGCAGGCGGTCGCTGCGGCCGCGTCCAAGACCTCTACGGAGGTGCAAACGG

ACCCGTGGATGTTTCGCGTTTCAGCCCCCCGGCGCCCGCGCGGTTCGAGGAAGTACGGCGCCGCCAGCGCGCT

ACTGCCCGAATATGCCCTACATCCTTCCATTGCGCCTACCCCCGGCTATCGTGGCTACACCTACCGCCCCAGA

AGACGAGCAACTACCCGACGCCGAACCACCACTGGAACCCGCCGCCGCCGTCGCCGTCGCCAGCCCGTGCTGG

CCCCGATTTCCGTGCGCAGGGTGGCTCGCGAAGGAGGCAGGACCCTGGTGCTGCCAACAGCGCGCTACCACCC

CAGCATCGTTTAAAAGCCGGTCTTTGTGGTTCTTGCAGATATGGCCCTCACCTGCCGCCTCCGTTTCCCGGTG

CCGGGATTCCGAGGAAGAATGCACCGTAGGAGGGGCATGGCCGGCCACGGCCTGACGGGCGGCATGCGTCGTG

CGCACCACCGGCGGCGGCGCGCGTCGCACCGTCGCATGCGCGGCGGTATCCTGCCCCTCCTTATTCCACTGAT

CGCCGCGGCGATTGGCGCCGTGCCCGGAATTGCATCCGTGGCCTTGCAGGCGCAGAGACACTGATTAAAAACA

AGTTGCATGTGGAAAAATCAAAATAAAAAGTCTGGACTCTCACGCTCGCTTGGTCCTGTAACTATTTTGTAGA

ATGGAAGACATCAACTTTGCGTCTCTGGCCCCGCGACACGGCTCGCGCCCGTTCATGGGAAACTGGCAAGATA

TCGGCACCAGCAATATGAGCGGTGGCGCCTTCAGCTGGGGCTCGCTGTGGAGCGGCATTAAAAATTTCGGTTC

CACCGTTAAGAACTATGGCAGCAAGGCCTGGAACAGCAGCACAGGCCAGATGCTGAGGGATAAGTTGAAAGAG

CAAAATTTCCAACAAAAGGTGGTAGATGGCCTGGCCTCTGGCATTAGCGGGGTGGTGGACCTGGCCAACCAGG

CAGTGCAAAATAAGATTAACAGTAAGCTTGATCCCCGCCCTCCCGTAGAGGAGCCTCCACCGGCCGTGGAGAC

AGTGTCTCCAGAGGGGCGTGGCGAAAAGCGTCCGCGCCCCGACAGGGAAGAAACTCTGGTGACGCAAATAGAC

GAGCCTCCCTCGTACGAGGAGGCACTAAAGCAAGGCCTGCCCACCACCCGTCCCATCGCGCCCATGGCTACCG

GAGTGCTGGGCCAGCACACACCCGTAACGCTGGACCTGCCTCCCCCCGCCGACACCCAGCAGAAACCTGTGCT

-continued

GCCAGGCCCGACCGCCGTTGTTGTAACCCGTCCTAGCCGCGCGTCCCTGCGCCGCGCCGCCAGCGGTCCGCGA

TCGTTGCGGCCCGTAGCCAGTGGCAACTGGCAAAGCACACTGAACAGCATCGTGGGTCTGGGGGTGCAATCCC

TGAAGCGCCGACGATGCTTCTGAATAGCTAACGTGTCGTATGTGTGTCATGTATGCGTCCATGTCGCCGCCAG

AGGAGCTGCTGAGCCGCCGCGCGCCCGCTTTCCAAGATGGCTACCCCTTCGATGATGCCGCAGTGGTCTTACA

TGCACATCTCGGGCCAGGACGCCTCGGAGTACCTGAGCCCCGGGCTGGTGCAGTTTGCCCGCGCCACCGAGAC

GTACTTCAGCCTGAATAACAAGTTTAGAAACCCCACGGTGGCGCCTACGCACGACGTGACCACAGACCGGTCC

CAGCGTTTGACGCTGCGGTTCATCCCTGTGGACCGTGAGGATACTGCGTACTCGTACAAGGCGCGGTTCACCC

TAGCTGTGGGTGATAACCGTGTGCTGGACATGGCTTCCACGTACTTTGACATCCGCGGCGTGCTGGACAGGGG

CCCTACTTTTAAGCCCTACTCTGGCACTGCCTACAACGCCCTGGCTCCCAAGGGTGCCCCAAATCCTTGCGAA

TGGGATGAAGCTGCTACTGCTCTTGAAATAAACCTAGAAGAAGAGGACGATGACAACGAAGACGAAGTAGACG

AGCAAGCTGAGCAGCAAAAAACTCACGTATTTGGGCAGGCGCCTTATTCTGGTATAAATATTACAAAGGAGGG

TATTCAAATAGGTGTCGAAGGTCAAACACCTAAATATGCCGATAAAACATTTCAACCTGAACCTCAAATAGGA

GAATCTCAGTGGTACGAAACTGAAATTAATCATGCAGCTGGGAGAGTCCTTAAAAAGACTACCCCAATGAAAC

CATGTTACGGTTCATATGCAAAACCCACAAATGAAAATGGAGGGCAAGGCATTCTTGTAAAGCAACAAAATGG

AAAGCTAGAAAGTCAAGTGGAAATGCAATTTTTCTCAACTACTGAGGCAGCCGCAGGCAATGGTGATAACTTG

ACTCCTAAAGTGGTATTGTACAGTGAAGATGTAGATATAGAAACCCCAGACACTCATATTTCTTACATGCCCA

CTATTAAGGAAGGTAACTCACGAGAACTAATGGGCCAACAATCTATGCCCAACAGGCCTAATTACATTGCTTT

TAGGGACAATTTTATTGGTCTAATGTATTACAACAGCACGGGTAATATGGGTGTTCTGGCGGGCCAAGCATCG

CAGTTGAATGCTGTTGTAGATTTGCAAGACAGAAACACAGAGCTTTCATACCAGCTTTTGCTTGATTCCATTG

GTGATAGAACCAGGTACTTTTCTATGTGGAATCAGGCTGTTGACAGCTATGATCCAGATGTTAGAATTATTGA

AAATCATGGAACTGAAGATGAACTTCCAAATTACTGCTTTCCACTGGGAGGTGTGATTAATACAGAGACTCTT

ACCAAGGTAAAACCTAAAACAGGTCAGGAAAATGGATGGGAAAAAGATGCTACAGAATTTTCAGATAAAAATG

AAATAAGAGTTGGAAATAATTTTGCCATGGAAATCAATCTAAATGCCAACCTGTGGAGAAATTTCCTGTACTC

CAACATAGCGCTGTATTTGCCCGACAAGCTAAAGTACAGTCCTTCCAACGTAAAAATTTCTGATAACCCAAAC

ACCTACGACTACATGAACAAGCGAGTGGTGGCTCCCGGGTTAGTGGACTGCTACATTAACCTTGGAGCACGCT

GGTCCCTTGACTATATGGACAACGTCAACCCATTTAACCACCACCGCAATGCTGGCCTGCGCTACCGCTCAAT

GTTGCTGGGCAATGGTCGCTATGTGCCCTTCCACATCCAGGTGCCTCAGAAGTTCTTTGCCATTAAAAACCTC

CTTCTCCTGCCGGGCTCATACACCTACGAGTGGAACTTCAGGAAGGATGTTAACATGGTTCTGCAGAGCTCCC

TAGGAAATGACCTAAGGGTTGACGGAGCCAGCATTAAGTTTGATAGCATTTGCCTTTACGCCACCTTCTTCCC

CATGGCCCACAACACCGCCTCCACGCTTGAGGCCATGCTTAGAAACGACACCAACGACCAGTCCTTTAACGAC

TATCTCTCCGCCGCCAACATGCTCTACCCTATACCCGCCAACGCTACCAACGTGCCCATATCCATCCCCTCCC

GCAACTGGGCGGCTTTCCGCGGCTGGGCCTTCACGCGCCTTAAGACTAAGGAAACCCCATCACTGGGCTCGGG

CTACGACCCTTATTACACCTACTCTGGCTCTATACCCTACCTAGATGGAACCTTTTACCTCAACCACACCTTT

AAGAAGGTGGCCATTACCTTTGACTCTTCTGTCAGCTGGCCTGGCAATGACCGCCTGCTTACCCCCAACGAGT

TTGAAATTAAGCGCTCAGTTGACGGGGAGGGTTACAACGTTGCCCAGTGTAACATGACCAAAGACTGGTTCCT

GGTACAAATGCTAGCTAACTACAACATTGGCTACCAGGGCTTCTATATCCCAGAGAGCTACAAGGACCGCATG

TACTCCTTCTTTAGAAACTTCCAGCCCATGAGCCGTCAGGTGGTGGATGATACTAAATACAAGGACTACCAAC

AGGTGGGCATCCTACACCAACACAACAACTCTGGATTTGTTGGCTACCTTGCCCCCACCATGCGCGAAGGACA

GGCCTACCCTGCTAACTTCCCCTATCCGCTTATAGGCAAGACCGCAGTTGACAGCATTACCCAGAAAAAGTTT

CTTTGCGATCGCACCCTTTGGCGCATCCCATTCTCCAGTAACTTTATGTCCATGGGCGCACTCACAGACCTGG

GCCAAAACCTTCTCTACGCCAACTCCGCCCACGCGCTAGACATGACTTTTGAGGTGGATCCCATGGACGAGCC

-continued

CACCCTTCTTTATGTTTTGTTTGAAGTCTTTGACGTGGTCCGTGTGCACCGGCCGCACCGCGGCGTCATCGAA

ACCGTGTACCTGCGCACGCCCTTCTCGGCCGGCAACGCCACAACATAAAGAAGCAAGCAACATCAACAACAGC

TGCCGCCATGGGCTCCAGTGAGCAGGAACTGAAAGCCATTGTCAAAGATCTTGGTTGTGGGCCATATTTTTTG

GGCACCTATGACAAGCGCTTTCCAGGCTTTGTTTCTCCACACAAGCTCGCCTGCGCCATAGTCAATACGGCCG

GTCGCGAGACTGGGGGCGTACACTGGATGGCCTTTGCCTGGAACCCGCACTCAAAAACATGCTACCTCTTTGA

GCCCTTTGGCTTTTCTGACCAGCGACTCAAGCAGGTTTACCAGTTTGAGTACGAGTCACTCCTGCGCCGTAGC

GCCATTGCTTCTTCCCCCGACCGCTGTATAACGCTGGAAAAGTCCACCCAAAGCGTACAGGGGCCCAACTCGG

CCGCCTGTGGACTATTCTGCTGCATGTTTCTCCACGCCTTTGCCAACTGGCCCCAAACTCCCATGGATCACAA

CCCCACCATGAACCTTATTACCGGGGTACCCAACTCCATGCTCAACAGTCCCCAGGTACAGCCCACCCTGCGT

CGCAACCAGGAACAGCTCTACAGCTTCCTGGAGCGCCACTCGCCCTACTTCCGCAGCCACAGTGCGCAGATTA

GGAGCGCCACTTCTTTTTGTCACTTGAAAAACATGTAAAAATAATGTACTAGAGACACTTTCAATAAAGGCAA

ATGCTTTTATTTGTACACTCTCGGGTGATTATTTACCCCCACCCTTGCCGTCTGCGCCGTTTAAAAATCAAAG

GGGTTCTGCCGCGCATCGCTATGCGCCACTGGCAGGGACACGTTGCGATACTGGTGTTTAGTGCTCCACTTAA

ACTCAGGCACAACCATCCGCGGCAGCTCGGTGAAGTTTTCACTCCACAGGCTGCGCACCATCACCAACGCGTT

TAGCAGGTCGGGCGCCGATATCTTGAAGTCGCAGTTGGGGCCTCCGCCCTGCGCGCGCGAGTTGCGATACACA

GGGTTGCAGCACTGGAACACTATCAGCGCCGGGTGGTGCACGCTGGCCAGCACGCTCTTGTCGGAGATCAGAT

CCGCGTCCAGGTCCTCCGCGTTGCTCAGGGCGAACGGAGTCAACTTTGGTAGCTGCCTTCCCAAAAAGGGCGC

GTGCCCAGGCTTTGAGTTGCACTCGCACCGTAGTGGCATCAAAAGGTGACCGTGCCCGGTCTGGGCGTTAGGA

TACAGCGCCTGCATAAAAGCCTTGATCTGCTTAAAAGCCACCTGAGCCTTTGCGCCTTCAGAGAAGAACATGC

CGCAAGACTTGCCGGAAAACTGATTGGCCGGACAGGCCGCGTCGTGCACGCAGCACCTTGCGTCGGTGTTGGA

GATCTGCACCACATTTCGGCCCCACCGGTTCTTCACGATCTTGGCCTTGCTAGACTGCTCCTTCAGCGCGCGC

TGCCCGTTTTCGCTCGTCACATCCATTTCAATCACGTGCTCCTTATTTATCATAATGCTTCCGTGTAGACACT

TAAGCTCGCCTTCGATCTCAGCGCAGCGGTGCAGCCACAACGCGCAGCCCGTGGGCTCGTGATGCTTGTAGGT

CACCTCTGCAAACGACTGCAGGTACGCCTGCAGGAATCGCCCCATCATCGTCACAAAGGTCTTGTTGCTGGTG

AAGGTCAGCTGCAACCCGCGGTGCTCCTCGTTCAGCCAGGTCTTGCATACGGCCGCCAGAGCTTCCACTTGGT

CAGGCAGTAGTTTGAAGTTCGCCTTTAGATCGTTATCCACGTGGTACTTGTCCATCAGCGCGCGCGCAGCCTC

CATGCCCTTCTCCCACGCAGACACGATCGGCACACTCAGCGGGTTCATCACCGTAATTTCACTTTCCGCTTCG

CTGGGCTCTTCCTCTTCCTCTTGCGTCCGCATACCACGCGCCACTGGGTCGTCTTCATTCAGCCGCCGCACTG

TGCGCTTACCTCCTTTGCCATGCTTGATTAGCACCGGTGGGTTGCTGAAACCCACCATTTGTAGCGCCACATC

TTCTCTTTCTTCCTCGCTGTCCACGATTACCTCTGGTGATGGCGGGCGCTCGGGCTTGGGAGAAGGGCGCTTC

TTTTTCTTCTTGGGCGCAATGGCCAAATCCGCCGCCGAGGTCGATGGCCGCGGGCTGGGTGTGCGCGGCACCA

GCGCGTCTTGTGATGAGTCTTCCTCGTCCTCGGACTCGATACGCCGCCTCATCCGCTTTTTTGGGGGCGCCCG

GGGAGGCGGCGGCGACGGGGACGGGGACGACACGTCCTCCATGGTTGGGGGACGTCGCGCCGCACCGCGTCCG

CGCTCGGGGGTGGTTTCGCGCTGCTCCTCTTCCCGACTGGCCATTTCCTTCTCCTATAGGCAGAAAAAGATCA

TGGAGTCAGTCGAGAAGAAGGACAGCCTAACCGCCCCCTCTGAGTTCGCCACCACCGCCTCCACCGATGCCGC

CAACGCGCCTACCACCTTCCCCGTCGAGGCACCCCCGCTTGAGGAGGAGGAAGTGATTATCGAGCAGGACCCA

GGTTTTGTAAGCGAAGACGACGAGGACCGCTCAGTACCAACAGAGGATAAAAAGCAAGACCAGGACAACGCAG

AGGCAAACGAGGAACAAGTCGGGCGGGGGGACGAAAGGCATGGCGACTACCTAGATGTGGGAGACGACGTGCT

GTTGAAGCATCTGCAGCGCCAGTGCGCCATTATCTGCGACGCGTTGCAAGAGCGCAGCGATGTGCCCCTCGCC

ATAGCGGATGTCAGCCTTGCCTACGAACGCCACCTATTCTCACCGCGCGTACCCCCCAAACGCCAAGAAAACG

-continued

GCACATGCGAGCCCAACCCGCGCCTCAACTTCTACCCCGTATTTGCCGTGCCAGAGGTGCTTGCCACCTATCA

CATCTTTTTCCAAAACTGCAAGATACCCCTATCCTGCCGTGCCAACCGCAGCCGAGCGGACAAGCAGCTGGCC

TTGCGGCAGGGCGCTGTCATACCTGATATCGCCTCGCTCAACGAAGTGCCAAAAATCTTTGAGGGTCTTGGAC

GCGACGAGAAGCGCGCGGCAAACGCTCTGCAACAGGAAAACAGCGAAAATGAAAGTCACTCTGGAGTGTTGGT

GGAACTCGAGGGTGACAACGCGCGCCTAGCCGTACTAAAACGCAGCATCGAGGTCACCCACTTTGCCTACCCG

GCACTTAACCTACCCCCCAAGGTCATGAGCACAGTCATGAGTGAGCTGATCGTGCGCCGTGCGCAGCCCCTGG

AGAGGGATGCAAATTTGCAAGAACAAACAGAGGAGGGCCTACCCGCAGTTGGCGACGAGCAGCTAGCGCGCTG

GCTTCAAACGCGCGAGCCTGCCGACTTGGAGGAGCGACGCAAACTAATGATGGCCGCAGTGCTCGTTACCGTG

GAGCTTGAGTGCATGCAGCGGTTCTTTGCTGACCCGGAGATGCAGCGCAAGCTAGAGGAAACATTGCACTACA

CCTTTCGACAGGGCTACGTACGCCAGGCCTGCAAGATCTCCAACGTGGAGCTCTGCAACCTGGTCTCCTACCT

TGGAATTTTGCACGAAAACCGCCTTGGGCAAAACGTGCTTCATTCCACGCTCAAGGGCGAGGCGCGCCGCGAC

TACGTCCGCGACTGCGTTTACTTATTTCTATGCTACACCTGGCAGACGGCCATGGGCGTTTGGCAGCAGTGCT

TGGAGGAGTGCAACCTCAAGGAGCTGCAGAAACTGCTAAAGCAAAACTTGAAGGACCTATGGACGGCCTTCAA

CGAGCGCTCCGTGGCCGCGCACCTGGCGGACATCATTTTCCCCGAACGCCTGCTTAAAACCCTGCAACAGGGT

CTGCCAGACTTCACCAGTCAAAGCATGTTGCAGAACTTTAGGAACTTTATCCTAGAGCGCTCAGGAATCTTGC

CCGCCACCTGCTGTGCACTTCCTAGCGACTTTGTGCCCATTAAGTACCGCGAATGCCCTCCGCCGCTTTGGGG

CCACTGCTACCTTCTGCAGCTAGCCAACTACCTTGCCTACCACTCTGACATAATGGAAGACGTGAGCGGTGAC

GGTCTACTGGAGTGTCACTGTCGCTGCAACCTATGCACCCCGCACCGCTCCCTGGTTTGCAATTCGCAGCTGC

TTAACGAAAGTCAAATTATCGGTACCTTTGAGCTGCAGGGTCCCTCGCCTGACGAAAAGTCCGCGGCTCCGGG

GTTGAAACTCACTCCGGGGCTGTGGACGTCGGCTTACCTTCGCAAATTTGTACCTGAGGACTACCACGCCCAC

GAGATTAGGTTCTACGAAGACCAATCCCGCCCGCCAAATGCGGAGCTTACCGCCTGCGTCATTACCCAGGGCC

ACATTCTTGGCCAATTGCAAGCCATCAACAAAGCCCGCCAAGAGTTTCTGCTACGAAAGGGACGGGGGGTTTA

CTTGGACCCCCAGTCCGGCGAGGAGCTCAACCCAATCCCCCCGCCGCCGCAGCCCTATCAGCAGCAGCCGCGG

GCCCTTGCTTCCCAGGATGGCACCCAAAAAGAAGCTGCAGCTGCCGCCGCCACCCACGGACGAGGAGGAATAC

TGGGACAGTCAGGCAGAGGAGGTTTTGGACGAGGAGGAGGAGGACATGATGGAAGACTGGGAGAGCCTAGACG

AGGAAGCTTCCGAGGTCGAAGAGGTGTCAGACGAAACACCGTCACCCTCGGTCGCATTCCCCTCGCCGGCGCC

CCAGAAATCGGCAACCGGTTCCAGCATGGCTACAACCTCCGCTCCTCAGGCGCCGCCGGCACTGCCCGTTCGC

CGACCCAACCGTAGATGGGACACCACTGGAACCAGGGCCGGTAAGTCCAAGCAGCCGCCGCCGTTAGCCCAAG

AGCAACAACAGCGCCAAGGCTACCGCTCATGGCGCGGGCACAAGAACGCCATAGTTGCTTGCTTGCAAGACTG

TGGGGGCAACATCTCCTTCGCCCGCCGCTTTCTTCTCTACCATCACGGCGTGGCCTTCCCCCGTAACATCCTG

CATTACTACCGTCATCTCTACAGCCCATACTGCACCGGCGGCAGCGGCAGCGGCAGCAACAGCAGCGGCCACA

CAGAAGCAAAGGCGACCGGATAGCAAGACTCTGACAAAGCCCAAGAAATCCACAGCGGCGGCAGCAGCAGGAG

GAGGAGCGCTGCGTCTGGCGCCCAACGAACCCGTATCGACCCGCGAGCTTAGAAACAGGATTTTTCCCACTCT

GTATGCTATATTTCAACAGAGCAGGGGCCAAGAACAAGAGCTGAAAATAAAAAACAGGTCTCTGCGATCCCTC

ACCCGCAGCTGCCTGTATCACAAAAGCGAAGATCAGCTTCGGCGCACGCTGGAAGACGCGGAGGCTCTCTTCA

GTAAATACTGCGCGCTGACTCTTAAGGACTAGTTTCGCGCCCTTTCTCAAATTTAAGCGCGAAAACTACGTCA

TCTCCAGCGGCCACACCCGGCGCCAGCACCTGTCGTCAGCGCCATTATGAGCAAGGAAATTCCCACGCCCTAC

ATGTGGAGTTACCAGCCACAAATGGGACTTGCGGCTGGAGCTGCCCAAGACTACTCAACCCGAATAAACTACA

TGAGCGCGGGACCCCACATGATATCCCGGGTCAACGGAATCCGCGCCCACCGAAACCGAATTCTCTTGGAACA

GGCGGCTATTACCACCACACCTCGTAATAACCTTAATCCCCGTAGTTGGCCCGCTGCCCTGGTGTACCAGGAA

AGTCCCGCTCCCACCACTGTGGTACTTCCCAGAGACGCCCAGGCCGAAGTTCAGATGACTAACTCAGGGGCGC

-continued

AGCTTGCGGGCGGCTTTCGTCACAGGGTGCGGTCGCCCGGGCAGGGTATAACTCACCTGACAATCAGAGGGCG

AGGTATTCAGCTCAACGACGAGTCGGTGAGCTCCTCGCTTGGTCTCCGTCCGGACGGGACATTTCAGATCGGC

GGCGCCGGCCGTCCTTCATTCACGCCTCGTCAGGCAATCCTAACTCTGCAGACCTCGTCCTCTGAGCCGCGCT

CTGGAGGCATTGGAACTCTGCAATTTATTGAGGAGTTTGTGCCATCGGTCTACTTTAACCCCTTCTCGGGACC

TCCCGGCCACTATCCGGATCAATTTATTCCTAACTTTGACGCGGTAAAGGACTCGGCGGACGGCTACGACTGA

ATGTTAAGTGGAGAGGCAGAGCAACTGCGCCTGAAACACCTGGTCCACTGTCGCCGCCACAAGTGCTTTGCCC

GCGACTCCGGTGAGTTTTGCTACTTTGAATTGCCCGAGGATCATATCGAGGGCCCGGCGCACGGCGTCCGGCT

TACCGCCCAGGGAGAGCTTGCCCGTAGCCTGATTCGGGAGTTTACCCAGCGCCCCCTGCTAGTTGAGCGGGAC

AGGGGACCCTGTGTTCTCACTGTGATTTGCAACTGTCCTAACCTTGGATTACATCAAGATCTTTGTTGCCATC

TCTGTGCTGAGTATAATAAATACAGAAATTAAAATATACTGGGGCTCCTATCGCCATCCTGTAAACGCCACCG

TCTTCACCCGCCCAAGCAAACCAAGGCGAACCTTACCTGGTACTTTTAACATCTCTCCCTCTGTGATTTACAA

CAGTTTCAACCCAGACGGAGTGAGTCTACGAGAGAACCTCTCCGAGCTCAGCTACTCCATCAGAAAAAACACC

ACCCTCCTTACCTGCCGGGAACGTACGAGTGCGTCACCGGCCGCTGCACCACACCTACCGCCTGACCGTAAAC

CAGACTTTTTCCGGACAGACCTCAATAACTCTGTTTACCAGAACAGGAGGTGAGCTTAGAAAACCCTTAGGGT

ATTAGGCCAAAGGCGCAGCTACTGTGGGGTTTATGAACAATTCAAGCAACTCTACGGGCTATTCTAATTCAGG

TTTCTCTAGAATCGGGGTTGGGGTTATTCTCTGTCTTGTGATTCTCTTTATTCTTATACTAACGCTTCTCTGC

CTAAGGCTCGCCGCCTGCTGTGTGCACATTTGCATTTATTGTCAGCTTTTTAAACGCTGGGGTCGCCACCCAA

GATGATTAGGTACATAATCCTAGGTTTACTCACCCTTGCGTCAGCCCACGGTACCACCCAAAAGGTGGATTTT

AAGGAGCCAGCCTGTAATGTTACATTCGCAGCTGAAGCTAATGAGTGCACCACTCTTATAAAATGCACCACAG

AACATGAAAAGCTGCTTATTCGCCACAAAAACAAAATTGGCAAGTATGCTGTTTATGCTATTTGGCAGCCAGG

TGACACTACAGAGTATAATGTTACAGTTTTCCAGGGTAAAAGTCATAAAACTTTTATGTATACTTTTCCATTT

TATGAAATGTGCGACATTACCATGTACATGAGCAAACAGTATAAGTTGTGGCCCCCACAAAATTGTGTGGAAA

ACACTGGCACTTTCTGCTGCACTGCTATGCTAATTACAGTGCTCGCTTTGGTCTGTACCCTACTCTATATTAA

ATACAAAAGCAGACGCAGCTTTATTGAGGAAAAGAAAATGCCTTAATTTACTAAGTTACAAAGCTAATGTCAC

CACTAACTGCTTTACTCGCTGCTTGCAAAACAAATTCAAAAAGTTAGCATTATAATTAGAATAGGATTTAAAC

CCCCCGGTCATTTCCTGCTCAATACCATTCCCCTGAACAATTGACTCTATGTGGGATATGCTCCAGCGCTACA

ACCTTGAAGTCAGGCTTCCTGGATGTCAGCATCTGACTTTGGCCAGCACCTGTCCCGCGGATTTGTTCCAGTC

CAACTACAGCGACCCACCCTAACAGAGATGACCAACACAACCAACGCGGCCGCCGCTACCGGACTTACATCTA

CCACAAATACACCCCAAGTTTCTGCCTTTGTCAATAACTGGGATAACTTGGGCATGTGGTGGTTCTCCATAGC

GCTTATGTTTGTATGCCTTATTATTATGTGGCTCATCTGCTGCCTAAAGCGCAAACGCGCCCGACCACCCATC

TATAGTCCCATCATTGTGCTACACCCAAACAATGATGGAATCCATAGATTGGACGGACTGAAACACATGTTCT

TTTCTCTTACAGTATGATTAAATGAGACATGATTCCTCGAGTTTTTATATTACTGACCCTTGTTGCGCTTTTT

TGTGCGTGCTCCACATTGGCTGCGGTTTCTCACATCGAAGTAGACTGCATTCCAGCCTTCACAGTCTATTTGC

TTTACGGATTTGTCACCCTCACGCTCATCTGCAGCCTCATCACTGTGGTCATCGCCTTTATCCAGTGCATTGA

CTGGGTCTGTGTGCGCTTTGCATATCTCAGACACCATCCCCAGTACAGGGACAGGACTATAGCTGAGCTTCTT

AGAATTCTTTAATTATGAAATTTACTGTGACTTTTCTGCTGATTATTTGCACCCTATCTGCGTTTTGTTCCCC

GACCTCCAAGCCTCAAAGACATATATCATGCAGATTCACTCGTATATGGAATATTCCAAGTTGCTACAATGAA

AAAAGCGATCTTTCCGAAGCCTGGTTATATGCAATCATCTCTGTTATGGTGTTCTGCAGTACCATCTTAGCCC

TAGCTATATATCCCTACCTTGACATTGGCTGGAAACGAATAGATGCCATGAACCACCCAACTTTCCCCGCGCC

CGCTATGCTTCCACTGCAACAAGTTGTTGCCGGCGGCTTTGTCCCAGCCAATCAGCCTCGCCCCACTTCTCCC

-continued

ACCCCCACTGAAATCAGCTACTTTAATCTAACAGGAGGAGATGACTGACACCCTAGATCTAGAAATGGACGGA

ATTATTACAGAGCAGCGCCTGCTAGAAAGACGCAGGGCAGCGGCCGAGCAACAGCGCATGAATCAAGAGCTCC

AAGACATGGTTAACTTGCACCAGTGCAAAAGGGGTATCTTTTGTCTGGTAAAGCAGGCCAAAGTCACCTACGA

CAGTAATACCACCGGACACCGCCTTAGCTACAAGTTGCCAACCAAGCGTCAGAAATTGGTGGTCATGGTGGGA

GAAAAGCCCATTACCATAACTCAGCACTCGGTAGAAACCGAAGGCTGCATTCACTCACCTTGTCAAGGACCTG

AGGATCTCTGCACCCTTATTAAGACCCTGTGCGGTCTCAAAGATCTTATTCCCTTTAACTAATAAAAAAAAAT

AATAAAGCATCACTTACTTAAAATCAGTTAGCAAATTTCTGTCCAGTTTATTCAGCAGCACCTCCTTGCCCTC

CTCCCAGCTCTGGTATTGCAGCTTCCTCCTGGCTGCAAACTTTCTCCACAATCTAAATGGAATGTCAGTTTCC

TCCTGTTCCTGTCCATCCGCACCCACTATCTTCATGTTGTTGCAGATGAAGCGCGCAAGACCGTCTGAAGATA

CCTTCAACCCCGTGTATCCATATGACACGGAAACCGGTCCTCCAACTGTGCCTTTTCTTACTCCTCCCTTTGT

ATCCCCCAATGGGTTTCAAGAGAGTCCCCCTGGGGTACTCTCTTTGCGCCTATCCGAACCTCTAGTTACCTCC

AATGGCATGCTTGCGCTCAAAATGGGCAACGGCCTCTCTCTGGACGAGGCCGGCAACCTTACCTCCCAAAATG

TAACCACTGTGAGCCCACCTCTCAAAAAAACCAAGTCAAACATAAACCTGGAAATATCTGCACCCCTCACAGT

TACCTCAGAAGCCCTAACTGTGGCTGCCGCCGCACCTCTAATGGTCGCGGGCAACACACTCACCATGCAATCA

CAGGCCCCGCTAACCGTGCACGACTCCAAACTTAGCATTGCCACCCAAGGACCCCTCACAGTGTCAGAAGGAA

AGCTAGCCCTGCAAACATCAGGCCCCCTCACCACCACCGATAGCAGTACCCTTACTATCACTGCCTCACCCCC

TCTAACTACTGCCACTGGTAGCTTGGGCATTGACTTGAAAGAGCCCATTTATACACAAAATGGAAAACTAGGA

CTAAAGTACGGGGCTCCTTTGCATGTAACAGACGACCTAAACACTTTGACCGTAGCAACTGGTCCAGGTGTGA

CTATTAATAATACTTCCTTGCAAACTAAAGTTACTGGAGCCTTGGGTTTTGATTCACAAGGCAATATGCAACT

TAATGTAGCAGGAGGACTAAGGATTGATTCTCAAAACAGACGCCTTATACTTGATGTTAGTTATCCGTTTGAT

GCTCAAAACCAACTAAATCTAAGACTAGGACAGGGCCCTCTTTTTATAAACTCAGCCCACAACTTGGATATTA

ACTACAACAAAGGCCTTTACTTGTTTACAGCTTCAAACAATTCCAAAAAGCTTGAGGTTAACCTAAGCACTGC

CAAGGGGTTGATGTTTGACGCTACAGCCATAGCCATTAATGCAGGAGATGGGCTTGAATTTGGTTCACCTAAT

GCACCAAACACAAATCCCCTCAAAACAAAAATTGGCCATGGCCTAGAATTTGATTCAAACAAGGCTATGGTTC

CTAAACTAGGAACTGGCCTTAGTTTTGACAGCACAGGTGCCATTACAGTAGGAAACAAAAATAATGATAAGCT

AACTTTGTGGACCACACCAGCTCCATCTCCTAACTGTAGACTAAATGCAGAGAAAGATGCTAAACTCACTTTG

GTCTTAACAAAATGTGGCAGTCAAATACTTGCTACAGTTTCAGTTTTGGCTGTTAAAGGCAGTTTGGCTCCAA

TATCTGGAACAGTTCAAAGTGCTCATCTTATTATAAGATTTGACGAAAATGGAGTGCTACTAAACAATTCCTT

CCTGGACCCAGAATATTGGAACTTTAGAAATGGAGATCTTACTGAAGGCACAGCCTATACAAACGCTGTTGGA

TTTATGCCTAACCTATCAGCTTATCCAAAATCTCACGGTAAAACTGCCAAAAGTAACATTGTCAGTCAAGTTT

ACTTAAACGGAGACAAAACTAAACCTGTAACACTAACCATTACACTAAACGGTACACAGGAAACAGGAGACAC

AACTCCAAGTGCATACTCTATGTCATTTTCATGGGACTGGTCTGGCCACAACTACATTAATGAAATATTTGCC

ACATCCTCTTACACTTTTTCATACATTGCCCAAGAATAAAGAATCGTTTGTGTTATGTTTCAACGTGTTTATT

TTTCAATTGCAGAAAATTTCAAGTCATTTTTCATTCAGTAGTATAGCCCCACCACCACATAGCTTATACAGAT

CACCGTACCTTAATCAAACTCACAGAACCCTAGTATTCAACCTGCCACCTCCCTCCCAACACACAGAGTACAC

AGTCCTTTCTCCCCGGCTGGCCTTAAAAAGCATCATATCATGGGTAACAGACATATTCTTAGGTGTTATATTC

CACACGGTTTCCTGTCGAGCCAAACGCTCATCAGTGATATTAATAAACTCCCCGGGCAGCTCACTTAAGTTCA

TGTCGCTGTCCAGCTGCTGAGCCACAGGCTGCTGTCCAACTTGCGGTTGCTTAACGGGCGGCGAAGGAGAAGT

CCACGCCTACATGGGGGTAGAGTCATAATCGTGCATCAGGATAGGGCGGTGGTGCTGCAGCAGCGCGCGAATA

AACTGCTGCCGCCGCCGCTCCGTCCTGCAGGAATACAACATGGCAGTGGTCTCCTCAGCGATGATTCGCACCG

CCCGCAGCATAAGGCGCCTTGTCCTCCGGGCACAGCAGCGCACCCTGATCTCACTTAAATCAGCACAGTAACT

-continued

GCAGCACAGCACCACAATATTGTTCAAAATCCCACAGTGCAAGGCGCTGTATCCAAAGCTCATGGCGGGGACC

ACAGAACCCACGTGGCCATCATACCACAAGCGCAGGTAGATTAAGTGGCGACCCCTCATAAACACGCTGGACA

TAAACATTACCTCTTTTGGCATGTTGTAATTCACCACCTCCCGGTACCATATAAACCTCTGATTAAACATGGC

GCCATCCACCACCATCCTAAACCAGCTGGCCAAAACCTGCCCGCCGGCTATACACTGCAGGGAACCGGGACTG

GAACAATGACAGTGGAGAGCCCAGGACTCGTAACCATGGATCATCATGCTCGTCATGATATCAATGTTGGCAC

AACACAGGCACACGTGCATACACTTCCTCAGGATTACAAGCTCCTCCCGCGTTAGAACCATATCCCAGGGAAC

AACCCATTCCTGAATCAGCGTAAATCCCACACTGCAGGGAAGACCTCGCACGTAACTCACGTTGTGCATTGTC

AAAGTGTTACATTCGGGCAGCAGCGGATGATCCTCCAGTATGGTAGCGCGGGTTTCTGTCTCAAAAGGAGGTA

GACGATCCCTACTGTACGGAGTGCGCCGAGACAACCGAGATCGTGTTGGTCGTAGTGTCATGCCAAATGGAAC

GCCGGACGTAGTCATATTTCCTGAAGCAAAACCAGGTGCGGGCGTGACAAACAGATCTGCGTCTCCGGTCTCG

CCGCTTAGATCGCTCTGTGTAGTAGTTGTAGTATATCCACTCTCTCAAAGCATCCAGGCGCCCCCTGGCTTCG

GGTTCTATGTAAACTCCTTCATGCGCCGCTGCCCTGATAACATCCACCACCGCAGAATAAGCCACACCCAGCC

AACCTACACATTCGTTCTGCGAGTCACACACGGGAGGAGCGGGAAGAGCTGGAAGAACCATGTTTTTTTTTTT

ATTCCAAAAGATTATCCAAAACCTCAAAATGAAGATCTATTAAGTGAACGCGCTCCCCTCCGGTGGCGTGGTC

AAACTCTACAGCCAAAGAACAGATAATGGCATTTGTAAGATGTTGCACAATGGCTTCCAAAAGGCAAACGGCC

CTCACGTCCAAGTGGACGTAAAGGCTAAACCCTTCAGGGTGAATCTCCTCTATAAACATTCCAGCACCTTCAA

CCATGCCCAAATAATTCTCATCTCGCCACCTTCTCAATATATCTCTAAGCAAATCCCGAATATTAAGTCCGGC

CATTGTAAAAATCTGCTCCAGAGCGCCCTCCACCTTCAGCCTCAAGCAGCGAATCATGATTGCAAAAATTCAG

GTTCCTCACAGACCTGTATAAGATTCAAAAGCGGAACATTAACAAAAATACCGCGATCCCGTAGGTCCCTTCG

CAGGGCCAGCTGAACATAATCGTGCAGGTCTGCACGGACCAGCGCGGCCACTTCCCCGCCAGGAACCTTGACA

AAAGAACCCACACTGATTATGACACGCATACTCGGAGCTATGCTAACCAGCGTAGCCCCGATGTAAGCTTTGT

TGCATGGGCGGCGATATAAAATGCAAGGTGCTGCTCAAAAAATCAGGCAAAGCCTCGCGCAAAAAAGAAAGCA

CATCGTAGTCATGCTCATGCAGATAAAGGCAGGTAAGCTCCGGAACCACCACAGAAAAAGACACCATTTTTCT

CTCAAACATGTCTGCGGGTTTCTGCATAAACACAAAATAAAATAACAAAAAAACATTTAAACATTAGAAGCCT

GTCTTACAACAGGAAAAACAACCCTTATAAGCATAAGACGGACTACGGCCATGCCGGCGTGACCGTAAAAAAA

CTGGTCACCGTGATTAAAAAGCACCACCGACAGCTCCTCGGTCATGTCCGGAGTCATAATGTAAGACTCGGTA

AACACATCAGGTTGATTCATCGGTCAGTGCTAAAAAGCGACCGAAATAGCCCGGGGGAATACATACCCGCAGG

CGTAGAGACAACATTACAGCCCCCATAGGAGGTATAACAAAATTAATAGGAGAGAAAAACACATAAACACCTG

AAAAACCCTCCTGCCTAGGCAAAATAGCACCCTCCCGCTCCAGAACAACATACAGCGCTTCACAGCGGCAGCC

TAACAGTCAGCCTTACCAGTAAAAAAGAAAACCTATTAAAAAAACACCACTCGACACGGCACCAGCTCAATCA

GTCACAGTGTAAAAAAGGGCCAAGTGCAGAGCGAGTATATATAGGACTAAAAAATGACGTAACGGTTAAAGTC

CACAAAAAACACCCAGAAAACCGCACGCGAACCTACGCCCAGAAACGAAAGCCAAAAAACCCACAACTTCCTC

AAATCGTCACTTCCGTTTTCCCACGTTACGTAACTTCCCATTTTAAGAAAACTACAATTCCCAACACATACAA

GTTACTCCGCCCTAAAACCTACGTCACCCGCCCCGTTCCCACGCCCCGCGCCACGTCACAAACTCCACCCCCT

CATTATCATATTGGCTTCAATCCAAAATAAGGTATATTATTGATGATGATTTAAATGGATCCATTTAAATCGG

TACCCAGCTTTTGTTCCCTTTAGTGAGGGTTAATTGCGCGCTTGGCGTAATCATGGTCATAGCTGTTTCCTGT

GTGAAATTGTTATCCGCTCACAATTCCACACAACATACGAGCCGGAAGCATAAAGTGTAAAGCCTGGGGTGCC

TAATGAGTGAGCTAACTCACATTAATTGCGTTGCGCTCACTGCCCGCTTTCCAGTCGGGAAACCTGTCGTGCC

AGCTGCATTAATGAATCGGCCAACGCGCGGGGAGAGGCGGTTTGCGTATTGGGCGCTCTTCCGCTTCCTCGCT

CACTGACTCGCTGCGCTCGGTCGTTCGGCTGCGGCGAGCGGTATCAGCTCACTCAAAGGCGGTAATACGGTTA

-continued

TCCACAGAATCAGGGGATAACGCAGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCATCACAAAAATCGACGCTCAAGTCA

GAGGTGGCGAAACCCGACAGGACTATAAAGATACCAGGCGTTTCCCCCTGGAAGCTCCCTCGTGCGCTCTCCT

GTTCCGACCCTGCCGCTTACCGGATACCTGTCCGCCTTTCTCCCTTCGGGAAGCGTGGCGCTTTCTCATAGCT

CACGCTGTAGGTATCTCAGTTCGGTGTAGGTCGTTCGCTCCAAGCTGGGCTGTGTGCACGAACCCCCCGTTCA

GCCCGACCGCTGCGCCTTATCCGGTAACTATCGTCTTGAGTCCAACCCGGTAAGACACGACTTATCGCCACTG

GCAGCAGCCACTGGTAACAGGATTAGCAGAGCGAGGTATGTAGGCGGTGCTACAGAGTTCTTGAAGTGGTGGC

CTAACTACGGCTACACTAGAAGGACAGTATTTGGTATCTGCGCTCTGCTGAAGCCAGTTACCTTCGGAAAAAG

AGTTGGTAGCTCTTGATCCGGCAAACAAACCACCGCTGGTAGCGGTGGTTTTTTTGTTTGCAAGCAGCAGATT

ACGCGCAGAAAAAAAGGATCTCAAGAAGATCCTTTGATCTTTTCTACGGGGTCTGACGCTCAGTGGAACGAAA

ACTCACGTTAAGGGATTTTGGTCATGAGATTATCAAAAAGGATCTTCACCTAGATCCTTTTAAATTAAAAATG

AAGTTTTAAATCAATCTAAAGTATATATGAGTAAACTTGGTCTGACAGTTACCAATGCTTAATCAGTGAGGCA

CCTATCTCAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTCCAGATTTATC

AGCAATAAACCAGCCAGCCGGAAGGGCCGAGCGCAGAAGTGGTCCTGCAACTTTATCCGCCTCCATCCAGTCT

ATTAATTGTTGCCGGGAAGCTAGAGTAAGTAGTTCGCCAGTTAATAGTTTGCGCAACGTTGTTGCCATTGCTA

CAGGCATCGTGGTGTCACGCTCGTCGTTTGGTATGGCTTCATTCAGCTCCGGTTCCCAACGATCAAGGCGAGT

TACATGATCCCCCATGTTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGCCATCCGTAAGATGCT

TTTCTGTGACTGGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAAAACGTTCTTCG

GGGCGAAAACTCTCAAGGATCTTACCGCTGTTGAGATCCAGTTCGATGTAACCCACTCGTGCACCCAACTGAT

CTTCAGCATCTTTTACTTTCACCAGCGTTTCTGGGTGAGCAAAAACAGGAAGGCAAAATGCCGCAAAAAAGGG

AATAAGGGCGACACGGAAATGTTGAATACTCATACTCTTCCTTTTTCAATATTATTGAAGCATTTATCAGGGT

TATTGTCTCATGAGCGGATACATATTTGAATGTATTTAGAAAAATAAACAAATAGGGGTTCCGCGCACATTTC

CCCGAAAAGTGCCACCTAAATTGTAAGCGTTAATATTTTGTTAAAATTCGCGTTAAATTTTTGTTAAATCAGC

TCATTTTTTAACCAATAGGCCGAAATCGGCAAAATCCCTTATAAATCAAAAGAATAGACCGAGATAGGGTTGA

GTGTTGTTCCAGTTTGGAACAAGAGTCCACTATTAAAGAACGTGGACTCCAACGTCAAAGGGCGAAAAACCGT

CTATCAGGGCGATGGCCCACTACGTGAACCATCACCCTAATCAAGTTTTTTGGGGTCGAGGTGCCGTAAAGCA

CTAAATCGGAACCCTAAAGGGAGCCCCCGATTTAGAGCTTGACGGGGAAAGCCGGCGAACGTGGCGAGAAAGG

AAGGGAAGAAAGCGAAAGGAGCGGGCGCTAGGGCGCTGGCAAGTGTAGCGGTCACGCTGCGCGTAACCACCAC

ACCCGCCGCGCTTAATGCGCCGCTACAGGGCGCGTCCCATTCGCCATTCAGGCTGCGCAACTGTTGGGAAGGG

CGATCGGTGCGGGCCTCTTCGCTATTACGCCAGCTGGCGAAAGGGGGATGTGCTGCAAGGCGATTAAGTTGGG

TAACGCCAGGGTTTTCCCAGTCACGACGTTGTAAAACGACGGCCAGTGAGCGCGCGTAATACGACTCACTATA

GGGCGAATTGGAGCTCCAC (pBSK-CMV-TPLIn-100K)

SEQ ID NO: 6 cacctaaattgtaagcgttaatattttgttaaaattcgcgttaaatttttgttaaatcagctcattttttaaccaatagg ccgaaatcggcaaaatcccttataaatcaaaagaatagaccgagatagggttgagtgttgttccagtttggaacaagagt ccactattaaagaacgtggactccaacgtcaaagggcgaaaaaccgtctatcagggcgatggcccactacgtgaaccatc accctaatcaagttttttggggtcgaggtgccgtaaagcactaaatcggaaccctaaagggagcccccgatttagagctt gacggggaaagccggcgaacgtggcgagaaaggaagggaagaaagcgaaaggagcgggcgctagggcgctggcaagtgta -continued gcggtcacgctgcgcgtaaccaccacacccgccgcgcttaatgcgccgctacagggcgcgtcccattcgccattcaggct gcgcaactgttgggaagggcgatcggtgcgggcctcttcgctattacgccagctggcgaaaggggatgtgctgcaaggc gattaagttgggtaacgccagggttttcccagtcacgacgttgtaaaacgacggccagtgaattgtaatacgactcacta tagggcgaattgGGTACCatttaaatacgcgtagatcttcaatattggccattagccatattattcattggttatatagc ataaatcaatattggctattggccattgcatacgttgtatctatatcataatatgtacatttatattggctcatgtccaa tatgaccgccatgttggcattgattattgactagttattaatagtaatcaattacggggtcattagttcatagcccatat atggagttccgcgttacataacttacggtaaatggcccgcctggctgaccgcccaacgacccccgcccattgacgtcaat aatgacgtatgttcccatagtaacgccaatagggactttccattgacgtcaatgggtggagtatttacggtaaactgccc acttggcagtacatcaagtgtatcatatgccaagtccgccccctattgacgtcaatgacggtaaatggcccgcctggcat tatgcccagtacatgaccttacgggactttcctacttggcagtacatctacgtattagtcatcgctattaccatggtgat gcggttttggcagtacaccaatgggcgtggatagcggtttgactcacggggatttccaagtctccaccccattgacgtca atgggagtttgttttggcaccaaaatcaacgggactttccaaaatgtcgtaataaccccgccccgttgacgcaaatgggc ggtaggcgtgtacggtgggaggtctatataagcaGAGCTCgtttagtgaaccgtcagatcactagaagctTACTCTCTTC

CGCATCGCTGTCTGCGAGGGCCAGCTGTTGGGCTCGCGGTTGAGGACAAACTCTTCGCGGTCTTTCCAGTACTCTTGGAT

CGGAAACCCGTCGGCCTCCGAACGGTACTCCGCCGCCGAGGGACCTGAGCGAGTCCGCATCGACCGGATCGGAAAACCTC

TCGAGAAAGGCGTCTAACCAGTCACAGTCGCAAGgtaagtatcaaggttacaagacaggtttaaggagaccaatagaaac tgggcttgtcgagacagagaagactcttgcgtttctgataggcacctattggtcttactgacatccactttgcctttctc tccacaggtGCggccGCgaccATGGAGTCAGTCGAGAAGAAGGACAGCCTAACCGCCCCCTCTGAGTTCGCCACCACCGC

CTCCACCGATGCCGCCAACGCGCCTACCACCTTCCCCGTCGAGGCACCCCCGCTTGAGGAGGAGGAAGTGATTATCGAGC

AGGACCCAGGTTTTGTAAGCGAAGACGACGAGGACCGCTCAGTACCAACAGAGGATAAAAAGCAAGACCAGGACAACGCA

GAGGCAAACGAGGAACAAGTCGGGCGGGGGGACGAAAGGCATGGCGACTACCTAGATGTGGGAGACGACGTGCTGTTGAA

GCATCTGCAGCGCCAGTGCGCCATTATCTGCGACGCGTTGCAAGAGCGCAGCGATGTGCCCCTCGCCATAGCGGATGTCA

GCCTTGCCTACGAACGCCACCTATTCTCACCGCGCGTACCCCCCAAACGCCAAGAAAACGGCACATGCGAGCCCAACCCG

CGCCTCAACTTCTACCCCGTATTTGCCGTGCCAGAGGTGCTTGCCACCTATCACATCTTTTTCCAAAACTGCAAGATACC

CCTATCCTGCCGTGCCAACCGCAGCCGAGCGGACAAGCAGCTGGCCTTGCGGCAGGGCGCTGTCATACCTGATATCGCCT

CGCTCAACGAAGTGCCAAAAATCTTTGAGGGTCTTGGACGCGACGAGAAGCGCGCGGCAAACGCTCTGCAACAGGAAAAC

AGCGAAAATGAAAGTCACTCTGGAGTGTTGGTGGAACTCGAGGGTGACAACGCGCGCCTAGCCGTACTAAAACGCAGCAT

CGAGGTCACCCACTTTGCCTACCCGGCACTTAACCTACCCCCCAAGGTCATGAGCACAGTCATGAGTGAGCTGATCGTGC

GCCGTGCGCAGCCCCTGGAGAGGGATGCAAATTTGCAAGAACAAACAGAGGAGGGCCTACCCGCAGTTGGCGACGAGCAG

CTAGCGCGCTGGCTTCAAACGCGCGAGCCTGCCGACTTGGAGGAGCGACGCAAACTAATGATGGCCGCAGTGCTCGTTAC

CGTGGAGCTTGAGTGCATGCAGCGGTTCTTTGCTGACCCGGAGATGCAGCGCAAGCTAGAGGAAACATTGCACTACACCT

TTCGACAGGGCTACGTACGCCAGGCCTGCAAGATCTCCAACGTGGAGCTCTGCAACCTGGTCTCCTACCTTGGAATTTTG

CACGAAAACCGCCTTGGGCAAAACGTGCTTCATTCCACGCTCAAGGGCGAGGCGCGCCGCGACTACGTCCGCGACTGCGT

TTACTTATTTCTATGCTACACCTGGCAGACGGCCATGGGCGTTTGGCAGCAGTGCTTGGAGGAGTGCAACCTCAAGGAGC

TGCAGAAACTGCTAAAGCAAAACTTGAAGGACCTATGGACGGCCTTCAACGAGCGCTCCGTGGCCGCGCACCTGGCGGAC

ATCATTTTCCCCGAACGCCTGCTTAAAACCCTGCAACAGGGTCTGCCAGACTTCACCAGTCAAAGCATGTTGCAGAACTT

TAGGAACTTTATCCTAGAGCGCTCAGGAATCTTGCCCGCCACCTGCTGTGCACTTCCTAGCGACTTTGTGCCCATTAAGT

ACCGCGAATGCCCTCCGCCGCTTTGGGGCCACTGCTACCTTCTGCAGCTAGCCAACTACCTTGCCTACCACTCTGACATA

ATGGAAGACGTGAGCGGTGACGGTCTACTGGAGTGTCACTGTCGCTGCAACCTATGCACCCCGCACCGCTCCCTGGTTTG

CAATTCGCAGCTGCTTAACGAAAGTCAAATTATCGGTACCTTTGAGCTGCAGGGTCCCTCGCCTGACGAAAAGTCCGCGG

-continued

CTCCGGGGTTGAAACTCACTCCGGGGCTGTGGACGTCGGCTTACCTTCGCAAATTTGTACCTGAGGACTACCACGCCCAC

GAGATTAGGTTCTACGAAGACCAATCCCGCCCGCCAAATGCGGAGCTTACCGCCTGCGTCATTACCCAGGGCCACATTCT

TGGCCAATTGCAAGCCATCAACAAAGCCCGCCAAGAGTTTCTGCTACGAAAGGGACGGGGGGTTTACTTGGACCCCCAGT

CCGGCGAGGAGCTCAACCCAATCCCCCCGCCGCCGCAGCCCTATCAGCAGCAGCCGCGGGCCCTTGCTTCCCAGGATGGC

ACCCAAAAAGAAGCTGCAGCTGCCGCCGCCACCCACGGACGAGGAGGAATACTGGGACAGTCAGGCAGAGGAGGTTTTGG

ACGAGGAGGAGGAGGACATGATGGAAGACTGGGAGAGCCTAGACGAGGAAGCTTCCGAGGTCGAAGAGGTGTCAGACGAA

ACACCGTCACCCTCGGTCGCATTCCCCTCGCCGGCGCCCCAGAAATCGGCAACCGGTTCCAGCATGGCTACAACCTCCGC

TCCTCAGGCGCCGCCGGCACTGCCCGTTCGCCGACCCAACCGTAGCCCGGGaatatcggccgcttcgagcagacatgata agatacattgatgagtttggacaaaccacaactagaatgcagtgaaaaaaatgctttatttgtgaaatttgtgatgctat tgctttatttgtaaccattataagctgcaataaacaagttaacaacaacaattgcattcattttatgtttcaggttcagg gggagatgtgggaggtttttaaagcaagtaaaacctctacaaatgtggtaaaatcgataaggatctgcGGCCggccgca tttaaatAGCTCcagcttttgttccctttagtgagggttaatttcgagcttggcgtaatcatggtcatagctgtttcctg tgtgaaattgttatccgctcacaattccacacaacatacgagccggaagcataaagtgtaaagcctggggtgcctaatga gtgagctaactcacattaattgcgttgcgctcactgcccgctttccagtcgggaaacctgtcgtgccagctgcattaatg aatcggccaacgcgcggggagaggcggtttgcgtattgggcgctcttccgcttcctcgctcactgactcgctgcgctcgg tcgttcggctgcggcgagcggtatcagctcactcaaaggcggtaatacggttatccacagaatcaggggataacgcagga aagaacatgtgagcaaaaggccagcaaaaggccaggaaccgtaaaaaggccgcgttgctggcgtttttccataggctccg cccccctgacgagcatcacaaaaatcgacgctcaagtcagaggtggcgaaacccgacaggactataaagataccaggcgt ttccccctggaagctccctcgtgcgctctcctgttccgaccctgccgcttaccggatacctgtccgcctttctcccttcg ggaagcgtggcgctttctcatagctcacgctgtaggtatctcagttcggtgtaggtcgttcgctccaagctgggctgtgt gcacgaaccccccgttcagcccgaccgctgcgccttatccggtaactatcgtcttgagtccaacccggtaagacacgact tatcgccactggcagcagccactggtaacaggattagcagagcgaggtatgtaggcggtgctacagagttcttgaagtgg tggcctaactacggctacactagaaggacagtatttggtatctgcgctctgctgaagccagttaccttcggaaaaagagt tggtagctcttgatccggcaaacaaaccaccgctggtagcggtggtttttttgtttgcaagcagcagattacgcgcagaa aaaaaggatctcaagaagatcctttgatcttttctacggggtctgacgctcagtggaacgaaaactcacgttaagggatt ttggtcatgagattatcaaaaaggatcttcacctagatccttttaaattaaaaatgaagttttaaatcaatctaaagtat atatgagtaaacttggtctgacagttaccaatgcttaatcagtgaggcacctatctcagcgatctgtctatttcgttcat ccatagttgcctgactccccgtcgtgtagataactacgatacgggagggcttaccatctggccccagtgctgcaatgata ccgcgagacccacgctcaccggctccagatttatcagcaataaaccagccagccggaagggccgagcgcagaagtggtcc tgcaactttatccgcctccatccagtctattaattgttgccgggaagctagagtaagtagttcgccagttaatagtttgc gcaacgttgttgccattgctacaggcatcgtggtgtcacgctcgtcgtttggtatggcttcattcagctccggttcccaa cgatcaaggcgagttacatgatcccccatgttgtgcaaaaaagcggttagctccttcggtcctccgatcgttgtcagaag taagttggccgcagtgttatcactcatggttatggcagcactgcataattctcttactgtcatgccatccgtaagatgct tttctgtgactggtgagtactcaaccaagtcattctgagaatagtgtatgcggcgaccgagttgctcttgcccggcgtca atacgggataataccgcgccacatagcagaactttaaaagtgctcatcattggaaaacgttcttcggggcgaaaactctc aaggatcttaccgctgttgagatccagttcgatgtaacccactcgtgcacccaactgatcttcagcatcttttactttca ccagcgtttctgggtgagcaaaaacaggaaggcaaaatgccgcaaaaaagggaataagggcgacacggaaatgttgaata ctcatactcttcctttttcaatattattgaagcatttatcagggttattgtctcatgagcggatacatatttgaatgtat ttagaaaaataaacaaataggggttccgcgcacatttccccgaaaagtgc -continued (Bacmid Ad5Δ100K)

SEQ ID NO: 7

ATTATTATAGTCAGCTGACGTGTAGTGTATTTATACCCGGTGAGTTCCTCAAGAGGCCACTCTTGAGTGCCAGCGAGTAG

AGTTTTCTCCTCCGAGCCGCTCCGACACCGGGACTGAAAATGAGACATATTATCTGCCACGGAGGTGTTATTACCGAAGA

AATGGCCGCCAGTCTTTTGGACCAGCTGATCGAAGAGGTACTGGCTGATAATCTTCCACCTCCTAGCCATTTTGAACCAC

CTACCCTTCACGAACTGTATGATTTAGACGTGACGGCCCCCGAAGATCCCAACGAGGAGGCGGTTTCGCAGATTTTTCCC

GACTCTGTAATGTTGGCGGTGCAGGAAGGGATTGACTTACTCACTTTTCCGCCGGCGCCCGGTTCTCCGGAGCCGCCTCA

CCTTTCCCGGCAGCCCGAGCAGCCGGAGCAGAGAGCCTTGGGTCCGGTTTCTATGCCAAACCTTGTACCGGAGGTGATCG

ATCTTACCTGCCACGAGGCTGGCTTTCCACCCAGTGACGACGAGGATGAAGAGGGTGAGGAGTTTGTGTTAGATTATGTG

GAGCACCCCGGGCACGGTTGCAGGTCTTGTCATTATCACCGGAGGAATACGGGGGACCCAGATATTATGTGTTCGCTTTG

CTATATGAGGACCTGTGGCATGTTTGTCTACAGTAAGTGAAAATTATGGGCAGTGGGTGATAGAGTGGTGGGTTTGGTGT

GGTAATTTTTTTTTTAATTTTTACAGTTTTGTGGTTTAAAGAATTTTGTATTGTGATTTTTTTAAAAGGTCCTGTGTCTG

AACCTGAGCCTGAGCCCGAGCCAGAACCGGAGCCTGCAAGACCTACCCGCCGTCCTAAAATGGCGCCTGCTATCCTGAGA

CGCCCGACATCACCTGTGTCTAGAGAATGCAATAGTAGTACGGATAGCTGTGACTCCGGTCCTTCTAACACACCTCCTGA

GATACACCCGGTGGTCCCGCTGTGCCCCATTAAACCAGTTGCCGTGAGAGTTGGTGGGCGTCGCCAGGCTGTGGAATGTA

TCGAGGACTTGCTTAACGAGCCTGGGCAACCTTTGGACTTGAGCTGTAAACGCCCCAGGCCATAAGGTGTAAACCTGTGA

TTGCGTGTGTGGTTAACGCCTTTGTTTGCTGAATGAGTTGATGTAAGTTTAATAAAGGGTGAGATAATGTTTAACTTGCA

TGGCGTGTTAAATGGGGCGGGGCTTAAAGGGTATATAATGCGCCGTGGGCTAATCTTGGTTACATCTGACCTCATGGAGG

CTTGGGAGTGTTTGGAAGATTTTTCTGCTGTGCGTAACTTGCTGGAACAGAGCTCTAACAGTACCTCTTGGTTTTGGAGG

TTTCTGTGGGGCTCATCCCAGGCAAAGTTAGTCTGCAGAATTAAGGAGGATTACAAGTGGGAATTTGAAGAGCTTTTGAA

ATCCTGTGGTGAGCTGTTTGATTCTTTGAATCTGGGTCACCAGGCGCTTTTCCAAGAGAAGGTCATCAAGACTTTGGATT

TTTCCACACCGGGGCGCGCTGCGGCTGCTGTTGCTTTTTTGAGTTTTATAAAGGATAAATGGAGCGAAGAAACCCATCTG

AGCGGGGGGTACCTGCTGGATTTTCTGGCCATGCATCTGTGGAGAGCGGTTGTGAGACACAAGAATCGCCTGCTACTGTT

GTCTTCCGTCCGCCCGGCGATAATACCGACGGAGGAGCAGCAGCAGCAGCAGGAGGAAGCCAGGCGGCGGCGGCAGGAGC

AGAGCCCATGGAACCCGAGAGCCGGCCTGGACCCTCGGGAATGAATGTTGTACAGGTGGCTGAACTGTATCCAGAACTGA

GACGCATTTTGACAATTACAGAGGATGGGCAGGGGCTAAAGGGGGTAAAGAGGGAGCGGGGGGCTTGTGAGGCTACAGAG

GAGGCTAGGAATCTAGCTTTTAGCTTAATGACCAGACACCGTCCTGAGTGTATTACTTTTCAACAGATCAAGGATAATTG

CGCTAATGAGCTTGATCTGCTGGCGCAGAAGTATTCCATAGAGCAGCTGACCACTTACTGGCTGCAGCCAGGGGATGATT

TTGAGGAGGCTATTAGGGTATATGCAAAGGTGGCACTTAGGCCAGATTGCAAGTACAAGATCAGCAAACTTGTAAATATC

AGGAATTGTTGCTACATTTCTGGGAACGGGGCCGAGGTGGAGATAGATACGGAGGATAGGGTGGCCTTTAGATGTAGCAT

GATAAATATGTGGCCGGGGGTGCTTGGCATGGACGGGGTGGTTATTATGAATGTAAGGTTTACTGGCCCCAATTTTAGCG

GTACGGTTTTCCTGGCCAATACCAACCTTATCCTACACGGTGTAAGCTTCTATGGGTTTAACAATACCTGTGTGGAAGCC

TGGACCGATGTAAGGGTTCGGGGCTGTGCCTTTTACTGCTGCTGGAAGGGGGTGGTGTGTCGCCCCAAAAGCAGGGCTTC

AATTAAGAAATGCCTCTTTGAAAGGTGTACCTTGGGTATCCTGTCTGAGGGTAACTCCAGGGTGCGCCACAATGTGGCCT

CCGACTGTGGTTGCTTCATGCTAGTGAAAAGCGTGGCTGTGATTAAGCATAACATGGTATGTGGCAACTGCGAGGACAGG

GCCTCTCAGATGCTGACCTGCTCGGACGGCAACTGTCACCTGCTGAAGACCATTCACGTAGCCAGCCACTCTCGCAAGGC

CTGGCCAGTGTTTGAGCATAACATACTGACCCGCTGTTCCTTGCATTTGGGTAACAGGAGGGGGGTGTTCCTACCTTACC

AATGCAATTTGAGTCACACTAAGATATTGCTTGAGCCCGAGAGCATGTCCAAGGTGAACCTGAACGGGGTGTTTGACATG

ACCATGAAGATCTGGAAGGTGCTGAGGTACGATGAGACCCGCACCAGGTGCAGACCCTGCGAGTGTGGCGGTAAACATAT

TAGGAACCAGCCTGTGATGCTGGATGTGACCGAGGAGCTGAGGCCCGATCACTTGGTGCTGGCCTGCACCCGCGCTGAGT

TTGGCTCTAGCGATGAAGATACAGATTGAGGTACTGAAATGTGtgggcgtggCttaagggtgggaaagaatatataaggt gggggtcttatgtagttttgtatctgttttgcagcagccgccgccgccatgagcaccaactcgtttgatggaagcattgt -continued gagctcatatttgacaacgcgcatgcccccatgggccggggtgcgtcagaatgtgatgggctccagcattgatggtcgcc ccgtcctgcccgcaaactctactaccttgacctacgagaccgtgtctggaacgccgttggagactgcagcctccgccgcc gcttcagccgctgcagccaccgcccgcgggattgtgactgactttgctttcctgagcccgcttgcaagcagtgcagcttc ccgttcatccgcccgcgatgacaagttgacggctcttttggcacaattggattctttgacccgggaacttaatgtcgttt ctcagcagctgttggatctgcgccagcaggtttctgccctgaaggcttcctcccctcccaatgcggtttaaaacataaat aaaaaaccagactctgtttggatttggatcaagcaagtgtcttgctgtctttatttaggggttttgcgcgcgcggtaggc ccgggaccagcggtctcggtcgttgagggtcctgtgtatttttttccaggacgtggtaaaggtgactctggatgttcagat acatgggcataagcccgtctctggggtggaggtagcaccactgcagagcttcatgctgcggggtggtgttgtagatgatc cagtcgtagcaggagcgctgggcgtggtgcctaaaaatgtctttcagtagcaagctgattgccaggggcaggcccttggt gtaagtgtttacaaagcggttaagctgggatgggtgcatacgtggggatatgagatgcatcttggactgtatttttaggt tggctatgttcccagccatatccctccggggattcatgttgtgcagaaccaccagcacagtgtatccggtgcacttggga aatttgtcatgtagcttagaaggaaatgcgtggaagaacttggagacgcccttgtgacctccaagattttccatgcattc gtccataatgatggcaatgggcccacgggcggcggcctgggcgaagatatttctgggatcactaacgtcatagttgtgtt ccaggatgagatcgtcataggccatttttacaaagcgcgggcggagggtgccagactgcggtataatggttccatccggc ccaggggcgtagttaccctcacagatttgcatttcccacgctttgagttcagatggggggatcatgtctacctgcggggc gatgaagaaaacggtttccggggtaggggagatcagctgggaagaaagcaggttcctgagcagctgcgacttaccgcagc cggtgggcccgtaaatcacacctattaccgggtgcaactggtagttaagagagctgcagctgccgtcatccctgagcagg ggggccacttcgttaagcatgtccctgactcgcatgttttccctgaccaaatccgccagaaggcgctcgccgcccagcga tagcagttcttgcaaggaagcaaagtttttcaacggtttgagaccgtccgccgtaggcatgcttttgagcgtttgaccaa gcagttccaggcggtcccacagctcggtcacctgctctacggcatctcgatccagcatatctcctcgtttcgcgggttgg ggcggctttcgctgtacggcagtagtcggtgctcgtccagacgggccagggtcatgtctttccacgggcgcagggtcctc gtcagcgtagtctgggtcacggtgaaggggtgcgctccgggctgcgcgctggccagggtgcgcttgaggctggtcctgct ggtgctgaagcgctgccggtcttcgccctgcgcgtcggccaggtagcatttgaccatggtgtcatagtccagcccctccg cggcgtggcccttggcgcgcagcttgcccttggaggaggcgccgcacgaggggcagtgcagacttttgagggcgtagagc ttgggcgcgagaaataccgattccggggagtaggcatccgcgccgcaggccccgcagacggtctcgcattccacgagcca ggtgagctctggccgttcggggtcaaaaaccaggtttcccccatgctttttgatgcgtttcttacctctggtttccatga gccggtgtccacgctcggtgacgaaaaggctgtccgtgtccccgtatacagacttgagaggcctgtcctcgagcggtgtt ccgcggtcctcctcgtatagaaactcggaccactctgagacaaaggctcgcgtccaggccagcacgaaggaggctaagtg ggaggggtagcggtcgttgtccactagggggtccactcgctccagggtgtgaagacacatgtcgccctcttcggcatcaa ggaaggtgattggtttgtaggtgtaggccacgtgaccgggtgttcctgaaggggggctataaaagggggtgggggcgcgt tcgtcctcactctcttccgcatcgctgtctgcgagggccagctgttggggtgagtactccctctgaaaagcgggcatgac ttctgcgctaagattgtcagtttccaaaaacgaggaggatttgatattcacctggcccgcggtgatgcctttgagggtgg ccgcatccatctggtcagaaaagacaatctttttgttgtcaagcttggtggcaaacgacccgtagagggcgttggacagc aacttggcgatggagcgcagggtttggtttttgtcgcgatcggcgcgctccttggccgcgatgtttagctgcacgtattc gcgcgcaacgcaccgccattcgggaaagacggtggtgcgctcgtcgggcaccaggtgcacgcgccaaccgcggttgtgca gggtgacaaggtcaacgctggtggctacctctccgcgtaggcgctcgttggtccagcagaggcggccgcccttgcgcgag cagaatggcggtagggggtctagctgcgtctcgtccgggggggtctgcgtccacggtaaagaccccgggcagcaggcgcgc gtcgaagtagtctatcttgcatccttgcaagtctagcgcctgctgccatgcgcgggcggcaagcgcgcgctcgtatgggt tgagtgggggaccccatggcatggggtgggtgagcgcggaggcgtacatgccgcaaatgtcgtaaacgtagaggggctct ctgagtattccaagatatgtagggtagcatcttccaccgcggatgctggcgcgcacgtaatcgtatagttcgtgcgaggg -continued agcgaggaggtcgggaccgaggttgctacgggcgggctgctctgctcggaagactatctgcctgaagatggcatgtgagt tggatgatatggttggacgctggaagacgttgaagctggcgtctgtgagacctaccgcgtcacgcacgaaggaggcgtag gagtcgcgcagcttgttgaccagctcggcggtgacctgcacgtctagggcgcagtagtccagggtttccttgatgatgtc atacttatcctgtcccttttttttccacagctcgcggttgaggacaaactcttcgcggtctttccagtactcttggatcg gaaacccgtcggcctccgaacggtaagagcctagcatgtagaactggttgacggcctggtaggcgcagcatccctttct acgggtagcgcgtatgcctgcgcggccttccggagcgaggtgtgggtgagcgcaaaggtgtccctgaccatgactttgag gtactggtatttgaagtcagtgtcgtcgcatccgccctgctcccagagcaaaaagtccgtgcgctttttggaacgcggat ttggcagggcgaaggtgacatcgttgaagagtatctttcccgcgcgaggcataaagttgcgtgtgatgcggaagggtccc ggcacctcggaacggttgttaattacctgggcggcgagcacgatctcgtcaaagccgttgatgttgtggcccacaatgta aagttccaagaagcgcgggatgcccttgatggaaggcaatttttaagttcctcgtaggtgagctcttcaggggagctga gcccgtgctctgaaagggcccagtctgcaagatgagggttggaagcgacgaatgagctccacaggtcacgggccattagc atttgcaggtggtcgcgaaaggtcctaaactggcgacctatggccatttttctggggtgatgcagtagaaggtaagcgg gtcttgttcccagcggtcccatccaaggttcgcggctaggtctcgcgcggcagtcactagaggctcatctccgccgaact tcatgaccagcatgaagggcacgagctgcttcccaaaggccccatccaagtataggtctctacatcgtaggtgacaaag agacgctcggtgcgaggatgcgagccgatcgggaagaactggatctcccgccaccaattggaggagtggctattgatgtg gtgaaagtagaagtccctgcgacgggccgaacactcgtgctggcttttgtaaaaacgtgcgcagtactggcagcggtgca cgggctgtacatcctgcacgaggttgacctgacgaccgcgcacaaggaagcagagtgggaatttgagcccctcgcctggc gggtttggctggtggtcttctacttcggctgcttgtccttgaccgtctggctgctcgaggggagttacggtggatcggac caccacgccgcgcgagcccaaagtccagatgtccgcgcgcggcggtcggagcttgatgacaacatcgcgcagatgggagc tgtccatggtctggagctcccgcggcgtcaggtcaggcgggagctcctgcaggtttacctcgcatagacgggtcagggcg cgggctagatccaggtgatacctaatttccaggggctggttggtggcggcgtcgatggcttgcaagaggccgcatccccg cggcgcgactacggtaccgcgcggcgggcggtgggccgcgggggtgtccttggatgatgcatctaaaagcggtgacgcgg gcgagcccccggaggtagggggggctccggacccgccgggagagggggcaggggcacgtcggcgccgcgcgcgggcagga gctggtgctgcgcgcgtaggttgctggcgaacgcgacgacgcggcggttgatctcctgaatctggcgcctctgcgtgaag acgacgggcccggtgagcttgagcctgaaagagagttcgacagaatcaatttcggtgtcgttgacggcggcctggcgcaa aatctcctgcacgtctcctgagttgtcttgataggcgatctcggccatgaactgctcgatctcttcctcctggagatctc cgcgtccggctcgctccacggtggcggcgaggtcgttggaaatgcgggccatgagctgcgagaaggcgttgaggcctccc tcgttccagacgcggctgtagaccacgcccccttcggcatcgcgggcgcgcatgaccacctgcgcgagattgagctccac gtgccgggcgaagacggcgtagtttcgcaggcgctgaaagaggtagttgagggtggtggcggtgtgttctgccacgaaga agtacataacccagcgtcgcaacgtggattcgttgatatcccccaaggcctcaaggcgctccatggcctcgtagaagtcc acggcgaagttgaaaaactgggagttgcgcgccgacacggttaactcctcctccagaagacggatgagctcggcgacagt gtcgcgcacctcgcgctcaaaggctacaggggcctcttcttcttcttcaatctcctcttccataagggcctccccttctt cttcttctggcggcggtgggggagggggacacggcggcgacgacggcgcaccgggaggcggtcgacaaagcgctcgatc atctccccgcggcgacggcgcatggtctcggtgacggcgcggccgttctcgcgggggcgcagttggaagacgccgcccgt catgtcccggttatgggttggcgggggctgccatgcggcagggatacggcgctaacgatgcatctcaacaattgttgtg taggtactccgccgccgagggacctgagcgagtccgcatcgaccggatcggaaaacctctcgagaaaggcgtctaaccag tcacagtcgcaaggtaggctgagcaccgtggcgggcggcagcgggcggcggtcggggttgtttctggcggaggtgctgct gatgatgtaattaaagtaggcggtcttgagacggcggatggtcgacagaagcaccatgtccttgggtccggcctgctgaa tgcgcaggcggtcggccatgccccaggcttcgttttgacatcggcgcaggtctttgtagtagtcttgcatgagcctttct accggcacttcttcttctccttcctcttgtcctgcatctcttgcatctatcgctgcggcggcggcggagtttggccgtag gtggcgccctcttcctcccatgcgtgtgaccccgaagcccctcatcggctgaagcagggctaggtcggcgacaacgcgct -continued cggctaatatggcctgctgcacctgcgtgagggtagactggaagtcatccatgtccacaaagcggtggtatgcgcccgtg
ttgatggtgtaagtgcagttggccataacggaccagttaacggtctggtgacccggctgcgagagctcggtgtacctgag
acgcgagtaagccctcgagtcaaatacgtagtcgttgcaagtccgcaccaggtactggtatcccaccaaaaagtgcggcg
gcggctggcggtagaggggccagcgtagggtggccggggctccgggggcgagatcttccaacataaggcgatgatatccg
tagatgtacctggacatccaggtgatgccggcggcggtggtggaggcgcgcggaaagtcgcggacgcggttccagatgtt
gcgcagcggcaaaaagtgctccatggtcgggacgctctggccggtcaggcgcgcgcaatcgttgacgctctagaccgtgc
aaaaggagagcctgtaagcgggcactcttccgtggtctggtggataaattcgcaagggtatcatggcggacgaccggggt
tcgagccccgtatccggccgtccgccgtgatccatgcggttaccgcccgcgtgtcgaacccaggtgtgcgacgtcagaca
acgggggagtgctccttttggcttccttccaggcgcggcggctgctgcgctagctttttggccactggccgcgcgcagc
gtaagcggttaggctggaaagcgaaagcattaagtggctcgctccctgtagccggagggttattttccaagggttgagtc
gcgggacccccggttcgagtctcggaccggccggactgcggcgaacgggggtttgcctccccgtcatgcaagaccccgct
tgcaaattcctccggaaacagggacgagcccctttttgcttttcccagatgcatccggtgctgcggcagatgcgccccc
ctcctcagcagcggcaagagcaagagcagcggcagacatgcagggcaccctcccctcctcctaccgcgtcaggaggggcg
acatccgcggttgacgcggcagcagatggtgattacgaacccccgcggcgccgggcccggcactacctggacttggagga
gggcgagggcctggcgcggctaggagcgccctctcctgagcggtacccaagggtgcagctgaagcgtgatacgcgtgagg
cgtacgtgccgcggcagaacctgtttcgcgaccgcgagggagaggagcccgaggagatgcgggatcgaaagttccacgca
gggcgcgagctgcggcatggcctgaatcgcgagcggttgctgcgcgaggaggactttgagcccgacgcgcgaaccgggat
tagtccccgtggcggccgccgacctggtaaccgcatacgagcagacggtgaaccaggagattaactttcaagcgcgcgca
caaaaagctttaacaaccacgtgcgtacgcttgtggcgcgcgaggaggtggctataggactgatgcatctgtgggacttt
gtaagcgcgctggagcaaaacccaaatagcaagccgctcatggcgcagctgttccttatagtgcagcacagcagggacaa
cgaggcattcagggatgcgctgctaaacatagtagagcccgagggccgctggctgctcgatttgataaacatcctgcaga
gcatagtggtgcaggagcgcagcttgagcctggctgacaaggtggccgccatcaactattccatgcttagcctgggcaag
ttttacgcccgcaagatataccataccccttacgttcccatagacaaggaggtaaagatcgaggggttctacatgcgcat
ggcgctgaaggtgcttaccttgagcgacgacctgggcgtttatcgcaacgagcgcatccacaaggccgtgagcgtgagcc
ggcggcgcgagctcagcgaccgcgagctgatgcacagcctgcaaagggccctggctggcacgggcagcggcgatagagag
gccgagtcctactttgacgcgggcgctgacctgcgctgggccccaagccgacgcgccctggaggcagctggggccggacc
tgggctggcggtggcacccgcgcgcgctggcaacgtcggcggcgtggaggaatatgacgaggacgatgagtacgagccag
aggacggcgagtactaagcggtgatgtttctgatcagatgatgcaagacgcaacggacccggcggtgcgggcggcgctgc
agagccagccgtccggccttaactccacggacgactggcgccaggtcatggaccgcatcatgtcgctgactgcgcgcaat
cctgacgcgttccggcagcagccgcaggccaaccggctctccgcaattctggaagcggtggtcccggcgcgcgcaaaccc
cacgcacgagaaggtgctggcgatcgtaaacgcgctggccgaaaacagggccatccggcccgacgaggccggcctggtct
acgacgcgctgcttcagcgcgtggctcgttacaacagcggcaacgtgcagaccaacctggaccggctggtgggggatgtg
cgcgaggccgtggcgcagcgtgagcgcgcgcagcagcagggcaacctgggctccatggttgcactaaacgccttcctgag
tacacagcccgccaacgtgccgcggggacaggaggactacaccaactttgtgagcgcactgcggctaatggtgactgaga
caccgcaaagtgaggtgtaccagtctgggccagactatttttccagaccagtagacaaggcctgcagaccgtaaacctg
agccaggctttcaaaaacttgcaggggctgtgggggtgcgggctcccacaggcgaccgcgcgaccgtgtctagcttgct
gacgcccaactcgcgcctgttgctgctgctaatagcgcccttcacggacagtggcagcgtgtcccgggacacatacctag
gtcacttgctgacactgtaccgcgaggccataggtcaggcgcatgtggacgagcatactttccaggagattacaagtgtc
agccgcgcgctggggcaggaggacacgggcagcctggaggcaaccctaaactacctgctgaccaaccggcggcagaagat
cccctcgttgcacagtttaaacagcgaggaggagcgcattttgcgctacgtgcagcagagcgtgagccttaacctgatgc -continued gcgacggggtaacgcccagcgtggcgctggacatgaccgcgcgcaacatggaaccgggcatgtatgcctcaaaccggccg tttatcaaccgcctaatggactacttgcatcgcgcggccgccgtgaaccccgagtatttcaccaatgccatcttgaaccc gcactggctaccgcccccctggtttctacaccgggggattcgaggtgcccgagggtaacgatggattcctctgggacgaca tagacgacagcgtgttttccccgcaaccgcagaccctgctagagttgcaacagcgcgagcaggcagaggcggcgctgcga aaggaaagcttccgcaggccaagcagcttgtccgatctaggcgctgcggccccgcggtcagatgctagtagcccatttcc aagcttgatagggtctcttaccagcactcgcaccacccgcccgcgcctgctgggcgaggaggagtacctaaacaactcgc tgctgcagccgcagcgcgaaaaaaacctgcctccggcatttcccaacaacgggatagagagcctagtggacaagatgagt agatggaagacgtacgcgcaggagcacagggacgtgccaggcccgcgcccgcccacccgtcgtcaaaggcacgaccgtca gcggggtctggtgtgggaggacgatgactcggcagacgacagcagcgtcctggatttgggagggagtggcaacccgtttg cgcaccttcgccccaggctggggagaatgttttaaaaaaaaaaaaagcatgatgcaaaataaaaaactcaccaaggccatg gcaccgagcgttggttttcttgtattccccttagtatgcggcgcgcggcgatgtatgaggaaggtcctcctccctcctac gagagtgtggtgagcgcggcgccagtggcggcggcgctgggttctcccttcgatgctcccctggacccgccgtttgtgcc tccgcggtacctgcggcctaccgggggggagaaacagcatccgttactctgagttggcacccctattcgacaccacccgtg tgtacctggtggacaacaagtcaacggatgtggcatccctgaactaccagaacgaccacagcaactttctgaccacggtc attcaaaacaatgactacagcccgggggaggcaagcacacagaccatcaatcttgacgaccggtcgcactggggcggcga cctgaaaaccatcctgcataccaacatgccaaatgtgaacgagttcatgtttaccaataagtttaaggcgcgggtgatgg tgtcgcgcttgcctactaaggacaatcaggtggagctgaaatacgagtgggtggagttcacgctgcccgagggcaactac tccgagaccatgaccatagaccttatgaacaacgcgatcgtggagcactacttgaaagtgggcagacagaacggggttct ggaaagcgacatcggggtaaagtttgacacccgcaacttcagactggggtttgaccccgtcactggtcttgtcatgcctg gggtatatacaaacgaagccttccatccagacatcattttgctgccaggatgcggggtggacttcacccacagccgcctg agcaacttgttgggcatccgcaagcggcaacccttccaggagggctttaggatcacctacgatgatctggagggtggtaa cattcccgcactgttggatgtggacgcctaccaggcgagcttgaaagatgacaccgaacagggcgggggtggcgcaggcg gcagcaacagcagtggcagcggcgcggaagagaactccaacgcggcagccgcggcaatgcagccggtggaggacatgaac gatcatgccattcgcggcgacacctttgccacacgggctgaggagaagcgcgctgaggccgaagcagcggccgaagctgc cgcccccgctgcgcaacccgaggtcgagaagcctcagaagaaaccggtgatcaaacccctgacagaggacagcaagaaac gcagttacaacctaataagcaatgacagcaccttcacccagtaccgcagctggtaccttgcatacaactacggcgaccct cagaccggaatccgctcatggaccctgctttgcactcctgacgtaacctgcggctcggagcaggtctactggtcgttgcc agacatgatgcaagaccccgtgaccttccgctccacgcgccagatcagcaactttccggtggtgggcgccgagctgttgc ccgtgcactccaagagcttctacaacgaccaggccgtctactcccaactcatccgccagtttacctctctgacccacgtg ttcaatcgctttcccgagaaccagattttggcgcgcccgccagcccccaccatcaccaccgtcagtgaaaacgttcctgc tctcacagatcacgggacgctaccgctgcgcaacagcatcggaggagtccagcgagtgaccattactgacgccagacgcc gcacctgcccctacgtttacaaggccctgggcatagtctcgccgcgcgtcctatcgagccgcactttttgagcaagcatg tccatccttatatcgcccagcaataacacaggctggggcctgcgcttcccaagcaagatgtttggcggggccaagaagcg ctccgaccaacacccagtgcgcgtgcgcgggcactaccgcgcgccctggggcgcgcacaaacgcggccgcactgggcgca ccaccgtcgatgacgccatcgacgcggtggtggaggaggcgcgcaactacacgcccacgccgccaccagtgtccacagtg gacgcggccattcagaccgtggtgcgcggagcccggcgctatgctaaaatgaagagacggcggaggcgcgtagcacgtcg ccaccgccgccgacccggcactgccgcccaacgcgcggcggcggccctgcttaaccgcgcacgtcgcaccggccgacggg cggccatgcgggccgctcgaaggctggccgcgggtattgtcactgtgccccccaggtccaggcgacgagcggccgccgca gcagccgcggccattagtgctatgactcagggtcgcaggggcaacgtgtattgggtgcgcgactcggttagcggcctgcg cgtgcccgtgcgcacccgcccccgcgcaactagattgcaagaaaaaactacttagactcgtactgttgtatgtatccag cggcggcggcgcgcaacgaagctatgtccaagcgcaaaatcaaagaagagatgctccaggtcatcgcgccggagatctat -continued ggcccccgaagaaggaagagcaggattacaagccccgaaagctaaagcgggtcaaaaagaaaaagaaagatgatgatga tgaacttgacgacgaggtggaactgctgcacgctaccgcgcccaggcgacgggtacagtggaaaggtcgacgcgtaaaac gtgttttgcgacccggcaccaccgtagtctttacgcccggtgagcgctccacccgcacctacaagcgcgtgtatgatgag gtgtacggcgacgaggacctgcttgagcaggccaacgagcgcctcggggagtttgcctacggaaagcggcataaggacat gctggcgttgccgctggacgagggcaacccaacacctagcctaaagcccgtaacactgcagcaggtgctgcccgcgcttg caccgtccgaagaaaagcgcggcctaaagcgcgagtctggtgacttggcacccaccgtgcagctgatggtacccaagcgc cagcgactggaagatgtcttggaaaaaatgaccgtggaacctgggctggagcccgaggtccgcgtgcggccaatcaagca ggtggcgccgggactgggcgtgcagaccgtggacgttcagatacccactaccagtagcaccagtattgccaccgccacag agggcatggagacacaaacgtccccggttgcctcagcggtggcggatgccgcggtgcaggcggtcgctgcggccgcgtcc aagacctctacggaggtgcaaacggacccgtggatgtttcgcgtttcagccccccggcgcccgcgcggttcgaggaagta cggcgccgccagcgcgctactgcccgaatatgccctacatccttccattgcgcctacccccggctatcgtggctacacct accgccccagaagacgagcaactacccgacgccgaaccaccactggaacccgccgccgccgtcgccgtcgccagcccgtg ctggccccgatttccgtgcgcagggtggctcgcgaaggaggcaggaccctggtgctgccaacagcgcgctaccaccccag catcgtttaaaagccggtctttgtggttcttgcagatatggccctcacctgccgcctccgtttcccggtgccgggattcc gaggaagaatgcaccgtaggaggggcatggccggccacggcctgacgggcggcatgcgtcgtgcgcaccaccggcggcgg cgcgcgtcgcaccgtcgcatgcgcggcggtatcctgcccctccttattccactgatcgccgcggcgattggcgccgtgcc cggaattgcatccgtggccttgcaggcgcagagacactgattaaaaacaagttgcatgtggaaaaatcaaaataaaaagt ctggactctcacgctcgcttggtcctgtaactattttgtagaatggaagacatcaactttgcgtctctggccccgcgaca cggctcgcgcccgttcatgggaaactggcaagatatcggcaccagcaatatgagcggtggcgccttcagctggggctcgc tgtggagcggcattaaaaatttcggttccaccgttaagaactatggcagcaaggcctggaacagcagcacaggccagatg ctgagggataagttgaaagagcaaaatttccaacaaaaggtggtagatggcctggcctctggcattagcggggtggtgga cctggccaaccaggcagtgcaaaataagattaacagtaagcttgatccccgccctcccgtagaggagcctccaccggccg tggagacagtgtctccagaggggcgtggcgaaaagcgtccgcgccccgacagggaagaaactctggtgacgcaaatagac gagcctccctcgtacgaggaggcactaaagcaaggcctgcccaccacccgtcccatcgcgcccatggctaccggagtgct gggccagcacacacccgtaacgctggacctgcctcccccgccgacacccagcagaaacctgtgctgccaggcccgaccg ccgttgttgtaacccgtcctagccgcgcgtccctgcgccgcgccgccagcggtccgcgatcgttgcggcccgtagccagt ggcaactggcaaagcacactgaacagcatcgtgggtctgggggtgcaatccctgaagcgccgacgatgcttctgaatagc taacgtgtcgtatgtgtgtcatgtatgcgtccatgtcgccgccagaggagctgctgagccgccgcgcgcccgctttccaa gatggctaccccttcgatgatgccgcagtggtcttacatgcacatctcgggccaggacgcctcggagtacctgagccccg ggctggtgcagtttgcccgcgccaccgagacgtacttcagcctgaataacaagtttagaaccccacggtggcgcctacg cacgacgtgaccacagaccggtcccagcgtttgacgctgcggttcatccctgtggaccgtgaggatactgcgtactcgta caaggcgcggttcaccctagctgtgggtgataaccgtgtgctggacatggcttccacgtactttgacatccgcggcgtgc tggacaggggccctacttttaagccctactctggcactgcctacaacgccctggctcccaagggtgccccaaatccttgc gaatgggatgaagctgctactgctcttgaaataaacctagaagaagaggacgatgacaacgaagacgaagtagacgagca agctgagcagcaaaaaactcacgtatttgggcaggcgccttattctggtataaatattacaaaggagggtattcaaatag gtgtcgaaggtcaaacacctaaatatgccgataaaacatttcaacctgaacctcaaataggagaatctcagtggtacgaa actgaaattaatcatgcagctgggagagtccttaaaaagactaccccaatgaaaccatgttacggttcatatgcaaaacc cacaaatgaaaatggagggcaaggcattcttgtaaagcaacaaaatggaaagctagaaagtcaagtggaaatgcaatttt tctcaactactgaggcgaccgcaggcaatggtgataacttgactcctaaagtggtattgtacagtgaagatgtagatata gaaaccccagacactcatatttcttacatgcccactattaaggaaggtaactcacgagaactaatgggccaacaatctat -continued gcccaacaggcctaattacattgcttttagggacaattttattggtctaatgtattacaacagcacgggtaatatgggtg ttctggcgggccaagcatcgcagttgaatgctgttgtagatttgcaagacagaaacacagagctttcataccagcttttg cttgattccattggtgatagaaccaggtacttttctatgtggaatcaggctgttgacagctatgatccagatgttagaat tattgaaaatcatggaactgaagatgaacttccaaattactgctttccactgggaggtgtgattaatacagagactctta ccaaggtaaaacctaaaacaggtcaggaaaatggatgggaaaaagatgctacagaattttcagataaaaatgaaataaga gttggaaataattttgccatggaaatcaatctaaatgccaacctgtggagaaatttcctgtactccaacatagcgctgta tttgcccgacaagctaaagtacagtccttccaacgtaaaaatttctgataacccaaacacctacgactacatgaacaagc gagtggtggctcccgggttagtggactgctacattaaccttggagcacgctggtcccttgactatatggacaacgtcaac ccatttaaccaccaccgcaatgctggcctgcgctaccgctcaatgttgctgggcaatggtcgctatgtgcccttccacat ccaggtgcctcagaagttctttgccattaaaaacctccttctcctgccgggctcatacacctacgagtggaacttcagga aggatgttaacatggttctgcagagctccctaggaaatgacctaagggttgacggagccagcattaagtttgatagcatt tgcctttacgccaccttcttccccatggcccacaacaccgcctccacgcttgaggccatgcttagaaacgacaccaacga ccagtcctttaacgactatctctccgccgccaacatgctctaccctatacccgccaacgctaccaacgtgcccatatcca tcccctcccgcaactgggcggctttccgcggctgggccttcacgcgccttaagactaaggaaaccccatcactgggctcg ggctacgacccttattacacctactctggctctataccctacctagatggaaccttttacctcaaccacacctttaagaa ggtggccattacctttgactcttctgtcagctggcctggcaatgaccgcctgcttacccccaacgagtttgaaattaagc gctcagttgacggggagggttacaacgttgcccagtgtaacatgaccaaagactggttcctggtacaaatgctagctaac tacaacattggctaccagggcttctatatcccagagagctacaaggaccgcatgtactccttctttagaaacttccagcc catgagccgtcaggtggtggatgatactaaatacaaggactaccaacaggtgggcatcctacaccaacacaacaactctg gatttgttggctaccttgcccccaccatgcgcgaaggacaggcctaccctgctaacttcccctatccgcttataggcaag accgcagttgacagcattacccagaaaaagtttctttgcgatcgcaccctttggcgcatcccattctccagtaactttat gtccatgggcgcactcacagacctgggccaaaaccttctctacgccaactccgcccacgcgctagacatgacttttgagg tggatcccatggacgagcccacccttctttatgttttgtttgaagtctttgacgtggtccgtgtgcaccggccgcaccgc ggcgtcatcgaaaccgtgtacctgcgcacgcccttctcggccggcaacgccacaacataaagaagcaagcaacatcaaca acagctgccgccatgggctccagtgagcaggaactgaaagccattgtcaaagatcttggttgtgggccatatttttggg cacctatgacaagcgctttccaggctttgtttctccacacaagctcgcctgcgccatagtcaatacggccggtcgcgaga ctgggggcgtacactggatggcctttgcctggaacccgcactcaaaaacatgctacctctttgagccctttggcttttct gaccagcgactcaagcaggtttaccagtttgagtacgagtcactcctgcgccgtagcgccattgcttcttcccccgaccg ctgtataacgctggaaaagtccacccaaagcgtacaggggcccaactcggccgcctgtggactattctgctgcatgtttc tccacgcctttgccaactggccccaaactcccatggatcacaaccccaccatgaaccttattaccggggtacccaactcc atgctcaacagtccccaggtacagcccaccctgcgtcgcaaccaggaacagctctacagcttcctggagcgccactcgcc ctacttccgcagccacagtgcgcagattaggagcgccacttctttttgtcacttgaaaaacatgtaaaaataatgtacta gagacactttcaataaaggcaaatgcttttatttgtacactctcgggtgattatttacccccacccttgccgtctgcgcc gtttaaaaatcaaaggggttctgccgcgcatcgctatgcgccactggcagggacacgttgcgatactggtgtttagtgct ccacttaaactcaggcacaaccatccgcggcagctcggtgaagttttcactccacaggctgcgcaccatcaccaacgcgt ttagcaggtcgggcgccgatatcttgaagtcgcagttggggcctccgccctgcgcgcgcgagttgcgatacacagggttg cagcactggaacactatcagcgccgggtggtgcacgctggccagcacgctcttgtcggagatcagatccgcgtccaggtc ctccgcgttgctcagggcgaacggagtcaactttggtagctgccttcccaaaaagggcgcgtgcccaggctttgagttgc actcgcaccgtagtggcatcaaaaggtgaccgtgcccggtctgggcgttaggatacagcgcctgcataaaagccttgatc tgcttaaaagccacctgagcctttgcgccttcagagaagaacatgccgcaagacttgccggaaaactgattggccggaca ggccgcgtcgtgcacgcagcaccttgcgtcggtgttggagatctgcaccacatttcggccccaccggttcttcacgatct -continued tggccttgctagactgctccttcagcgcgcgctgcccgttttcgctcgtcacatccatttcaatcacgtgctccttattt
atcataatgcttccgtgtagacacttaagctcgccttcgatctcagcgcagcggtgcagccacaacgcgcagcccgtggg
ctcgtgatgcttgtaggtcacctctgcaaacgactgcaggtacgcctgcaggaatcgccccatcatcgtcacaaaggtct
tgttgctggtgaaggtcagctgcaacccgcggtgctcctcgttcagccaggtcttgcatacggccgccagagcttccact
tggtcaggcagtagtttgaagttcgcctttagatcgttatccacgtggtacttgtccatcagcgcgcgcgcagcctccat
gcccttctcccacgcagacacgatcggcacactcagcgggttcatcaccgtaatttcactttccgcttcgctgggctctt
cctcttcctcttgcgtccgcataccacgcgccactgggtcgtcttcattcagccgccgcactgtgcgcttacctcctttg
ccatgcttgattagcaccggtgggttgctgaaacccaccatttgtagcgccacatcttctctttcttcctcgctgtccac
gattacctctggtgatggcgggcgctcgggcttgggagaagggcgcttctttttcttcttgggcgcaatggccaaatccg
ccgccgaggtcgatggccgcgggctgggtgtgcgcggcaccagcgcgtcttgtgatgagtcttcctcgtcctcggactcg
atacgccgcctcatccgctttttggggggcgcccggggaggcggcggcgacggggacggggacgacacgtcctccatggt
tgggggacgtcgcgccgcaccgcgtccgcgctcgggggtggtttcgcgctgctcctcttcccgactggccatttccttct
cctataggcagaaaaagatcatggagtcagtcgagaagaaggacagcctaaccgcccccctctgagttcgccaccaccgcc
tccaccgatgccgccaacgcgcctaccaccttccccgtcgaggcacccccgcttgaggaggaggaagtgattatcgagca
ggacccaggttttgtaagcgaagacgacgaggaccgctcagtaccaacagaggataaaaagcaagaccaggacaacgcag
aggcaaacgaggaacaagtcgggcgggggacgaaaggcatggcgactacctagatgtgggagacgacgtgctgttgaag
catctgcagcgccagtgcgccattatctgcgacgcgttgcaagagcgcagcgatgtgcccctcgccatagcggatgtcag
ccttgcctacgaacgccacctattctcaccgcgcgtacccccaaacgccaagaaaacggcacatgcgagcccaacccgc
gcctcaacttctaccccgtatttgccgtgccagaggtgcttgccacctatcacatctttttccaaaactgcaagataccc
ctatcctgccgtgccaaccgcagccgagcggacaagcagctggccttgcggcagggcgctgtcatacctgatatcgcctc
gctcaacgaagtgccaaaaatctttgagggtcttggacgcgacgagaagcgcgcggcaaacgctctgcaacaggaaaaca
gcgaaaatgaaagtcactctggagtgttggtggaactcgagggtgacaacgcgcgcctagccgtactaaaacgcagcaTC
GAGGTCACCCACTTTGCCTACCCGGCACTTAACCTACCCCCCAAGGTCTTGCCTACCACTCTGACATAATGGAAGACGTG
AGCGGTGACGGTCTACTGgagtgtcactgtcgctgcaacctatgcaccccgcaccgctccctggtttgcaattcgcagct
gcttaacgaaagtcaaattatcggtacctttgagctgcagggtccctcgcctgacgaaaagtccgcggctccggggttga
aactcactccggggctgtggacgtcggcttaccttcgcaaatttgtacctgaggactaccacgcccacgagattaggttc
tacgaagaccaatcccgcccgccaaatgcggagcttaccgcctgcgtcattacccagggccacattcttggccaattgca
agccatcaacaaagcccgccaagagtttctgctacgaaagggacgggggtttacttggacccccagtccggcgaggagc
tcaacccaatcccccgccgccgcagccctatcagcagcagccgcgggcccttgcttcccaggatggcacccaaaaagaa
gctgcagctgccgccgccacccacggacgaggaggaatactgggacagtcaggcagaggaggttttggacgaggaggagg
aggacatgatggaagactgggagagcctagacgaggaagcttccgaggtcgaagaggtgtcagacgaaacaccgtcaccc
tcggtcgcattcccctcgccggcgccccagaaatcggcaaccggttccagcatggctacaacctccgctcctcaggcgcc
gccggcactgcccgttcgccgacccaaccgtagatgggacaccactggaaccagggccggtaagtccaagcagccgccgc
cgttagcccaagagcaacaacagcgccaaggctaccgctcatggcgcgggcacaagaacgccatagttgcttgcttgcaa
gactgtgggggcaacatctccttcgcccgccgctttcttctctaccatcacggcgtggccttcccccgtaacatcctgca
ttactaccgtcatctctacagcccatactgcaccggcggcagcggcagcggcagcaacagcagcggccacacagaagcaa
aggcgaccggatagcaagactctgacaaagcccaagaaatccacagcggcggcagcagcaggaggaggagcgctgcgtct
ggcgcccaacgaacccgtatcgacccgcgagcttagaaacaggatttttcccactctgtatgctatatttcaacagagca
ggggccaagaacaagagctgaaaataaaaaacaggtctctgcgatccctcacccgcagctgcctgtatcacaaaagcgaa
gatcagcttcggcgcacgctggaagacgcggaggctctcttcagtaaatactgcgcgctgactcttaaggactagtttcg -continued cgccctttctcaaatttaagcgcgaaaactacgtcatctccagcggccacacccggcgccagcacctgtcgtcagcgcca ttatgagcaaggaaattcccacgccctacatgtggagttaccagccacaaatgggacttgcggctggagctgcccaagac tactcaacccgaataaactacatgagcgcgggaccccacatgatatcccgggtcaacggaatccgcgcccaccgaaaccg aattctcttggaacaggcggctattaccaccacacctcgtaataaccttaatccccgtagttggcccgctgccctggtgt accaggaaagtcccgctcccaccactgtggtacttcccagagacgcccaggccgaagttcagatgactaactcaggggcg cagcttgcgggcggctttcgtcacagggtgcggtcgcccgggcagggtataactcacctgacaatcagagggcgaggtat tcagctcaacgacgagtcggtgagctcctcgcttggtctccgtccggacgggacatttcagatcggcggcgccggccgtc cttcattcacgcctcgtcaggcaatcctaactctgcagacctcgtcctctgagccgcgctctggaggcattggaactctg caatttattgaggagtttgtgccatcggtctactttaaccccttctcgggacctcccggccactatccggatcaatttat tcctaactttgacgcggtaaaggactcggcggacggctacgactgaatgttaagtggagaggcagagcaactgcgcctga aacacctggtccactgtcgccgccacaagtgctttgcccgcgactccggtgagttttgctactttgaattgcccgaggat catatcgagggcccggcgcacggcgtccggcttaccgcccagggagagcttgcccgtagcctgattcgggagtttaccca gcgcccccctgctagttgagcgggacaggggaccctgtgttctcactgtgatttgcaactgtcctaaccttggattacatc aagatctttgttgccatctctgtgctgagtataataaatacagaaattaaaatatactggggctcctatcgccatcctgt aaacgccaccgtcttcacccgcccaagcaaaccaaggcgaaccttacctggtacttttaacatctctccctctgtgattt acaacagtttcaacccagacggagtgagtctacgagagaacctctccgagctcagctactccatcagaaaaaacaccacc ctccttacctgccgggaacgtacgagtgcgtcaccggccgctgcaccacacctaccgcctgaccgtaaaccagactttt t ccggacagacctcaataactctgtttaccagaacaggaggtgagcttagaaaacccttagggtattaggccaaaggcgca gctactgtggggtttatgaacaattcaagcaactctacgggctattctaattcaggtttctctagaatcggggttggggt tattctctgtcttgtgattctctttattcttatactaacgcttctctgcctaaggctcgccgcctgctgtgtgcacattt gcatttattgtcagctttttaaacgctggggtcgccacccaagatgattaggtacataatcctaggtttactcacccttg cgtcagcccacggtaccacccaaaaggtggattttaaggagccagcctgtaatgttacattcgcagctgaagctaatgag tgcaccactcttataaaatgcaccacagaacatgaaaagctgcttattcgccacaaaaacaaaattggcaagtatgctgt ttatgctatttggcagccaggtgacactacagagtataatgttacagttttccagggtaaaagtcataaaacttttatgt atacttttccattttatgaaatgtgcgacattaccatgtacatgagcaaacagtataagttgtggcccccacaaaattgt gtggaaaacactggcactttctgctgcactgctatgctaattacagtgctcgctttggtctgtaccctactctatattaa atacaaaagcagacgcagctttattgaggaaaagaaaatgccttaatttactaagttacaaagctaatgtcaccactaac tgctttactcgctgcttgcaaaacaaattcaaaaagttagcattataattagaataggatttaaaccccccggtcatttc ctgctcaataccattcccctgaacaattgactctatgtgggatatgctccagcgctacaaccttgaagtcaggcttcctg gatgtcagcatctgactttggccagcacctgtcccgcggatttgttccagtccaactacagcgacccaccctaacagaga tgaccaacacaaccaacgcggccgccgctaccggacttacatctaccacaaatacaccccaagtttctgcctttgtcaat aactgggataacttgggcatgtggtggttctccatagcgcttatgtttgtatgccttattattatgtggctcatctgctg cctaaagcgcaaacgcgcccgaccacccatctatagtcccatcattgtgctacacccaaacaatgatggaatccatagat tggacggactgaaacacatgttcttttctcttacagtatgattaaatgagacatgattcctcgagtttttatattactga cccttgttgcgctttttttgtgcgtgctccacattggctgcggtttctcacatcgaagtagactgcattccagccttcaca gtctatttgctttacggatttgtcaccctcacgctcatctgcagcctcatcactgtggtcatcgcctttatccagtgcat tgactgggtctgtgtgcgctttgcatatctcagacaccatccccagtacagggacaggactatagctgagcttcttagaa ttctttaattatgaaatttactgtgacttttctgctgattatttgcaccctatctgcgttttgttccccgacctccaagc ctcaaagacatatatcatgcagattcactcgtatatggaatattccaagttgctacaatgaaaaaagcgatctttccgaa gcctggttatatgcaatcatctctgttatggtgttctgcagtaccatcttagccctagctatatatccctaccttgacat tggctggaaacgaatagatgccatgaaccacccaactttccccgcgcccgctatgcttccactgcaacaagttgttgccg -continued gcggctttgtcccagccaatcagcctcgccccacttctcccacccccactgaaatcagctactttaatctaacaggagga gatgactgacaccctagatctagaaatggacggaattattacagagcagcgcctgctagaaagacgcagggcagcggccg agcaacagcgcatgaatcaagagctccaagacatggttaacttgcaccagtgcaaaaggggtatcttttgtctggtaaag caggccaaagtcacctacgacagtaataccaccggacaccgccttagctacaagttgccaaccaagcgtcagaaattggt ggtcatggtgggagaaaagcccattaccataactcagcactcggtagaaaccgaaggctgcattcactcaccttgtcaag gacctgaggatctctgcacccttattaagaccctgtgcggtctcaaagatcttattccctttaactaataaaaaaaaata ataaagcatcacttacttaaaatcagttagcaaatttctgtccagtttattcagcagcacctccttgccctcctcccagc tctggtattgcagcttcctcctggctgcaaactttctccacaatctaaatggaatgtcagtttcctcctgttcctgtcca tccgcacccactatcttcatgttgttgcagatgaagcgcgcaagaccgtctgaagataccttcaaccccgtgtatccata tgacacggaaaccggtcctccaactgtgccttttcttactcctccctttgtatcccccaatgggtttcaagagagtcccc ctggggtactctctttgcgcctatccgaacctctagttacctccaatggcatgcttgcgctcaaaatgggcaacggcctc tctctggacgaggccggcaaccttacctcccaaaatgtaaccactgtgagcccacctctcaaaaaaaccaagtcaaacat aaacctggaaatatctgcacccctcacagttacctcagaagccctaactgtggctgccgccgcacctctaatggtcgcgg gcaacacactcaccatgcaatcacaggccccgctaaccgtgcacgactccaaacttagcattgccacccaaggacccctc acagtgtcagaaggaaagctagccctgcaaacatcaggcccccctcaccaccaccgatagcagtacccttactatcactgc ctcacccccctctaactactgccactggtagcttgggcattgacttgaaagagcccatttatacacaaaatggaaaactag gactaaagtacggggctcctttgcatgtaacagacgacctaaacactttgaccgtagcaactggtccaggtgtgactatt aataatacttccttgcaaactaaagttactggagccttgggttttgattcacaaggcaatatgcaacttaatgtagcagg aggactaaggattgattctcaaaacagacgccttatacttgatgttagttatccgtttgatgctcaaaaccaactaaatc taagactaggacagggccctctttttataaactcagcccacaacttggatattaactacaacaaaggcctttacttgttt acagcttcaaacaattccaaaaagcttgaggttaacctaagcactgccaaggggttgatgtttgacgctacagccatagc cattaatgcaggagatgggcttgaatttggttcacctaatgcaccaaacacaaatcccctcaaaacaaaaattggccatg gcctagaatttgattcaaacaaggctatggttcctaaactaggaactggccttagttttgacagcacaggtgccattaca gtaggaaacaaaaataatgataagctaactttgtggaccacaccagctccatctcctaactgtagactaaatgcagagaa agatgctaaactcactttggtcttaacaaaatgtggcagtcaaatacttgctacagtttcagttttggctgttaaaggca gtttggctccaatatctggaacagttcaaagtgctcatcttattataagatttgacgaaaatggagtgctactaaacaat tccttcctggacccagaatattggaactttagaaatggagatcttactgaaggcacagcctatacaaacgctgttggatt tatgcctaacctatcagcttatccaaaatctcacggtaaaactgccaaaagtaacattgtcagtcaagtttacttaaacg gagacaaaactaaacctgtaacactaaccattacactaaacggtacacaggaaacaggagacacaactccaagtgcatac tctatgtcattttcatgggactggtctggccacaactacattaatgaaatatttgccacatcctcttacactttttcata cattgcccaagaataaagaatcgtttgtgttatgtttcaacgtgtttatttttcaattgcagaaaatttcaagtcatttt tcattcagtagtatagccccaccaccacatagcttatacagatcaccgtaccttaatcaaactcacagaaccctagtatt caacctgccacctccctcccaacacacagagtacacagtcctttctccccggctggccttaaaaagcatcatatcatggg taacagacatattcttaggtgttatattccacacggtttcctgtcgagccaaacgctcatcagtgatattaataaactcc ccgggcagctcacttaagttcatgtcgctgtccagctgctgagccacaggctgctgtccaacttgcggttgcttaacggg cggcgaaggagaagtccacgcctacatgggggtagagtcataatcgtgcatcaggatagggcggtggtgctgcagcagcg cgcgaataaactgctgccgccgccgctccgtcctgcaggaatacaacatggcagtggtctcctcagcgatgattcgcacc gcccgcagcataaggcgccttgtcctccgggcacagcagcgcaccctgatctcacttaaatcagcacagtaactgcagca cagcaccacaatattgttcaaaatcccacagtgcaaggcgctgtatccaaagctcatggcggggaccacagaacccacgt ggccatcataccacaagcgcaggtagattaagtggcgacccctcataaacacgctggacataaacattacctcttttggc -continued atgttgtaattcaccacctcccggtaccatataaacctctgattaaacatggcgccatccaccaccatcctaaaccagct ggccaaaacctgcccgccggctatacactgcagggaaccgggactggaacaatgacagtggagagcccaggactcgtaac catggatcatcatgctcgtcatgatatcaatgttggcacaacacaggcacacgtgcatacacttcctcaggattacaagc tcctcccgcgttagaaccatatcccagggaacaacccattcctgaatcagcgtaaatcccacactgcagggaagacctcg cacgtaactcacgttgtgcattgtcaaagtgttacattcgggcagcagcggatgatcctccagtatggtagcgcgggttt ctgtctcaaaaggaggtagacgatccctactgtacggagtgcgccgagacaaccgagatcgtgttggtcgtagtgtcatg ccaaatggaacgccggacgtagtcatatttcctgaagcaaaaccaggtgcgggcgtgacaaacagatctgcgtctccggt ctcgccgcttagatcgctctgtgtagtagttgtagtatatccactctctcaaagcatccaggcgcccccctggcttcgggt tctatgtaaactccttcatgcgccgctgccctgataacatccaccaccgcagaataagccacacccagccaacctacaca ttcgttctgcgagtcacacacgggaggagcgggaagagctggaagaaccatgtttttttttttattccaaaagattatcc aaaacctcaaaatgaagatctattaagtgaacgcgctcccctccggtggcgtggtcaaactctacagccaaagaacagat aatggcatttgtaagatgttgcacaatggcttccaaaaggcaaacggccctcacgtccaagtggacgtaaaggctaaacc cttcagggtgaatctcctctataaacattccagcaccttcaaccatgcccaaataattctcatctcgccaccttctcaat atatctctaagcaaatcccgaatattaagtccggccattgtaaaaatctgctccagagcgccctccaccttcagcctcaa gcagcgaatcatgattgcaaaaattcaggttcctcacagacctgtataagattcaaaagcggaacattaacaaaaatacc gcgatcccgtaggtcccttcgcagggccagctgaacataatcgtgcaggtctgcacggaccagcgcggccacttccccgc caggaaccttgacaaaagaacccacactgattatgacacgcatactcggagctatgctaaccagcgtagccccgatgtaa gctttgttgcatgggcggcgatataaaatgcaaggtgctgctcaaaaaatcaggcaaagcctcgcgcaaaaaagaaagca catcgtagtcatgctcatgcagataaaggcaggtaagctccggaaccaccacagaaaaagacaccatttttctctcaaac atgtctgcgggtttctgcataaacacaaaataaaataacaaaaaaacatttaaacattagaagcctgtcttacaacagga aaaacaacccttataagcataagacggactacggccatgccggcgtgaccgtaaaaaaactggtcaccgtgattaaaaag caccaccgacagctcctcggtcatgtccggagtcataatgtaagactcggtaaacacatcaggttgattcatcggtcagt gctaaaaagcgaccgaaatagcccgggggaatacatacccgcaggcgtagagacaacattacagcccccataggaggtat aacaaaattaataggagagaaaaacacataaacacctgaaaaaccctcctgcctaggcaaaatagcaccctcccgctcca gaacaacatacagcgcttcacagcggcagcctaacagtcagccttaccagtaaaaaagaaaacctattaaaaaaacacca ctcgacacggcaccagctcaatcagtcacagtgtaaaaaagggccaagtgcagagcgagtatatataggactaaaaaatg acgtaacggttaaagtccacaaaaaacacccagaaaaccgcacgcgaacctacgcccagaaacgaaagccaaaaaaccca caacttcctcaaatcgtcacttccgttttcccacgttacgtaacttcccattttaagaaaactacaattcccaacacata caagttactccgccctaaaacctacgtcacccgccccgttcccacgccccgcgccacgtcacaaactccacccccctcatt atcatattggcttcaatccaaaataaggtatattattgatgatgatttaaatgccgcagtactgttgtaattcattaagc attctgccgacatggaagccatcacaaacggcatgatgaacctgaatcgccagcggcatcagcaccttgtcgccttgcgt ataatatttgcccatggtgaaaacgggggcgaagaagttgtccatattggccacgtttaaatcaaaactggtgaaactca cccagggattggctgagacgaaaaacatattctcaataaaccctttagggaaataggccaggttttcaccgtaacacgcc acatcttgcgaatatatgtgtagaaactgccggaaatcgtcgtggtattcactccagagcgatgaaaacgtttcagtttg ctcatggaaaacggtgtaacaagggtgaacactatcccatatcaccagctcaccgtctttcattgccatacggaattccg gatgagcattcatcaggcgggcaagaatgtgaataaaggccggataaaacttgtgcttatttttctttacggtctttaaa aaggccgtaatatccagctgaacggtctggttataggtacattgagcaactgactgaaatgcctcaaaatgttctttacg atgccattgggatatatcaacggtggtatatccagtgatttttttctccattttagcttccttagctcctgaaaatctcg ataactcaaaaaatacgcccggtagtgatcttatttcattatggtgaaagttggaacctcttacgtgccgatcaacgtct cattttcgccaaaagttggcccagggcttcccggtatcaacagggacaccaggatttatttattctgcgaagtgatcttc cgtcacaggtatttattcgcgataagctcatggagcggcgtaaccgtcgcacaggaaggacagagaaagcgcggatctgg -continued gaagtgacggacagaacggtcaggacctggattggggaggcggttgccgccgctgctgctgacggtgtgacgttctctgt tccggtcacaccacatacgttccgccattcctatgcgatgcacatgctgtatgccggtataccgctgaaagttctgcaaa gcctgatgggacataagtccatcagttcaacggaagtctacacgaaggtttttgcgctggatgtggctgcccggcaccgg gtgcagtttgcgatgccggagtctgatgcggttgcgatgctgaaacaattatcctgagaataaatgccttggcctttata tggaaatgtggaactgagtggatatgctgtttttgtctgttaaacagagaagctggctgttatccactgagaagcgaacg aaacagtcgggaaaatctcccattatcgtagagatccgcattattaatctcaggagcctgtgtagcgtttataggaagta gtgttctgtcatgatgcctgcaagcggtaacgaaaacgatttgaatatgccttcaggaacaatagaaatcttcgtgcggt gttacgttgaagtggagcggattatgtcagcaatggacagaacaacctaatgaacacagaaccatgatgtggtctgtcct tttacagccagtagtgctcgccgcagtcgagcgacagggcgaagccctcgagtgagcgaggaagcaccagggaacagcac ttatatattctgcttacacacgatgcctgaaaaaacttcccttggggttatccacttatccacggggatatttttataat tatttttttatagtttttagatcttctttttagagcgccttgtaggcctttatccatgctggttctagagaaggtgtt gtgacaaattgccctttcagtgtgacaaatcaccctcaaatgacagtcctgtctgtgacaaattgcccttaaccctgtga caaattgccctcagaagaagctgtttttcacaaagttatccctgcttattgactctttttatttagtgtgacaatcta aaaacttgtcacacttcacatggatctgtcatggcggaaacagcggttatcaatcacaagaaacgtaaaaatagcccgcg aatcgtccagtcaaacgacctcactgaggcggcatatagtctctcccgggatcaaaaacgtatgctgtatctgttcgttg accagatcagaaaatctgatggcaccctacaggaacatgacggtatctgcgagatccatgttgctaaatatgctgaaata ttcggattgacctctgcggaagccagtaaggatatacggcaggcattgaagagtttcgcggggaaggaagtggtttttta tcgccctgaagaggatgccggcgatgaaaaaggctatgaatcttttccttggtttatcaaacgtgcgcacagtccatcca gagggctttacagtgtacatatcaacccatatctcattcccttctttatcgggttacagaaccggtttacgcagtttcgg cttagtgaaacaaaagaaatcaccaatccgtatgccatgcgtttatacgaatccctgtgtcagtatcgtaagccggatgg ctcaggcatcgtctctctgaaaatcgactggatcatagagcgttaccagctgcctcaaagttaccagcgtatgcctgact tccgccgccgcttcctgcaggtctgtgttaatgagatcaacagcagaactccaatgcgcctctcatacattgagaaaaag aaaggccgccagacgactcatatcgtattttccttccgcgatatcacttccatgacgacaggatagtctgagggttatct gtcacagatttgagggtggttcgtcacatttgttctgacctactgagggtaatttgtcacagttttgctgtttccttcag cctgcatggattttctcatactttttgaactgtaattttaaggaagccaaatttgagggcagtttgtcacagttgattt ccttctctttcccttcgtcatgtgacctgatatcgggggttagttcgtcatcattgatgagggttgattatcacagttta ttactctgaattggctatccgcgtgtgtacctctacctggagtttttcccacggtggatatttcttcttgcgctgagcgt aagagctatctgacagaacagttcttctttgcttcctcgccagttcgctcgctatgctcggttacacggctgcggcgagc gctagtgataataagtgactgaggtatgtgctcttcttatctccttttgtagtgttgctcttattttaaacaactttgcg gtttttttgatgactttgcgattttgttgttgctttgcagtaaattgcaagatttaataaaaaaacgcaaagcaatgatta aaggatgttcagaatgaaactcatggaaacacttaaccagtgcataaacgctggtcatgaaatgacgaaggctatcgcca ttgcacagtttaatgatgacagcccggaagcgaggaaaataacccggcgctggagaataggtgaagcagcggatttagtt ggggtttcttctcaggctatcagagatgccgagaaagcagggcgactaccgcacccggatatggaaattcgaggacgggt tgagcaacgtgttggttatacaattgaacaaattaatcatatgcgtgatgtgtttggtacgcgattgcgacgtgctgaag acgtatttccaccggtgatcggggttgctgcccataaaggtggcgtttacaaaacctcagtttctgttcatcttgctcag gatctggctctgaaggggctacgtgttttgctcgtggaaggtaacgacccccagggaacagcctcaatgtatcacggatg ggtaccagatcttcatattcatgcagaagacactctcctgcctttctatcttggggaaaaggacgatgtcacttatgcaa taaagcccacttgctggccggggcttgacattattccttcctgtctggctctgcaccgtattgaaactgagttaatgggc aaatttgatgaaggtaaactgcccaccgatccacacctgatgctccgactggccattgaaactgttgctcatgactatga tgtcatagttattgacagcgcgcctaacctgggtatcggcacgattaatgtcgtatgtgctgctgatgtgctgattgttc -continued ccacgcctgctgagttgtttgactacacctccgcactgcagtttttcgatatgcttcgtgatctgctcaagaacgttgat cttaaagggttcgagcctgatgtacgtattttgcttaccaaatacagcaatagtaatggctctcagtccccgtggatgga ggagcaaattcgggatgcctggggaagcatggttctaaaaaatgttgtacgtgaaacggatgaagttggtaaaggtcaga tccggatgagaactgtttttgaacaggccattgatcaacgctcttcaactggtgcctggagaaatgctctttctatttgg gaacctgtctgcaatgaaattttcgatcgtctgattaaaccacgctgggagattagataatgaagcgtgcgcctgttatt ccaaaacatacgctcaatactcaaccggttgaagatacttcgttatcgacaccagctgccccgatggtggattcgttaat tgcgcgcgtaggagtaatggctcgcggtaatgccattactttgcctgtatgtggtcgggatgtgaagtttactcttgaag tgctccggggtgatagtgttgagaagacctctcgggtatggtcaggtaatgaacgtgaccaggagctgcttactgaggac gcactggatgatctcatcccttcttttctactgactggtcaacagacaccggcgttcggtcgaagagtatctggtgtcat agaaattgccgatgggagtcgccgtcgtaaagctgctgcacttaccgaaagtgattatcgtgttctggttggcgagctgg atgatgagcagatggctgcattatccagattgggtaacgattatcgcccaacaagtgcttatgaacgtggtcagcgttat gcaagccgattgcagaatgaatttgctggaaatatttctgcgctggctgatgcggaaaatatttcacgtaagattattac ccgctgtatcaacaccgccaaattgcctaaatcagttgttgctcttttttctcaccccggtgaactatctgcccggtcag gtgatgcacttcaaaaagcctttacagataaagaggaattacttaagcagcaggcatctaaccttcatgagcagaaaaaa gctggggtgatatttgaagctgaagaagttatcactcttttaacttctgtgcttaaaacgtcatctgcatcaagaactag tttaagctcacgacatcagtttgctcctggagcgacagtattgtataagggcgataaaatggtgcttaacctggacaggt ctcgtgttccaactgagtgtatagagaaaattgaggccattcttaaggaacttgaaaagccagcaccctgatgcgaccac gttttagtctacgtttatctgtctttacttaatgtcctttgttacaggccagaaagcataactggcctgaatattctctc tgggcccactgttccacttgtatcgtcggtctgataatcagactgggaccacggtcccactcgtatcgtcggtctgatta ttagtctgggaccacggtcccactcgtatcgtcggtctgattattagtctgggaccacggtcccactcgtatcgtcggtc tgataatcagactgggaccacggtcccactcgtatcgtcggtctgattattagtctgggaccatggtcccactcgtatcg tcggtctgattattagtctgggaccacggtcccactcgtatcgtcggtctgattattagtctggaaccacggtcccactc gtatcgtcggtctgattattagtctgggaccacggtcccactcgtatcgtcggtctgattattagtctgggaccacgatc ccactcgtgttgtcggtctgattatcggtctgggaccacggtcccacttgtattgtcgatcagactatcagcgtgagact acgattccatcaatgcctgtcaagggcaagtattgacatgtcgtcgtaacctgtagaacggagtaacctcggtgtgcggt tgtatgcctgctgtggattgctgctgtgtcctgcttatccacaacattttgcgcacggttatgtggacaaaatacctgtt accatttccatttaaatcatcatcaataatataccttattttggattgaagccaatatgataatgagggggtggagtttg tgacgtggcgcggggcgtgggaacggggcgggtgacgtagtagtgtggcggaagtgtgatgttgcaagtgtggcggaaca catgtaagcgacggatgtggcaaaagtgacgtttttggtgtgcgcccggtgtacacaggaagtgacaattttcgcgcggtt ttaggcggatgttgtagtaaatttgggcgtaaccgagtaagatttggccattttcgcgggaaaactgaataagaggaagt gaaatctgaataattttgtgttactcatagcgcgtaatatttgtctagggccgcggggactttgaccgtttacgtggaga ctcgcccaggtgtttttctcaggtgttttccgcgttccgggtcaaagttggcgtttt (Human Adenovirus 5 complete genome, 35938 nucleotides)

SEQ ID NO: 46

1 catcatcaat aatatacctt attttggatt gaagccaata tgataatgag ggggtggagt 61 ttgtgacgtg gcgcggggcg tgggaacggg gcgggtgacg tagtagtgtg gcggaagtgt 121 gatgttgcaa gtgtggcgga acacatgtaa gcgacggatg tggcaaaagt gacgtttttg 181 gtgtgcgccg gtgtacacag gaagtgacaa ttttcgcgcg gttttaggcg gatgttgtag 241 taaatttggg cgtaaccgag taagatttgg ccattttcgc gggaaaactg aataagagga 301 agtgaaatct gaataatttt gtgttactca tagcgcgtaa tatttgtcta gggccgcggg 361 gactttgacc gtttacgtgg agactcgccc aggtgttttt ctcaggtgtt ttccgcgttc 421 cgggtcaaag ttggcgtttt attattatag tcagctgacg tgtagtgtat ttatacccgg -continued

```
 481 tgagttcctc aagaggccac tcttgagtgc cagcgagtag agttttctcc tccgagccgc
 541 tccgacaccg ggactgaaaa tgagacatat tatctgccac ggaggtgtta ttaccgaaga
 601 aatggccgcc agtcttttgg accagctgat cgaagaggta ctggctgata atcttccacc
 661 tcctagccat tttgaaccac ctacccttca cgaactgtat gatttagacg tgacggcccc
 721 cgaagatccc aacgaggagg cggtttcgca gatttttccc gactctgtaa tgttggcggt
 781 gcaggaaggg attgacttac tcacttttcc gccggcgccc ggttctccgg agccgcctca
 841 cctttcccgg cagcccgagc agccggagca gagagccttg ggtccggttt ctatgccaaa
 901 ccttgtaccg gaggtgatcg atcttacctg ccacgaggct ggctttccac ccagtgacga
 961 cgaggatgaa gagggtgagg agtttgtgtt agattatgtg gagcaccccg ggcacggttg
1021 caggtcttgt cattatcacc ggaggaatac gggggaccca gatattatgt gttcgctttg
1081 ctatatgagg acctgtggca tgtttgtcta cagtaagtga aaattatggg cagtgggtga
1141 tagagtggtg ggtttggtgt ggtaattttt tttttaattt ttacagtttt gtggtttaaa
1201 gaattttgta ttgtgatttt tttaaaaggt cctgtgtctg aacctgagcc tgagcccgag
1261 ccagaaccgg agcctgcaag acctacccgc cgtcctaaaa tggcgcctgc tatcctgaga
1321 cgcccgacat cacctgtgtc tagagaatgc aatagtagta cggatagctg tgactccggt
1381 ccttctaaca cacctcctga gatacacccg gtggtcccgc tgtgccccat taaaccagtt
1441 gccgtgagag ttggtgggcg tcgccaggct gtggaatgta tcgaggactt gcttaacgag
1501 cctgggcaac ctttggactt gagctgtaaa cgccccaggc cataaggtgt aaacctgtga
1561 ttgcgtgtgt ggttaacgcc tttgtttgct gaatgagttg atgtaagttt aataaagggt
1621 gagataatgt ttaacttgca tggcgtgtta aatggggcgg ggcttaaagg gtatataatg
1681 cgccgtgggc taatcttggt tacatctgac ctcatggagg cttgggagtg tttggaagat
1741 ttttctgctg tgcgtaactt gctggaacag agctctaaca gtacctcttg gttttggagg
1801 tttctgtggg gctcatccca ggcaaagtta gtctgcagaa ttaaggagga ttacaagtgg
1861 gaatttgaag agcttttgaa atcctgtggt gagctgtttg attctttgaa tctgggtcac
1921 caggcgcttt tccaagagaa ggtcatcaag actttggatt tttccacacc ggggcgcgct
1981 gcggctgctg ttgctttttt gagttttata aaggataaat ggagcgaaga aacccatctg
2041 agcggggggt acctgctgga ttttctggcc atgcatctgt ggagagcggt tgtgagacac
2101 aagaatcgcc tgctactgtt gtcttccgtc cgcccggcga taataccgac ggaggagcag
2161 cagcagcagc aggaggaagc caggcggcgg cggcaggagc agagcccatg gaacccgaga
2221 gccggcctgg accctcggga atgaatgttg tacaggtggc tgaactgtat ccagaactga
2281 gacgcatttt gacaattaca gaggatgggc aggggctaaa gggggtaaag agggagcggg
2341 gggcttgtga ggctacagag gaggctagga atctagcttt tagcttaatg accagacacc
2401 gtcctgagtg tattactttt caacagatca aggataattg cgctaatgag cttgatctgc
2461 tggcgcagaa gtattccata gagcagctga ccacttactg gctgcagcca ggggatgatt
2521 ttgaggaggc tattagggta tatgcaaagg tggcacttag gccagattgc aagtacaaga
2581 tcagcaaact tgtaaatatc aggaattgtt gctacatttc tgggaacggg gccgaggtgg
2641 agatagatac ggaggatagg gtggccttta gatgtagcat gataaatatg tggccggggg
2701 tgcttggcat ggacggggtg gttattatga atgtaaggtt tactggcccc aattttagcg
2761 gtacggtttt cctggccaat accaacctta tcctacacgg tgtaagcttc tatgggttta
2821 acaatacctg tgtggaagcc tggaccgatg taagggttcg ggctgtgcc ttttactgct
```

-continued 2881 gctggaaggg ggtggtgtgt cgccccaaaa gcagggcttc aattaagaaa tgcctctttg 2941 aaaggtgtac cttgggtatc ctgtctgagg gtaactccag ggtgcgccac aatgtggcct 3001 ccgactgtgg ttgcttcatg ctagtgaaaa gcgtggctgt gattaagcat aacatggtat 3061 gtggcaactg cgaggacagg gcctctcaga tgctgacctg ctcggacggc aactgtcacc 3121 tgctgaagac cattcacgta gccagccact ctcgcaaggc ctggccagtg tttgagcata 3181 acatactgac ccgctgttcc ttgcatttgg gtaacaggag gggggtgttc ctaccttacc 3241 aatgcaattt gagtcacact aagatattgc ttgagcccga gagcatgtcc aaggtgaacc 3301 tgaacggggt gtttgacatg accatgaaga tctggaaggt gctgaggtac gatgagaccc 3361 gcaccaggtg cagaccctgc gagtgtggcg gtaaacatat taggaaccag cctgtgatgc 3421 tggatgtgac cgaggagctg aggcccgatc acttggtgct ggcctgcacc cgcgctgagt 3481 ttggctctag cgatgaagat acagattgag gtactgaaat gtgtgggcgt ggcttaaggg 3541 tgggaaagaa tatataaggt gggggtctta tgtagttttg tatctgtttt gcagcagccg 3601 ccgccgccat gagcaccaac tcgtttgatg gaagcattgt gagctcatat ttgacaacgc 3661 gcatgccccc atgggccggg gtgcgtcaga atgtgatggg ctccagcatt gatggtcgcc 3721 ccgtcctgcc cgcaaactct actaccttga cctacgagac cgtgtctgga acgccgttgg 3781 agactgcagc ctccgccgcc gcttcagccg ctgcagccac cgcccgcggg attgtgactg 3841 actttgcttt cctgagcccg cttgcaagca gtgcagcttc ccgttcatcc gcccgcgatg 3901 acaagttgac ggctcttttg gcacaattgg attctttgac ccgggaactt aatgtcgttt 3961 ctcagcagct gttggatctg cgccagcagg tttctgccct gaaggcttcc tcccctccca 4021 atgcggttta aaacataaat aaaaaaccag actctgtttg gatttggatc aagcaagtgt 4081 cttgctgtct ttatttaggg gttttgcgcg cgcggtaggc ccgggaccag cggtctcggt 4141 cgttgagggt cctgtgtatt ttttccagga cgtggtaaag gtgactctgg atgttcagat 4201 acatgggcat aagcccgtct ctggggtgga ggtagcacca ctgcagagct tcatgctgcg 4261 gggtggtgtt gtagatgatc cagtcgtagc aggagcgctg ggcgtggtgc ctaaaaatgt 4321 ctttcagtag caagctgatt gccaggggca ggcccttggt gtaagtgttt acaaagcggt 4381 taagctggga tgggtgcata cgtggggata tgagatgcat cttggactgt atttttaggt 4441 tggctatgtt cccagccata tccctccggg gattcatgtt gtgcagaacc accagcacag 4501 tgtatccggt gcacttggga aatttgtcat gtagcttaga aggaaatgcg tggaagaact 4561 tggagacgcc cttgtgacct ccaagatttt ccatgcattc gtccataatg atggcaatgg 4621 gcccacgggc ggcggcctgg gcgaagatat ttctgggatc actaacgtca tagttgtgtt 4681 ccaggatgag atcgtcatag gccattttta caaagcgcgg gcggagggtg ccagactgcg 4741 gtataatggt tccatccggc ccaggggcgt agttaccctc acagatttgc atttcccacg 4801 ctttgagttc agatgggggg atcatgtcta cctgcggggc gatgaagaaa acggtttccg 4861 gggtagggga gatcagctgg gaagaaagca ggttcctgag cagctgcgac ttaccgcagc 4921 cggtgggccc gtaaatcaca cctattaccg ggtgcaactg gtagttaaga gagctgcagc 4981 tgccgtcatc cctgagcagg ggggccactt cgttaagcat gtccctgact cgcatgtttt 5041 ccctgaccaa atccgccaga aggcgctcgc cgcccagcga tagcagttct tgcaaggaag 5101 caaagttttt caacggtttg agaccgtccg ccgtaggcat gcttttgagc gtttgaccaa 5161 gcagttccag gcggtcccac agctcggtca cctgctctac ggcatctcga tccagcatat 5221 ctcctcgttt cgcgggttgg ggcggctttc gctgtacggc agtagtcggt gctcgtccag 5281 acgggccagg gtcatgtctt tccacgggcg cagggtcctc gtcagcgtag tctgggtcac -continued 5341 ggtgaagggg tgcgctccgg gctgcgcgct ggccagggtg cgcttgaggc tggtcctgct
5401 ggtgctgaag cgctgccggt cttcgccctg cgcgtcggcc aggtagcatt tgaccatggt
5461 gtcatagtcc agcccctccg cggcgtggcc cttggcgcgc agcttgccct tggaggaggc
5521 gccgcacgag gggcagtgca gacttttgag ggcgtagagc ttgggcgcga gaaataccga
5581 ttccggggag taggcatccg cgccgcaggc cccgcagacg gtctcgcatt ccacgagcca
5641 ggtgagctct ggccgttcgg ggtcaaaaac caggtttccc ccatgctttt tgatgcgttt
5701 cttacctctg gtttccatga gccggtgtcc acgctcggtg acgaaaaggc tgtccgtgtc
5761 cccgtataca gacttgagag gcctgtcctc gagcggtgtt ccgcggtcct cctcgtatag
5821 aaactcggac cactctgaga caaaggctcg cgtccaggcc agcacgaagg aggctaagtg
5881 ggaggggtag cggtcgttgt ccactagggg gtccactcgc tccagggtgt gaagacacat
5941 gtcgccctct tcggcatcaa ggaaggtgat tggtttgtag gtgtaggcca cgtgaccggg
6001 tgttcctgaa ggggggctat aaaagggggt gggggcgcgt tcgtcctcac tctcttccgc
6061 atcgctgtct gcgagggcca gctgttgggg tgagtactcc ctctgaaaag cgggcatgac
6121 ttctgcgcta agattgtcag tttccaaaaa cgaggaggat ttgatattca cctggcccgc
6181 ggtgatgcct ttgagggtgg ccgcatccat ctggtcagaa aagacaatct ttttgttgtc
6241 aagcttggtg gcaaacgacc cgtagagggc gttggacagc aacttggcga tggagcgcag
6301 ggtttggttt ttgtcgcgat cggcgcgctc cttggccgcg atgtttagct gcacgtattc
6361 gcgcgcaacg caccgccatt cgggaaagac ggtggtgcgc tcgtcgggca ccaggtgcac
6421 gcgccaaccg cggttgtgca gggtgacaag gtcaacgctg gtggctacct ctccgcgtag
6481 gcgctcgttg gtccagcaga ggcggccgcc cttgcgcgag cagaatggcg gtagggggtc
6541 tagctgcgtc tcgtccgggg ggtctgcgtc cacggtaaag accccgggca gcaggcgcgc
6601 gtcgaagtag tctatcttgc atccttgcaa gtctagcgcc tgctgccatg cgcgggcggc
6661 aagcgcgcgc tcgtatgggt tgagtggggg accccatggc atggggtggg tgagcgcgga
6721 ggcgtacatg ccgcaaatgt cgtaaacgta gaggggctct ctgagtattc caagatatgt
6781 agggtagcat cttccaccgc ggatgctggc gcgcacgtaa tcgtatagtt cgtgcgaggg
6841 agcgaggagg tcgggaccga ggttgctacg ggcgggctgc tctgctcgga agactatctg
6901 cctgaagatg gcatgtgagt tggatgatat ggttggacgc tggaagacgt tgaagctggc
6961 gtctgtgaga cctaccgcgt cacgcacgaa ggaggcgtag gagtcgcgca gcttgttgac
7021 cagctcggcg gtgacctgca cgtctagggc gcagtagtcc agggtttcct tgatgatgtc
7081 atacttatcc tgtccctttt ttttccacag ctcgcggttg aggacaaact cttcgcggtc
7141 tttccagtac tcttggatcg gaaacccgtc ggcctccgaa cggtaagagc ctagcatgta
7201 gaactggttg acggcctggt aggcgcagca tcccttttct acgggtagcg cgtatgcctg
7261 cgcggccttc cggagcgagg tgtgggtgag cgcaaaggtg tccctgacca tgactttgag
7321 gtactggtat ttgaagtcag tgtcgtcgca tccgccctgc tcccagagca aaaagtccgt
7381 gcgctttttg gaacgcggat ttggcagggc gaaggtgaca tcgttgaaga gtatctttcc
7441 cgcgcgaggc ataaagttgc gtgtgatgcg gaagggtccc ggcacctcgg aacggttgtt
7501 aattacctgg gcggcgagca cgatctcgtc aaagccgttg atgttgtggc ccacaatgta
7561 aagttccaag aagcgcggga tgcccttgat ggaaggcaat tttttaagtt cctcgtaggt
7621 gagctcttca ggggagctga gcccgtgctc tgaaagggcc cagtctgcaa gatgagggtt
7681 ggaagcgacg aatgagctcc acaggtcacg ggccattagc atttgcaggt ggtcgcgaaa -continued 7741 ggtcctaaac tggcgaccta tggccatttt ttctggggtg atgcagtaga aggtaagcgg 7801 gtcttgttcc cagcggtccc atccaaggtt cgcggctagg tctcgcgcgg cagtcactag 7861 aggctcatct ccgccgaact tcatgaccag catgaagggc acgagctgct tcccaaaggc 7921 ccccatccaa gtataggtct ctacatcgta ggtgacaaag agacgctcgg tgcgaggatg 7981 cgagccgatc gggaagaact ggatctcccg ccaccaattg gaggagtggc tattgatgtg 8041 gtgaaagtag aagtccctgc gacgggccga acactcgtgc tggcttttgt aaaaacgtgc 8101 gcagtactgg cagcggtgca cgggctgtac atcctgcacg aggttgacct gacgaccgcg 8161 cacaaggaag cagagtggga atttgagccc ctcgcctggc gggtttggct ggtggtcttc 8221 tacttcggct gcttgtcctt gaccgtctgg ctgctcgagg ggagttacgg tggatcggac 8281 caccacgccg cgcgagccca aagtccagat gtccgcgcgc ggcggtcgga gcttgatgac 8341 aacatcgcgc agatgggagc tgtccatggt ctggagctcc cgcggcgtca ggtcaggcgg 8401 gagctcctgc aggtttacct cgcatagacg ggtcagggcg cgggctagat ccaggtgata 8461 cctaatttcc aggggctggt tggtggcggc gtcgatggct tgcaagaggc cgcatccccg 8521 cggcgcgact acggtaccgc gcggcgggcg gtgggccgcg ggggtgtcct tggatgatgc 8581 atctaaaagc ggtgacgcgg gcgagccccc ggaggtaggg ggggctccgg acccgccggg 8641 agagggggca ggggcacgtc ggcgccgcgc gcgggcagga gctggtgctg cgcgcgtagg 8701 ttgctggcga acgcgacgac gcggcggttg atctcctgaa tctggcgcct ctgcgtgaag 8761 acgacgggcc cggtgagctt gagcctgaaa gagagttcga cagaatcaat ttcggtgtcg 8821 ttgacggcgg cctggcgcaa aatctcctgc acgtctcctg agttgtcttg ataggcgatc 8881 tcggccatga actgctcgat ctcttcctcc tggagatctc cgcgtccggc tcgctccacg 8941 gtggcggcga ggtcgttgga aatgcgggcc atgagctgcg agaaggcgtt gaggcctccc 9001 tcgttccaga cgcggctgta gaccacgccc ccttcggcat cgcgggcgcg catgaccacc 9061 tgcgcgagat tgagctccac gtgccgggcg aagacggcgt agtttcgcag gcgctgaaag 9121 aggtagttga gggtggtggc ggtgtgttct gccacgaaga agtacataac ccagcgtcgc 9181 aacgtggatt cgttgatatc ccccaaggcc tcaaggcgct ccatggcctc gtagaagtcc 9241 acggcgaagt tgaaaaactg ggagttgcgc gccgacacgg ttaactcctc ctccagaaga 9301 cggatgagct cggcgacagt gtcgcgcacc tcgcgctcaa aggctacagg ggcctcttct 9361 tcttcttcaa tctcctcttc cataagggcc tccccttctt cttcttctgg cggcggtggg 9421 ggaggggggga cacggcggcg acgacggcgc accgggaggc ggtcgacaaa gcgctcgatc 9481 atctccccgc ggcgacggcg catggtctcg gtgacggcgc ggccgttctc gcgggggcgc 9541 agttggaaga cgccgcccgt catgtcccgg ttatgggttg gcgggggggct gccatgcggc 9601 agggatacgg cgctaacgat gcatctcaac aattgttgtg taggtactcc gccgccgagg 9661 gacctgagcg agtccgcatc gaccggatcg gaaaacctct cgagaaaggc gtctaaccag 9721 tcacagtcgc aaggtaggct gagcaccgtg gcgggcggca gcgggcggcg gtcggggttg 9781 tttctggcgg aggtgctgct gatgatgtaa ttaaagtagg cggtcttgag acggcggatg 9841 gtcgacagaa gcaccatgtc cttgggtccg gcctgctgaa tgcgcaggcg gtcggccatg 9901 ccccaggctt cgttttgaca tcggcgcagg tctttgtagt agtcttgcat gagcctttct 9961 accggcactt cttcttctcc ttcctcttgt cctgcatctc ttgcatctat cgctgcggcg 10021 gcggcggagt ttggccgtag gtggcgccct cttcctccca tgcgtgtgac cccgaagccc 10081 ctcatcggct gaagcagggc taggtcggcg acaacgcgct cggctaatat ggcctgctgc 10141 acctgcgtga gggtagactg gaagtcatcc atgtccacaa agcggtggta tgcgcccgtg -continued 10201 ttgatggtgt aagtgcagtt ggccataacg gaccagttaa cggtctggtg acccggctgc 10261 gagagctcgg tgtacctgag acgcgagtaa gccctcgagt caaatacgta gtcgttgcaa 10321 gtccgcacca ggtactggta tcccaccaaa aagtgcggcg gcggctggcg gtagaggggc 10381 cagcgtaggg tggccggggc tccgggggcg agatcttcca acataaggcg atgatatccg 10441 tagatgtacc tggacatcca ggtgatgccg gcggcggtgg tggaggcgcg cggaaagtcg 10501 cggacgcggt tccagatgtt gcgcagcggc aaaaagtgct ccatggtcgg gacgctctgg 10561 ccggtcaggc gcgcgcaatc gttgacgctc tagaccgtgc aaaaggagag cctgtaagcg 10621 ggcactcttc cgtggtctgg tggataaatt cgcaagggta tcatggcgga cgaccggggt 10681 tcgagccccg tatccggccg tccgccgtga tccatgcggt taccgcccgc gtgtcgaacc 10741 caggtgtgcg acgtcagaca acgggggagt gctccttttg gcttccttcc aggcgcggcg 10801 gctgctgcgc tagctttttt ggccactggc cgcgcgcagc gtaagcggtt aggctggaaa 10861 gcgaaagcat taagtggctc gctccctgta gccggagggt tattttccaa gggttgagtc 10921 gcgggacccc cggttcgagt ctcggaccgg ccggactgcg gcgaacgggg gtttgcctcc 10981 ccgtcatgca agaccccgct tgcaaattcc tccggaaaca gggacgagcc cctttttttgc 11041 ttttcccaga tgcatccggt gctgcggcag atgcgccccc ctcctcagca gcggcaagag 11101 caagagcagc ggcagacatg cagggcaccc tcccctcctc ctaccgcgtc aggaggggcg 11161 acatccgcgg ttgacgcggc agcagatggt gattacgaac ccccgcggcg ccgggcccgg 11221 cactacctgg acttggagga gggcgagggc ctggcgcggc taggagcgcc ctctcctgag 11281 cggtacccaa gggtgcagct gaagcgtgat acgcgtgagg cgtacgtgcc gcggcagaac 11341 ctgtttcgcg accgcgaggg agaggagccc gaggagatgc gggatcgaaa gttccacgca 11401 gggcgcgagc tgcggcatgg cctgaatcgc gagcggttgc tgcgcgagga ggactttgag 11461 cccgacgcgc gaaccgggat tagtcccgcg cgcgcacacg tggcggccgc cgacctggta 11521 accgcatacg agcagacggt gaaccaggag attaactttc aaaaaagctt taacaaccac 11581 gtgcgtacgc ttgtggcgcg cgaggaggtg gctataggac tgatgcatct gtgggacttt 11641 gtaagcgcgc tggagcaaaa cccaaatagc aagccgctca tggcgcagct gttccttata 11701 gtgcagcaca gcagggacaa cgaggcattc agggatgcgc tgctaaacat agtagagccc 11761 gagggccgct ggctgctcga tttgataaac atcctgcaga gcatagtggt gcaggagcgc 11821 agcttgagcc tggctgacaa ggtggccgcc atcaactatt ccatgcttag cctgggcaag 11881 ttttacgccc gcaagatata ccatacccct tacgttccca tagacaagga ggtaaagatc 11941 gaggggttct acatgcgcat ggcgctgaag gtgcttacct tgagcgacga cctgggcgtt 12001 tatcgcaacg agcgcatcca caaggccgtg agcgtgagcc ggcggcgcga gctcagcgac 12061 cgcgagctga tgcacagcct gcaaagggcc ctggctggca cgggcagcgg cgatagagag 12121 gccgagtcct actttgacgc gggcgctgac ctgcgctggg ccccaagccg acgcgccctg 12181 gaggcagctg gggccggacc tgggctggcg gtggcacccg cgcgcgctgg caacgtcggc 12241 ggcgtggagg aatatgacga ggacgatgag tacgagccag aggacggcga gtactaagcg 12301 gtgatgtttc tgatcagatg atgcaagacg caacggaccc ggcggtgcgg gcggcgctgc 12361 agagccagcc gtccggcctt aactccacgg acgactggcg ccaggtcatg gaccgcatca 12421 tgtcgctgac tgcgcgcaat cctgacgcgt tccggcagca gccgcaggcc aaccggctct 12481 ccgcaattct ggaagcggtg gtcccggcgc gcgcaaaccc cacgcacgag aaggtgctgg 12541 cgatcgtaaa cgcgctggcc gaaaacaggg ccatccggcc cgacgaggcc ggcctggtct -continued 12601 acgacgcgct gcttcagcgc gtggctcgtt acaacagcgg caacgtgcag accaacctgg 12661 accggctggt gggggatgtg cgcgaggccg tggcgcagcg tgagcgcgcg cagcagcagg 12721 gcaacctggg ctccatggtt gcactaaacg ccttcctgag tacacagccc gccaacgtgc 12781 cgcggggaca ggaggactac accaactttg tgagcgcact gcggctaatg gtgactgaga 12841 caccgcaaag tgaggtgtac cagtctgggc cagactattt tttccagacc agtagacaag 12901 gcctgcagac cgtaaacctg agccaggctt tcaaaaactt gcaggggctg tggggggtgc 12961 gggctcccac aggcgaccgc gcgaccgtgt ctagcttgct gacgcccaac tcgcgcctgt 13021 tgctgctgct aatagcgccc ttcacggaca gtggcagcgt gtcccgggac acatacctag 13081 gtcacttgct gacactgtac cgcgaggcca taggtcaggc gcatgtggac gagcatactt 13141 tccaggagat tacaagtgtc agccgcgcgc tggggcagga ggacacgggc agcctggagg 13201 caaccctaaa ctacctgctg accaaccggc ggcagaagat cccctcgttg cacagtttaa 13261 acagcgagga ggagcgcatt ttgcgctacg tgcagcagag cgtgagcctt aacctgatgc 13321 gcgacggggt aacgcccagc gtggcgctgg acatgaccgc gcgcaacatg gaaccgggca 13381 tgtatgcctc aaaccggccg tttatcaacc gcctaatgga ctacttgcat cgcgcggccg 13441 ccgtgaaccc cgagtatttc accaatgcca tcttgaaccc gcactggcta ccgccccctg 13501 gtttctacac cgggggattc gaggtgcccg agggtaacga tggattcctc tgggacgaca 13561 tagacgacag cgtgttttcc ccgcaaccgc agaccctgct agagttgcaa cagcgcgagc 13621 aggcagaggc ggcgctgcga aaggaaagct tccgcaggcc aagcagcttg tccgatctag 13681 gcgctgcggc cccgcggtca gatgctagta gcccatttcc aagcttgata gggtctctta 13741 ccagcactcg caccacccgc ccgcgcctgc tgggcgagga ggagtaccta aacaactcgc 13801 tgctgcagcc gcagcgcgaa aaaaacctgc ctccggcatt tcccaacaac gggatagaga 13861 gcctagtgga caagatgagt agatggaaga cgtacgcgca ggagcacagg gacgtgccag 13921 gcccgcgccc gcccacccgt cgtcaaaggc acgaccgtca gcggggtctg gtgtgggagg 13981 acgatgactc ggcagacgac agcagcgtcc tggatttggg agggagtggc aacccgtttg 14041 cgcaccttcg ccccaggctg gggagaatgt tttaaaaaaa aaaaagcatg atgcaaaata 14101 aaaaactcac caaggccatg gcaccgagcg ttggttttct tgtattcccc ttagtatgcg 14161 gcgcgcggcg atgtatgagg aaggtcctcc tccctcctac gagagtgtgg tgagcgcggc 14221 gccagtggcg gcggcgctgg gttctccctt cgatgctccc ctggacccgc cgtttgtgcc 14281 tccgcggtac ctgcggccta ccggggggag aaacagcatc cgttactctg agttggcacc 14341 cctattcgac accacccgtg tgtacctggt ggacaacaag tcaacggatg tggcatccct 14401 gaactaccag aacgaccaca gcaactttct gaccacggtc attcaaaaca atgactacag 14461 cccgggggag gcaagcacac agaccatcaa tcttgacgac cggtcgcact ggggcggcga 14521 cctgaaaacc atcctgcata ccaacatgcc aaatgtgaac gagttcatgt ttaccaataa 14581 gtttaaggcg cgggtgatgg tgtcgcgctt gcctactaag gacaatcagg tggagctgaa 14641 atacgagtgg gtggagttca cgctgcccga gggcaactac tccgagacca tgaccataga 14701 ccttatgaac aacgcgatcg tggagcacta cttgaaagtg ggcagacaga acggggttct 14761 ggaaagcgac atcggggtaa agtttgacac ccgcaacttc agactggggt ttgaccccgt 14821 cactggtctt gtcatgcctg gggtatatac aaacgaagcc ttccatccag acatcatttt 14881 gctgccagga tgcggggtgg acttcaccca cagccgcctg agcaacttgt tgggcatccg 14941 caagcggcaa cccttccagg agggctttag gatcacctac gatgatctgg agggtggtaa 15001 cattcccgca ctgttggatg tggacgccta ccaggcgagc ttgaaagatg acaccgaaca -continued 15061 gggcgggggt ggcgcaggcg gcagcaacag cagtggcagc ggcgcggaag agaactccaa
15121 cgcggcagcc gcggcaatgc agccggtgga ggacatgaac gatcatgcca ttcgcggcga
15181 cacctttgcc acacgggctg aggagaagcg cgctgaggcc gaagcagcgg ccgaagctgc
15241 cgcccccgct gcgcaacccg aggtcgagaa gcctcagaag aaaccggtga tcaaacccct
15301 gacagaggac agcaagaaac gcagttacaa cctaataagc aatgacagca ccttcaccca
15361 gtaccgcagc tggtaccttg catacaacta cggcgaccct cagaccggaa tccgctcatg
15421 gaccctgctt tgcactcctg acgtaacctg cggctcggag caggtctact ggtcgttgcc
15481 agacatgatg caagaccccg tgaccttccg ctccacgcgc cagatcagca actttccggt
15541 ggtgggcgcc gagctgttgc ccgtgcactc caagagcttc tacaacgacc aggccgtcta
15601 ctcccaactc atccgccagt ttacctctct gacccacgtg ttcaatcgct ttcccgagaa
15661 ccagattttg gcgcgcccgc cagcccccac catcaccacc gtcagtgaaa acgttcctgc
15721 tctcacagat cacgggacgc taccgctgcg caacagcatc ggaggagtcc agcgagtgac
15781 cattactgac gccagacgcc gcacctgccc ctacgtttac aaggccctgg gcatagtctc
15841 gccgcgcgtc ctatcgagcc gcactttttg agcaagcatg tccatcctta tatcgcccag
15901 caataacaca ggctggggcc tgcgcttccc aagcaagatg tttggcgggg ccaagaagcg
15961 ctccgaccaa cacccagtgc gcgtgcgcgg gcactaccgc gcgccctggg gcgcgcacaa
16021 acgcggccgc actgggcgca ccaccgtcga tgacgccatc gacgcggtgg tggaggaggc
16081 gcgcaactac acgcccacgc cgccaccagt gtccacagtg gacgcggcca ttcagaccgt
16141 ggtgcgcgga gcccggcgct atgctaaaat gaagagacgg cggaggcgcg tagcacgtcg
16201 ccaccgccgc cgacccggca ctgccgccca acgcgcggcg gcggccctgc ttaaccgcgc
16261 acgtcgcacc ggccgacggg cggccatgcg ggccgctcga aggctggccg cgggtattgt
16321 cactgtgccc cccaggtcca ggcgacgagc ggccgccgca gcagccgcgg ccattagtgc
16381 tatgactcag ggtcgcaggg gcaacgtgta ttgggtgcgc gactcggtta gcggcctgcg
16441 cgtgcccgtg cgcacccgcc ccccgcgcaa ctagattgca agaaaaaact acttagactc
16501 gtactgttgt atgtatccag cggcggcggc gcgcaacgaa gctatgtcca agcgcaaaat
16561 caaagaagag atgctccagg tcatcgcgcc ggagatctat ggccccccga agaaggaaga
16621 gcaggattac aagccccgaa agctaaagcg ggtcaaaaag aaaaagaaag atgatgatga
16681 tgaacttgac gacgaggtgg aactgctgca cgctaccgcg cccaggcgac gggtacagtg
16741 gaaaggtcga cgcgtaaaac gtgttttgcg acccggcacc accgtagtct ttacgcccgg
16801 tgagcgctcc acccgcacct acaagcgcgt gtatgatgag gtgtacggcg acgaggacct
16861 gcttgagcag gccaacgagc gcctcgggga gtttgcctac ggaaagcggc ataaggacat
16921 gctggcgttg ccgctggacg agggcaaccc aacacctagc ctaaagcccg taacactgca
16981 gcaggtgctg cccgcgcttg caccgtccga agaaaagcgc ggcctaaagc gcgagtctgg
17041 tgacttggca cccaccgtgc agctgatggt acccaagcgc cagcgactgg aagatgtctt
17101 ggaaaaaatg accgtggaac ctgggctgga gcccgaggtc cgcgtgcggc caatcaagca
17161 ggtggcgccg ggactgggcg tgcagaccgt ggacgttcag atacccacta ccagtagcac
17221 cagtattgcc accgccacag agggcatgga gacacaaacg tccccggttg cctcagcggt
17281 ggcggatgcc gcggtgcagg cggtcgctgc ggccgcgtcc aagacctcta cggaggtgca
17341 aacggacccg tggatgtttc gcgtttcagc cccccggcgc ccgcgcggtt cgaggaagta
17401 cggcgccgcc agcgcgctac tgcccgaata tgccctacat ccttccattg cgcctacccc -continued 17461 cggctatcgt ggctacacct accgccccag aagacgagca actacccgac gccgaaccac 17521 cactggaacc cgccgccgcc gtcgccgtcg ccagcccgtg ctggccccga tttccgtgcg 17581 cagggtggct cgcgaaggag gcaggaccct ggtgctgcca acagcgcgct accaccccag 17641 catcgtttaa aagccggtct ttgtggttct tgcagatatg gccctcacct gccgcctccg 17701 tttcccggtg ccgggattcc gaggaagaat gcaccgtagg aggggcatgg ccggccacgg 17761 cctgacgggc ggcatgcgtc gtgcgcacca ccggcggcgg cgcgcgtcgc accgtcgcat 17821 gcgcggcggt atcctgcccc tccttattcc actgatcgcc gcggcgattg gcgccgtgcc 17881 cggaattgca tccgtggcct tgcaggcgca gagacactga ttaaaaacaa gttgcatgtg 17941 gaaaaatcaa aataaaaagt ctggactctc acgctcgctt ggtcctgtaa ctattttgta 18001 gaatggaaga catcaacttt gcgtctctgg ccccgcgaca cggctcgcgc ccgttcatgg 18061 gaaactggca agatatcggc accagcaata tgagcggtgg cgccttcagc tggggctcgc 18121 tgtggagcgg cattaaaaat ttcggttcca ccgttaagaa ctatggcagc aaggcctgga 18181 acagcagcac aggccagatg ctgagggata agttgaaaga gcaaaatttc caacaaaagg 18241 tggtagatgg cctggcctct ggcattagcg gggtggtgga cctggccaac caggcagtgc 18301 aaaataagat taacagtaag cttgatcccc gccctcccgt agaggagcct ccaccggccg 18361 tggagacagt gtctccagag gggcgtggcg aaaagcgtcc gcgccccgac agggaagaaa 18421 ctctggtgac gcaaatagac gagcctccct cgtacgagga ggcactaaag caaggcctgc 18481 ccaccacccg tcccatcgcg cccatggcta ccggagtgct gggccagcac acacccgtaa 18541 cgctggacct gcctcccccc gccgacaccc agcagaaacc tgtgctgcca ggcccgaccg 18601 ccgttgttgt aacccgtcct agccgcgcgt ccctgcgccg cgccgccagc ggtccgcgat 18661 cgttgcggcc cgtagccagt ggcaactggc aaagcacact gaacagcatc gtgggtctgg 18721 gggtgcaatc cctgaagcgc cgacgatgct tctgaatagc taacgtgtcg tatgtgtgtc 18781 atgtatgcgt ccatgtcgcc gccagaggag ctgctgagcc gccgcgcgcc cgctttccaa 18841 gatggctacc ccttcgatga tgccgcagtg gtcttacatg cacatctcgg gccaggacgc 18901 ctcggagtac ctgagccccg ggctggtgca gtttgcccgc gccaccgaga cgtacttcag 18961 cctgaataac aagtttagaa accccacggt ggcgcctacg cacgacgtga ccacagaccg 19021 gtcccagcgt ttgacgctgc ggttcatccc tgtggaccgt gaggatactg cgtactcgta 19081 caaggcgcgg ttcaccctag ctgtgggtga taaccgtgtg ctggacatgg cttccacgta 19141 ctttgacatc cgcggcgtgc tggacagggg ccctactttt aagccctact ctggcactgc 19201 ctacaacgcc ctggctccca agggtgcccc aaatccttgc gaatgggatg aagctgctac 19261 tgctcttgaa ataaacctag aagaagagga cgatgacaac gaagacgaag tagacgagca 19321 agctgagcag caaaaaactc acgtatttgg gcaggcgcct tattctggta taaatattac 19381 aaaggagggt attcaaatag gtgtcgaagg tcaaacacct aaatatgccg ataaaacatt 19441 tcaacctgaa cctcaaatag gagaatctca gtggtacgaa actgaaatta atcatgcagc 19501 tgggagagtc cttaaaaaga ctaccccaat gaaaccatgt tacggttcat atgcaaaacc 19561 cacaaatgaa aatggagggc aaggcattct tgtaaagcaa caaaatggaa agctagaaag 19621 tcaagtggaa atgcaatttt tctcaactac tgaggcgacc gcaggcaatg gtgataactt 19681 gactcctaaa gtggtattgt acagtgaaga tgtagatata gaaaccccag acactcatat 19741 ttcttacatg cccactatta aggaaggtaa ctcacgagaa ctaatgggcc aacaatctat 19801 gcccaacagg cctaattaca ttgcttttag ggacaatttt attggtctaa tgtattacaa 19861 cagcacgggt aatatgggtg ttctggcggg ccaagcatcg cagttgaatg ctgttgtaga -continued 19921 tttgcaagac agaaacacag agctttcata ccagcttttg cttgattcca ttggtgatag 19981 aaccaggtac ttttctatgt ggaatcaggc tgttgacagc tatgatccag atgttagaat 20041 tattgaaaat catggaactg aagatgaact tccaaattac tgctttccac tgggaggtgt 20101 gattaataca gagactctta ccaaggtaaa acctaaaaca ggtcaggaaa atggatggga 20161 aaaagatgct acagaatttt cagataaaaa tgaaataaga gttggaaata attttgccat 20221 ggaaatcaat ctaaatgcca acctgtggag aaatttcctg tactccaaca tagcgctgta 20281 tttgcccgac aagctaaagt acagtccttc caacgtaaaa atttctgata acccaaacac 20341 ctacgactac atgaacaagc gagtggtggc tcccgggtta gtggactgct acattaacct 20401 tggagcacgc tggtcccttg actatatgga caacgtcaac ccatttaacc accaccgcaa 20461 tgctggcctg cgctaccgct caatgttgct gggcaatggt cgctatgtgc ccttccacat 20521 ccaggtgcct cagaagttct ttgccattaa aaacctcctt ctcctgccgg gctcatacac 20581 ctacgagtgg aacttcagga aggatgttaa catggttctg cagagctccc taggaaatga 20641 cctaagggtt gacggagcca gcattaagtt tgatagcatt tgcctttacg ccaccttctt 20701 ccccatggcc cacaacaccg cctccacgct tgaggccatg cttagaaacg acaccaacga 20761 ccagtccttt aacgactatc tctccgccgc caacatgctc taccctatac ccgccaacgc 20821 taccaacgtg cccatatcca tcccctcccg caactgggcg gctttccgcg gctgggcctt 20881 cacgcgcctt aagactaagg aaaccccatc actgggctcg ggctacgacc cttattacac 20941 ctactctggc tctataccct acctagatgg aaccttttac ctcaaccaca cctttaagaa 21001 ggtggccatt acctttgact cttctgtcag ctggcctggc aatgaccgcc tgcttacccc 21061 caacgagttt gaaattaagc gctcagttga cggggagggt tacaacgttg cccagtgtaa 21121 catgaccaaa gactggttcc tggtacaaat gctagctaac tacaacattg gctaccaggg 21181 cttctatatc ccagagagct acaaggaccg catgtactcc ttctttagaa acttccagcc 21241 catgagccgt caggtggtgg atgatactaa atacaaggac taccaacagg tgggcatcct 21301 acaccaacac aacaactctg gatttgttgg ctaccttgcc cccaccatgc gcgaaggaca 21361 ggcctaccct gctaacttcc cctatccgct tataggcaag accgcagttg acagcattac 21421 ccagaaaaag tttctttgcg atcgcaccct ttggcgcatc ccattctcca gtaactttat 21481 gtccatgggc gcactcacag acctgggcca aaaccttctc tacgccaact ccgcccacgc 21541 gctagacatg acttttgagg tggatcccat ggacgagccc acccttcttt atgttttgtt 21601 tgaagtcttt gacgtggtcc gtgtgcaccg gccgcaccgc ggcgtcatcg aaaccgtgta 21661 cctgcgcacg cccttctcgg ccggcaacgc cacaacataa agaagcaagc aacatcaaca 21721 acagctgccg ccatgggctc cagtgagcag gaactgaaag ccattgtcaa agatcttggt 21781 tgtgggccat atttttttggg cacctatgac aagcgctttc caggctttgt ttctccacac 21841 aagctcgcct gcgccatagt caatacggcc ggtcgcgaga ctgggggcgt acactggatg 21901 gcctttgcct ggaacccgca ctcaaaaaca tgctacctct ttgagccctt tggcttttct 21961 gaccagcgac tcaagcaggt ttaccagttt gagtacgagt cactcctgcg ccgtagcgcc 22021 attgcttctt cccccgaccg ctgtataacg ctggaaaagt ccacccaaag cgtacagggg 22081 cccaactcgg ccgcctgtgg actattctgc tgcatgtttc tccacgcctt tgccaactgg 22141 ccccaaactc ccatggatca caaccccacc atgaacctta ttaccggggt acccaactcc 22201 atgctcaaca gtccccaggt acagcccacc ctgcgtcgca accaggaaca gctctacagc 22261 ttcctggagc gccactcgcc ctacttccgc agccacagtg cgcagattag gagcgccact -continued 22321 tctttttgtc acttgaaaaa catgtaaaaa taatgtacta gagacacttt caataaaggc 22381 aaatgctttt atttgtacac tctcgggtga ttatttaccc ccacccttgc cgtctgcgcc 22441 gtttaaaaat caaaggggtt ctgccgcgca tcgctatgcg ccactggcag ggacacgttg 22501 cgatactggt gtttagtgct ccacttaaac tcaggcacaa ccatccgcgg cagctcggtg 22561 aagttttcac tccacaggct gcgcaccatc accaacgcgt ttagcaggtc gggcgccgat 22621 atcttgaagt cgcagttggg gcctccgccc tgcgcgcgcg agttgcgata cacagggttg 22681 cagcactgga acactatcag cgccgggtgg tgcacgctgg ccagcacgct cttgtcggag 22741 atcagatccg cgtccaggtc ctccgcgttg ctcagggcga acggagtcaa ctttggtagc 22801 tgccttccca aaaagggcgc gtgcccaggc tttgagttgc actcgcaccg tagtggcatc 22861 aaaaggtgac cgtgcccggt ctgggcgtta ggatacagcg cctgcataaa agccttgatc 22921 tgcttaaaag ccacctgagc ctttgcgcct tcagagaaga acatgccgca agacttgccg 22981 gaaaactgat tggccggaca ggccgcgtcg tgcacgcagc accttgcgtc ggtgttggag 23041 atctgcacca catttcggcc ccaccggttc ttcacgatct tggccttgct agactgctcc 23101 ttcagcgcgc gctgcccgtt ttcgctcgtc acatccattt caatcacgtg ctccttattt 23161 atcataatgc ttccgtgtag acacttaagc tcgccttcga tctcagcgca gcggtgcagc 23221 cacaacgcgc agcccgtggg ctcgtgatgc ttgtaggtca cctctgcaaa cgactgcagg 23281 tacgcctgca ggaatcgccc catcatcgtc acaaaggtct tgttgctggt gaaggtcagc 23341 tgcaacccgc ggtgctcctc gttcagccag gtcttgcata cggccgccag agcttccact 23401 tggtcaggca gtagtttgaa gttcgccttt agatcgttat ccacgtggta cttgtccatc 23461 agcgcgcgcg cagcctccat gcccttctcc cacgcagaca cgatcggcac actcagcggg 23521 ttcatcaccg taatttcact ttccgcttcg ctgggctctt cctcttcctc ttgcgtccgc 23581 ataccacgcg ccactgggtc gtcttcattc agccgccgca ctgtgcgctt acctcctttg 23641 ccatgcttga ttagcaccgg tgggttgctg aaacccacca tttgtagcgc cacatcttct 23701 ctttcttcct cgctgtccac gattacctct ggtgatggcg ggcgctcggg cttgggagaa 23761 gggcgcttct ttttcttctt gggcgcaatg gccaaatccg ccgccgaggt cgatggccgc 23821 gggctgggtg tgcgcggcac cagcgcgtct tgtgatgagt cttcctcgtc ctcggactcg 23881 atacgccgcc tcatccgctt ttttgggggc gcccggggag gcggcggcga cggggacggg 23941 gacgacacgt cctccatggt tgggggacgt cgcgccgcac cgcgtccgcg ctcgggggtg 24001 gtttcgcgct gctcctcttc ccgactggcc atttccttct cctataggca gaaaaagatc 24061 atggagtcag tcgagaagaa ggacagccta accgccccct ctgagttcgc caccaccgcc 24121 tccaccgatg ccgccaacgc gcctaccacc ttccccgtcg aggcaccccc gcttgaggag 24181 gaggaagtga ttatcgagca ggacccaggt tttgtaagcg aagacgacga ggaccgctca 24241 gtaccaacag aggataaaaa gcaagaccag gacaacgcag aggcaaacga ggaacaagtc 24301 gggcgggggg acgaaaggca tggcgactac ctagatgtgg gagacgacgt gctgttgaag 24361 catctgcagc gccagtgcgc cattatctgc gacgcgttgc aagagcgcag cgatgtgccc 24421 ctcgccatag cggatgtcag ccttgcctac gaacgccacc tattctcacc gcgcgtaccc 24481 cccaaacgcc aagaaaacgg cacatgcgag cccaacccgc gcctcaactt ctaccccgta 24541 tttgccgtgc cagaggtgct tgccacctat cacatctttt tccaaaactg caagataccc 24601 ctatcctgcc gtgccaaccg cagccgagcg gacaagcagc tggccttgcg gcagggcgct 24661 gtcatacctg atatcgcctc gctcaacgaa gtgccaaaaa tctttgaggg tcttggacgc 24721 gacgagaagc gcgcggcaaa cgctctgcaa caggaaaaca gcgaaaatga aagtcactct -continued 24781 ggagtgttgg tggaactcga gggtgacaac gcgcgcctag ccgtactaaa acgcagcatc 24841 gaggtcaccc actttgccta cccggcactt aacctacccc ccaaggtcat gagcacagtc 24901 atgagtgagc tgatcgtgcg ccgtgcgcag cccctggaga gggatgcaaa tttgcaagaa 24961 caaacagagg agggcctacc cgcagttggc gacgagcagc tagcgcgctg gcttcaaacg 25021 cgcgagcctg ccgacttgga ggagcgacgc aaactaatga tggccgcagt gctcgttacc 25081 gtggagcttg agtgcatgca gcggttcttt gctgacccgg agatgcagcg caagctagag 25141 gaaacattgc actacacctt tcgacagggc tacgtacgcc aggcctgcaa gatctccaac 25201 gtggagctct gcaacctggt ctcctacctt ggaattttgc acgaaaaccg ccttgggcaa 25261 aacgtgcttc attccacgct caagggcgag gcgcgccgcg actacgtccg cgactgcgtt 25321 tacttatttc tatgctacac ctggcagacg gccatgggcg tttggcagca gtgcttggag 25381 gagtgcaacc tcaaggagct gcagaaactg ctaaagcaaa acttgaagga cctatggacg 25441 gccttcaacg agcgctccgt ggccgcgcac ctggcggaca tcattttccc cgaacgcctg 25501 cttaaaaccc tgcaacaggg tctgccagac ttcaccagtc aaagcatgtt gcagaacttt 25561 aggaacttta tcctagagcg ctcaggaatc ttgcccgcca cctgctgtgc acttcctagc 25621 gactttgtgc ccattaagta ccgcgaatgc cctccgccgc tttggggcca ctgctacctt 25681 ctgcagctag ccaactacct tgcctaccac tctgacataa tggaagacgt gagcggtgac 25741 ggtctactgg agtgtcactg tcgctgcaac ctatgcaccc cgcaccgctc cctggtttgc 25801 aattcgcagc tgcttaacga aagtcaaatt atcggtacct ttgagctgca gggtccctcg 25861 cctgacgaaa agtccgcggc tccggggttg aaactcactc cggggctgtg gacgtcggct 25921 taccttcgca aatttgtacc tgaggactac cacgcccacg agattaggtt ctacgaagac 25981 caatcccgcc cgccaaatgc ggagcttacc gcctgcgtca ttacccaggg ccacattctt 26041 ggccaattgc aagccatcaa caaagcccgc caagagtttc tgctacgaaa gggacggggg 26101 gtttacttgg acccccagtc cggcgaggag ctcaacccaa tcccccgcc gccgcagccc 26161 tatcagcagc agccgcgggc ccttgcttcc caggatggca cccaaaaaga agctgcagct 26221 gccgccgcca cccacggacg aggaggaata ctgggacagt caggcagagg aggttttgga 26281 cgaggaggag gaggacatga tggaagactg ggagagccta gacgaggaag cttccgaggt 26341 cgaagaggtg tcagacgaaa caccgtcacc ctcggtcgca ttcccctcgc cggcgcccca 26401 gaaatcggca accggttcca gcatggctac aacctccgct cctcaggcgc cgccggcact 26461 gcccgttcgc cgacccaacc gtagatggga caccactgga accagggccg gtaagtccaa 26521 gcagccgccg ccgttagccc aagagcaaca acagcgccaa ggctaccgct catggcgcgg 26581 gcacaagaac gccatagttg cttgcttgca agactgtggg ggcaacatct ccttcgcccg 26641 ccgctttctt ctctaccatc acggcgtggc cttcccccgt aacatcctgc attactaccg 26701 tcatctctac agcccatact gcaccggcgg cagcggcagc ggcagcaaca gcagcggcca 26761 cacagaagca aaggcgaccg gatagcaaga ctctgacaaa gcccaagaaa tccacagcgg 26821 cggcagcagc aggaggagga gcgctgcgtc tggcgcccaa cgaacccgta tcgacccgcg 26881 agcttagaaa caggattttt cccactctgt atgctatatt tcaacagagc aggggccaag 26941 aacaagagct gaaaataaaa aacaggtctc tgcgatccct cacccgcagc tgcctgtatc 27001 acaaaagcga agatcagctt cggcgcacgc tggaagacgc ggaggctctc ttcagtaaat 27061 actgcgcgct gactcttaag gactagtttc gcgccctttc tcaaatttaa gcgcgaaaac 27121 tacgtcatct ccagcggcca cacccggcgc cagcacctgt cgtcagcgcc attatgagca -continued 27181 aggaaattcc cacgccctac atgtggagtt accagccaca aatgggactt gcggctggag
27241 ctgcccaaga ctactcaacc cgaataaact acatgagcgc gggaccccac atgatatccc
27301 gggtcaacgg aatccgcgcc caccgaaacc gaattctctt ggaacaggcg gctattacca
27361 ccacacctcg taataacctt aatccccgta gttggcccgc tgccctggtg taccaggaaa
27421 gtcccgctcc caccactgtg gtacttccca gagacgccca ggccgaagtt cagatgacta
27481 actcaggggc gcagcttgcg ggcggctttc gtcacagggt gcggtcgccc gggcagggta
27541 taactcacct gacaatcaga gggcgaggta ttcagctcaa cgacgagtcg gtgagctcct
27601 cgcttggtct ccgtccggac gggacatttc agatcggcgg cgccggccgt ccttcattca
27661 cgcctcgtca ggcaatccta actctgcaga cctcgtcctc tgagccgcgc tctggaggca
27721 ttggaactct gcaatttatt gaggagtttg tgccatcggt ctactttaac cccttctcgg
27781 gacctcccgg ccactatccg gatcaattta ttcctaactt tgacgcggta aaggactcgg
27841 cggacggcta cgactgaatg ttaagtggag aggcagagca actgcgcctg aaacacctgg
27901 tccactgtcg ccgccacaag tgctttgccc gcgactccgg tgagttttgc tactttgaat
27961 tgcccgagga tcatatcgag ggcccggcgc acggcgtccg gcttaccgcc cagggagagc
28021 ttgcccgtag cctgattcgg gagtttaccc agcgccccct gctagttgag cgggacaggg
28081 gaccctgtgt tctcactgtg atttgcaact gtcctaacct tggattacat caagatcttt
28141 gttgccatct ctgtgctgag tataataaat acagaaatta aaatatactg gggctcctat
28201 cgccatcctg taaacgccac cgtcttcacc cgcccaagca aaccaaggcg aaccttacct
28261 ggtactttta acatctctcc ctctgtgatt tacaacagtt tcaacccaga cggagtgagt
28321 ctacgagaga acctctccga gctcagctac tccatcagaa aaaacaccac cctccttacc
28381 tgccgggaac gtacgagtgc gtcaccggcc gctgcaccac acctaccgcc tgaccgtaaa
28441 ccagactttt tccggacaga cctcaataac tctgtttacc agaacaggag gtgagcttag
28501 aaaaccctta gggtattagg ccaaaggcgc agctactgtg gggtttatga acaattcaag
28561 caactctacg ggctattcta attcaggttt ctctagaatc ggggttgggg ttattctctg
28621 tcttgtgatt ctctttattc ttatactaac gcttctctgc ctaaggctcg ccgcctgctg
28681 tgtgcacatt tgcatttatt gtcagctttt taaacgctgg ggtcgccacc caagatgatt
28741 aggtacataa tcctaggttt actcaccctt gcgtcagccc acggtaccac ccaaaaggtg
28801 gattttaagg agccagcctg taatgttaca ttcgcagctg aagctaatga gtgcaccact
28861 cttataaaat gcaccacaga acatgaaaag ctgcttattc gccacaaaaa caaaattggc
28921 aagtatgctg tttatgctat ttggcagcca ggtgacacta cagagtataa tgttacagtt
28981 ttccagggta aaagtcataa aacttttatg tatactttc cattttatga aatgtgcgac
29041 attaccatgt acatgagcaa acagtataag ttgtggcccc cacaaaattg tgtggaaaac
29101 actggcactt tctgctgcac tgctatgcta attacagtgc tcgctttggt ctgtacccta
29161 ctctatatta aatacaaaag cagacgcagc tttattgagg aaaagaaaat gccttaattt
29221 actaagttac aaagctaatg tcaccactaa ctgctttact cgctgcttgc aaaacaaatt
29281 caaaaagtta gcattataat tagaatagga tttaaacccc ccggtcattt cctgctcaat
29341 accattcccc tgaacaattg actctatgtg ggatatgctc cagcgctaca accttgaagt
29401 caggcttcct ggatgtcagc atctgacttt ggccagcacc tgtcccgcgg atttgttcca
29461 gtccaactac agcgacccac cctaacagag atgaccaaca caaccaacgc ggccgccgct
29521 accggactta catctaccac aaatacaccc caagtttctg cctttgtcaa taactgggat
29581 aacttgggca tgtggtggtt ctccatagcg cttatgtttg tatgccttat tattatgtgg -continued 29641 ctcatctgct gcctaaagcg caaacgcgcc cgaccaccca tctatagtcc catcattgtg
29701 ctacacccaa acaatgatgg aatccataga ttggacggac tgaaacacat gttcttttct
29761 cttacagtat gattaaatga gacatgattc ctcgagtttt tatattactg acccttgttg
29821 cgctttttttg tgcgtgctcc acattggctg cggtttctca catcgaagta gactgcattc
29881 cagccttcac agtctatttg ctttacggat ttgtcaccct cacgctcatc tgcagcctca
29941 tcactgtggt catcgccttt atccagtgca ttgactgggt ctgtgtgcgc tttgcatatc
30001 tcagacacca tccccagtac agggacagga ctatagctga gcttcttaga attctttaat
30061 tatgaaattt actgtgactt ttctgctgat tatttgcacc ctatctgcgt tttgttcccc
30121 gacctccaag cctcaaagac atatatcatg cagattcact cgtatatgga atattccaag
30181 ttgctacaat gaaaaaagcg atctttccga agcctggtta tatgcaatca tctctgttat
30241 ggtgttctgc agtaccatct tagccctagc tatatatccc taccttgaca ttggctggaa
30301 acgaatagat gccatgaacc acccaacttt ccccgcgccc gctatgcttc cactgcaaca
30361 agttgttgcc ggcggctttg tcccagccaa tcagcctcgc cccacttctc ccaccccccac
30421 tgaaatcagc tactttaatc taacaggagg agatgactga caccctagat ctagaaatgg
30481 acggaattat tacagagcag cgcctgctag aaagacgcag ggcagcggcc gagcaacagc
30541 gcatgaatca agagctccaa gacatggtta acttgcacca gtgcaaaagg ggtatctttt
30601 gtctggtaaa gcaggccaaa gtcacctacg acagtaatac caccggacac cgccttagct
30661 acaagttgcc aaccaagcgt cagaaattgg tggtcatggt gggagaaaag cccattacca
30721 taactcagca ctcggtagaa accgaaggct gcattcactc accttgtcaa ggacctgagg
30781 atctctgcac ccttattaag accctgtgcg gtctcaaaga tcttattccc tttaactaat
30841 aaaaaaaaat aataaagcat cacttactta aaatcagtta gcaaatttct gtccagttta
30901 ttcagcagca cctccttgcc ctcctcccag ctctggtatt gcagcttcct cctggctgca
30961 aactttctcc acaatctaaa tggaatgtca gtttcctcct gttcctgtcc atccgcaccc
31021 actatcttca tgttgttgca gatgaagcgc gcaagaccgt ctgaagatac cttcaacccc
31081 gtgtatccat atgacacgga aaccggtcct ccaactgtgc cttttcttac tcctcccttt
31141 gtatccccca atgggtttca agagagtccc cctggggtac tctctttgcg cctatccgaa
31201 cctctagtta cctccaatgg catgcttgcg ctcaaaatgg gcaacggcct ctctctggac
31261 gaggccggca accttacctc ccaaaatgta accactgtga gcccacctct caaaaaaacc
31321 aagtcaaaca taaacctgga aatatctgca cccctcacag ttacctcaga agccctaact
31381 gtggctgccg ccgcacctct aatggtcgcg ggcaacacac tcaccatgca atcacaggcc
31441 ccgctaaccg tgcacgactc caaacttagc attgccaccc aaggacccct cacagtgtca
31501 gaaggaaagc tagccctgca aacatcaggc cccctcacca ccaccgatag cagtaccctt
31561 actatcactg cctcaccccc tctaactact gccactggta gcttgggcat tgacttgaaa
31621 gagcccattt atacacaaaa tggaaaacta ggactaaagt acggggctcc tttgcatgta
31681 acagacgacc taaacacttt gaccgtagca actggtccag gtgtgactat taataatact
31741 tccttgcaaa ctaaagttac tggagccttg ggttttgatt cacaaggcaa tatgcaactt
31801 aatgtagcag gaggactaag gattgattct caaaacagac gccttatact tgatgttagt
31861 tatccgtttg atgctcaaaa ccaactaaat ctaagactag gacagggccc tctttttata
31921 aactcagccc acaacttgga tattaactac aacaaaggcc tttacttgtt tacagcttca
31981 aacaattcca aaaagcttga ggttaaccta agcactgcca aggggttgat gtttgacgct -continued 32041 acagccatag ccattaatgc aggagatggg cttgaatttg gttcacctaa tgcaccaaac 32101 acaaatcccc tcaaaacaaa aattggccat ggcctagaat ttgattcaaa caaggctatg 32161 gttcctaaac taggaactgg ccttagtttt gacagcacag gtgccattac agtaggaaac 32221 aaaaataatg ataagctaac tttgtggacc acaccagctc catctcctaa ctgtagacta 32281 aatgcagaga aagatgctaa actcactttg gtcttaacaa aatgtggcag tcaaatactt 32341 gctacagttt cagttttggc tgttaaaggc agtttggctc caatatctgg aacagttcaa 32401 agtgctcatc ttattataag atttgacgaa aatggagtgc tactaaacaa ttccttcctg 32461 gacccagaat attggaactt tagaaatgga gatcttactg aaggcacagc ctatacaaac 32521 gctgttggat ttatgcctaa cctatcagct tatccaaaat ctcacggtaa aactgccaaa 32581 agtaacattg tcagtcaagt ttacttaaac ggagacaaaa ctaaacctgt aacactaacc 32641 attacactaa acggtacaca ggaaacagga gacacaactc caagtgcata ctctatgtca 32701 ttttcatggg actggtctgg ccacaactac attaatgaaa tatttgccac atcctcttac 32761 actttttcat acattgccca agaataaaga atcgtttgtg ttatgtttca acgtgtttat 32821 ttttcaattg cagaaaattt caagtcattt ttcattcagt agtatagccc caccaccaca 32881 tagcttatac agatcaccgt accttaatca aactcacaga accctagtat tcaacctgcc 32941 acctccctcc caacacacag agtacacagt cctttctccc cggctggcct taaaaagcat 33001 catatcatgg gtaacagaca tattcttagg tgttatattc cacacggttt cctgtcgagc 33061 caaacgctca tcagtgatat taataaactc cccgggcagc tcacttaagt tcatgtcgct 33121 gtccagctgc tgagccacag gctgctgtcc aacttgcggt tgcttaacgg gcggcgaagg 33181 agaagtccac gcctacatgg gggtagagtc ataatcgtgc atcaggatag ggcggtggtg 33241 ctgcagcagc gcgcgaataa actgctgccg ccgccgctcc gtcctgcagg aatacaacat 33301 ggcagtggtc tcctcagcga tgattcgcac cgcccgcagc ataaggcgcc ttgtcctccg 33361 ggcacagcag cgcaccctga tctcacttaa atcagcacag taactgcagc acagcaccac 33421 aatattgttc aaaatcccac agtgcaaggc gctgtatcca aagctcatgg cggggaccac 33481 agaacccacg tggccatcat accacaagcg caggtagatt aagtggcgac ccctcataaa 33541 cacgctggac ataaacatta cctcttttgg catgttgtaa ttcaccacct cccggtacca 33601 tataaacctc tgattaaaca tggcgccatc caccaccatc ctaaaccagc tggccaaaac 33661 ctgcccgccg gctatacact gcagggaacc gggactggaa caatgacagt ggagagccca 33721 ggactcgtaa ccatggatca tcatgctcgt catgatatca atgttggcac aacacaggca 33781 cacgtgcata cacttcctca ggattacaag ctcctcccgc gttagaacca tatcccaggg 33841 aacaacccat tcctgaatca gcgtaaatcc cacactgcag ggaagacctc gcacgtaact 33901 cacgttgtgc attgtcaaag tgttacattc gggcagcagc ggatgatcct ccagtatggt 33961 agcgcgggtt tctgtctcaa aaggaggtag acgatcccta ctgtacggag tgcgccgaga 34021 caaccgagat cgtgttggtc gtagtgtcat gccaaatgga acgccggacg tagtcatatt 34081 tcctgaagca aaaccaggtg cgggcgtgac aaacagatct gcgtctccgg tctcgccgct 34141 tagatcgctc tgtgtagtag ttgtagtata tccactctct caaagcatcc aggcgccccc 34201 tggcttcggg ttctatgtaa actccttcat gcgccgctgc cctgataaca tccaccaccg 34261 cagaataagc cacacccagc caacctacac attcgttctg cgagtcacac acgggaggag 34321 cgggaagagc tggaagaacc atgttttttt ttttattcca aaagattatc caaaacctca 34381 aaatgaagat ctattaagtg aacgcgctcc cctccggtgg cgtggtcaaa ctctacagcc 34441 aaagaacaga taatggcatt tgtaagatgt tgcacaatgg cttccaaaag gcaaacggcc -continued 34501 ctcacgtcca agtggacgta aaggctaaac ccttcagggt gaatctcctc tataaacatt 34561 ccagcacctt caaccatgcc caaataattc tcatctcgcc accttctcaa tatatctcta 34621 agcaaatccc gaatattaag tccggccatt gtaaaaatct gctccagagc gccctccacc 34681 ttcagcctca agcagcgaat catgattgca aaaattcagg ttcctcacag acctgtataa 34741 gattcaaaag cggaacatta acaaaaatac cgcgatcccg taggtccctt cgcagggcca 34801 gctgaacata atcgtgcagg tctgcacgga ccagcgcggc cacttccccg ccaggaacca 34861 tgacaaaaga acccacactg attatgacac gcatactcgg agctatgcta accagcgtag 34921 ccccgatgta agcttgttgc atgggcggcg atataaaatg caaggtgctg ctcaaaaaat 34981 caggcaaagc ctcgcgcaaa aaagaaagca catcgtagtc atgctcatgc agataaaggc 35041 aggtaagctc cggaaccacc acagaaaaag acaccatttt tctctcaaac atgtctgcgg 35101 gtttctgcat aaacacaaaa taaaataaca aaaaaacatt taaacattag aagcctgtct 35161 tacaacagga aaaacaaccc ttataagcat aagacggact acggccatgc cggcgtgacc 35221 gtaaaaaaac tggtcaccgt gattaaaaag caccaccgac agctcctcgg tcatgtccgg 35281 agtcataatg taagactcgg taaacacatc aggttgattc acatcggtca gtgctaaaaa 35341 gcgaccgaaa tagcccgggg gaatacatac ccgcaggcgt agagacaaca ttacagcccc 35401 cataggaggt ataacaaaat taataggaga gaaaaacaca taaacacctg aaaaaccctc 35461 ctgcctaggc aaaatagcac cctcccgctc cagaacaaca tacagcgctt ccacagcggc 35521 agccataaca gtcagcctta ccagtaaaaa agaaaaccta ttaaaaaaac accactcgac 35581 acggcaccag ctcaatcagt cacagtgtaa aaaagggcca agtgcagagc gagtatatat 35641 aggactaaaa aatgacgtaa cggttaaagt ccacaaaaaa cacccagaaa accgcacgcg 35701 aacctacgcc cagaaacgaa agccaaaaaa cccacaactt cctcaaatcg tcacttccgt 35761 tttcccacgt tacgtaactt cccattttaa gaaaactaca attcccaaca catacaagtt 35821 actccgccct aaaacctacg tcacccgccc cgttcccacg ccccgcgcca cgtcacaaac 35881 tccacccccct cattatcata ttggcttcaa tccaaaataa ggtatattat tgatgatg (L4-100K)

SEQ ID NO: 47

ATGGAGTCAGTCGAGAAGAAGGACAGCCTAACCGCCCCCTCTGAGTTCGCCACCACCGCCT

CCACCGATGCCGCCAACGCGCCTACCACCTTCCCCGTCGAGGCACCCCCGCTTGAGGAGGA

GGAAGTGATTATCGAGCAGGACCCAGGTTTTGTAAGCGAAGACGACGAGGACCGCTCAGTA

CCAACAGAGGATAAAAAGCAAGACCAGGACAACGCAGAGGCAAACGAGGAACAAGTCGGGC

GGGGGGACGAAAGGCATGGCGACTACCTAGATGTGGGAGACGACGTGCTGTTGAAGCATCT

GCAGCGCCAGTGCGCCATTATCTGCGACGCGTTGCAAGAGCGCAGCGATGTGCCCCTCGCC

ATAGCGGATGTCAGCCTTGCCTACGAACGCCACCTATTCTCACCGCGCGTACCCCCCAAAC

GCCAAGAAAACGGCACATGCGAGCCCAACCCGCGCCTCAACTTCTACCCCGTATTTGCCGT

GCCAGAGGTGCTTGCCACCTATCACATCTTTTTCCAAAACTGCAAGATACCCCTATCCTGC

CGTGCCAACCGCAGCCGAGCGGACAAGCAGCTGGCCTTGCGGCAGGGCGCTGTCATACCTG

ATATCGCCTCGCTCAACGAAGTGCCAAAAATCTTTGAGGGTCTTGGACGCGACGAGAAGCG

CGCGGCAAACGCTCTGCAACAGGAAAACAGCGAAAATGAAAGTCACTCTGGAGTGTTGGTG

GAACTCGAGGGTGACAACGCGCGCCTAGCCGTACTAAAACGCAGCATCGAGGTCACCCACT

TTGCCTACCCGGCACTTAACCTACCCCCCAAGGTCATGAGCACAGTCATGAGTGAGCTGAT

CGTGCGCCGTGCGCAGCCCCTGGAGAGGGATGCAAATTTGCAAGAACAAACAGAGGAGGGC

-continued

CTACCCGCAGTTGGCGACGAGCAGCTAGCGCGCTGGCTTCAAACGCGCGAGCCTGCCGACT

TGGAGGAGCGACGCAAACTAATGATGGCCGCAGTGCTCGTTACCGTGGAGCTTGAGTGCAT

GCAGCGGTTCTTTGCTGACCCGGAGATGCAGCGCAAGCTAGAGGAAACATTGCACTACACC

TTTCGACAGGGCTACGTACGCCAGGCCTGCAAGATCTCCAACGTGGAGCTCTGCAACCTGG

TCTCCTACCTTGGAATTTTGCACGAAAACCGCCTTGGGCAAAACGTGCTTCATTCCACGCT

CAAGGGCGAGGCGCGCCGCGACTACGTCCGCGACTGCGTTTACTTATTTCTATGCTACACC

TGGCAGACGGCCATGGGCGTTTGGCAGCAGTGCTTGGAGGAGTGCAACCTCAAGGAGCTGC

AGAAACTGCTAAAGCAAAACTTGAAGGACCTATGGACGGCCTTCAACGAGCGCTCCGTGGC

CGCGCACCTGGCGGACATCATTTTCCCCGAACGCCTGCTTAAAACCCTGCAACAGGGTCTG

CCAGACTTCACCAGTCAAAGCATGTTGCAGAACTTTAGGAACTTTATCCTAGAGCGCTCAG

GAATCTTGCCCGCCACCTGCTGTGCACTTCCTAGCGACTTTGTGCCCATTAAGTACCGCGA

ATGCCCTCCGCCGCTTTGGGGCCACTGCTACCTTCTGCAGCTAGCCAACTACCTTGCCTAC

CACTCTGACATAATGGAAGACGTGAGCGGTGACGGTCTACTGGAGTGTCACTGTCGCTGCA

ACCTATGCACCCCGCACCGCTCCCTGGTTTGCAATTCGCAGCTGCTTAACGAAAGTCAAAT

TATCGGTACCTTTGAGCTGCAGGGTCCCTCGCCTGACGAAAAGTCCGCGGCTCCGGGGTTG

AAACTCACTCCGGGGCTGTGGACGTCGGCTTACCTTCGCAAATTTGTACCTGAGGACTACC

ACGCCCACGAGATTAGGTTCTACGAAGACCAATCCCGCCCGCCAAATGCGGAGCTTACCGC

CTGCGTCATTACCCAGGGCCACATTCTTGGCCAATTGCAAGCCATCAACAAAGCCCGCCAA

GAGTTTCTGCTACGAAAGGGACGGGGGGTTTACTTGGACCCCCAGTCCGGCGAGGAGCTCA

ACCCAATCCCCCCGCCGCCGCAGCCCTATCAGCAGCAGCCGCGGGCCCTTGCTTCCCAGGA

TGGCACCCAAAAAGAAGCTGCAGCTGCCGCCGCCACCCACGGACGAGGAGGAATACTGGGA

CAGTCAGGCAGAGGAGGTTTTGGACGAGGAGGAGGAGGACATGATGGAAGACTGGGAGAGC

CTAGACGAGGAAGCTTCCGAGGTCGAAGAGGTGTCAGACGAAACACCGTCACCCTCGGTCG

CATTCCCCTCGCCGGCGCCCCAGAAATCGGCAACCGGTTCCAGCATGGCTACAACCTCCGC

TCCTCAGGCGCCGCCGGCACTGCCCGTTCGCCGACCCAACCGTAG (52/55K)

SEQ ID NO: 48

ATGCATCCGGTGCTGCGGCAGATGCGCCCCCCTCCTCAGCAGCGGCAAGAGCAAGAGCAGC

GGCAGACATGCAGGGCACCCTCCCCTCCTCCTACCGCGTCAGGAGGGGCGACATCCGCGGT

TGACGCGGCAGCAGATGGTGATTACGAACCCCCGCGGCGCCGGGCCCGGCACTACCTGGAC

TTGGAGGAGGGCGAGGGCCTGGCGCGGCTAGGAGCGCCCTCTCCTGAGCGGCACCCAAGGG

TGCAGCTGAAGCGTGATACGCGTGAGGCGTACGTGCCGCGGCAGAACCTGTTTCGCGACCG

CGAGGGAGAGGAGCCCGAGGAGATGCGGGATCGAAAGTTCCACGCAGGGCGCGAGCTGCGG

CATGGCCTGAATCGCGAGCGGTTGCTGCGCGAGGAGGACTTTGAGCCCGACGCGCGAACCG

GGATTAGTCCCGCGCGCGCACACGTGGCGGCCGCCGACCTGGTAACCGCATACGAGCAGAC

GGTGAACCAGGAGATTAACTTTCAAAAAAGCTTTAACAACCACGTGCGTACGCTTGTGGCG

CGCGAGGAGGTGGCTATAGGACTGATGCATCTGTGGGACTTTGTAAGCGCGCTGGAGCAAA

ACCCAAATAGCAAGCCGCTCATGGCGCAGCTGTTCCTTATAGTGCAGCACAGCAGGGACAA

CGAGGCATTCAGGGATGCGCTGCTAAACATAGTAGAGCCCGAGGGCCGCTGGCTGCTCGAT

TTGATAAACATCCTGCAGAGCATAGTGGTGCAGGAGCGCAGCTTGAGCCTGGCTGACAAGG

TGGCCGCCATCAACTATTCCATGCTTAGCCTGGGCAAGTTTTACGCCCGCAAGATATACCA

TACCCCTTACGTTCCCATAGACAAGGAGGTAAAGATCGAGGGGTTCTACATGCGCATGGCG

-continued

CTGAAGGTGCTTACCTTGAGCGACGACCTGGGCGTTTATCGCAACGAGCGCATCCACAAGG

CCGTGAGCGTGAGCCGGCGGCGCGAGCTCAGCGACCGCGAGCTGATGCACAGCCTGCAAAG

GGCCCTGGCTGGCACGGGCAGCGGCGATAGAGAGGCCGAGTCCTACTTTGACGCGGGCGCT

GACCTGCGCTGGGCCCCAAGCCGACGCGCCCTGGAGGCAGCTGGGGCCGGACCTGGGCTGG

CGGTGGCACCCGCGCGCGCTGGCAACGTCGGCGGCGTGGAGGAATATGACGAGGACGATGA

GTACGAGCCAGAGGACGGCGAGTACTAA (pTP)

SEQ ID NO: 49

ATGGCCTTGAGCGTCAACGATTGCGCGCGCCTGACCGGCCAGAGCGTCCCGACCATGGAGC

ACTTTTTGCCGCTGCGCAACATCTGGAACCGCGTCCGCGACTTTCCGCGCGCCTCCACCAC

CGCCGCCGGCATCACCTGGATGTCCAGGTACATCTACGGATATCATCGCCTTATGTTGGAA

GATCTCGCCCCCGGAGCCCCGGCCACCCTACGCTGGCCCCTCTACCGCCAGCCGCCGCCGC

ACTTTTTGGTGGGATACCAGTACCTGGTGCGGACTTGCAACGACTACGTATTTGACTCGAG

GGCTTACTCGCGTCTCAGGTACACCGAGCTCTCGCAGCCGGGTCACCAGACCGTTAACTGG

TCCGTTATGGCCAACTGCACTTACACCATCAACACGGGCGCATACCACCGCTTTGTGGACA

TGGATGACTTCCAGTCTACCCTCACGCAGGTGCAGCAGGCCATATTAGCCGAGCGCGTTG

TCGCCGACCTAGCCCTGCTTCAGCCGATGAGGGGCTTCGGGGTCACACGCATGGGAGGAAG

AGGGCGCCACCTACGGCCAAACTCCGCCGCCGCCGCAGCGATAGATGCAAGAGATGCAGGA

CAAGAGGAAGGAGAAGAAGAAGTGCCGGTAGAAAGGCTCATGCAAGACTACTACAAAGACC

TGCGCCGATGTCAAAACGAAGCCTGGGGCATGGCCGACCGCCTGCGCATTCAGCAGGCCGG

ACCCAAGGACATGGTGCTTCTGTCGACCATCCGCCGTCTCAAGACCGCCTACTTTAATTAC

ATCATCAGCAGCACCTCCGCCAGAAACAACCCCGACCGCCGCCCGCTGCCGCCCGCCACGG

TGCTCAGCCTACCTTGCGACTGTGACTGGTTAGACGCCTTTCTCGAGAGGTTTTCCGATCC

GGTCGATGCGGACTCGCTCAGGTCCCTCGGCGGCGGAGTACCTACACAACAATTGTTGAGA

TGCATCGTTAGCGCCGTATCCCTGCCGCATGGCAGCCCCCCGCCAACCCATAACCGGGACA

TGACGGGCGGCGTCTTCCAACTGCGCCCCCGCGAGAACGGCCGCGCCGTCACCGAGACCAT

GCGCCGTCGCCGCGGGGAGATGATCGAGCGCTTTGTCGACCGCCTCCCGGTGCGCCGTCGT

CGCCGCCGTGTCCCCCCTCCCCCACCGCCGCCAGAAGAAGAAGAAGGGGAGGCCCTTATGG

AAGAGGAGATTGAAGAAGAAGAAGAGGCCCCTGTAGCCTTTGAGCGCGAGGTGCGCGACAC

TGTCGCCGAGCTCATCCGTCTTCTGGAGGAGGAGTTAACCGTGTCGGCGCGCAACTCCCAG

TTTTTCAACTTCGCCGTGGACTTCTACGAGGCCATGGAGCGCCTTGAGGCCTTGGGGGATA

TCAACGAATCCACGTTGCGACGCTGGGTTATGTACTTCTTCGTGGCAGAACACACCGCCAC

CACCCTCAACTACCTCTTTCAGCGCCTGCGAAACTACGCCGTCTTCGCCCGGCACGTGGAG

CTCAATCTCGCGCAGGTGGTCATGCGCGCCCGCGATGCCGAAGGGGGCGTGGTCTACAGCC

GCGTCTGGAACGAGGGAGGCCTCAACGCCTTCTCGCAGCTCATGGCCCGCATTTCCAACGA

CCTCGCCGCCACCGTGGAGCGAGCCGGACGCGGAGATCTCCAGGAGGAAGAGATCGAGCAG

TTCATGGCCGAGATCGCCTATCAAGACAACTCAGGAGACGTGCAGGAGATTTTGCGCCAGG

CCGCCGTCAACGACACCGAAATTGATTCTGTCGAACTCTCTTTCAGGCTCAAGCTCACCGG

GCCCGTCGTCTTCACGCAGAGGCGCCAGATTCAGGAGATCAACCGCCGCGTCGTCGCGTTC

-continued

GCCAGCAACCTACGCGCGCAGCACCAGCTCCTGCCCGCGCGCGGCGCCGACGTGCCCCTGC

CCCCTCTCCCGGCGGGTCCGGAGCCCCCCCTACCTCCGGGGGCTCGCCCGCGTCACCGCTT

TTAG

The invention claimed is:

1. A life-cycle-defective Adenovirus helper vector construct or a life-cycle-defective Adenovirus helper virus containing a temperature sensitive (ts) mutation in the L4-100K protein and a ts mutation in the hexon protein, wherein
   (i) the ts mutation in the L4-100K protein is: a TCC to CCC mutation located at positions 25456-25458 of SEQ ID NO: 46, and
   (ii) the ts mutation in the hexon protein is: a GGC to GAT mutation located at positions 21170-21172 of SEQ ID NO: 46.

2. The life-cycle-defective Adenovirus helper vector construct or the life-cycle defective Adenovirus helper virus according to claim 1, wherein the remaining L4-100K coding sequence comprises the sequence of SEQ ID NO: 1.

3. The life-cycle-defective Adenovirus helper vector construct or the life-cycle defective Adenovirus helper virus according to claim 1, wherein the remaining L4-100K coding sequence consists of the sequence of SEQ ID NO: 1.

4. The life-cycle-defective Adenovirus helper vector construct or the life-cycle-defective Adenovirus helper virus according to claim 1, wherein said helper vector construct or said helper virus codes for functional viral associated (VA) RNA I and II.

5. The life-cycle-defective Adenovirus helper vector construct or the life-cycle-defective Adenovirus helper virus according to claim 1, wherein the life-cycle-defective Adenovirus helper virus is selected or derived from a serotype of subgroup A, B, C, D, E, F, or G.

6. A method for producing a life-cycle-defective Adenovirus helper virus, said method comprising introducing a life-cycle-defective Adenovirus helper vector construct according to claim 1 into a suitable host cell, and incubating the host cell until the life-cycle-defective Adenovirus helper virus is produced, wherein the suitable host cell is a host cell containing at least one of: an Adenovirus complementing gene, a L4-100K complementing cell, an Adenovirus L1-52/55K complementing cell, an Adenovirus pTP complementing cell, an Adenovirus EIA complementing cell, or an Adenovirus EIB complementing cell.

7. The method for producing a life-cycle-defective Adenovirus helper virus according to claim 6, wherein the method is further characterized by at least one of (i)-(iv):
   (i) the host cell is transiently transfected with or has stably integrated at least one of:
   an Adenovirus complementing gene, an Adenovirus L4-100K complementing gene, an Adenovirus L1-52/55K complementing gene, an Adenovirus pTP complementing gene, an Adenovirus EIA, or an Adenovirus EIB complementing gene;
   (ii) the host cell expresses at least one of: an Adenovirus L4-100K, an Adenovirus L1-52/55K protein, or an Adenovirus pTP;
   (iii) the host cell expresses at least one of: an Adenovirus L4-100K protein, or an Adenovirus pTP, and wherein the L4-100K protein and the pTP are under the control of a constitutive promoter; or
   (iv) the host cell expresses at least one of: an Adenovirus L4-100K protein, an Adenovirus L1-52/55K protein or an Adenovirus pTP, wherein the L4-100K protein, then L 1-52/55K protein and the pTP are under the control of an inducible promoter.

8. The method for producing a life-cycle-defective Adenovirus helper virus according to claim 6, wherein the method is further characterized by at least one of (i)-(vi):
   (i) incubating the host cell comprises incubating in a serum-free medium;

(ii) incubating the host cell comprises incubating at least transiently in the presence of an inducer;

(iii) incubating the host cell comprises incubating at a temperature below 37° C., from about 28° C. to about 36° C., from about 30° C. to about 34° C., or at about 32° C.;

(iv) the produced life-cycle-defective Adenovirus helper virus is harvested and purified, by means of at least one of: at least one CsC1 gradient centrifugation step, at least one filtration step, at least one ion exchange chromatography step, at least one size exclusion chromatography step, at least one affinity chromatography step, at least one hydrophobic interaction chromatography step or combinations thereof;

(v) the produced life-cycle-defective Adenovirus helper virus is concentrated by ultrafiltration; and/or (vi) the produced life-cycle-defective Adenovirus helper virus has a titer of at least about 1×10E5 i.u./μL, at least about 1×10E7 i.u./μL, at least about 1×10E9 i.u./μL, at least 1×10E10 i.u./μL, from about 10E6 to about 10E11 particles/μL, or from about 10E8 to about 10E10 particles/μL.

9. A method for producing a recombinant adeno-associated virus (rAAV), said method comprising the steps of: (1) infecting a suitable host cell containing at least one rAAV construct with a life-cycle-defective Adenovirus helper vector construct or a life-cycle-defective Adenovirus helper virus according to claim 1, and (2) incubating the host cell until the rAAV is produced.

10. The method for producing rAAV according to claim 9, wherein the remaining L4-100K coding sequence comprises the sequence of SEQ ID NO: 1.

11. The method for producing rAAV according to claim 9, wherein the remaining L4-100K coding sequence consists of the sequence of SEQ ID NO: 1.

12. The method for producing rAAV according to claim 9, wherein the life-cycle-defective Adenovirus helper virus codes for a functional viral associated (VA) RNA I and IL.

13. The method for producing rAAV according to claim 9, wherein the life-cycle-defective Adenovirus helper virus is selected or derived from a serotype of subgroup A, B, C, D, E, F, or G.

14. The method for producing rAAV according to claim 9, wherein the suitable host cell is infected with the life-cycle-defective Adenovirus helper virus at a multiplicity of infection (MOI) of at least about 1, at least about 10, at least about 100, at least about 500, or at least about 1000.

15. The method for producing rAAV according to claim 9, wherein the at least one rAAV construct is (a) episomally maintained in the host cell or (b) chromosomally integrated into the host cell.

16. The method for producing rAAV according to claim 9, wherein the host cell is selected from the group consisting of: a BHK cell, a COS cell, a Vero cell, a EB66 cell, a Hela cell, a A549 cell, a SF9 cell, a SF plus cell, a Hi5 cell, a S2 cell, a HEK293 cell, a HEK293T cell, a HEK293EBNA cell, a C139 cell, a CAP cell, a CAPT cell, a PERC6 cell, and a AGE1 cell.

17. The method for producing rAAV according to claim 9, wherein the host cell codes for at least one of: a functional Adeno virus E1 A protein, a functional Adenovirus EIB protein, or a functional Adenovirus EIB 55K protein.

18. The method for producing rAAV according to claim 9, wherein incubating the host cell comprises incubation in a serum-free medium.

19. The method for producing rAAV according to claim 9, further comprising purifying the rAAV by at least one of: at least one CsCl gradient centrifugation step, at least one filtration step, at least one ion exchange chromatography step, at least one hydrophobic interaction chromatography step, or combinations thereof.

20. The method for producing rAAV according to claim 9, further comprising concentrating the rAAV by ultrafiltration.

21. The method for producing rAAV according to claim 9, further comprising formulating the rAAV with one or more pharmaceutically acceptable excipients into a pharmaceutical preparation.

22. The method for producing rAAV according to claim 9, wherein the method is further characterized by at least one of (i)-(iii): (i) the method reduces generation of progeny Adenovirus; (ii) the rAAV produced by the method is substantially free of Adenovirus; or (iii) the method reduces generation of progeny Adenovirus and the rAAV produced by the method is substantially free of Adenovirus.

* * * * *